US011866434B2

(12) United States Patent
Wang et al.

(10) Patent No.: US 11,866,434 B2
(45) Date of Patent: Jan. 9, 2024

(54) PROCESS FOR MAKING A PD-1/PD-L1 INHIBITOR AND SALTS AND CRYSTALLINE FORMS THEREOF

(71) Applicant: Incyte Corporation, Wilmington, DE (US)

(72) Inventors: Dengjin Wang, Wilmington, DE (US); Daniel Carper, Wilmington, DE (US); Zhongjiang Jia, Kennett Square, PA (US); Bo Shen, Garnet Valley, PA (US); Joseph A. Sclafani, Malvern, PA (US); Robert Wilson, Wilmington, DE (US); Jiacheng Zhou, Newark, DE (US); Osama Suleiman, Cambridge (GB); Mark Wright, Cambridge (GB)

(73) Assignee: Incyte Corporation, Wilmington, DE (US)

( * ) Notice: Subject to any disclaimer, the term of this patent is extended or adjusted under 35 U.S.C. 154(b) by 38 days.

(21) Appl. No.: 17/520,174

(22) Filed: Nov. 5, 2021

(65) Prior Publication Data

US 2022/0144831 A1 May 12, 2022

Related U.S. Application Data

(60) Provisional application No. 63/110,792, filed on Nov. 6, 2020.

(51) Int. Cl.
*C07D 471/04* (2006.01)

(52) U.S. Cl.
CPC ........ *C07D 471/04* (2013.01); *C07B 2200/13* (2013.01)

(58) Field of Classification Search
CPC .................................................... C07D 471/04
USPC ...................................................... 514/258.1
See application file for complete search history.

(56) References Cited

U.S. PATENT DOCUMENTS

| | | | |
|---|---|---|---|
| 3,272,781 | A | 9/1966 | Goodrow |
| 4,208,328 | A | 6/1980 | Lavallee et al. |
| 4,789,711 | A | 12/1988 | Monnier et al. |
| 5,077,164 | A | 12/1991 | Ueda et al. |
| 6,114,497 | A | 9/2000 | Tada et al. |
| 6,297,351 | B1 | 10/2001 | Murayama et al. |
| 6,372,907 | B1 | 4/2002 | Lee et al. |
| 6,521,618 | B2 | 2/2003 | Boschelli et al. |
| 6,867,200 | B1 | 3/2005 | Allen et al. |
| 7,320,989 | B2 | 1/2008 | Anderson et al. |
| 7,417,065 | B2 | 8/2008 | Mi et al. |
| 7,488,802 | B2 | 2/2009 | Collins et al. |
| 7,491,245 | B2 | 2/2009 | Glenn et al. |
| 7,691,870 | B2 | 4/2010 | Buchstaller et al. |
| 7,851,489 | B2 | 12/2010 | Borzilleri et al. |
| 7,943,743 | B2 | 5/2011 | Korman et al. |
| 8,008,449 | B2 | 8/2011 | Korman et al. |
| 8,163,743 | B2 | 4/2012 | Baldwin et al. |
| 8,168,757 | B2 | 5/2012 | Finnefrock et al. |
| 8,217,149 | B2 | 7/2012 | Irving et al. |
| 8,541,424 | B2 | 9/2013 | DeGoey et al. |
| 8,993,604 | B2 | 3/2015 | Byrd et al. |
| 9,085,576 | B2 | 7/2015 | Minatti et al. |
| 9,163,017 | B2 | 10/2015 | DeGoey et al. |
| 9,394,365 | B1 | 7/2016 | Eisenbach-Schwartz et al. |
| 9,540,322 | B2 | 1/2017 | Jorgensen et al. |
| 9,603,950 | B1 | 3/2017 | Li et al. |
| 9,611,261 | B2 | 4/2017 | Minatti et al. |
| 9,643,922 | B2 | 5/2017 | Jorgensen et al. |
| 10,017,520 | B2 | 7/2018 | Koehler et al. |
| 10,202,343 | B2 | 2/2019 | Jorgensen et al. |
| 10,308,644 | B2 * | 6/2019 | Wu ........................ A61P 37/00 |
| 10,618,916 | B2 | 4/2020 | Wu et al. |
| 10,669,271 | B2 | 6/2020 | Wu et al. |
| 10,793,565 | B2 | 10/2020 | Wu et al. |
| 10,800,768 | B2 | 10/2020 | Wu et al. |
| 10,806,785 | B2 | 10/2020 | Liu et al. |
| 10,906,920 | B2 | 2/2021 | Wu et al. |
| 11,124,511 | B2 | 9/2021 | Wu et al. |
| 11,339,149 | B2 | 5/2022 | Wu et al. |
| 11,401,279 | B2 | 8/2022 | Li et al. |
| 11,407,749 | B2 | 8/2022 | Wu et al. |
| 11,414,433 | B2 | 8/2022 | Wu et al. |
| 11,465,981 | B2 | 10/2022 | Wu et al. |
| 11,566,026 | B2 | 1/2023 | Wu et al. |
| 11,572,366 | B2 | 2/2023 | Li et al. |
| 11,596,692 | B1 | 3/2023 | Wu et al. |
| 11,608,337 | B2 | 3/2023 | Li et al. |

(Continued)

FOREIGN PATENT DOCUMENTS

| | | |
|---|---|---|
| CA | 2355249 | 6/2000 |
| CA | 3099994 | 11/2019 |

(Continued)

OTHER PUBLICATIONS

Indian Office Action in Indian Application No. 202017053661, dated Jun. 3, 2022, 5 pages.
Stahl et al., "Handbook of Pharmaceutical Salts: Properties, Selection, and Use," Wiley, 2002, p. 329-350.
Abdellaoui et al., "Palladium-catalyzed non-directed C-H bond arylation of difluorobenzenes and dichlorobenzenes bearing benzoxazole or benzothiazole," Catalysis Communications, 2015, 71:13-16.
Ahmed et al., "Enantioselective Polymerization of Epoxides Using Biaryl-Linked Bimetallic Cobalt Catalysts: A Mechanistic Study," J Am Chem Soc., 2013, 135(50):18901-18911.
Alverez et al., "Structure—Activity Study of Bioisosteric Trifluoromethyl and Pentafluorosulfanyl Indole Inhibitors of the AAA ATPase p. 97," ACS Med Chem., 2015, 6(12):1225-1230.

(Continued)

*Primary Examiner* — Niloofar Rahmani
(74) *Attorney, Agent, or Firm* — Fish & Richardson P.C.

(57) ABSTRACT

This application relates to processes and intermediates for the preparation of the PD-1/PD-L1 inhibitor (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl) piperidine-4-carboxylic acid, and salts and crystalline forms thereof, where the PD-1/PD-L1 inhibitor and solid forms and salt forms thereof are useful in the treatment of various diseases including infectious diseases and cancer.

41 Claims, 6 Drawing Sheets

(56) References Cited

U.S. PATENT DOCUMENTS

| | | | |
|---|---|---|---|
| 11,613,536 | B2 | 3/2023 | Wu et al. |
| 11,673,883 | B2 | 6/2023 | Lu et al. |
| 11,718,605 | B2 | 8/2023 | Yu et al. |
| 2002/0082266 | A1 | 6/2002 | Gallant et al. |
| 2003/0134843 | A1 | 7/2003 | Lubisch et al. |
| 2003/0191115 | A1 | 10/2003 | Pinto et al. |
| 2004/0018986 | A1 | 1/2004 | Pitlik et al. |
| 2004/0058938 | A1 | 3/2004 | Cullmann et al. |
| 2004/0063963 | A1 | 4/2004 | Ueno et al. |
| 2004/0082635 | A1 | 4/2004 | Hashimoto et al. |
| 2004/0186114 | A1 | 9/2004 | Cirillo et al. |
| 2004/0214040 | A1 | 10/2004 | Lee et al. |
| 2005/0187230 | A1 | 8/2005 | Ding et al. |
| 2005/0245536 | A1 | 11/2005 | Hao et al. |
| 2005/0260126 | A1 | 11/2005 | Kudo et al. |
| 2005/0288295 | A1 | 12/2005 | Currie et al. |
| 2006/0004010 | A1 | 1/2006 | Habashita et al. |
| 2006/0084650 | A1 | 4/2006 | Dong et al. |
| 2006/0089362 | A1 | 4/2006 | Seno et al. |
| 2006/0178367 | A1 | 8/2006 | Currie et al. |
| 2006/0183746 | A1 | 8/2006 | Currie et al. |
| 2006/0229337 | A1 | 10/2006 | Brittelli et al. |
| 2006/0270686 | A1 | 11/2006 | Kelly et al. |
| 2007/0099938 | A1 | 5/2007 | Ohmoto et al. |
| 2007/0191395 | A1 | 8/2007 | Kawakami et al. |
| 2008/0045536 | A1 | 2/2008 | Vaccaro et al. |
| 2008/0139557 | A1 | 6/2008 | Blomgren et al. |
| 2008/0153834 | A1 | 6/2008 | Blomgren et al. |
| 2008/0280891 | A1 | 11/2008 | Kelly et al. |
| 2009/0163545 | A1 | 6/2009 | Goldfarb |
| 2009/0253735 | A1 | 10/2009 | Almario-Garcia et al. |
| 2009/0281075 | A1 | 11/2009 | Roughton et al. |
| 2009/0281120 | A1 | 11/2009 | Nakai et al. |
| 2009/0304821 | A1 | 12/2009 | Notoya et al. |
| 2010/0155712 | A1 | 6/2010 | Kitamura |
| 2010/0160292 | A1 | 6/2010 | Whitney et al. |
| 2010/0160303 | A1 | 6/2010 | Liu et al. |
| 2010/0249151 | A1 | 9/2010 | Klein et al. |
| 2010/0267775 | A1 | 10/2010 | Negoro et al. |
| 2010/0267778 | A1 | 10/2010 | Kusuda et al. |
| 2010/0273832 | A1 | 10/2010 | Jung et al. |
| 2010/0292227 | A1 | 11/2010 | Yoakim et al. |
| 2011/0053915 | A1 | 3/2011 | Ivaschenko et al. |
| 2011/0062858 | A1 | 3/2011 | Yersin et al. |
| 2011/0065699 | A1 | 3/2011 | De Peretti et al. |
| 2011/0065700 | A1 | 3/2011 | De Peretti et al. |
| 2011/0065745 | A1 | 3/2011 | De Peretti et al. |
| 2011/0124640 | A1 | 5/2011 | Liu et al. |
| 2011/0294781 | A1 | 12/2011 | Yamamoto et al. |
| 2011/0301145 | A1 | 12/2011 | Barbosa, Jr. et al. |
| 2012/0058996 | A1 | 3/2012 | Liu et al. |
| 2012/0295884 | A1 | 11/2012 | Altmann et al. |
| 2012/0323002 | A1 | 12/2012 | Yamamoto et al. |
| 2012/0328569 | A1 | 12/2012 | McComas et al. |
| 2013/0096118 | A1 | 4/2013 | Liu et al. |
| 2013/0131063 | A1 | 5/2013 | Castro et al. |
| 2013/0203741 | A1 | 8/2013 | Suzuki et al. |
| 2013/0203747 | A1 | 8/2013 | Yoakim et al. |
| 2013/0203754 | A1 | 8/2013 | Yang et al. |
| 2013/0253011 | A1 | 9/2013 | Jung et al. |
| 2014/0058097 | A1 | 2/2014 | Kobayashi et al. |
| 2014/0088117 | A1 | 3/2014 | Burch et al. |
| 2014/0128382 | A1 | 5/2014 | Wu et al. |
| 2014/0243306 | A1 | 8/2014 | Heng et al. |
| 2014/0275058 | A1 | 9/2014 | Minatti et al. |
| 2014/0288094 | A1 | 9/2014 | Bennett et al. |
| 2014/0378447 | A1 | 12/2014 | Okano et al. |
| 2015/0005279 | A1 | 1/2015 | Bonafoux et al. |
| 2015/0011751 | A1 | 1/2015 | Kawakami et al. |
| 2015/0073024 | A1 | 3/2015 | Sasikumar et al. |
| 2015/0181880 | A1 | 7/2015 | Takahashi |
| 2015/0210680 | A1 | 7/2015 | Kobayashi et al. |
| 2015/0232478 | A1 | 8/2015 | Ishida et al. |
| 2015/0239868 | A1 | 8/2015 | Pais et al. |
| 2015/0252011 | A1 | 9/2015 | Minatti et al. |
| 2015/0258505 | A1 | 9/2015 | Hironaka et al. |
| 2015/0291549 | A1 | 10/2015 | Chupak et al. |
| 2015/0299227 | A1 | 10/2015 | Wolkenberg et al. |
| 2015/0307465 | A1 | 10/2015 | Scott et al. |
| 2015/0376172 | A1 | 12/2015 | Guba et al. |
| 2016/0015690 | A1 | 1/2016 | Babaoglu et al. |
| 2016/0046648 | A1 | 2/2016 | Petrukhin et al. |
| 2016/0130251 | A1 | 5/2016 | Graupe et al. |
| 2016/0194295 | A1 | 7/2016 | Sasikumar et al. |
| 2016/0229816 | A1 | 8/2016 | Sato et al. |
| 2016/0280695 | A1 | 9/2016 | Minatti et al. |
| 2017/0107216 | A1 | 4/2017 | Wu et al. |
| 2017/0145025 | A1 | 5/2017 | Li et al. |
| 2017/0174671 | A1 | 6/2017 | Wu et al. |
| 2017/0174679 | A1 | 6/2017 | Lajkiewicz et al. |
| 2017/0304282 | A1 | 10/2017 | Rocco et al. |
| 2017/0320875 | A1 | 11/2017 | Li et al. |
| 2017/0342060 | A1 | 11/2017 | Lu et al. |
| 2017/0362253 | A1 | 12/2017 | Xiao et al. |
| 2018/0016260 | A1 | 1/2018 | Yu et al. |
| 2018/0057486 | A1 | 3/2018 | Wu et al. |
| 2018/0177784 | A1 | 6/2018 | Wu et al. |
| 2018/0177870 | A1 | 6/2018 | Liu et al. |
| 2018/0179179 | A1 | 6/2018 | Wu et al. |
| 2018/0179197 | A1 | 6/2018 | Wu et al. |
| 2018/0179201 | A1 | 6/2018 | Wu et al. |
| 2018/0179202 | A1 | 6/2018 | Wu et al. |
| 2018/0273519 | A1 | 9/2018 | Wu et al. |
| 2019/0040082 | A1 | 2/2019 | Xiao et al. |
| 2019/0062345 | A1 | 2/2019 | Xiao et al. |
| 2019/0071439 | A1 | 3/2019 | Li et al. |
| 2019/0144439 | A1 | 5/2019 | Wu et al. |
| 2019/0202824 | A1 | 7/2019 | Wu et al. |
| 2019/0225601 | A1 | 7/2019 | Wu et al. |
| 2019/0270706 | A1 | 9/2019 | Jorgensen et al. |
| 2019/0300524 | A1 | 10/2019 | Wu et al. |
| 2019/0345170 | A1 | 11/2019 | Wu et al. |
| 2020/0172533 | A1 | 6/2020 | Wu et al. |
| 2020/0172541 | A1 | 6/2020 | Li et al. |
| 2020/0181126 | A1 | 6/2020 | Lu et al. |
| 2020/0255424 | A1 | 8/2020 | Wu et al. |
| 2020/0277309 | A1 | 9/2020 | Wu et al. |
| 2020/0283423 | A1 | 9/2020 | Yu et al. |
| 2020/0325115 | A1 | 10/2020 | Wu et al. |
| 2020/0397893 | A1 | 12/2020 | Liu et al. |
| 2020/0407357 | A1 | 12/2020 | Lajkiewicz et al. |
| 2021/0002276 | A1 | 1/2021 | Wu et al. |
| 2021/0017164 | A1 | 1/2021 | Lu et al. |
| 2021/0017175 | A1 | 1/2021 | Li et al. |
| 2021/0040090 | A1 | 2/2021 | Jia et al. |
| 2021/0094976 | A1 | 4/2021 | Li et al. |
| 2021/0107900 | A1 | 4/2021 | Wu et al. |
| 2021/0115025 | A1 | 4/2021 | Yu et al. |
| 2021/0115068 | A1 | 4/2021 | Wu et al. |
| 2021/0139511 | A1 | 5/2021 | Jia et al. |
| 2021/0221819 | A1 | 7/2021 | Li et al. |
| 2021/0317139 | A1 | 10/2021 | Xiao et al. |
| 2021/0347771 | A1 | 11/2021 | Wu et al. |
| 2021/0363137 | A1 | 11/2021 | Wu et al. |
| 2021/0380584 | A1 | 12/2021 | Wu et al. |
| 2022/0089588 | A1 | 3/2022 | Wu et al. |
| 2022/0144830 | A1 | 5/2022 | Zhou et al. |
| 2022/0144832 | A1 | 5/2022 | Jia et al. |
| 2022/0193050 | A1 | 6/2022 | Yang et al. |
| 2022/0194931 | A1 | 6/2022 | Wu et al. |
| 2022/0213090 | A1 | 7/2022 | Wu et al. |
| 2022/0340600 | A1 | 10/2022 | Li et al. |
| 2022/0348594 | A1 | 11/2022 | Wu et al. |
| 2022/0412976 | A1 | 12/2022 | Lovat |
| 2023/0100875 | A1 | 3/2023 | Lajkiewicz et al. |
| 2023/0146129 | A1 | 5/2023 | Wu et al. |
| 2023/0149409 | A1 | 5/2023 | Geschwindt et al. |
| 2023/0181605 | A1 | 6/2023 | Mohanlal et al. |
| 2023/0226062 | A1 | 7/2023 | Wu et al. |

FOREIGN PATENT DOCUMENTS

| | | |
|---|---|---|
| CL | 2018001531 | 7/2018 |
| CL | 2018003734 | 2/2019 |

(56) References Cited

FOREIGN PATENT DOCUMENTS

| | | | |
|---|---|---|---|
| CL | 2018003701 | | 4/2019 |
| CL | 2018003697 | | 5/2019 |
| CL | 2019001744 | | 10/2019 |
| CL | 2020002511 | | 9/2020 |
| CN | 1344256 | | 4/2002 |
| CN | 101891895 | | 11/2010 |
| CN | 101910158 | | 12/2010 |
| CN | 101993415 | | 3/2011 |
| CN | 103933036 | | 7/2014 |
| CN | 104045552 | | 9/2014 |
| CN | 104211726 | | 12/2014 |
| CN | 105164121 | | 12/2015 |
| CN | 105705489 | | 6/2016 |
| EP | 0361069 | | 4/1990 |
| EP | 0644460 | | 3/1995 |
| EP | 1505068 | | 2/2005 |
| EP | 1644370 | | 4/2006 |
| EP | 1942105 | | 7/2008 |
| EP | 2233474 | | 9/2010 |
| EP | 2402345 | | 1/2012 |
| EP | 2871179 | | 5/2015 |
| EP | 2824099 | | 1/2018 |
| FR | 1425700 | | 1/1966 |
| JP | H 10316853 | | 12/1998 |
| JP | 2000128986 | | 5/2000 |
| JP | 2000128987 | | 5/2000 |
| JP | 2000212281 | | 8/2000 |
| JP | 2001114893 | | 4/2001 |
| JP | 2001163975 | | 6/2001 |
| JP | 3461397 | | 10/2003 |
| JP | 2003287634 | | 10/2003 |
| JP | 2004059761 | | 2/2004 |
| JP | 2004091369 | | 3/2004 |
| JP | 2004294556 | | 10/2004 |
| JP | 2005002330 | | 1/2005 |
| JP | 2005248082 | | 9/2005 |
| JP | 2005290301 | | 10/2005 |
| JP | 2006290883 | | 10/2006 |
| JP | 2008218327 | | 9/2008 |
| JP | 2010202530 | | 9/2010 |
| JP | 2010540452 | | 12/2010 |
| JP | 2013084945 | | 5/2013 |
| JP | 2014520866 | | 8/2014 |
| JP | 2014532066 | | 12/2014 |
| JP | 2015155397 | | 8/2015 |
| JP | 2015193612 | | 11/2015 |
| JP | 2016135778 | | 7/2016 |
| JP | 2016532710 | | 10/2016 |
| JP | 2019523231 | | 8/2019 |
| JP | 2019530732 | | 10/2019 |
| JP | 2020504737 | | 2/2020 |
| JP | 2020504739 | | 2/2020 |
| JP | 2020514271 | | 5/2020 |
| JP | 2020514272 | | 5/2020 |
| JP | 6911031 | | 7/2021 |
| KR | 1715090 | | 3/2015 |
| KR | 1717601 | | 12/2015 |
| KR | 1653560 | | 2/2016 |
| MX | 2019007651 | | 2/2020 |
| TW | 103143948 | | 12/2014 |
| TW | 201625527 | | 7/2016 |
| WO | WO 98/27108 | | 6/1998 |
| WO | WO 1999/018096 | | 4/1999 |
| WO | WO 99/44992 | A1 | 9/1999 |
| WO | WO 00/35886 | | 6/2000 |
| WO | WO 01/07409 | | 2/2001 |
| WO | WO 2001/047883 | | 7/2001 |
| WO | WO 01/74815 | | 10/2001 |
| WO | WO 2002/000196 | | 1/2002 |
| WO | WO 02/14321 | | 2/2002 |
| WO | WO 02/48147 | | 6/2002 |
| WO | WO 02/066477 | | 8/2002 |
| WO | WO 02/071827 | | 9/2002 |
| WO | WO 02/078700 | | 10/2002 |
| WO | WO 02/083672 | | 10/2002 |
| WO | WO 02/088124 | | 11/2002 |
| WO | WO 03/022845 | | 3/2003 |
| WO | WO 03/030901 | | 4/2003 |
| WO | WO 03/031587 | | 4/2003 |
| WO | WO 2003/042402 | | 5/2003 |
| WO | WO 2004/006906 | | 1/2004 |
| WO | WO 2004/033454 | | 4/2004 |
| WO | WO 2004/035588 | | 4/2004 |
| WO | WO 2004/085385 | | 10/2004 |
| WO | WO 2004/089940 | | 10/2004 |
| WO | WO 2005/000833 | | 1/2005 |
| WO | WO 2005/005429 | | 1/2005 |
| WO | WO 2005/014543 | | 2/2005 |
| WO | WO 2005/014599 | | 2/2005 |
| WO | WO 2005/023761 | | 3/2005 |
| WO | WO 2005/034869 | | 4/2005 |
| WO | WO 2005/047290 | | 5/2005 |
| WO | WO 2005/063710 | | 7/2005 |
| WO | WO 2005/077948 | | 8/2005 |
| WO | WO 2005/079802 | | 9/2005 |
| WO | WO 2005/080316 | | 9/2005 |
| WO | WO 2005/086808 | | 9/2005 |
| WO | WO 2005/086904 | | 9/2005 |
| WO | WO 2005/097751 | | 10/2005 |
| WO | WO 2005/103022 | | 11/2005 |
| WO | WO 2005/105798 | | 11/2005 |
| WO | WO 2006/034317 | | 3/2006 |
| WO | WO 2006/034337 | | 3/2006 |
| WO | WO 2006/050803 | | 5/2006 |
| WO | WO 2006/053121 | | 5/2006 |
| WO | WO 2006/094235 | | 9/2006 |
| WO | WO 2006/099075 | | 9/2006 |
| WO | WO 2006/125101 | | 11/2006 |
| WO | WO 2007/004954 | | 1/2007 |
| WO | WO 2007/034282 | | 3/2007 |
| WO | WO 2007/038314 | | 4/2007 |
| WO | WO 2007/061764 | | 5/2007 |
| WO | WO 2007/067711 | | 6/2007 |
| WO | WO 2007/069565 | | 6/2007 |
| WO | WO 2007/096764 | | 8/2007 |
| WO | WO 2007/113226 | | 10/2007 |
| WO | WO 2007/146712 | | 12/2007 |
| WO | WO 2008/011560 | | 1/2008 |
| WO | WO 2008/021745 | | 2/2008 |
| WO | WO 2008/027812 | | 3/2008 |
| WO | WO 2008/032171 | | 3/2008 |
| WO | WO 2008/033854 | | 3/2008 |
| WO | WO 2008/033857 | | 3/2008 |
| WO | WO 2008/033858 | | 3/2008 |
| WO | WO 2008/057254 | | 5/2008 |
| WO | WO 2008/062182 | | 5/2008 |
| WO | WO 2008/064317 | | 5/2008 |
| WO | WO 2008/064318 | | 5/2008 |
| WO | WO 2008/071944 | | 6/2008 |
| WO | WO 2008/079965 | | 7/2008 |
| WO | WO 2008/104077 | | 9/2008 |
| WO | WO 2008/104278 | | 9/2008 |
| WO | WO 2008/104279 | | 9/2008 |
| WO | WO 2008/111299 | | 9/2008 |
| WO | WO 2008/114002 | | 9/2008 |
| WO | WO 2008/118122 | | 10/2008 |
| WO | WO 2008/133274 | | 11/2008 |
| WO | WO 2008/134553 | | 11/2008 |
| WO | WO 2008/141249 | | 11/2008 |
| WO | WO 2008/156712 | | 12/2008 |
| WO | WO 2009/027733 | | 3/2009 |
| WO | WO 2009/038759 | | 3/2009 |
| WO | WO 2009/039397 | | 3/2009 |
| WO | WO 2009/059162 | | 5/2009 |
| WO | WO 2009/062059 | | 5/2009 |
| WO | WO 2009/075830 | | 6/2009 |
| WO | WO 2009/077197 | | 6/2009 |
| WO | WO 2009/079683 | | 7/2009 |
| WO | WO 2009/106539 | | 9/2009 |
| WO | WO 2009/106597 | | 9/2009 |
| WO | WO 2009/123986 | | 10/2009 |
| WO | WO 2009/139576 | | 11/2009 |
| WO | WO 2009/143156 | | 11/2009 |
| WO | WO 2009/146358 | | 12/2009 |

(56) References Cited

FOREIGN PATENT DOCUMENTS

| | | |
|---|---|---|
| WO | WO 2010/011837 | 1/2010 |
| WO | WO 2010/029950 | 3/2010 |
| WO | WO 2010/036959 | 4/2010 |
| WO | WO 2010/056875 | 5/2010 |
| WO | WO 2010/064020 | 6/2010 |
| WO | WO 2010/071885 | 6/2010 |
| WO | WO 2010/075376 | 7/2010 |
| WO | WO 2010/080474 | 7/2010 |
| WO | WO 2010/089411 | 8/2010 |
| WO | WO 2010/104306 | 9/2010 |
| WO | WO 2010/115736 | 10/2010 |
| WO | WO 2010/119264 | 10/2010 |
| WO | WO 2010/130034 | 11/2010 |
| WO | WO 2011/002635 | 1/2011 |
| WO | WO 2011/008709 | 1/2011 |
| WO | WO 2011/018170 | 2/2011 |
| WO | WO 2011/044181 | 4/2011 |
| WO | WO 2011/047129 | 4/2011 |
| WO | WO 2011/047319 | 4/2011 |
| WO | WO 2011/050245 | 4/2011 |
| WO | WO 2009/096202 | 5/2011 |
| WO | WO 2011/066342 | 6/2011 |
| WO | WO 2011/082400 | 7/2011 |
| WO | WO 2011/097607 | 8/2011 |
| WO | WO 2011/113606 | 9/2011 |
| WO | WO 2011/117264 | 9/2011 |
| WO | WO 2011/140202 | 11/2011 |
| WO | WO 2011/159877 | 12/2011 |
| WO | WO 2011/161699 | 12/2011 |
| WO | WO 2012/016133 | 2/2012 |
| WO | WO 2012/033735 | 3/2012 |
| WO | WO 2012/034363 | 3/2012 |
| WO | WO 2012/047856 | 4/2012 |
| WO | WO 2012/052730 | 4/2012 |
| WO | WO 2012/052745 | 4/2012 |
| WO | WO 2012/068406 | 5/2012 |
| WO | WO 2012/080376 | 6/2012 |
| WO | WO 2012/088411 | 6/2012 |
| WO | WO 2012/100342 | 8/2012 |
| WO | WO 2012/125886 | 9/2012 |
| WO | WO 2012/129562 | 9/2012 |
| WO | WO 2012/139425 | 10/2012 |
| WO | WO 2012/159565 | 11/2012 |
| WO | WO 2012/166951 | 12/2012 |
| WO | WO 2012/168733 | 12/2012 |
| WO | WO 2012/175991 | 12/2012 |
| WO | WO 2013/008095 | 1/2013 |
| WO | WO 2013/033901 | 3/2013 |
| WO | WO 2013/040528 | 3/2013 |
| WO | WO 2013/057650 | 4/2013 |
| WO | WO 2013/059594 | 4/2013 |
| WO | WO 2013/120040 | 8/2013 |
| WO | WO 2013/134113 | 9/2013 |
| WO | WO 2013/157021 | 10/2013 |
| WO | WO 2013/163404 | 10/2013 |
| WO | WO 2014/009295 | 1/2014 |
| WO | WO 2014/009296 | 1/2014 |
| WO | WO 2014/017087 | 1/2014 |
| WO | WO 2014/039595 | 3/2014 |
| WO | WO 2014/061693 | 4/2014 |
| WO | WO 2014/081878 | 5/2014 |
| WO | WO 2014/113388 | 7/2014 |
| WO | WO 2014/114532 | 7/2014 |
| WO | WO 2014/121085 | 8/2014 |
| WO | WO 2014/133046 | 9/2014 |
| WO | WO 2014/138484 | 9/2014 |
| WO | WO 2014/138791 | 9/2014 |
| WO | WO 2014/151634 | 9/2014 |
| WO | WO 2014/152536 | 9/2014 |
| WO | WO 2014/159959 | 10/2014 |
| WO | WO 2014/181287 | 11/2014 |
| WO | WO 2014/186035 | 11/2014 |
| WO | WO 2014/210255 | 12/2014 |
| WO | WO 2015/000715 | 1/2015 |
| WO | WO 2015/013635 | 1/2015 |
| WO | WO 2015/018940 | 2/2015 |
| WO | WO 2015/033299 | 3/2015 |
| WO | WO 2015/033301 | 3/2015 |
| WO | WO 2015/034820 | 3/2015 |
| WO | WO 2015/036927 | 3/2015 |
| WO | WO 2015/086498 | 6/2015 |
| WO | WO 2015/086499 | 6/2015 |
| WO | WO 2015/086502 | 6/2015 |
| WO | WO 2015/086512 | 6/2015 |
| WO | WO 2015/095337 | 6/2015 |
| WO | WO 2015/101622 | 7/2015 |
| WO | WO 2015/120364 | 8/2015 |
| WO | WO 2015/150097 | 10/2015 |
| WO | WO 2015/160641 | 10/2015 |
| WO | WO 2015/175678 | 11/2015 |
| WO | WO 2015/197028 | 12/2015 |
| WO | WO 2016/044604 | 3/2016 |
| WO | WO 2016/094688 | 6/2016 |
| WO | WO 2016/116525 | 7/2016 |
| WO | WO 2016/118404 | 7/2016 |
| WO | WO 2016/156282 | 10/2016 |
| WO | WO 2017/035405 | 3/2017 |
| WO | WO 2017/066227 | 4/2017 |
| WO | WO 2017/070089 | 4/2017 |
| WO | WO 2017/070320 | 4/2017 |
| WO | WO 2017/087777 | 5/2017 |
| WO | WO 2017/106634 | 6/2017 |
| WO | WO 2017/108569 | 6/2017 |
| WO | WO 2017/109041 | 6/2017 |
| WO | WO 2017/112617 | 6/2017 |
| WO | WO 2017/112730 | 6/2017 |
| WO | WO 2017/192961 | 11/2017 |
| WO | WO 2017/205464 | 11/2017 |
| WO | WO 2017/222976 | 12/2017 |
| WO | WO 2017/223239 | 12/2017 |
| WO | WO 2018/013789 | 1/2018 |
| WO | WO 2018/026971 | 2/2018 |
| WO | WO 2018/044783 | 3/2018 |
| WO | WO 2018/045084 | 3/2018 |
| WO | WO 2016/057500 | 4/2018 |
| WO | WO 2018/116259 | 6/2018 |
| WO | WO 2018/119036 | 6/2018 |
| WO | WO 2018/119221 | 6/2018 |
| WO | WO 2018/119224 | 6/2018 |
| WO | WO 2018/119236 | 6/2018 |
| WO | WO 2018/119263 | 6/2018 |
| WO | WO 2018/119266 | 6/2018 |
| WO | WO 2018/119286 | 6/2018 |
| WO | WO 2018/195321 | 10/2018 |
| WO | WO 2019/023575 | 1/2019 |
| WO | WO 2019/032547 | 2/2019 |
| WO | WO 2019/034172 | 2/2019 |
| WO | WO 2019/191707 | 10/2019 |
| WO | WO 2019/192506 | 10/2019 |
| WO | WO 2019/204609 | 10/2019 |
| WO | WO 2020/086556 | 4/2020 |
| WO | WO 2020/088357 | 5/2020 |
| WO | WO 2020/156323 | 8/2020 |
| WO | WO 2021/030162 | 2/2021 |
| WO | WO 2021/053207 | 3/2021 |

OTHER PUBLICATIONS

Amaya et al., “Synthesis of three-dimensionally arranged bis-biphenol ligand on hexaaryl benzene scaffold and its application for cross-pinacol coupling reaction,” Tetrahedron Letters, 2011, 52(35):4567-4569.

Anyika et al., “Point-to-Axial Chirality Transfer—A New Probe for “Sensing” the Absolute Configurations of Monoamines,” J Am Chem Soc., 2014, 136(2):550-553.

Argentina Office Action in Argentina Application No. 20170103634, dated Jan. 27, 2022, 7 pages.

Arkin et al., “Small-Molecule Inhibitors of Protein-Protein Interactions: Progressing toward the Reality,” Chemistry & Biology, Sep. 2014, 21:1102-1114.

Arkin et al., “Small-Molecule Inhibitors of Protein-Protein Interactions: Progressing Towards the Dream,” Nature Reviews, Apr. 2004, 3:301-317.

(56) References Cited

OTHER PUBLICATIONS

Artz et al., "Host-guest complexation. 28. Hemispherands with four self-organizing units," J Am Chem Soc., 1984, 106(7):2160-2171.
Atzrodt et al., "The Renaissance of H/D Exchange," Angew Chem Int Ed., 2007, 7744-7765.
Australian Office Action in Australian Application No. 2016358100, dated May 8, 2020, 5 pages.
Australian Notice of Allowance in Australian Application No. 2017382870, dated Mar. 15, 2022, 4 pages.
Azuma et al., "B7-H1 is a ubiquitous antiapoptotic receptor on cancer cells," Blood, Apr. 1, 2018, 111(7):3635-3643.
Barakat, "Do We Need Small Molecule Inhibitors for the Immune Checkpoints?" J. Pharma. Care Health Sys., 2014, 1(4):1000e119.
Barber et al., "Restoring function in exhausted CD8 T cells during chronic viral infection," Nature, Feb. 2006, 439:682-687.
Bastin et al., "Salt Selection and Optimisation for Pharmaceutical New Chemical Entities," Org Proc Res Dev., dated Jan. 1, 2000, pp. 4(5):427-435.
Bentley et al., "Antenna Biphenols: Development of Extended Wavelength Chiroptical Reporters," J Org Chem., 2016, 81(3):1185-1191.
Berg, "Modulation of Protein-Protein Interactions with Small Organic Molecules," Angew. Chem. Int. Ed., 2003, 42:2462-2481.
Berge et al., "Pharmaceutical Salts," J. Pharm. Sci., Jan. 1977, 66(1):1-19.
Blank et al., "PD-L1/B7H-1 Inhibits the Effector Phase of Tumor Rejection by T Cell Receptor (TCR) Transgenic CD8+ T Cells," Cancer Res., Feb. 2004, 64(3):1140-5.
Blom et al., "Optimizing Preparative LC-MS Configurations and Methods for Parallel Synthesis Purification", J. Combi. Chem., 2003, 5:670-83.
Blom et al., "Preparative LC-MS Purification: Improved Compound Specific Method Optimization", J. Combi. Chem., Nov. 2004, 6:874-883.
Blom, "Two-Pump At Column Dilution Configuration for Preparative LC-Ms", K. Blom, J. Combi. Chem., 2002, 4:295-301.
Brazilian Office Action in Brazilian Application No. BR112018012756-6, dated Jan. 5, 2021, 6 pages.
Bross et al., "Radiation damage to 2-(2'-hydroxyphenyl)benzothiazoles," Radiation Physics and Chemistry, Jul. 1992, 41:379-387.
Buisman et al., "Chiral Cooperativity in Diastereomeric Diphosphite Ligands: Effects on the Rhodium-Catalyzed Enantioselective Hydroformylation of Styrene," Organometallics, 1997, 16(13):2929-2939.
Caira, "Crystalline Polymorphism of Organic Compounds," Topics in Current Chemistry, Jan. 1, 1998, 198:163-208.
Camara et al., "Multiple dermatofibromas: Dermoscopic patterns," Indian journal of dermatology, 2013, 58(3):243.
Carter et al., "PD-1:PD-L inhibitory pathway affects both CD4+ and CD8+ T cells and is overcome by IL-2," Eur. J. Immunol., 2002, 32(3):634-643.
Chang et al., "Blocking of the PD-1/PD-L1 Interaction by a d-Peptide Antagonist for Cancer Immunotherapy" Angew. Chem. Int. Ed., 2015, 26 pages; Supporting Information for 127(40):11926-11930.
Chang et al., "Blocking of the PD-1/PD-L1 Interaction by a d-Peptide Antagonist for Cancer Immunotherapy," Angew. Chem. Int. Ed., 2015, 127(40):11926-11930.
Chen et al., "Anti-PD-1/PD-L1 therapy of human cancer: past, present, and future," J. Clin. Invest., Sep. 2015, 125(9):3384-3391.
Cheng et al., "Cancer-associated fibroblasts induce PDL1+ neutrophils through the IL6-STAT3 pathway that foster immune suppression in hepatocellular carcinoma," Cell Death and Disease, 2018, 9:422.
Cheng et al., "Recent Advances in Small Molecule Based Cancer Immunotherapy," Eur J Med Chem., 2018, 157:582-598.
Cheng et al., "Structure and Interactions of the Human Programmed Cell Death 1 Receptor," J. Bio. Chem., Apr. 2013, 288(17):11771-11785.
Cheng et al., "Synthetic connections to the aromatic directed metalation reaction. Iterative ortho metalation-cross coupling tactics for the construction of polyphenyls," Tetrahedron Letters, 1978, 28(43):5097-5098.
Chilean Office Action in Chilean Application No. 201801685, dated Aug. 20, 2019, 18 pages.
Chilean Office Action in Chilean Application No. 201803701, dated Nov. 22, 2019, 18 pages.
Chilean Office Action in Chilean Application No. 201901744, dated Apr. 14, 2020, 19 pages.
Chilean Office Action in Chilean Application No. 2922-2020, dated Dec. 8, 2021, 21 pages.
Chinese Office Action in Chinese Application No. 201680077700.8, dated Jul. 2, 2021, 23 pages.
Chinese Search Report in Chinese Application No. 201780049752.9, dated Dec. 28, 2020, 5 pages.
Clayden et al., "Conformational Preference and Remote (1,10) Stereocontrol in Bipheny1-2,2'-dicarboxamides," Org. Lett., 2001, 3(26):4133-4136.
Colombian Office Action in Colombian Application No. NC2019/0000386, dated Sep. 25, 2020, 18 pages.
Cram et al., "Host-guest complexation. 29. Expanded hemispherands," J Am Chem Soc., 1984, 106(11):6386-3292.
Cram et al., "Host-guest complexation. 32. Spherands composed of cyclic urea and anisyl units," J Am Chem Soc., 1984, 106(23):7150-7167.
Cram et al., "Host-guest complexation. 26. Cavitands composed of fluorobenzene units bonded in their 2,6-positions to form macrocycles," J Am Chem Soc., 1984, 106(3):695-701.
Cram et al., "Spherand hosts containing cyclic urea units," J Am Chem Soc., 1982, 104(24):6828-6830.
Curis, "Overview and Path for Growth," Aurigene Strategic Collaboration, Jan. 21, 2015, 13 slides.
Database accession No. 1478989-52-4 abstract, Nov. 22, 2013, 1 page.
Database Accession No. 1568738-04-4 abstract, Mar. 14, 2014, 1 page.
Database Accession No. 1580823-55-7 abstract, Apr. 6, 2014, 1 page.
Database Accession No. 1581556-71-9 abstract, Apr. 8, 2014, 1 page.
Database Accession No. 1590700-72-3 abstract, Apr. 27, 2014, 1 page.
Database accession No. 2013:447446 abstract, 2013, 1 page.
De Lucca et al., "Small Molecule Reversible Inhibitors of Bruton's Tyrosine Kinase (BTK): Structure Activity Relationships Leading to the Identification of 7-(2-Hydroxypropan-2-yl)-4-[2-methyl-3-(4-oxo-3,4-dihydroquinazolin-3-yl)phenyl]-9H-carbazole-1-carboxamide (BMS-935177)," Journal of Medicinal Chemistry, 2016, 59(17):7915-7935.
Dhanunjayarao et al., "Synthesis and Optical Properties of Salicylaldimine-Based Diboron Complexes," Eur J Inorg Chem., 2014, 3:539-545.
Differding, "AUNP-12—A Novel Peptide Therapeutic Targeting PD-1 Immune Checkpoint Pathway for Cancer Immunotherapy—Structure Activity Relationships & Peptide / Peptidomimetic Analogs," Differding Consulting s.p.r.l. (Belgium), Feb. 26, 2014, 12 pages.
Dolan et al., "PD-1 Pathway Inhibitors: Changing the Landscape of Cancer Immunotherapy," Cancer Control, Jul. 2014, 21(3):231-237.
Domling et al., "Programmed Death-1: Therapeutic Success after More than 100 Years of Cancer Immunotherapy," Angew. Chem. Int. Ed., 2014, 53:2283-2288.
Dong et al., "Tumor-associated B7-H1 promotes T-cell apoptosis: a potential mechanism of immune evasion," Nature Medicine, Aug. 2002, 8(8):793-800.
Ecuador Opposition in Ecuador Application No. SENADI-2019-3773, dated Oct. 10, 2019, 29 pages.
Escarcega-Bobadilla et al., "A Recyclable Trinuclear Bifunctional Catalyst Derived from a Tetraoxo Bis-Zn(salphen) Metalloligand," Chemistry—A European Journal., 2013, 19(8):2641-2648.

(56) References Cited

OTHER PUBLICATIONS

Escarcega-Bobadilla et al., "Metal-directed assembly of chiral bis-Zn(II) Schiff base structures," Dalton Transactions, 2012, 41(32):9766-9772.
Escarcega-Bobadilla et al., "Versatile Switching in Substrate Topicity: Supramolecular Chirality Induction in Di- and Trinuclear Host Complexes," Chemistry—A European Journal, 2012:8(22):6805-6810.
Eurasian Office Action in Eurasian Application No. 201990074/28, dated Oct. 3, 2019, 5 pages.
European Communication in European Application No. 16805690.1, dated Jan. 22, 2020, 5 pages.
European Communication in European Application No. 16805690.1, dated Jul. 10, 2018, 6 pages.
European Communication in European Application No. 16805690.1, dated Nov. 5, 2020, 4 pages.
European Communication in European Application No. 17743174.9, dated Jan. 31, 2020, 5 pages.
European Communication in European Application No. 20202254.7, dated Apr. 1, 2022, 4 pages.
Fabris et al., "Central to Axial Transfer of Chirality in Menthone or Camphor-Derived 2,2'-Biphenols," J Org Chem., 1997, 62(21):7156-7164.
FDA Report, "22 Case Studies Where Phase 2 and Phase 3 Trials Had Divergent Results," U.S. Food and Drug Administration, Jan. 2017, 44 pages.
Francisco et al., "The PD-1 Pathway in Tolerance and Autoimmunity," Immunol. Rev., Jul. 2010, 236:219-242.
Freeman et al., "Engagement of the Pd-1 Immunoinhibitory Receptor by a Novel B7 Family Member Leads to Negative Regulation of Lymphocyte Activation," J. Exp. Med., Oct. 2000, 192(7):1027-34.
Freeman, "Structures of PD-1 with its ligands: Sideways and dancing cheek to cheek," PNAS, Jul. 2008, 105(30):10275-10276.
Freindorf, M., "Vibronic couplings in an excited state of hydrogen bond dimeric systems," Acta Physica Polonica, 1990, A78(6):825-839.
Gong et al., "Rhodium(I)-catalyzed regiospecific dimerization of aromatic acids: two direct C-H bond activations in water," Angewandte Chemie, 2015, 54(19):5718-5721.
Goswami et al., "A turn on ESIPT probe for rapid and ratiometric fluorogenic detection of homocysteine and cysteine in water with live cell-imaging," Tetrahedron Letters, 2014, 55(2):490-494.
Gould et al. "Salt selection for basic drugs," Int J Pharma., 1986, 33(1-3):201-217.
Green et al., "Synthesis and investigation of the configurational stability of some dimethylammonium borate salts," J. Chem. Soc., Perkin Trans. 1, 2000, 24:4403-4408.
Greenwald et al., "The B7 Family Revisited," Annu. Rev. Immunol., 2005, 23:515-548.
Gu et al., "Undo the brake of tumour immune tolerance with antibodies, peptide mimetics and small molecule compounds targeting PD-1/PD-L1 checkpoint at different locations for acceleration of cytotoxic immunity to cancer cells," Clinical and Experimental Pharmacology and Physiology, 2019, 46(2):105-115.
Han et al., "Synthesis of binuclear phenoxyimino organoaluminum complexes and their use as the catalyst precursors for efficient ring-opening polymerisation of E-caprolactone," Dalton Transactions, 2013, 41:12346-12353.
Helgeson et al., "Host-guest complexation. 66. 18-Membered-ring spherands containing five anisyl groups," J Am Chem Soc., 1993, 1115(24):11506-11511.
Hilfiker "Relevance of Solid-state Properties for Pharmaceutical Products," Polymorphism in the Pharmaceutical Industry, Jan. 1, 2006, pp. 1-19.
Highlights Prescribing Information, "OPDIVO," Revised Apr. 2019, 90 pages.
Highlights Prescribing Information, "Keytruda," Revised Feb. 2019, 66 pages.
Hu et al., "Novel highly active binuclear neutral nickel and palladium complexes as precatalysts for norbornene polymerization," Journal of Molecular Catalysis A: Chemical 253, 2006, 155-164.
Hu et al., "Syntheses and Ethylene Polymerization Behavior of Supported Salicylaldimine-Based Neutral Nickel(II) Catalysts," Organometallics, 2007, 26(10):2609-2615.
Hu et al., "Synthesis and Ethylene Polymerization Activity of a Novel, Highly Active Single-Component Binuclear Neutral Nickel(II) Catalyst," Organometallics, 2005, 24(11):2628-2632.
Huang et al., "The prognostic significance of PD-L1 in bladder cancer," Oncol. Rep., 2015, 33:3075-3084.
Huang et al., "Pharmacological treatment for keloids," Expert opinion on pharmacotherapy, 2013, 14(15):2087-2100.
Huddle et al., "Reactions of alkyl-lithium compounds with aryl halides," J Chem Soc., Perkin I, 1980, 12:2617-2625.
HuGEMM™ and HuCELL™ Models, "FactSheet," CrownBio, Oct. 2016, 8 pages.
Indian Office Action with Indian Application No. 201817026809, dated Apr. 29, 2020, 6 pages.
Indian Office Action with Indian Application No. 201917001998, dated Nov. 24, 2020, 7 pages.
Indian Office Action with Indian Application No. 201917028273, dated Feb. 15, 2021, 5 pages.
International Preliminary Report on Patentability in International Application No. PCT/US2017/041899, dated Jan. 15, 2019, 7 pages.
International Preliminary Report on Patentability in International Application No. PCT/US2016/057487, dated May 3, 2018, 7 pages.
International Preliminary Report on Patentability in International Application No. PCT/US2016/062730, dated May 31, 2018, 7 pages.
International Preliminary Report on Patentability in International Application No. PCT/US2016/067155, dated Jun. 19, 2018, 10 pages.
International Preliminary Report on Patentability in International Application No. PCT/US2016/067925, dated Jun. 26, 2018, 8 pages.
International Preliminary Report on Patentability in International Application No. PCT/US2017/031242, dated Nov. 6, 2018, 7 pages.
International Preliminary Report on Patentability in International Application No. PCT/US2017/034173, dated Nov. 27, 2018, 8 pages.
International Preliminary Report on Patentability in International Application No. PCT/US2017/038120, dated Dec. 25, 2018, 6 pages.
International Preliminary Report on Patentability in International Application No. PCT/US2017/048880, dated March, 5, 2019, 9 pages.
International Preliminary Report on Patentability in International Application No. PCT/US2017/067880, dated Jun. 25, 2019, 7 pages.
International Preliminary Report on Patentability in International Application No. PCT/US2017/067886, dated Jun. 25, 2019, 9 pages.
International Preliminary Report on Patentability in International Application No. PCT/US2017/067904, dated Jun. 25, 2019, 7 pages.
International Preliminary Report on Patentability in International Application No. PCT/US2017/067946, dated Jun. 25, 2019, 9 pages.
International Preliminary Report on Patentability in International Application No. PCT/US2017/067951, dated Jun. 25, 2019, 8 pages.
International Preliminary Report on Patentability in International Application No. PCT/US2017/067984, dated Jun. 25, 2019, 7 pages.
International Preliminary Report on Patentability in International Application No. PCT/US2019/025036, dated Oct. 15, 2020, 7 pages.
International Preliminary Report on Patentability in International Application No. PCT/US2019/031728, dated Nov. 17, 2020, 7 pages.

(56) References Cited

OTHER PUBLICATIONS

International Preliminary Report on Patentability in International Application No. PCT/US2020/045311, dated Feb. 17, 2022, 8 pages.
International Preliminary Report on Patentability in International Application No. PCT/US2020/053190, dated Apr. 5, 2022, 7 pages.
International Preliminary Report on Patentability in International Application No. PCT/US2020/059817, dated May 17, 2022, 12 pages.
International Search Report and Written Opinion in International Application No. PCT/US2016/057487, dated Dec. 8, 2016, 11 pages.
International Search Report and Written Opinion in International Application No. PCT/US2016/062730, dated Feb. 9, 2017, 12 pages.
International Search Report and Written Opinion in International Application No. PCT/US2016/067155, dated Apr. 24, 2017, 26 pages.
International Search Report and Written Opinion in International Application No. PCT/US2016/067925, dated Mar. 27, 2017, 13 pages.
International Search Report and Written Opinion in International Application No. PCT/US2017/031242, dated Jun. 20, 2017, 22 pages.
International Search Report and Written Opinion in International Application No. PCT/US2017/034173, dated Aug. 8, 2017, 15 pages.
International Search Report and Written Opinion in International Application No. PCT/US2017/038120, dated Aug. 1, 2017, 14 pages.
International Search Report and Written Opinion in International Application No. PCT/US2017/041899, dated Sep. 5, 2017, 12 pages.
International Search Report and Written Opinion in International Application No. PCT/US2017/048880, dated Oct. 23, 2017, 15 pages.
International Search Report and Written Opinion in International Application No. PCT/US2017/067880, dated Mar. 21, 2018, 13 pages.
International Search Report and Written Opinion in International Application No. PCT/US2017/067886, dated Mar. 23, 2018, 24 pages.
International Search Report and Written Opinion in International Application No. PCT/US2017/067904, dated Mar. 22, 2018, 14 pages.
International Search Report and Written Opinion in International Application No. PCT/US2017/067946, dated May 22, 2018, 16 pages.
International Search Report and Written Opinion in International Application No. PCT/US2017/067951, dated Mar. 27, 2018, 15 pages.
International Search Report and Written Opinion in International Application No. PCT/US2017/067984, dated Mar. 22, 2018, 14 pages.
International Search Report and Written Opinion in International Application No. PCT/US2019/025036, dated Jul. 3, 2019, 12 pages.
International Search Report and Written Opinion in International Application No. PCT/US2019/031728, dated Jun. 25, 2019, 12 pages.
International Search Report and Written Opinion in International Application No. PCT/US2020/045311, dated Oct. 2, 2020, 14 pages.
International Search Report and Written Opinion in International Application No. PCT/US2020/059817, dated Mar. 29, 2021, 19 pages.
International Search Report and Written Opinion in International Application No. PCT/US2020/053190, dated Jan. 29, 2021, 13 pages.
International Search Report and Written Opinion in International Application No. PCT/US2021/058338, dated Feb. 9, 2022, 15 pages.
International Search Report and Written Opinion in International Application No. PCT/US2021/058334, dated Apr. 25, 2022, 23 pages.
International Search Report and Written Opinion in International Application No. PCT/US2021/063965, dated Apr. 12, 2022, 20 pages.
International Search Report and Written Opinion in International Application No. PCT/US2021/058268, dated Apr. 21, 2022, 22 pages.
Invitation to Pay Fee's in International Application No. PCT/US2021/058268, dated Jan. 31, 2022, 16 pages.
Invitation to Pay Fee's in International Application No. PCT/US2021/058334, dated Feb. 3, 2022, 12 pages.
Israeli Office Action in Israeli Application No. 259,406, dated Mar. 11, 2020, 10 pages.
Israeli Office Action in Israeli Application No. 260,166, dated Jun. 2, 2020, 13 pages.
Israeli Office Action in Israeli Application No. 287,267, dated Feb. 15, 2022, 4 pages.
Iwai et al., "Involvement of PD-L1 on tumor cells in the escape from host immune system and tumor immunotherapy by PD-L1 blockade, " PNAS, Sep. 2002, 99(19):12293-12297.
Japanese Office Action in Japanese Application No. 2018526213, dated Oct. 13, 2020, 10 pages.
Japanese Office Action in Japanese Application No. 2019-534122, dated Oct. 19, 2021, 10 pages.
Japanese Office Action in Japanese Application No. 2019-534195, dated Nov. 1, 2021, 8 pages.
Japanese Office Action in Japanese Application No. 2019-534196, dated Nov. 9, 2021, 8 pages.
Jiang et al., "Self-immobilizing binuclear neutral nickel catalyst for ethylene polymerization: Synthesis and catalytic studies," J Mol Cat., 2013, 380:139-143.
Kayal et al., "3,3'-Bis(triphenylsilyl)biphenoxide as a Sterically Hindered Ligand on Fe(II), Fe(III), and Cr(II)," Inorg Chem., 2002, 41(2):321-330.
Keir et al., "PD-1 and Its Ligands in Tolerance and Immunity," Annu. Rev. Immunol., 2008, 26:677-704.
Kerekes et al., "Aurora kinase inhibitors based on the imidazo[1,2-a]pyrazine core: fluorine and deuterium incorporation improve oral absorption and exposure," J Med Chem., 2011, 54(1):201-210.
Koch et al., "Nucleophilic reactions of pyridines and imidazoles with vinyl and aromatic halides, " J Org Chem., 1993, 58(6):1409-1414.
Komiyama et al., "IL-17 Plays an Important Role in the Development of Experimental Autoimmune Encephalomyelitis," J. Immunol., Jul. 2006, 177:566-73.
Latchman et al., "PD-L2 is a second ligand for PD-1 and inhibits T cell activation," Nat. Immunol., Mar. 2001, 2(3):261-268.
Lazar-Molnar et al., "Crystal structure of the complex between programmed death-1 (PD-1) and its ligand PD-L2," PNAS, Jul. 2008, 105(30):10483-10488.
Legon'kova et al., "Interaction of o,o-dihalo o'-hydroxy azo compounds with metallic copper. II. Preparation of oligomeric azo compounds from monoazo compounds," Mosk Khim-Tekhnol Inst im Mendeleeva., 1968, 11(11):1281-1284 Machine Translation.
Legon'kova et al., "Interaction of o,o-dihalogeno o-hydroxy azo compounds with metallic copper," Trudy Instituta—Moskovskii Khimiko-Tekhnologicheskii Institut imeni D. I. Mendeleeva, 1965, 48:120-125 Machine Translation.
Lehtonen et al., "Comparison of quaternary methyl-, ethyl- and butylammonium hydroxides as alkylating reagents in pyrolysis-GC/MS studies of aquatic fulvic acid," Journal of Analytical and Applied Pyrolysis, 2003, 68-69:315-329.
Lexico.com, "Synonyms of Enhance," Oxford Dictionary, retrieved on Dec. 9, 2021, retrieved from URL <https://www.lexico.conn/synonynns/enhance>, 4 pages.
Li et al., "A 3D Mesomeric Supramolecular Structure of a Cu(II) Coordination Polymer with 1,1'-Biphenyl-2,2',3,3'-tetracarboxylic

(56) References Cited

OTHER PUBLICATIONS

Acid and 5,5'-Dimethyl-2,2'-bipyridine Ligands," J Inorg and Organomet Poly Mat., 2012, 22(6):1320-1324.
Li et al., "A Mini-Review for Cancer Immunotherapy: Molecular Understanding of PD-1/PD-L1 Pathway & Translational Blockade of Immune Checkpoints," Int. J. Mol. Soc., 2016, 17:1151, 22 pages.
Li et al., "Analysis of Receptor Tyrosine Kinase Internalization Using Flow Cytometry," Methods Mol. Biol., 2008, 457:305-317.
Li et al., "Asymmetric Alternating Copolymerization of Meso-epoxides and Cyclic Anhydrides: Efficient Access to Enantiopure Polyesters," J. Am. Chem. Soc., 2016, 138(36):11493-11496.
Li et al., "Discovery of peptide inhibitors targeting human programmed death 1 (PD-1) receptor," Oncotarget, Aug. 2016, 7(40):64967-64976.
Lin et al., "The PD-1/PD-L1 complex resembles the antigen-binding Fv domains of antibodies and T cell receptors," PNAS, Feb. 2008, 105(8):3011-3016.
Lipson et al., "From Discovery to Development: Blocking PD-1 and its Ligands," The Melanoma Letter, A Publication of The Skin Cancer Foundation, vol. 31, Summer 2013, 6 pages.
Liu et al., "Asymmetric Copolymerization of CO2 with meso-Epoxides Mediated by Dinuclear Cobalt(III) Complexes: Unprecedented Enantioselectivity and Activity," Angewandte Chemie, 2013, 52(44):11594-11598.
Liu et al., "Development of amino- and dimethylcarbamate-substituted resorcinol as programmed cell death-1 (PD-1) inhibitor," Eur J Pharm Sci, 2016, 88:50-58.
Mahoney et al., "The Next Immune-Checkpoint Inhibitors:PD-1/PD-L1 Blockade in Melanoma," Clin. Therapeutics, Nov. 2015, 37(4):761-782.
Maier et al., "Effects of the stationary phase and the solvent on the stereodynamics of biphep ligands quantified by dynamic three-column HPLC," Angewante Chemie, 2012, 51(12):2985-2988.
Manecke et al., "Preparation and properties of chelate-forming monomeric and polymeric Schiff bases derived from salicylaldehyde and 2,5-dihydroxyterephthalaldehyde. I," Makromolekulare Chemie, 1970, 133:61-82 English Abstract.
Manecke et al., "Preparation and properties of monomeric and polymeric Schiff bases derived from salicylaldehyde and 2,5-dihydroxyterephthalaldehyde. II. Electrical conductivity," Makromolekulare Chemie, 1972, 160:111-126 English Abstract.
Mexican Office Action in Mexican Application No. MX/a/2018/007774, dated Apr. 8, 2021, 5 pages.
Mexican Office Action in Mexican Application No. MX/a/2018/016273, dated Mar. 26, 2021, 5 pages.
Miyaura and Suzuki, "Palladium-Catalyzed Cross-Coupling Reactions of Organoboron Compounds," Chem Rev., 1995, 95:2457-2483.
Mochida et al., "Rhodium-Catalyzed Regioselective Olefination Directed by a Carboxylic Group," J Org Chem, 2011, 76(9):3024-3033.
Moneta et al., "Boron templated synthesis of macrocyclic hosts containing convergent hydroxy or methoxy groups," Bulletin de la Societe Chimique de France, 1988, 6:995-1004 (English Abstract).
Nallasivam et al., "Development of Unimolecular Tetrakis(piperidin-4-ol) as a Ligand for Suzuki-Miyaura Cross-Coupling Reactions: Synthesis of Incrustoporin and Preclamol," 2015, Eur J Org Chem., 2015(16):3558-3567.
Nero et al., "Oncogenic protein interfaces: small molecules, big challenges," Nature Reviews, Apr. 2014, 14:248-262.
Nishimura et al., "Autoimmune Dilated Cardiomyopathy in PD-1 Receptor-Deficient Mice," Science, Jan. 2001, 291:319-322.
Nishimura et al., "Development of Lupus-like Autoimmune Diseases by Disruption of the PD-1 Gene Encoding an ITIM Motif-Carrying Immunoreceptor," Immunity, Aug. 1999, 11:141-151.
Nishimura et al., "PD-1: an inhibitory immunoreceptor involved in peripheral tolerance," Trends in Immunology, May 2001, 22(5):265-268.
Nishino et al., "Copper-Mediated C-H/C-H Biaryl Coupling of Benzoic Acid Derivatives and 1,3-Azoles," Angew. Chem. Int. Ed., 2013, 52:4457-4461.
Normand et al., "Dinuclear vs. mononuclear complexes: accelerated, metal-dependent ring-opening polymerization of lactide," Chem. Commun., 2013, 49(99):11692-11694.
Okazaki and Honjo, "The PD-1-PD-L pathway in immunological tolerance," Trends Immunol., Apr. 2006, 4:195-201.
Okazaki et al., "A rheostat for immune responses: the unique properties of PD-1 and their advantages for clinical application," Nature Immunology, Dec. 2013, 14(12):1212-1218.
Paek et al., "Chiral host. Attempted synthesis using McMurray reaction as a final ring closure method," Bulletin of the Korean Chemical Society, 1989, 10(6):572-577.
Paek et al.., "Facile syntheses and multi-orthofunctionalizations of tertiary benzamides," Bulletin of the Korean Chemical Society, 1993, 14(6):732-739.
Pardoll, "The blockade of immune checkpoints in cancer immunotherapy," Nature, Apr. 2012, 12:252-264.
Parry et al., "CTLA-4 and PD-1 Receptors Inhibit T-Cell Activation by Distinct Mechanisms," Mol. Cell. Biol., Nov. 2005, 25(21):9543-9553.
Parsons et al., "Directed ortho metalation reactions. Expedient synthesis of 3,3'-disubstituted 1,1'-bi-(2- phenols) (BIPOLS)," Tetrahedron Letters, 1994, 35(41):7537-7540.
Pascolutti et al., "Structure and Dynamics of PD-L1 and an Ultra-High-Affinity PD-1 Receptor Mutant," Structure, Oct. 2016, 24:1719-1728.
Paulini et al., "Orthogonal Multipolar Interactions in Structural Chemistry and Biology," Angew. Chem. Int. Ed., 2005, 44:1788-1805.
Pearson et al., "The formation of complexes between aza-derivatives of crown ethers and primary alkylammonium salts. Part 5. Chiral macrocyclic diamines," J. Chem. Soc., Perkin I, 1979, 12:3113-3126.
Pfeiffer et al., "Inner complex salts of the aldimine and azo series," Journal fuer Praktische Chemie, 1937, 149:217-296 Machine Translation.
Pierre et al., "Synthesis of a new macrobicyclic siderophoric host molecule with six converging phenolate groups," Angewandte Chemie, 1991, 103(1):75-76 Machine Translation.
Postow et al., "Immune Checkpoint Blockade in Cancer Therapy," J. Clinical Oncology, Jun. 2015, 33(17):1974-1982.
Press Release Archive, "Boehringer Ingelheim and Yale University collaborate to investigate novel immunotherapy targets across several therapeutic areas," Boehringer Ingelheim, Jan. 13, 2015, 2 pages.
Puehlhofer et al., "SASAPOS cascades of perfluorinated aromatic carboxylic acids: low-temperature decarboxylation triggered by electrostatic effects of polycationic ligand sets," Euro J of Org Chem., 2004, 5:1002-1007.
Punniyamurthy et al., "Enantiomerically pure bicyclo[3.3.1]nona-2,6-diene as the sole source of enantioselectivity in BIPHEP-Rh asymmetric hydrogenation," Chem Comm., 2008, 41:5092-5094.
Qin et al., "The Diverse Function of PD-1/PD-L Pathway Beyond Cancer," Frontiers In Immunology, Oct. 2019, 10(2298):1-16.
Reck et al., "Pembrolizumab versus Chemotherapy for PD-L1-Positive Non-Small-Cell Lung Cancer," N Engl J Med., Nov. 10, 2016, 375(19):1823-1833.
Rowe et al., "Fumaric Acid" Handbook of pharmaceutical excipients, Jan. 1, 2009, pp. 276-277, 309-310, 393-396.
Sabatier et al., "Prognostic and predictive value of PDL1 expression in breast cancer," Oncotarget, Mar. 2015, 6(7):5449-5464.
Sharma et al., "Palladium-Catalyzed Decarboxylative Acylation of O-Phenyl Carbamates with Alpha- Oxocarboxylic Acids at Room Temperature," Advanced Synthesis & Catalysis, 2013, 355(4):667-672.
Sharpe et al., "The function of programmed cell death 1 and its ligands in regulating autoimmunity and infection," Nat. Immunol., Mar. 2007 8(3):239-245.
Sharpe et al., "The B7-CD28 Superfamily," Nature Reviews, Feb. 2002, 2:116-126.

(56) References Cited

OTHER PUBLICATIONS

Sorrell et al., "3,3'-Disubstituted 2,2'-biphenols. Synthesis of nonplanar, tetradentate chelating ligands," J Org Chem., 1985, 50(26):5765-5769.
STN Search Report dated Dec. 20, 2016, 117 pages.
STN Search Report dated Apr. 14, 2016, 79 pages.
STN Search Report dated Apr. 29, 2016, 69 pages.
STN Search Report dated Apr. 30, 2018, 8 pages.
STN Search Report dated Aug. 19, 2016, 23 pages.
STN Search Report dated Aug. 30, 2016, 4 pages.
STN Search Report dated Dec. 15, 2016, 4 pages.
STN Search Report dated Dec. 16, 2016, 25 pages.
STN Search Report dated Dec. 16, 2016, 4 pages.
STN Search Report dated Dec. 19, 2016, 11 pages.
STN Search Report dated Jul. 12, 2016, 4 pages.
STN Search Report dated Jun. 16, 2016, 8 pages.
STN Search Report dated Jun. 6, 2016, 115 pages.
STN Search Report dated Mar. 27, 2018, 4 pages.
STN Search Report dated May 24, 2016, 92 pages.
STN Search Report dated Sep. 12, 2016, 4 pages.
STN Search Report dated Sep. 12, 2016, 17 pages.
STN Search Report dated Sep. 2, 2016, 115 pages.
STN Search Report dated Sep. 27, 2017, 4 pages.
STN Search Report, dated May 1, 2016, 12 pages.
Storz, "Intellectual property issues of immune checkpoint inhibitors," mAbs, Jan. 2016, 8(1):10-26.
Suarez et al., "Inhibitors of TAM subfamily of tyrosine kinases: synthesis and biological evaluation," European Journal of Medicinal Chemistry, 2013, 61:2-25.
Sumrit et al., "Aluminum complexes containing salicylbenzoxazole ligands and their application in the ring-opening polymerization of rac-lactide and ϵ-caprolactone," Dalton Transactions (2016), 45(22), 9250-9266.
Sun et al., "Studies on Synthesis and Properties of Some New Dibenzocyclobromonium," Chemical Journal of Chinese Universities, 1998, 19(12), 6 pages (English Abstract).
Sznol et al., "Antagonist Antibodies to PD-1 and B7-H1 (PD-L1) in the Treatment of Advanced Human Cancer," Clin Cancer Res., Mar. 1, 2013, 19(5):1021-1034.
Taiwan Office Action in Taiwan Application No. 105133530, dated Oct. 15, 2020, 8 pages.
Taiwan Office Action in Taiwan Application No. 105137807, dated Nov. 12, 2020, 12 pages.
Taiwan Office Action in Taiwan Application No. 105141804, dated Nov. 9, 2020, 9 pages.
Tang et al., "Facile synthesis of enantioenriched phenol-sulfoxides and their aluminum complexes," Org Biomol Chem., 2016, 14(24):5580-5585.
Thiel et al., "Small-Molecule Stabilization of Protein-Protein Interactions: An Underestimated Concept in Drug Discovery?" Angew. Chem. Int. Ed., 2012, 51:2012-2018.
Tucker et al., "Host-guest complexation. 52. Bridged and chiral hemispherands," J Org Chem., 1989, 54(23):5460-5482.
Ukraine Office Action in Ukraine Application No. a 2019 00525, dated Jan. 14, 2021, 11 pages.
Unrau et al., "Directed ortho metalation. Suzuki cross coupling connections. Convenient regiospecific routes to functionalized m- and p-teraryls and m-quinquearyls," Tetrahedron Letters, 1992, 33(20):2773-2776.
Vaddepally et al., "Review of Indications of FDA-Approved Immune Checkpoint Inhibitors per NCCN Guidelines with the Level of Evidence," Cancers, 2020, 12(3):738.
Velcheti et al., "Programmed death-1/programmed death-1 ligand axis as a therapeutic target in oncology: current insights," Journal of Receptor Ligand and Channel Research, Dec. 2014, 8(23):1-7.
Wang et al., "The prognostic value of PD-L1 expression for non-small cell lung cancer patients: A meta-analysis," Eur. J. Surg. Oncol., 2015, 41:450-456.
Wang et al., "A binuclear Zn(II)-Zn(II) complex from a 2-hydroxybenzohydrazide-derived Schiff base for selective detection of pyrophosphate," Dalton Transactions, Oct. 2014, 43(37):14142-14146.
Wang et al., "Molecular Modeling and Functional Mapping of B7-H1 and B7-DC Uncouple Costimulatory Function from PD-1 Interaction," J. Exp. Med., Apr. 2013, 197(3):1083-1091.
Wei et al., "Strength of PD-1 signaling differentially affects T-cell effector functions," PNAS, Apr. 2013, E2480-E2489.
Weinmann, "Cancer Immunotherapy: Selected Targets and Small-Molecule Modulators," Chem. Med. Chem., 2016, 11:450-466.
Weiss et al., "Electrostatic activation of SNAr-reactivity by sulfonylonio substituents," Zeitschrift fuer Naturforschung, 2001, 56(12):1360-1368 English Abstract.
Weiss et al., "Electrostatics and color: Massive electrostatic perturbation of chromophores by ion cluster ligands," J Am Chem Soc., 2007, 129(3):547-553.
Weiss et al., "First-ever per(onio) substitution of benzene: the role of the counterion," Angewandte Chemie, 1995, 34(12):1319-1321.
Weiss et al., "Massive electrostatic effects on heteropolar C-C disconnections: Transforming a phenyl anion into a potent leaving group," Euro J Org Chem., 2005, 16:3530-3535.
Weiss et al., "Poly-onio substituted quinones as strong electron acceptors," Inst Org Chem., 1986, 98(10):925-926.
Weiss et al., "SASAPOS, not Sisyphus: highly efficient 20-step one-pot synthesis of a discrete organic-inorganic ion cluster with a porphyrin core," Angewandte Chemie International Edition, 2002, 41(20):3815-3817.
Weiss et al., "Syntheses and Reactions of Polycationically Substituted Azido- and Diazidobenzenes," Eur J Org Chem., Nov. 2007, 31:5270-5276.
Wells et al., "Reaching for high-hanging fruit in drug discovery at protein-protein interfaces," Nature, Dec. 2007, 450:1001-1009.
Wu et al., "Targeting the BACE1 Active Site Flap Leads to a Potent Inhibitor That Elicits Robust Brain Aβ Reduction in Rodents," ACS Medicinal Chemistry Letters, 2016, 7(3):271-276.
Wuts et al., "Protective Groups in Organic Synthesis," 4th Ed., 2007, 1111 pages.
www.medscape.com [online]. "The 'Family Business' Behind the Flurry of PD-1 Inhibitors," Sep. 10, 2014. [Retrieved on Jan. 29, 2015]. Retrieved from the Internet: URL<http://www.medscape.com/viewarticle/831448_print>. 3 pages.
Xiong et al., "Biaryl-Bridged Salalen Ligands and Their Application in Titanium-Catalyzed Asymmetric Epoxidation of Olefins with Aqueous H2O2," Eur J Org Chem., 2011, 23:4289-4292.
Xu et al., "Design, synthesis and biological evaluation of deuterated nintedanib for improving pharmacokinetic properties," J Label Compd RadioPharm., Jun. 15, 2015, 58(7):308-312.
Xu et al., "Quantitative structure-activity relationship study on BTK inhibitors by modified multivariate adaptive regression spline and CoMSIA methods," SAR QSAR Environ Res., 2015, 26(4):279-300.
Yao et al., "PD-1 as an Immune Modulatory Receptor," Cancer J., 2014, 20(4):262-264.
Yin et al., "Strategies for Targeting Protein-Protein Interactions With Synthetic Agents," Angew. Chem. Int. Ed., 2005, 44:4130-4163.
Young et al., "Discovery of highly potent and selective Bruton's tyrosine kinase inhibitors: Pyridazinone analogs with improved metabolic stability," Bioorganic & Medicinal Chemistry Letters, 2016, 26(2):575-579.
Young et al., "Potent and selective Bruton's tyrosine kinase inhibitors: Discovery of GDC-0834," Bioorganic & Medicinal Chemistry Letters , 2015, 25(6):1333-1337.
Zak et al., "Structural basis for small molecule targeting of the programmed death ligand 1 (PD-L1)" Oncotarget, Apr. 2016, 19 pages; Supplemental Material for 2016, 7(21):30323-30335.
Zak et al., "Structural basis for small molecule targeting of the programmed death ligand 1 (PD-L1)," Oncotarget, 2016, 7(21):30323-30335.
Zak et al., "Structure of the Complex of Human Programmed Death 1, PD-1, and Its Ligand PD-L1: with Supplemental Information," Structure, Dec. 2015, 23:2341-2348.

(56) References Cited

OTHER PUBLICATIONS

Zang et al., "Four 2D metal-organic networks incorporating Cd-cluster SUBs: hydrothermal synthesis, structures and photoluminescent properties," CrystEngComm, 2009, 11(1):122-129.
Zarganes-Tzitzikas, "Inhibitors of programmed cell death 1 (PD-1): a patent review (2010-2015)," Expert Opinion on Therapeutic Patents, Sep. 19, 2016, 26(9):973-977.
Zhan et al., "From monoclonal antibodies to small molecules: the development of inhibitors targeting the PD-1/PD-L1 pathway," Drug Discovery Today, Apr. 2016, 10 pages.
Zhang et al., "Biaryl-Based Macrocyclic and Polymeric Chiral (Salophen)Ni(II) Complexes: Synthesis and Spectroscopic Study," J Org Chem., 2001, 66(2):481-487.
Zhang et al., "Electrospray mass spectrum of a per(onio)-substituted benzene: retention of Coulombic charge upon collisionally activated decomposition," J Am Soc. Mass. Spectrom., 1998, 9(1):15-20.
Zhang et al., "Non-symmetrical diarylcarboxylic acids via rhodium(I)-catalyzed regiospecific cross-dehydrogenation coupling of aromatic acids: twofold direct C-H bond activations in water," RSC Advances, 2016, 6(64):91617-91620.
Zhang et al., "Structural and Functional Analysis of the Costimulatory Receptor Programmed Death-1," Immunity, Mar. 2004, 20:337-347.
Zhao et al., "Design, synthesis and organocatalysis of 2,2'-biphenol-based prolinamide organocatalysts in the asymmetric direct aldol reaction in water," Synlett, 2013, 24(20):2743-2747.
European Communication in European Application No. 23189545.9, dated Aug. 28, 2023, 1 page.
Japanese Notice of Allowance in Japanese Application No. 2020-552827, dated Aug. 22, 2023, 4 pages (with English Translation).
Japanese Office Action in Japanese Application No. 2022-108265, dated Aug. 22, 2023, 3 pages (with English Translation).
Methot et al., "Exploration of the internal cavity of histone deacetylase (H Dac) with selective HDAC1/HDAC2 inhibitors (SHIT-1:2)," Bioorganic & Medicinal Chemistry Letters, 2008, 18:973-978.
Mexican Office Action in Mexican Application No. MX/a/2020/012045, dated Jul. 12, 2023, 8 pages (with Machine Translation).
Otter et al., "The human papillomavirus as a common pathogen in oropharyngeal, anal and cervical cancers," Clin Oncol (R Coll Radiol), Feb. 2019, 31(2):81-90.
Pajouhesh et al., "Medicinal Chemical Properties of Successful Central Nervous System Drugs," NeuroRx, 2005, 2, 541-553.
Poljak, "Nucleic Acid Tests for the Detection of Alpha Human Papillomaviruses," Vaccine, 2012, 30S:F100-F106.
Rowe et al., "Fumaric Acid," Handbook of pharmaceutical excipients, Jan. 1, 2009, pp. 276-277, 318-321, 663-666.
Venuti, "HPV Detection Methods in Head and Neck Cancer," Head and Neck Pathol, 2012, 6:S63-S74.
Vietnamese Office Action in Vietnamese Application No. 2022-108265, dated Jul. 31, 2023, 3 pages (with English Translation).

* cited by examiner

PROCESS FOR MAKING A PD-1/PD-L1 INHIBITOR AND SALTS AND CRYSTALLINE FORMS THEREOF

CROSS-REFERENCE TO RELATED APPLICATIONS

The present application claims the benefit of U.S. Provisional Application No. 63/110,792, filed Nov. 6, 2020, which is incorporated herein by reference in its entirety.

FIELD OF THE INVENTION

This application relates to processes and intermediates for the preparation of the PD-1/PD-L1 inhibitor (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl) piperidine-4-carboxylic acid, and salts and crystalline forms thereof, where the PD-1/PD-L1 inhibitor and solid forms and crystalline forms thereof are useful in the treatment of various diseases including infectious diseases and cancer.

BACKGROUND OF THE INVENTION

The immune system plays an important role in controlling and eradicating diseases such as cancer. However, cancer cells often develop strategies to evade or to suppress the immune system in order to favor their growth. One such mechanism is altering the expression of co-stimulatory and co-inhibitory molecules expressed on immune cells (Postow et al, J. Clinical Oncology 2015, 1-9). Blocking the signaling of an inhibitory immune checkpoint, such as PD-1, has proven to be a promising and effective treatment modality.

Programmed cell death-1 (PD-1), also known as CD279, is a cell surface receptor expressed on activated T cells, natural killer T cells, B cells, and macrophages (Greenwald et al, Annu. Rev. Immunol. 2005, 23:515-548; Okazaki and Honjo, Trends Immunol 2006, (4):195-201). It functions as an intrinsic negative feedback system to prevent the activation of T-cells, which in turn reduces autoimmunity and promotes self-tolerance. In addition, PD-1 is also known to play a critical role in the suppression of antigen-specific T cell response in diseases like cancer and viral infection (Sharpe et al, *Nat Immunol* 2007 8, 239-245; Postow et al, J. Clinical Oncol. 2015, 1-9).

The structure of PD-1 consists of an extracellular immunoglobulin variable-like domain followed by a transmembrane region and an intracellular domain (Parry et al, Mol Cell Biol 2005, 9543-9553). The intracellular domain contains two phosphorylation sites located in an immunoreceptor tyrosine-based inhibitory motif and an immunoreceptor tyrosine-based switch motif, which suggests that PD-1 negatively regulates T cell receptor-mediated signals. PD-1 has two ligands, PD-L1 and PD-L2 (Parry et al, Mol Cell Biol 2005, 9543-9553; Latchman et al, Nat Immunol 2001, 2, 261-268), and they differ in their expression patterns. PD-L1 protein is upregulated on macrophages and dendritic cells in response to lipopolysaccharide and GM-CSF treatment, and on T cells and B cells upon T cell receptor and B cell receptor signaling. PD-L1 is also highly expressed on almost all tumor cells, and the expression is further increased after IFN-γ treatment (Iwai et al, PNAS 2002, 99(19):12293-7; Blank et al, Cancer Res 2004, 64(3):1140-5). In fact, tumor PD-L1 expression status has been shown to be prognostic in multiple tumor types (Wang et al, Eur J Surg Oncol 2015; Huang et al, Oncol Rep 2015; Sabatier et al, Oncotarget 2015, 6(7): 5449-5464). PD-L2 expression, in contrast, is more restricted and is expressed mainly by dendritic cells (Nakae et al, J Immunol 2006, 177:566-73). Ligation of PD-1 with its ligands PD-L1 and PD-L2 on T cells delivers a signal that inhibits IL-2 and IFN-γ production, as well as cell proliferation induced upon T cell receptor activation (Carter et al, Eur J Immunol 2002, 32(3):634-43; Freeman et al, J Exp Med 2000, 192(7):1027-34). The mechanism involves recruitment of SHP-2 or SHP-1 phosphatases to inhibit T cell receptor signaling such as Syk and Lck phosphorylation (Sharpe et al, Nat Immunol 2007, 8, 239-245). Activation of the PD-1 signaling axis also attenuates PKC-θ activation loop phosphorylation, which is necessary for the activation of NF-□B and AP1 pathways, and for cytokine production such as IL-2, IFN-γ and TNF (Sharpe et al, Nat Immunol 2007, 8, 239-245; Carter et al, Eur J Immunol 2002, 32(3):634-43; Freeman et al, J Exp Med 2000, 192(7):1027-34).

Several lines of evidence from preclinical animal studies indicate that PD-1 and its ligands negatively regulate immune responses. PD-1-deficient mice have been shown to develop lupus-like glomerulonephritis and dilated cardiomyopathy (Nishimura et al, Immunity 1999, 11:141-151; Nishimura et al, Science 2001, 291:319-322). Using an LCMV model of chronic infection, it has been shown that PD-1/PD-L1 interaction inhibits activation, expansion and acquisition of effector functions of virus-specific CD8 T cells (Barber et al, Nature 2006, 439, 682-7). Together, these data support the development of a therapeutic approach to block the PD-1-mediated inhibitory signaling cascade in order to augment or "rescue" T cell response. Accordingly, there is a need for new compounds and salts that block PD-1/PD-L1 protein/protein interaction.

SUMMARY OF THE INVENTION

The present disclosure is directed to a process of preparing (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidine-4-carboxylic acid (compound of formula 1), or a salt thereof, comprising:

reacting a compound of formula A-3:

A-3

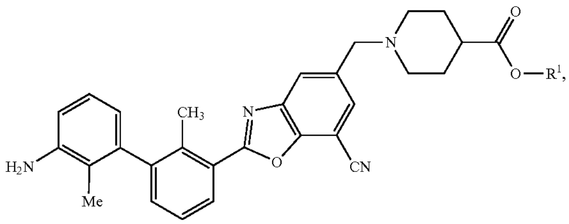

or a salt thereof, with a compound of formula A-4:

A-4

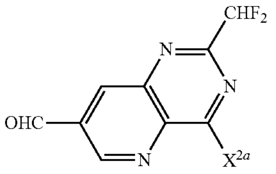

or a salt thereof, to form a compound of formula A-5:

A-5

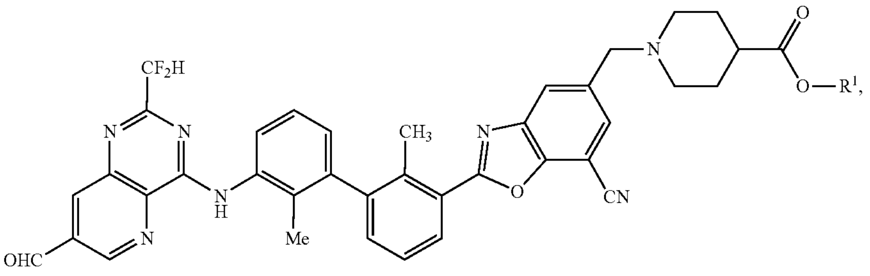

or a salt thereof, wherein $R^1$ is $C_{1-6}$ alkyl; and $X^{2a}$ is halo.

The present disclosure is further directed to a process of preparing (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidine-4-carboxylic acid (compound of formula 1), or a salt thereof, comprising:

reacting a compound of formula A-5:

A-5

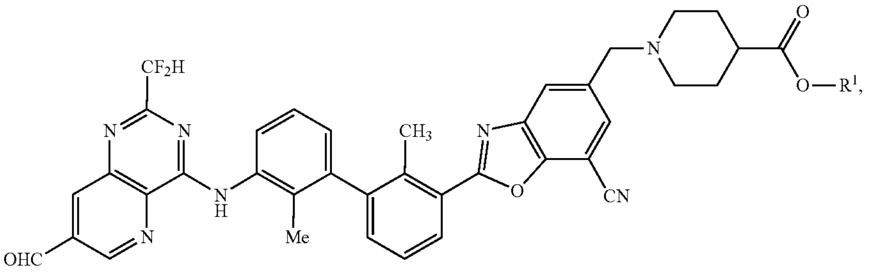

or a salt thereof, with a compound of formula A-6:

A-6

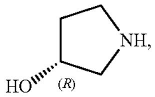

or a salt thereof, in the presence of a reducing agent to form a compound of formula A-7:

A-7

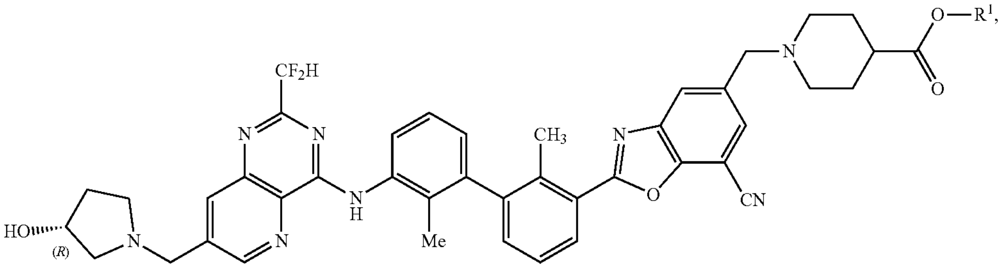

or a salt thereof, wherein $R^1$ is $C_{1-6}$ alkyl.

The present disclosure is further directed to a process of preparing (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidine-4-carboxylic acid (compound of formula 1), or a salt thereof, comprising:

reacting a compound of formula A-3:

A-3

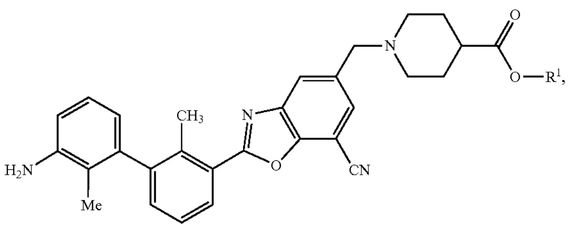

or a salt thereof, with a compound of formula B-1:

B-1

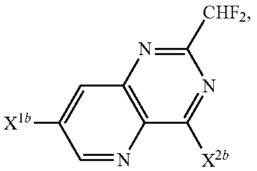

or a salt thereof, in the presence of a base to form a compound of formula B-2:

B-2

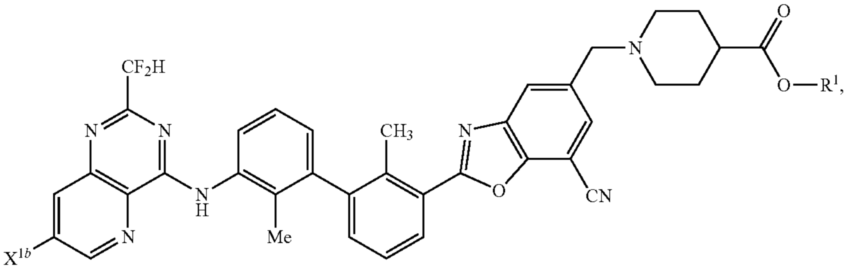

or a salt thereof, wherein $R^1$ is $C_{1-6}$ alkyl; and $X^{1b}$ and $X^{2b}$ are independently halo.

The present disclosure is further directed to a process of preparing (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidine-4-carboxylic acid (compound of formula 1), or a salt thereof, comprising:

reacting a compound of formula B-2:

B-2

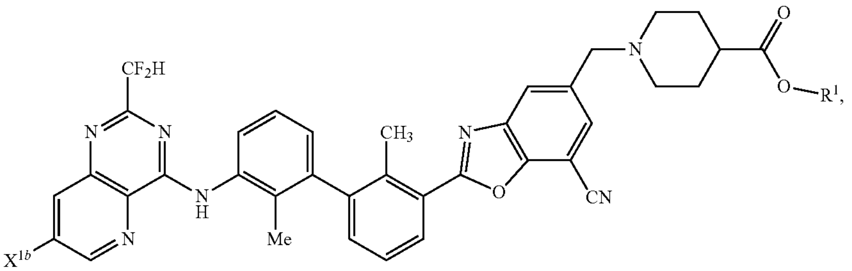

or a salt thereof, with a salt of formula B-3:

B-3

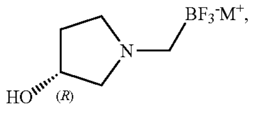

wherein $M^+$ is $Li^+$, $Na^+$, $K^+$, or $Cs^+$, in the presence of a Suzuki catalyst and a base to form a compound of formula A-7:

A-7

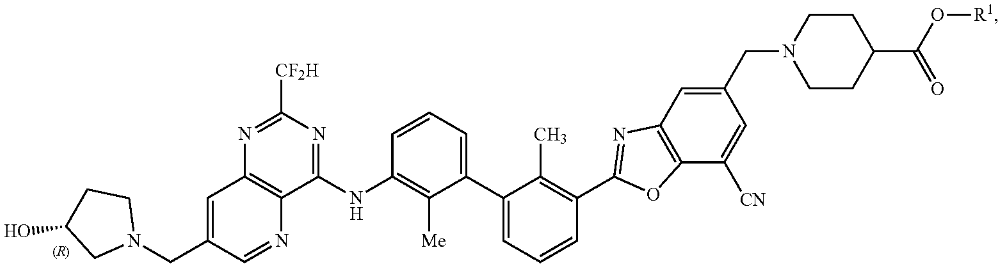

or a salt thereof, wherein $R^1$ is $C_{1-6}$ alkyl and $X^{1b}$ is halo.

The present disclosure is further directed to a process of preparing (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidine-4-carboxylic acid (compound of formula 1), or a salt thereof, comprising:

a) reacting a compound of formula A-3a:

A-3a

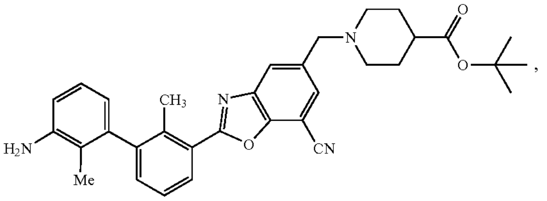

or a salt thereof, with a compound of formula A-4a:

A-4a

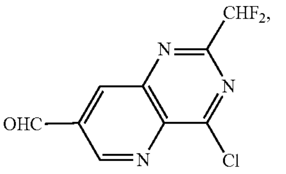

or a salt thereof, in the presence of an alkali metal halide and a base, to form a compound of formula A-5a:

A-5a

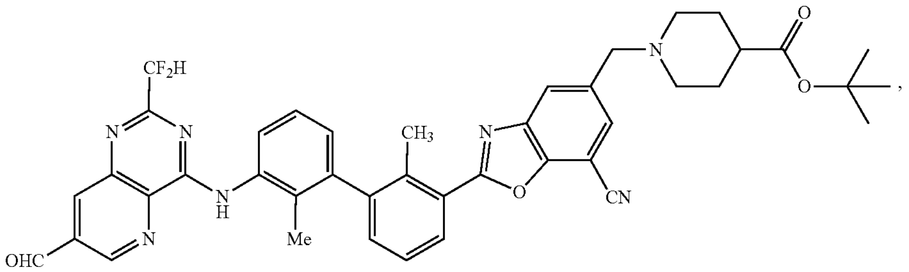

or a salt thereof;

b) reacting the compound of formula A-5a:

A-5a

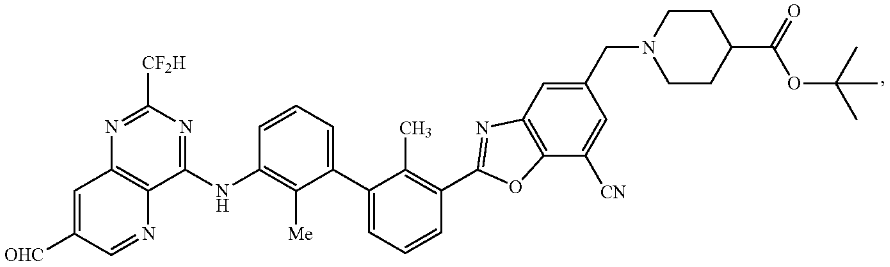

or a salt thereof, with a compound of formula A-6:
A-6
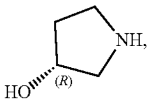
or a salt thereof, in the presence of a reducing agent to form a compound of formula A-7a:
A-7a
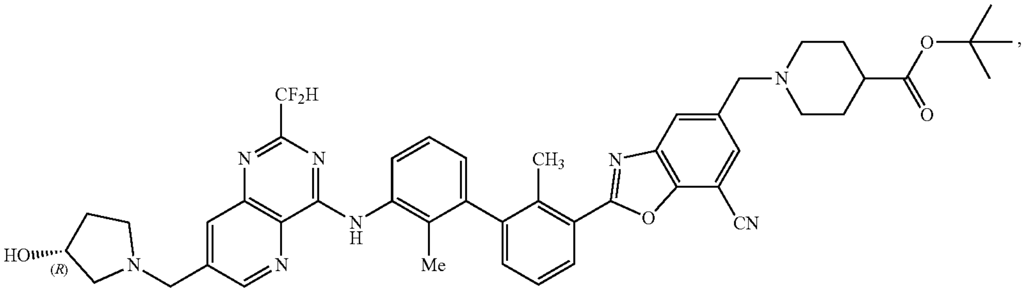
or a salt thereof, and
c) reacting the compound of formula A-7a:
A-7a
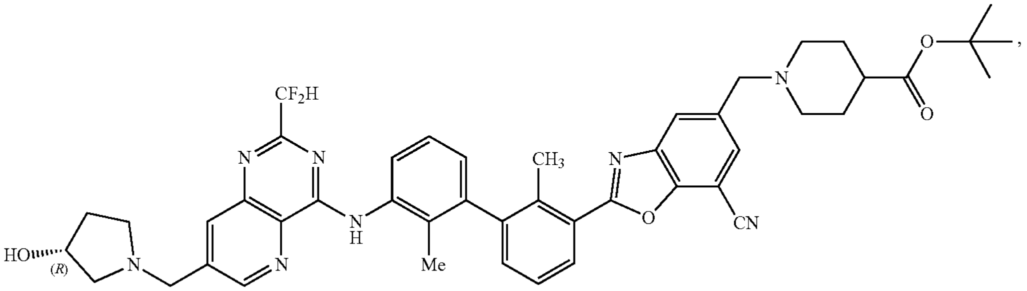
or a salt thereof, with a Lewis acid to form the compound of formula 1:
1
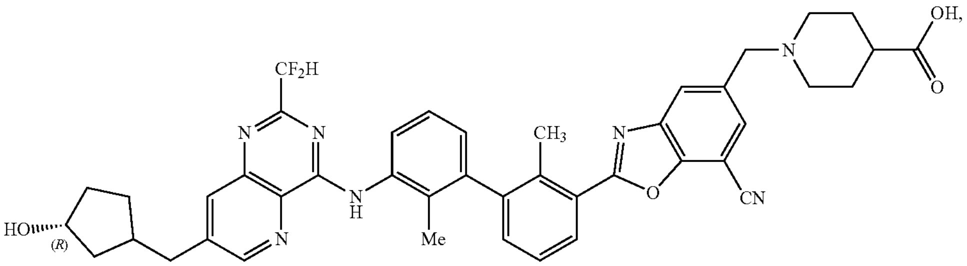
or a salt thereof.

The present disclosure is further directed to a process of preparing (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidine-4-carboxylic acid (compound of formula 1), or a salt thereof, comprising:

a) reacting a compound of formula A-3a:

A-3a

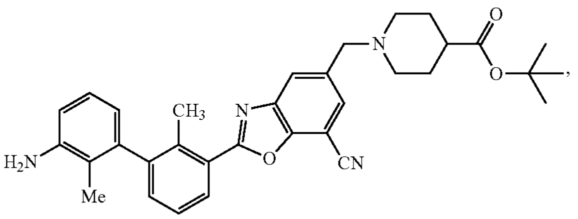

or a salt thereof, with a compound of formula B-1a:

B-1a

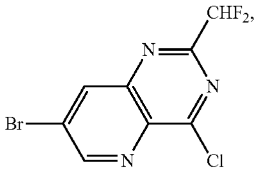

or a salt thereof, in the presence of a base, to form a compound of formula B-2a:

B-2a

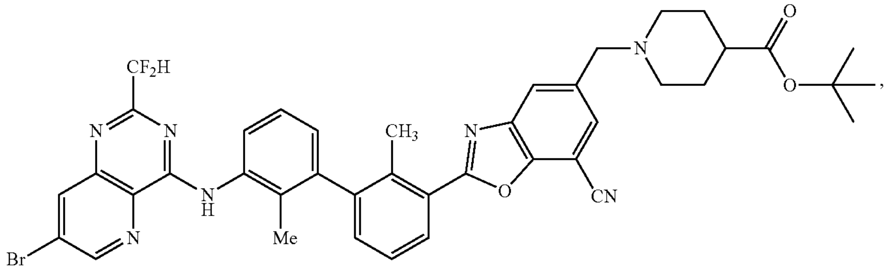

or a salt thereof;

b) reacting the compound of formula B-2a or a salt thereof, with a salt of formula B-3a:

B-3a

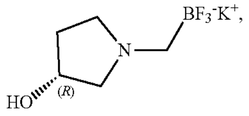

in the presence of a Suzuki catalyst and a base to form a compound of formula A-7a:

A-7a

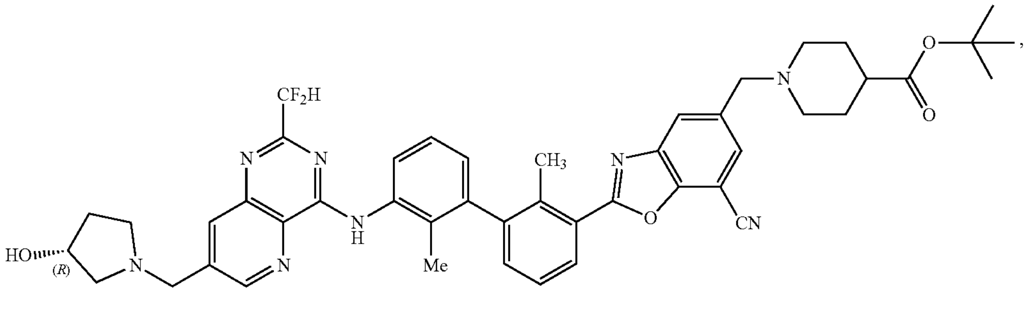

or a salt thereof, and c) reacting the compound of formula A-7a:

A-7a

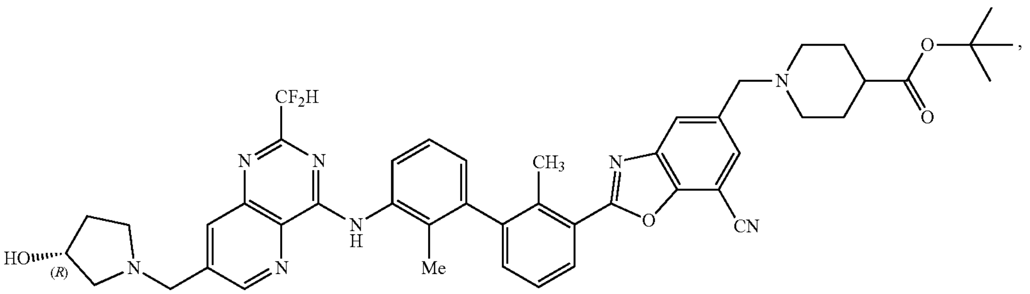

or a salt thereof, with a Lewis acid to form the compound of formula 1:

1

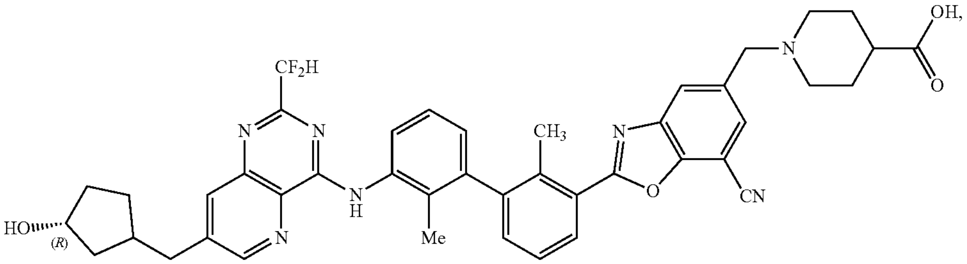

or a salt thereof.

The present disclosure is further directed to a process of preparing (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidine-4-carboxylic acid (compound of formula 1), or a salt thereof, comprising:

a) reacting a compound of formula A-3a':

A-3a'

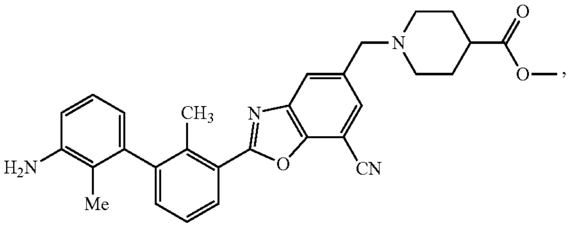

or a salt thereof, with a compound of formula B-1a:
B-1a
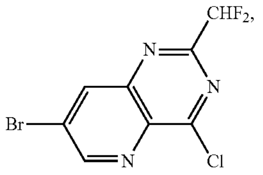
or a salt thereof, in the presence of a base, to form a compound of formula B-2a':
B-2a'
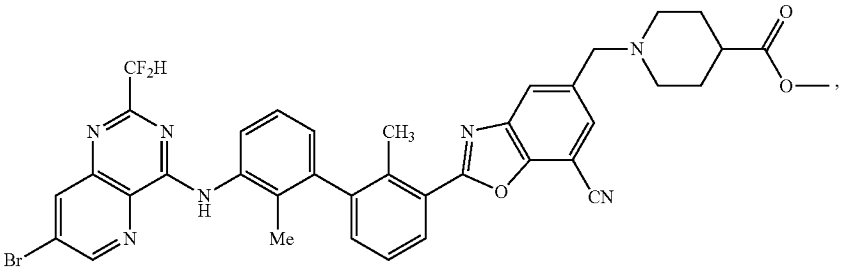
or a salt thereof;
b) reacting the compound of formula B-2a' or a salt thereof, with a salt of formula B-3a:
B-3a
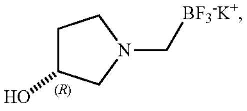
in the presence of a Suzuki catalyst and a base to form a compound of formula A-7a':
A-7a'
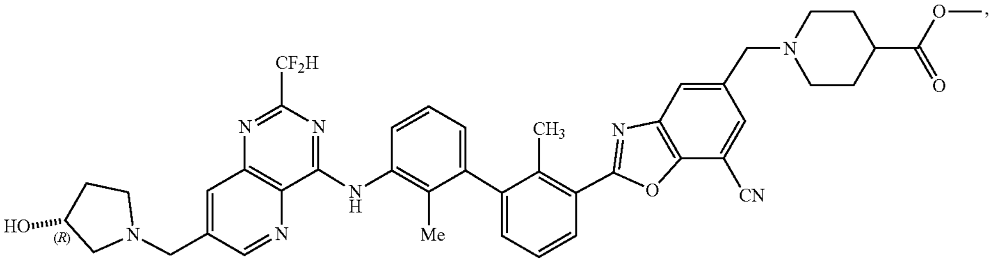
or a salt thereof, and c) deprotecting the compound of formula A-7a':

A-7a'

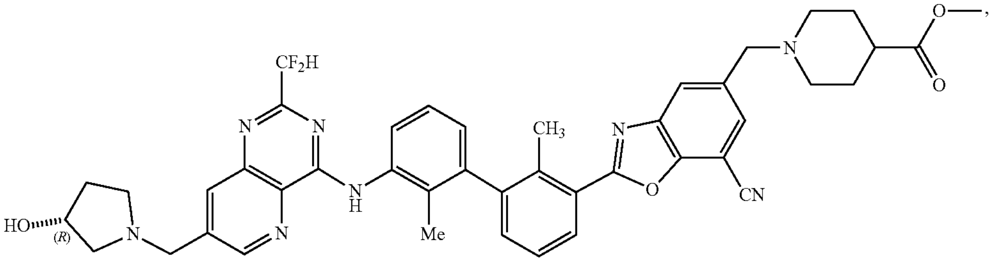

or a salt thereof, in the presence of a base to form the compound of formula 1:

1

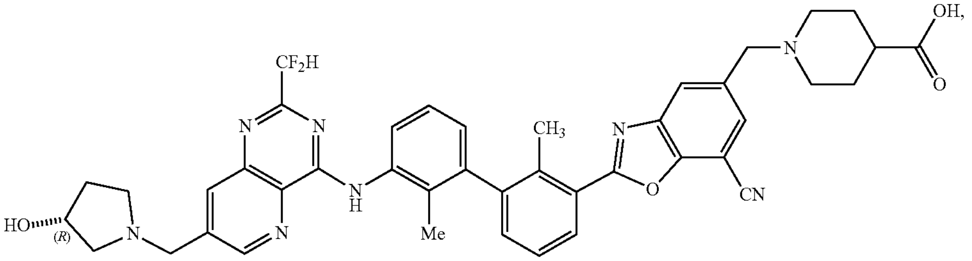

or a salt thereof.

The present disclosure also provides a process of preparing (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidine-4-carboxylic acid, or a salt thereof, comprising:

(a) reacting a compound of formula A-1a':

A-1a'

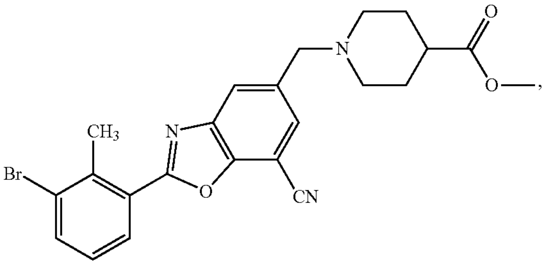

or a salt thereof, with a compound of formula A-2a:

A-2a

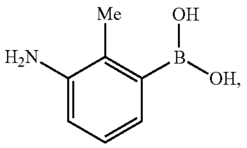

or a salt thereof, in the presence of a Suzuki catalyst and a base to form a compound of formula 3a':

A-3a'

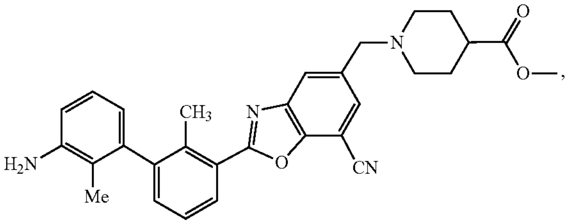

or a salt thereof;

(b) reacting the compound of formula A-3a', or the salt thereof with a compound of formula B-1a:

B-1a

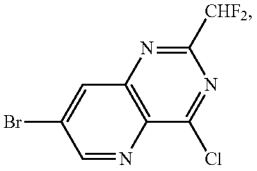

or a salt thereof, in the presence of a base, to form a compound of formula B-2a':

B-2a'

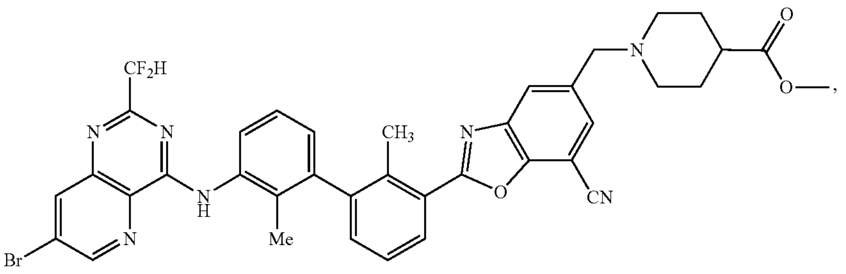

or a salt thereof;

(c) reacting the compound of formula B-2a', or the salt thereof, with a salt of formula B-3a:

B-3a

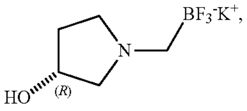

in the presence of a Suzuki catalyst and a base to form a compound of formula A-7a':

A-7a'

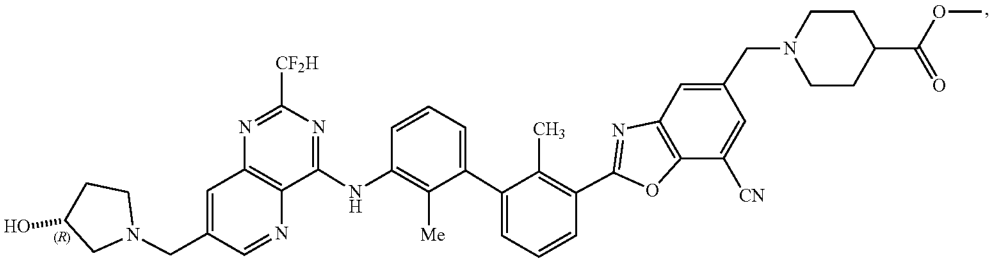

or a salt thereof, and (d) deprotecting the compound of formula A-7a', or the salt thereof, in the presence of a base to form the (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidine-4-carboxylic acid, or the salt thereof.

The present disclosure is further directed to a process of preparing a compound of formula A-1:

A-1

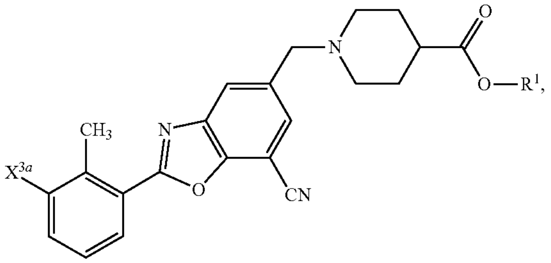

or a salt thereof, comprising: converting a compound of formula 6:

6

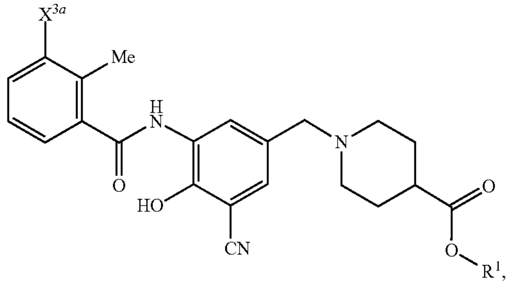

or a salt thereof, under oxidation conditions to form the compound of formula A-1, or the salt thereof, wherein $R^1$ is $C_{1-6}$ alkyl and $X^{3a}$ is halo.

The present disclosure is further directed to solid forms and salt forms of (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidine-4-carboxylic acid (compound of Formula 1, an inhibitor of PD-1/PD-L1 interaction).

Compound of Formula 1

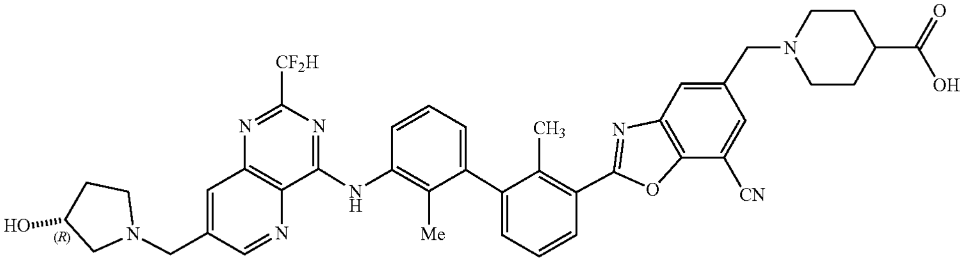

The present disclosure is further directed to the crystalline free base forms and the methanesulfonic acid salt of the compound of Formula 1.

The present disclosure is further directed to crystalline forms of salts of Compound of Formula 1.

The present disclosure is further directed to pharmaceutical compositions comprising a solid form or salt form described herein and at least one pharmaceutically acceptable carrier or excipient. The present disclosure is further directed to solid dosage forms comprising the pharmaceutical compositions described herein.

The present disclosure is further directed to a method of inhibiting PD-1/PD-L1 interaction comprising administering to a patient the solid forms or salt forms described herein.

The present disclosure is further directed to treating a disease or disorder associated with inhibition of PD-1/PD-L1 interaction comprising administering to a patient the solid forms and salt forms described herein. The present disclosure is further directed to enhancing, stimulating and/or increasing the immune response in a patient comprising administering to a patient the solid forms and salt forms described herein.

The present disclosure also provides uses of the solid forms and salt forms described herein for manufacture of a medicament for use in any of the methods described herein.

The present disclosure also provides uses of the solid forms and salt forms described herein for use in any of the methods described herein.

The present disclosure further provides processes of preparing compound of Formula 1, or a pharmaceutically acceptable salt thereof, comprising the steps detailed infra.

The present disclosure is further directed to processes for preparing the solid forms and salt forms described herein.

The present disclosure is further directed to a compound of formula A-1:

A-1

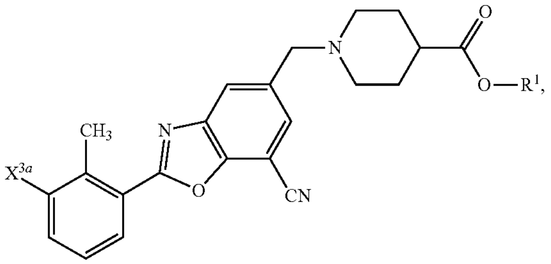

or a salt thereof, wherein $R^1$ is $C_{1-6}$ alkyl; and $X^{3a}$ is halo.

The present disclosure is further directed to a compound of formula A-3:

A-3

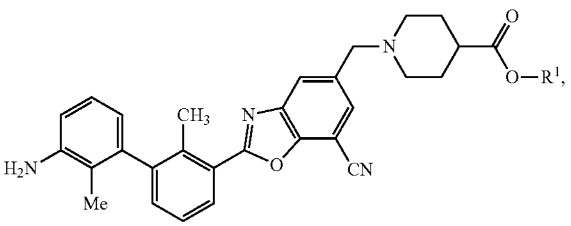

or a salt thereof, wherein $R^1$ is $C_{1-6}$ alkyl.

The present disclosure is further directed to a compound of formula A-4:

A-4

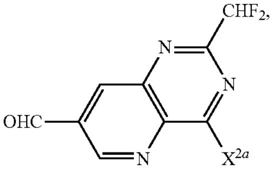

or a salt thereof, wherein $X^{2a}$ is halo.

The present disclosure is further directed to a compound of formula A-5:

A-5
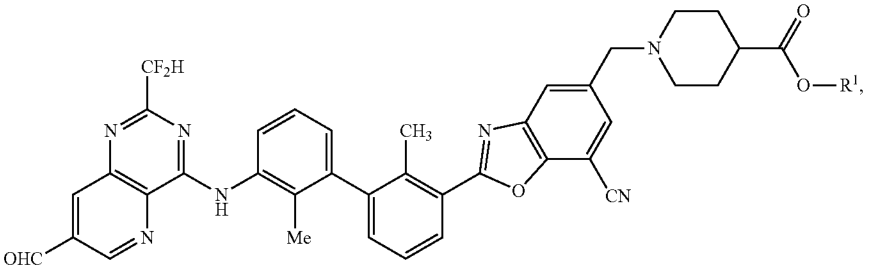
or a salt thereof, wherein $R^1$ is $C_{1-6}$ alkyl.
The present disclosure is further directed to a compound of formula A-7:
A-7
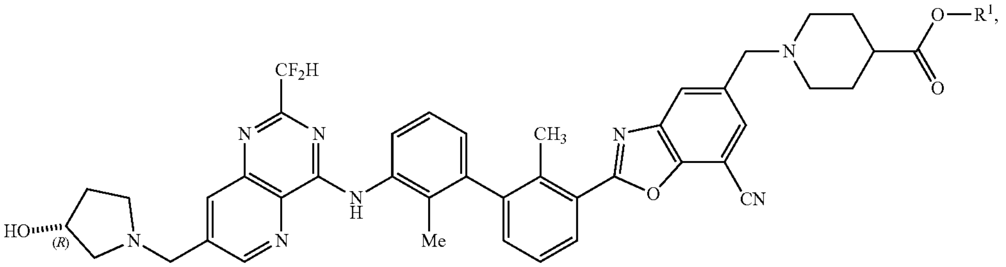
or a salt thereof, wherein $R^1$ is $C_{1-6}$ alkyl.
The present disclosure is further directed to a compound of formula B-2:
B-2
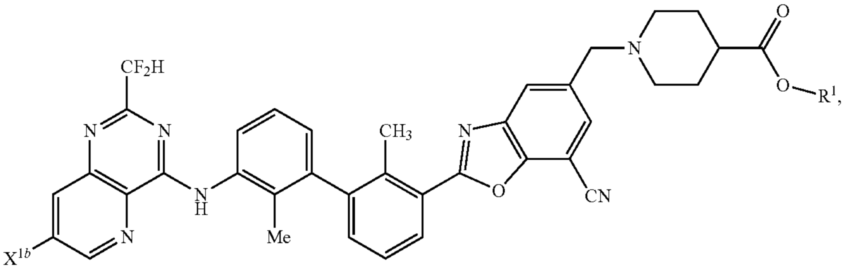
or a salt thereof, wherein $R^1$ is $C_{1-6}$ alkyl, wherein $X^{1b}$ is halo.

The present disclosure is further directed to a compound selected from a compound of formula 4, a compound of formula 5, and a compound of formula 6:

4

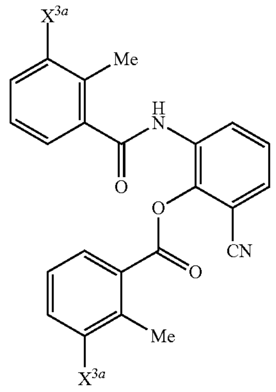

5

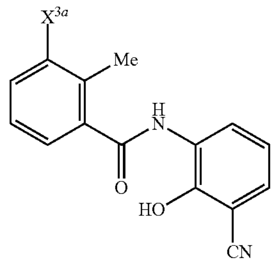

6

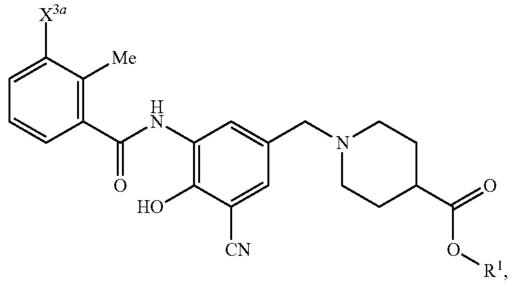

or a salt thereof, wherein each $X^{3a}$ is independently halo; and $R^1$ is t-butyl.

The present disclosure is further directed to a compound of formula 11:

11

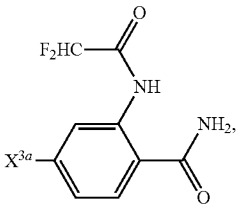

or a salt thereof, wherein $X^{3a}$ is halo.

DETAILED DESCRIPTION

Synthetic Processes

Figure 1:
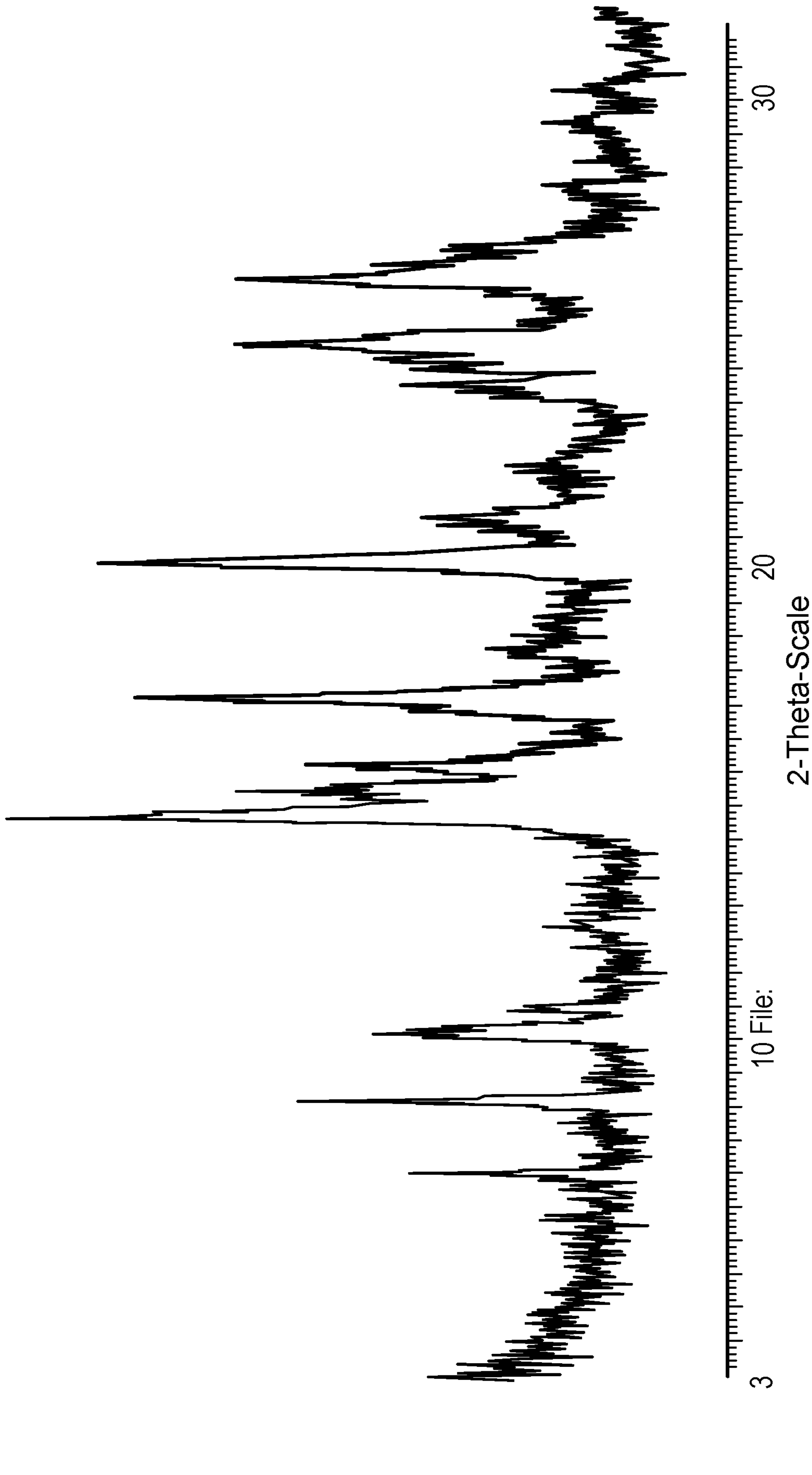
FIG. 1 shows an XRPD pattern of Form I of the compound of Formula 1 crystalline free base.

The present disclosure is directed to, inter alia, processes of preparing (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidine-4-carboxylic acid (Compound of Formula 1), or salts thereof.

The compound of Formula 1, including salts thereof, can be prepared using known organic synthesis techniques and can be synthesized according to any of numerous possible synthetic routes. The compound of Formula 1 is described in U.S. Patent Publication No. 2019/0300524, the entirety of which is incorporated herein by reference.

In some embodiments, the present disclosure provides a process of preparing the compound of Formula 1, or a salt thereof, comprising:

reacting a compound of formula A-3:

(A-3)

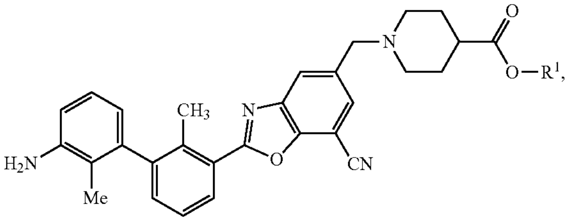

or a salt thereof, with a compound of formula A-4:

(A-4)

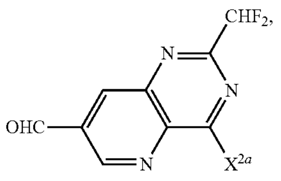

or a salt thereof, to form a compound of formula A-5:

(A-5)

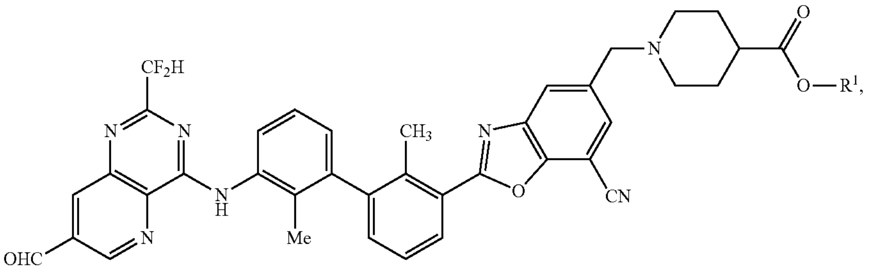

or a salt thereof, $R^1$ is $C_{1-6}$ alkyl and $X^{2a}$ is halo.

In some embodiments, $R^1$ is t-butyl. In some embodiments, $R^1$ is methyl.

In some embodiments, the reacting of the compound of formula A-3, or the salt thereof, with the compound of formula A-4, or the salt thereof, is conducted in the presence of an alkali metal halide and a base. In some embodiments, the alkali metal halide is LiBr.

In some embodiments, the alkali metal halide is an alkali metal bromide. In some embodiments, the base is a tertiary amine. In some embodiments, the base is selected from N,N-diisopropylamine, methylamine, dimethylamine, trimethylamine, and ethylamine. In some embodiments, the base is N,N-diisopropylamine.

In some embodiments, from about 1 to about 1.5 molar equivalents of the compound of formula A-4, or the salt thereof, is utilized relative to the compound of formula A-3, or the salt thereof. In some embodiments, about 1 molar equivalent of the compound of formula A-4, or the salt thereof, is utilized relative to the compound of formula A-3, or the salt thereof. In some embodiments, from about 3 to about 5 molar equivalents of the base is utilized relative to the compound of formula A-3, or the salt thereof. In some embodiments, about 4 molar equivalents of the base is utilized relative to the compound of formula A-3, or the salt thereof.

In some embodiments, from about 0.1 to about 1 molar equivalent of alkali metal halide is utilized relative to the compound of formula A-3, or the salt thereof. In some embodiments, from about 0.4 to about 0.6 molar equivalents of alkali metal halide is utilized relative to the compound of formula A-3, or the salt thereof. In some embodiments, about 0.5 molar equivalents of alkali metal halide is utilized relative to the compound of formula A-3, or the salt thereof.

In some embodiments, the reacting of the compound of formula A-3, or the salt thereof, with the compound of formula A-4, or the salt thereof, is carried out at a temperature of from about 40° C. to about 50° C.

In some embodiments, the reacting of the compound of formula A-3, or the salt thereof, with the compound of formula A-4, or the salt thereof, is carried out in a solvent component. In some embodiments, the solvent component comprises a di-$C_{1-6}$ alkyl ether or a 4-10 membered heterocycloalkyl ether. In some embodiments, the solvent component comprises tetrahydrofuran.

In some embodiments, the compound of formula A-3, or the salt thereof, is a compound of formula A-3a:

(A-3a)

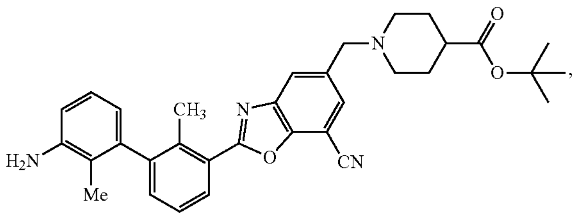

or a salt thereof.

In some embodiments, the compound of formula A-4, or the salt thereof, is a compound of formula A-4a:

(A-4a)

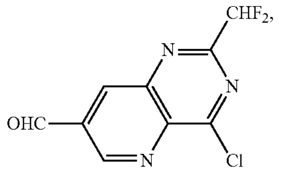

or a salt thereof.

In some embodiments, the compound of formula A-5, or the salt thereof, is a compound of formula A-5a:

(A-5a)

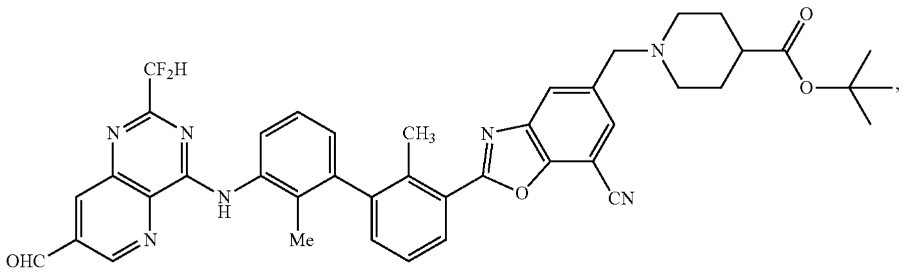

or a salt thereof.

In some embodiments, the process comprises: reacting a compound of formula A-3a:

(A-3a)

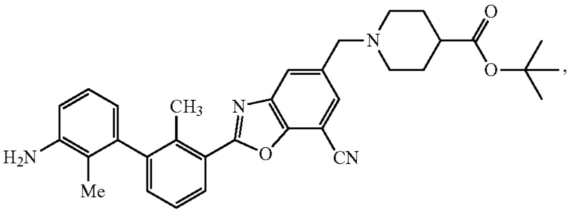

or a salt thereof, with a compound of formula A-4a:

(A-4a)

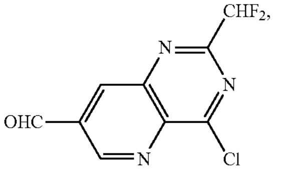

or a salt thereof, in the presence of an alkali metal halide and a base, to form a compound of formula A-5a:

(A-5a)

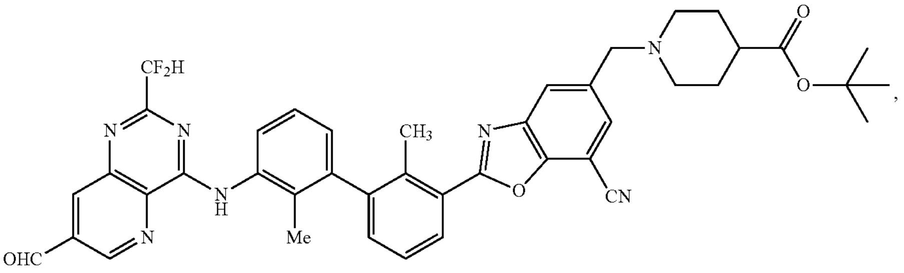

or a salt thereof.

In some embodiments, the process comprises:

a) reacting a compound of formula A-3a:

A-3a

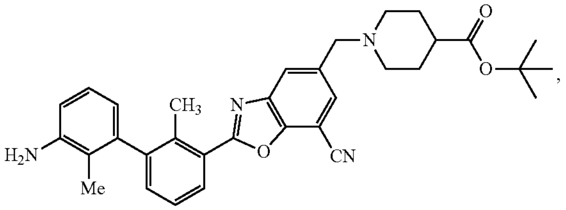

or a salt thereof, with a compound of formula A-4a:

A-4a

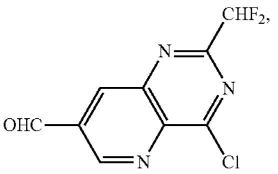

or a salt thereof, in the presence of an alkali metal halide and a base, to form a compound of formula A-5a:

A-5a
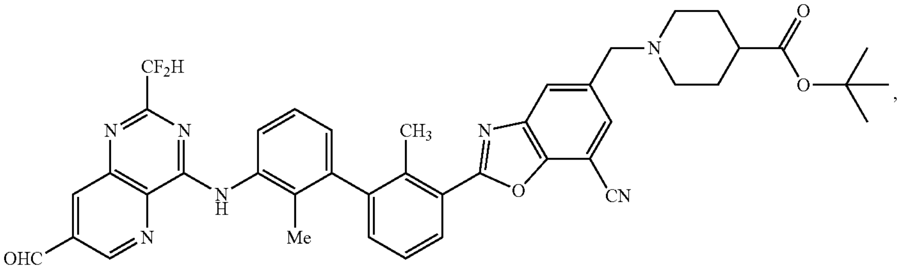
or a salt thereof;
b) reacting the compound of formula A-5a:
A-5a
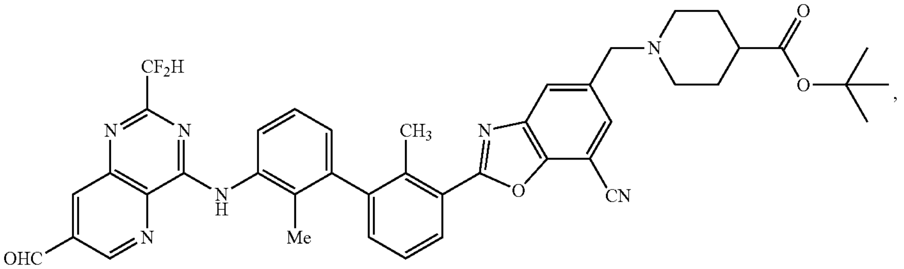
or a salt thereof, with a compound of formula A-6:
A-6
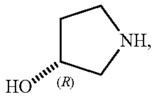
or a salt thereof, in the presence of a reducing agent to form a compound of formula A-7a:
A-7a
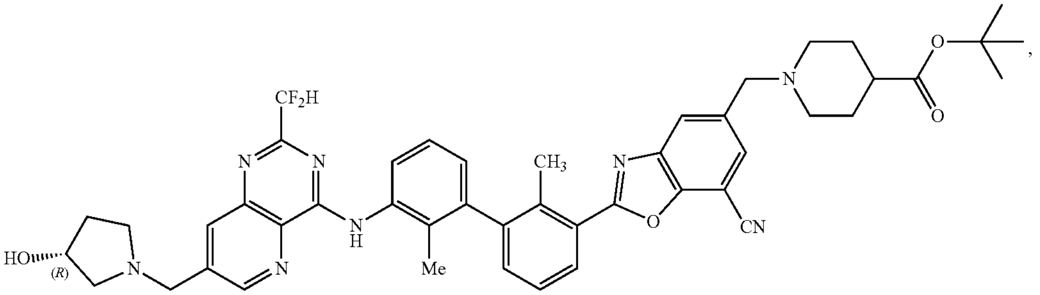
or a salt thereof, and c) reacting the compound of formula A-7a:

A-7a

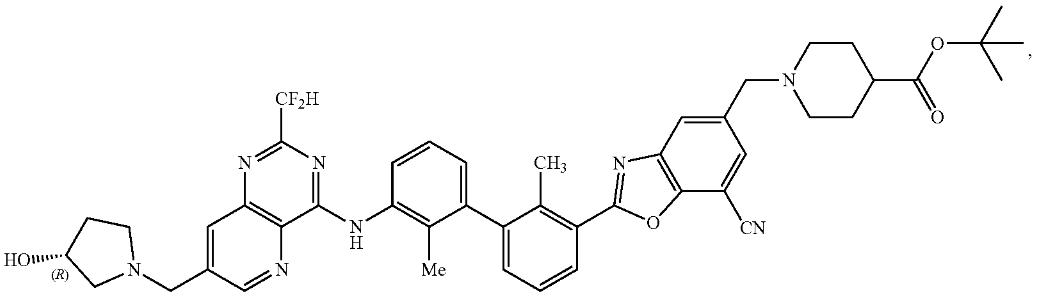

or a salt thereof, with a Lewis acid to form the compound of formula 1:

1

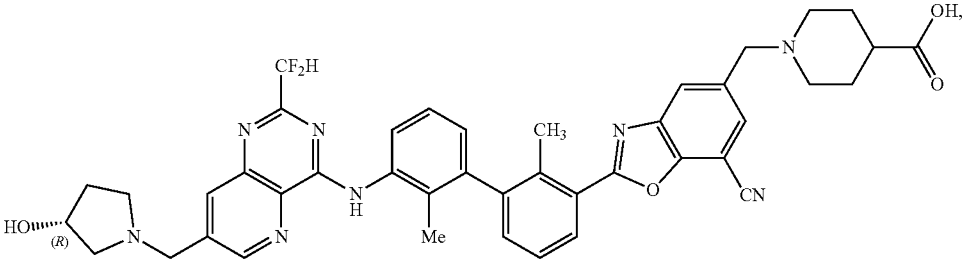

or a salt thereof.

Accordingly, the present disclosure further provides a process of preparing (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidine-4-carboxylic acid, or a salt thereof, comprising:

reacting a compound of formula A-5:

(A-5)

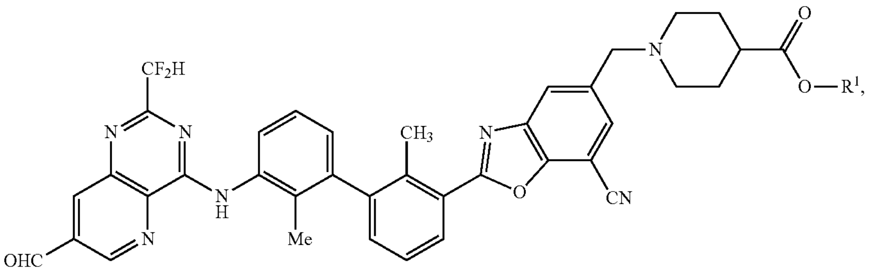

or a salt thereof, with a compound of formula A-6:

(A-6)

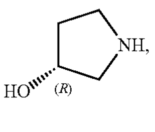

or a salt thereof, in the presence of a reducing agent to form a compound of formula A-7:

(A-7)

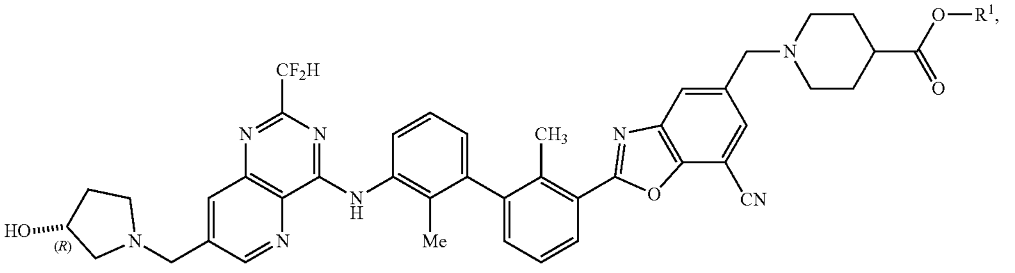

or a salt thereof, wherein $R^1$ is $C_{1-6}$ alkyl.

In some embodiments, $R^1$ is t-butyl. In some embodiments, $R^1$ is methyl.

In some embodiments, the reducing agent is a borohydride reducing agent. In some embodiments, the reducing agent is selected from $NaBH_4$, $NaBH_3CN$ and $NaBH(OAc)_3$. In some embodiments, wherein the reducing agent is $NaBH(OAc)_3$.

In some embodiments, the reacting of the compound of formula A-5, or the salt thereof, with the compound of formula A-6, or the salt thereof, is carried out in the presence of a catalyst. In some embodiments, the catalyst is a reductive amination catalyst. In some embodiments, the catalyst is a Lewis acid. In some embodiments, the Lewis acid is trimethyl borate. In some embodiments, the catalyst is trimethyl borate. In some embodiments, from about 1 to about 4 molar equivalents of the compound of formula A-6, or the salt thereof, is utilized relative to the compound of formula A-5, or the salt thereof. In some embodiments, from about 2 to about 3 molar equivalents of the compound of formula A-6, or the salt thereof, is utilized relative to the compound of formula A-5, or the salt thereof. In some embodiments, from about 1.5 to about 2.5 molar equivalents of the compound of formula A-6, or the salt thereof, is utilized relative to the compound of formula A-5, or the salt thereof. In some embodiments, from about 2 to about 2.5 molar equivalents of the compound of formula A-6, or the salt thereof, is utilized relative to the compound of formula A-5, or the salt thereof. In some embodiments, about 2 molar equivalents of the compound of formula A-6, or the salt thereof, is utilized relative to the compound of formula A-5, or the salt thereof.

In some embodiments, from about 1 to about 4 molar equivalents of the catalyst is utilized relative to the compound of formula A-5, or the salt thereof. In some embodiments, from about 1.5 to about 2.5 molar equivalents of the catalyst is utilized relative to A-5, or the salt thereof. In some embodiments, about 2 molar equivalents of the catalyst is utilized relative to the compound of formula A-5, or the salt thereof.

In some embodiments, from about 1 to about 4 molar equivalents of the reducing agent is utilized relative to the compound of formula A-5, or the salt thereof. In some embodiments, from about 2 to about 3 molar equivalents of the reducing agent is utilized relative to the compound of formula A-5, or the salt thereof. In some embodiments, from about 1.5 to about 2.5 molar equivalents of the reducing agent is utilized relative to the compound of formula A-5, or the salt thereof. In some embodiments, from about 2 to about 2.5 molar equivalents of the reducing agent is utilized relative to the compound of formula A-5, or the salt thereof. In some embodiments, about 2 molar equivalents of the reducing agent is utilized relative to the compound of formula A-5, or the salt thereof.

In some embodiments, the reacting of the compound of formula A-5, or the salt thereof, with the compound of formula A-6, or salt thereof, is carried out at a temperature of about 15° C. to about 25° C.

In some embodiments, the reacting of the compound of formula A-5, or the salt thereof, with the compound of formula A-6, or salt thereof, is carried out in a solvent component. In some embodiments, the reacting of the compound of formula A-5, or the salt thereof, with the compound of formula A-6, or salt thereof, is carried out in a solvent component comprising a polar aprotic solvent. In some embodiments, the reacting of the compound of formula A-5, or the salt thereof, with the compound of formula A-6, or salt thereof, is carried out in a solvent component comprising an organic solvent. In some embodiments, the reacting of the compound of formula A-5, or the salt thereof, with the compound of formula A-6, or salt thereof, is carried out in a solvent component comprising an organonitrile and an organohalide. In some embodiments, the reacting of the compound of formula A-5, or the salt thereof, with the compound of formula A-6, or salt thereof, is carried out in a solvent component comprising dichloromethane and acetonitrile.

In some embodiments, the compound of formula A-5, or the salt thereof, is a compound of formula A-5a:

(A-5a)

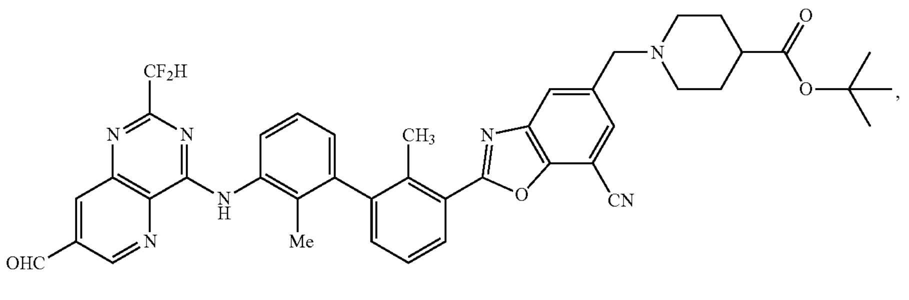

or a salt thereof.

In some embodiments, the compound of formula A-7, or the salt thereof, is a compound of formula A-7a:
(A-7a)
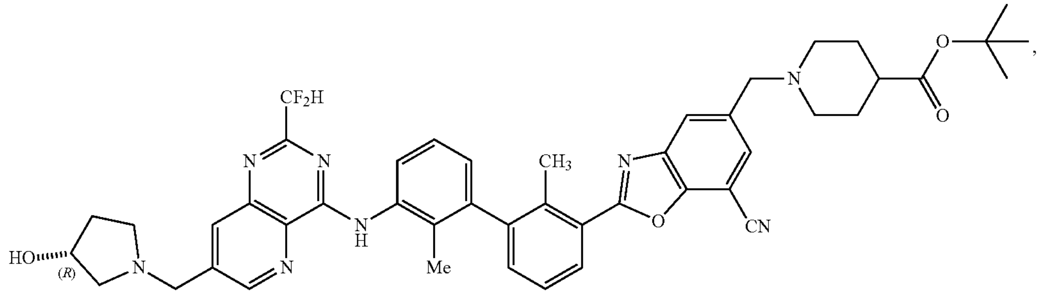
or a salt thereof.
In some embodiments, the process comprises:
reacting a compound of formula A-5a:
(A-5a)
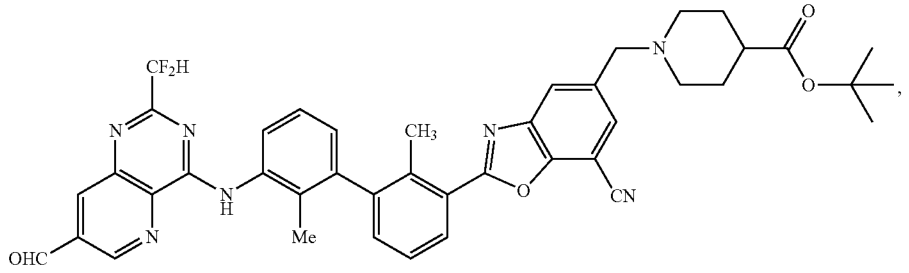
or a salt thereof, with a compound of formula A-6:
(A-6)
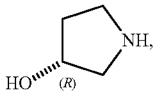
or a salt thereof, in the presence of a reducing agent to form a compound of formula A-7a:
(A-7a)
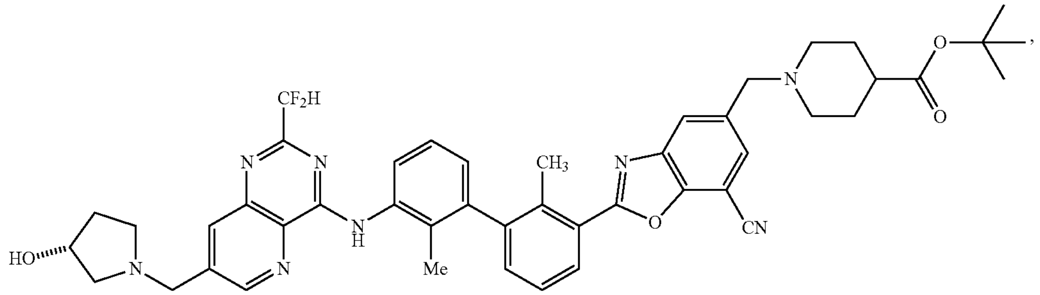
or a salt thereof.

The present disclosure further provides a process of preparing Compound of Formula 1, or a salt thereof, comprising:

reacting a compound of formula A-3:

(A-3)

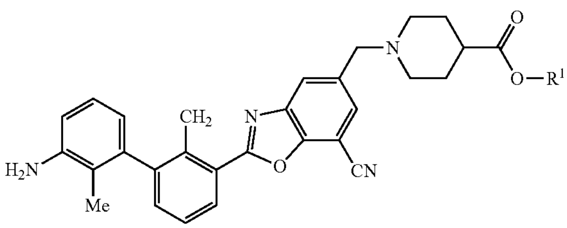

or a salt thereof, with a compound of formula B-1:

(B-1)

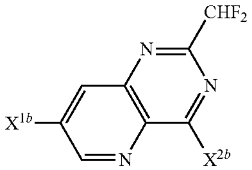

or a salt thereof, in the presence of a base, to form a compound of formula B-2:

(B-2)

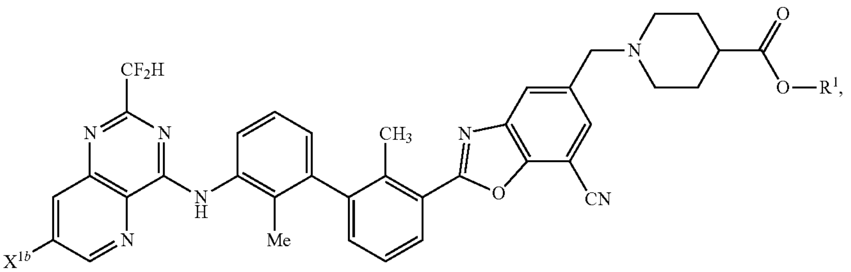

or a salt thereof, wherein $R^1$ is $C_{1-6}$ alkyl; and $X^{1b}$ and $X^{2b}$ are independently halo. In some embodiments, $R^1$ is t-butyl. In some embodiments, $R^1$ is methyl.

In some embodiments, the base, present in the reacting of the compound of formula A-3, or the salt thereof, with the compound of formula B-1, or the salt thereof, is an alkali metal base. In some embodiments, the base, present in the reacting of the compound of formula A-3, or the salt thereof, with the compound of formula B-1, or the salt thereof, is an alkali metal carbonate. In some embodiments, the base, present in the reacting of the compound of formula A-3, or the salt thereof, with the compound of formula B-1, or the salt thereof, is selected from cesium carbonate, lithium carbonate, sodium carbonate, and potassium carbonate. In some embodiments, the base, present in the reacting of the compound of formula A-3, or the salt thereof, with the compound of formula B-1, or the salt thereof, is potassium carbonate.

In some embodiments, from about 1 to about 1.5 molar equivalents of the compound of formula B-1, or the salt thereof, is utilized relative to the compound of formula A-3, or the salt thereof. In some embodiments, about 1 molar equivalent of the compound of formula B-1, or the salt thereof, is utilized relative to the compound of formula A-3, or the salt thereof.

In some embodiments, from about 1 to about 4 molar equivalents of the base is utilized relative to the compound of formula A-3, or the salt thereof. In some embodiments, from about 1.5 to about 2.5 molar equivalents of the base is utilized relative to the compound of formula A-3, or the salt thereof. In some embodiments, from about 2 to about 3 molar equivalents of the base is utilized relative to the compound of formula A-3, or the salt thereof. In some embodiments, from about 2 to about 2.5 molar equivalents of the base is utilized relative to the compound of formula A-3, or the salt thereof. In some embodiments, about 2 molar equivalents of the base is utilized relative to the compound of formula A-3, or the salt thereof. In some embodiments, about 1 molar equivalent of the base is utilized relative to the compound of formula A-3, or the salt thereof.

In some embodiments, the reacting the compound of formula A-3, or the salt thereof, with the compound of formula B-1, or the salt thereof, is carried out at a temperature of about 70° C. to about 90° C. In some embodiments, the reacting the compound of formula A-3, or the salt thereof, with the compound of formula B-1, or the salt thereof, is carried out at a temperature of about 80° C. In some embodiments, the reacting the compound of formula A-3, or the salt thereof, with the compound of formula B-1, or the salt thereof, is carried out at a temperature of about 40° C. to about 70° C. In some embodiments, the reacting the compound of formula A-3, or the salt thereof, with the compound of formula B-1, or the salt thereof, is carried out at a temperature of about 50° C.

In some embodiments, the reacting the compound of formula A-3, or the salt thereof, with the compound of formula B-1, or the salt thereof, is carried out in a solvent component. In some embodiments, the solvent component comprises an organic ether. In some embodiments, the solvent component comprises diglyme. In some embodiments, the solvent component comprises tetrahydrofuran.

In some embodiments, $X^{1b}$ is bromo. In some embodiments, $X^{1b}$ is chloro. In some embodiments, $X^{2b}$ is chloro.

In some embodiments, the compound of formula A-3, or the salt thereof, is a compound of formula A-3a:

(A-3a)

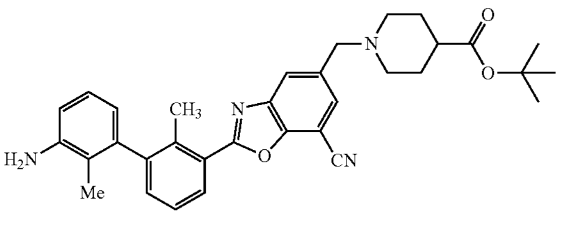

or a salt thereof.

In some embodiments, the compound of formula A-3, or the salt thereof, is a compound of formula A-3a':

(A-3a')

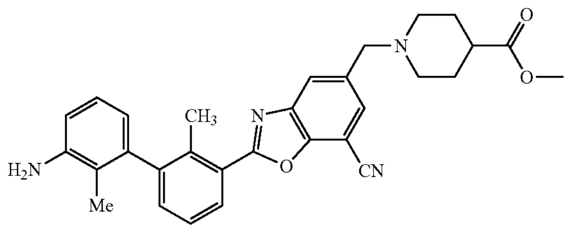

or a salt thereof.

In some embodiments, the compound of formula B-1, or the salt thereof, is a compound of formula B-1a:

(B-1a)

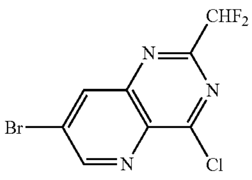

or a salt thereof.

In some embodiments, the compound of formula B-2, or the salt thereof, is a compound of formula B-2a:

In some embodiments, the process comprises:

reacting a compound of formula A-3a:

(A-3a)

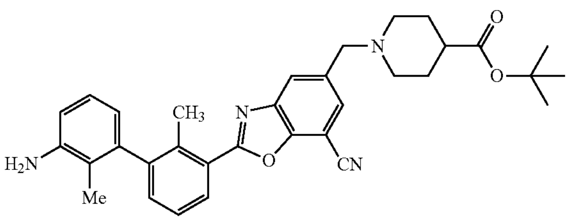

or a salt thereof, with a compound of formula B-1a:

(B-1a)

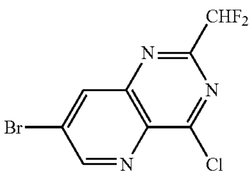

or a salt thereof, in the presence of a base, to form a compound of formula B-2a:

(B-2a)

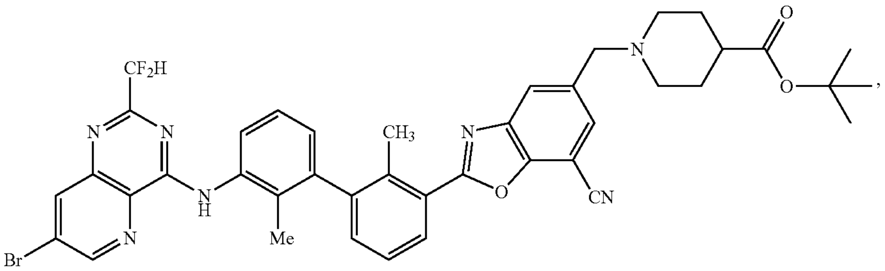

or a salt thereof.

In some embodiments, the compound of formula B-2, or the salt thereof, is a compound of formula B-2a':

(B-2a)

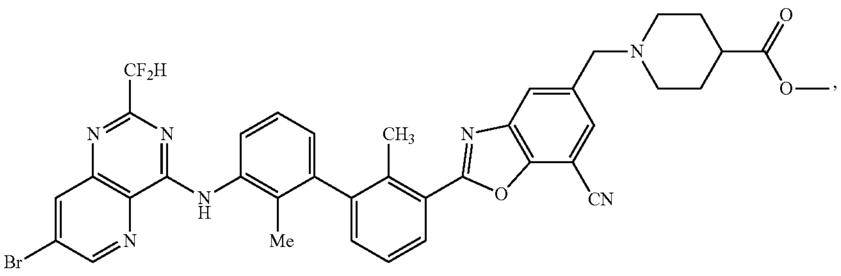

or a salt thereof.

(B-2a)

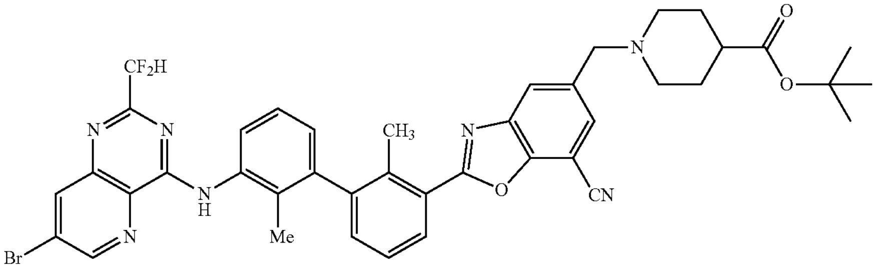

or a salt thereof.

In some embodiments, the process comprises:

reacting a compound of formula A-3a':

(A-3')

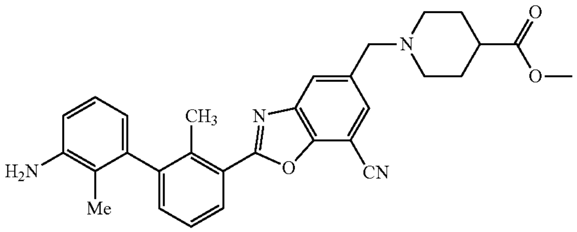

or a salt thereof, with a compound of formula B-1a:

(B-1a)

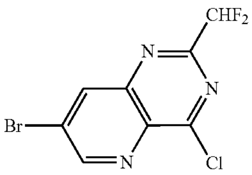

or a salt thereof, in the presence of a base, to form a compound of formula B-2a':

(B-2a')

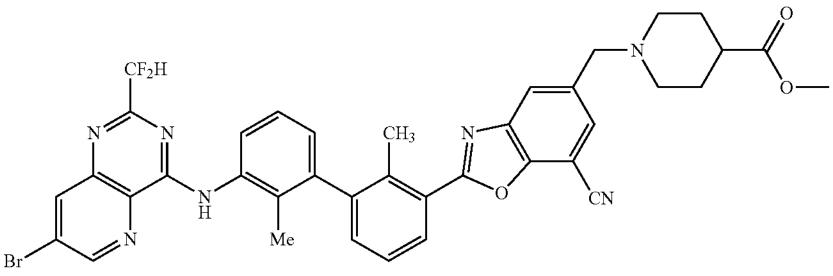

or a salt thereof.

The present disclosure further provides a process of preparing Compound of Formula 1, or a salt thereof, comprising:

reacting a compound of formula B-2:

(B-2)

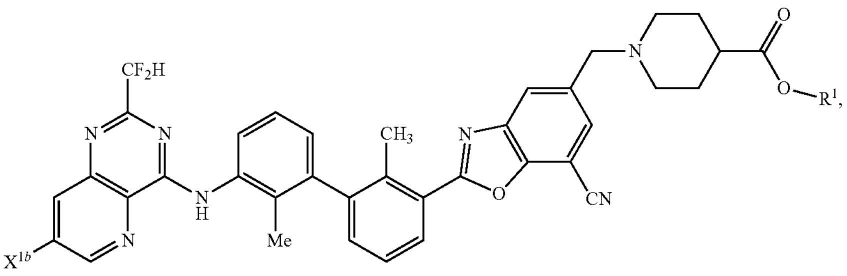

or a salt thereof, with a salt of formula B-3:

(B-3)

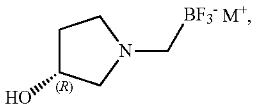

wherein $M^+$ is $Li^+$, $Na^+$, $K^+$, or $Cs^+$, in the presence of a Suzuki catalyst and a base to form a compound of formula A-7:

(A-7)

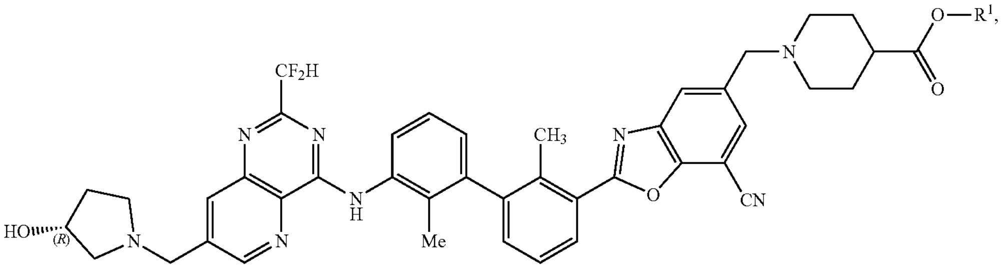

or a salt thereof, wherein $R^1$ is $C_{1-6}$ alkyl and $X^{1b}$ is halo. In some embodiments, $R^1$ is t-butyl. In some embodiments, $R^1$ is methyl.

In some embodiments, the process further comprises: reacting a compound of formula B-2:

(B-2)

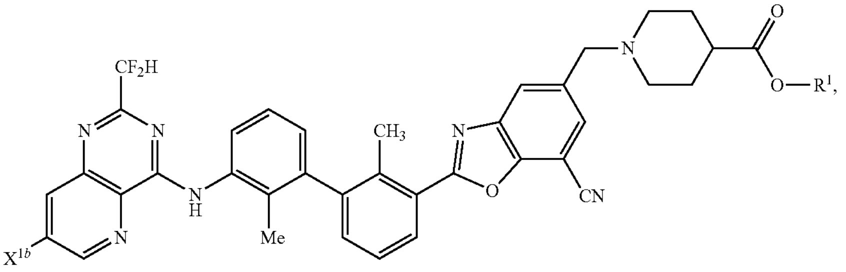

or a salt thereof, with a salt of formula B-3:

(B-3)

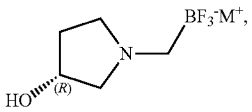

wherein $M^+$ is $Li^+$, $Na^+$, $K^+$, or $Cs^+$, in the presence of a Suzuki catalyst and a base to form a compound of formula A-7:

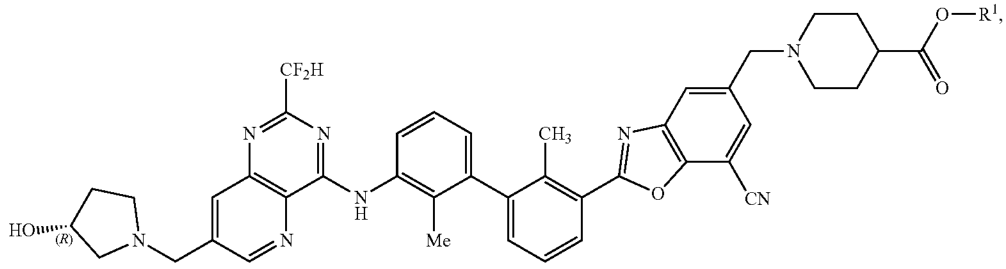

(A-7)

or a salt thereof, wherein $R^1$ is $C_{1-6}$ alkyl and $X^{1b}$ is halo.

In some embodiments, $R^1$ is t-butyl. In some embodiments, $R^1$ is methyl.

In some embodiments, $X^{1b}$ is bromo.

In some embodiments, the Suzuki catalyst is a palladium catalyst. In some embodiments, the Suzuki catalyst is selected from CataCXium® Pd G4, $Pd(PPh_3)_4$, $Pd(dppf)_2Cl_2$, dichlorobis[di-tert-butyl(p-dimethylaminophenyl)phosphino]palladium and $PdCl_2(dtbpf)$ (Pd-118). In some embodiments, the Suzuki catalyst is CataCXium® Pd G4. In some embodiments, the Suzuki catalyst is selected from CataCXium® Pd G4 ((2'-(methylamino)-[1,1'-biphenyl]-2-yl)((methylsulfonyl)oxy)palladium di(1-adamantyl)-n-butylphosphine complex), CataCXium® $[Pd(allyl)Cl]_2$, $Pd(PPh_3)_4$, $Pd(dppf)_2Cl_2$, dichlorobis[di-tert-butyl(p-dimethylaminophenyl)phosphino]palladium and $PdCl_2(dtbpf)$ (Pd-118). In some embodiments, wherein the Suzuki catalyst is CataCXium® $[Pd(allyl)Cl]_2$.

In some embodiments, the base, present in the reacting of the compound of formula B-2, or the salt thereof, with the salt of formula B-3, is an alkali metal base. In some embodiments, wherein the base, present in the reacting of the compound of formula B-2, or the salt thereof, with the salt of formula B-3, is an alkali metal carbonate. In some embodiments, the base, present in the reacting of the compound of formula B-2, or the salt thereof, with the salt of formula B-3, is selected from cesium carbonate, lithium carbonate, sodium carbonate, and potassium carbonate. In some embodiments, the base, present in the reacting of the compound of formula B-2, or the salt thereof, with the salt of formula B-3, is cesium carbonate.

In some embodiments, from about 1 to about 4 molar equivalents of the salt of formula B-3 is utilized relative to the compound of formula B-2, or the salt thereof. In some embodiments, from about 1.5 to about 2.5 molar equivalents of the salt of formula B-3 is utilized relative to the compound of formula B-2, or the salt thereof. In some embodiments, about 1.6 molar equivalents of the salt of formula B-3 is utilized relative to the compound of formula B-2, or the salt thereof. In some embodiments, from about 2 to about 3 molar equivalents of the salt of formula B-3 is utilized relative to the compound of formula B-2, or the salt thereof. In some embodiments, from about 2 to about 2.5 molar equivalents of the salt of formula B-3 is utilized relative to the compound of formula B-2, or the salt thereof. In some embodiments, about 2 molar equivalents of the salt of formula B-3 is utilized relative to the compound of formula B-2, or the salt thereof.

In some embodiments, from about 3 to about 9 molar equivalents of the base is utilized relative to the compound of formula B-2, or the salt thereof. In some embodiments, from about 5 to about 7 molar equivalents of the base is utilized relative to the compound of formula B-2, or the salt thereof. In some embodiments, about 6 molar equivalents of the base is utilized relative to the compound of formula B-2, or the salt thereof.

In some embodiments, from about 0.01 to about 0.5 molar equivalent of the Suzuki catalyst is utilized relative to the compound of formula B-2, or the salt thereof. In some embodiments, from about 0.01 to about 0.1 molar equivalent of the Suzuki catalyst is utilized relative to the compound of formula B-2, or the salt thereof. In some embodiments, from about 0.03 to about 0.05 molar equivalent of the Suzuki catalyst is utilized relative to the compound of formula B-2, or the salt thereof. In some embodiments, about 0.04 molar equivalent of the Suzuki catalyst is utilized relative to the compound of formula B-2, or the salt thereof.

In some embodiments, wherein the reacting the compound of formula B-2, or the salt thereof, with the salt of formula B-3, is carried out at a temperature of about 80° C. to about 120° C. In some embodiments, the reacting of the compound of formula B-2, or the salt thereof, with the salt of formula B-3, is carried out at a temperature of about 100° C. In some embodiments, the reacting of the compound of formula B-2, or the salt thereof, with the salt of formula B-3, is carried out at a temperature of about 90° C.

In some embodiments, the reacting of the compound of B-2, or the salt thereof, with the salt of formula B-3, is carried out in a solvent component. In some embodiments, the reacting of the compound of B-2, or the salt thereof, with the salt of formula B-3, is carried out in a solvent component comprising a non-protic organic solvent. In some embodiments, the reacting of the compound of B-2, or the salt thereof, with the salt of formula B-3, is carried out in a solvent component comprising a di-$C_{1-6}$ alkyl ether or a 4-10 membered heterocycloalkyl ether. In some embodiments, the solvent component comprises dioxane.

In some embodiments, the compound of formula B-2, or the salt thereof, is a compound of formula B-2a:

(B-2a)
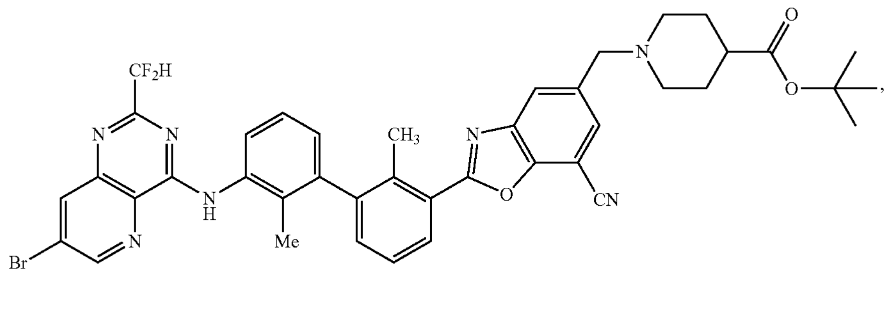
or a salt thereof.
In some embodiments, the compound of formula B-2, or the salt thereof, is a compound of formula B-2a':
(B-2a')
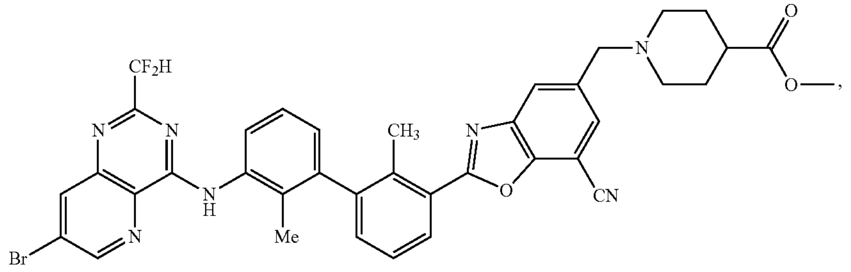
or a salt thereof.
In some embodiments, the salt of formula B-3, or the salt thereof, is a salt of formula B-3a:
(B-3a)
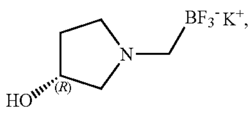
or a salt thereof.
In some embodiments, the compound of formula A-7, or the salt thereof, is a compound of formula A-7a:
(A-7a)
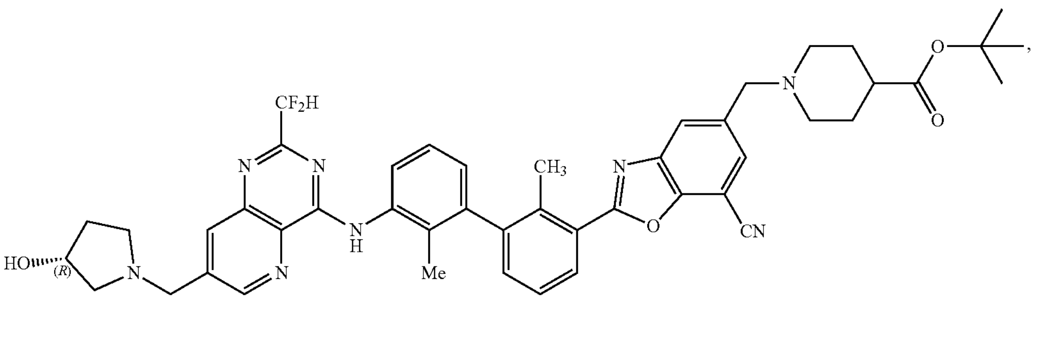
or a salt thereof.

In some embodiments, the compound of formula A-7, or the salt thereof, is a compound of formula A-7a':
(A-7a')
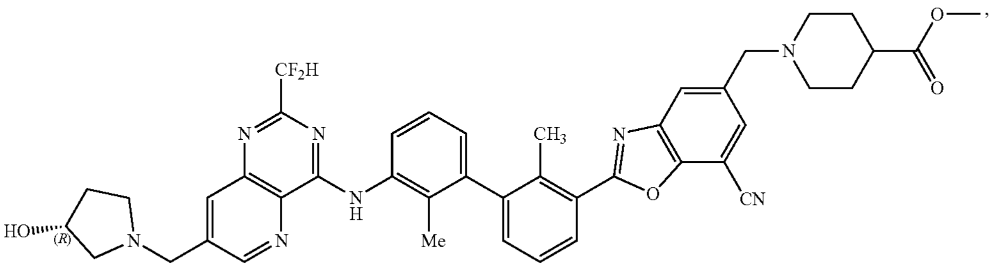
or a salt thereof.
In some embodiments, the process comprises:
reacting a compound of formula B-2a:
(B-2a)
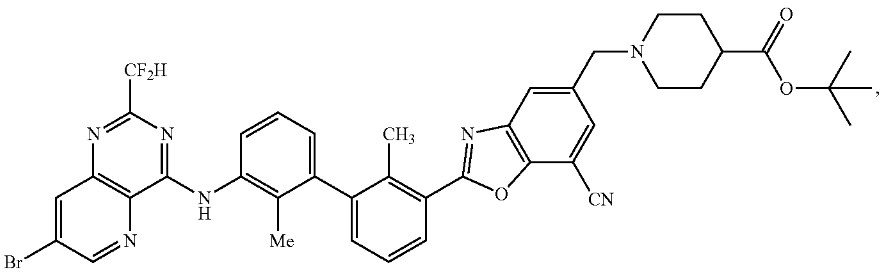
or a salt thereof, with a salt of formula B-3a:
(B-3a)
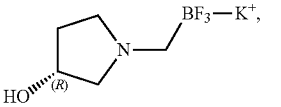
in the presence of a Suzuki catalyst and a base to form a compound of formula A-7a:
(A-7a)
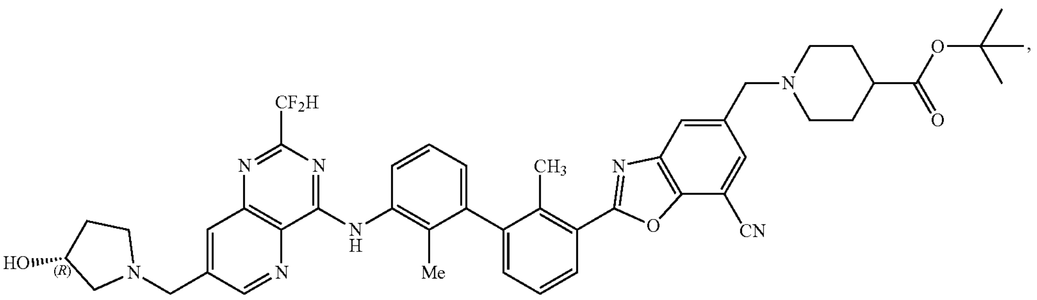
or a salt thereof.

In some embodiments, the process comprises: reacting a compound of formula B-2a':

(B-2a')

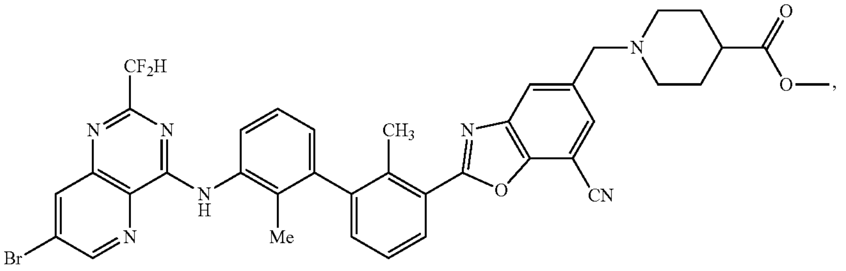

or a salt thereof, with a salt of formula B-3a:

(B-3a)

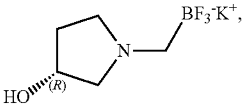

in the presence of a Suzuki catalyst and a base to form a compound of formula A-7a':

(A-7a')

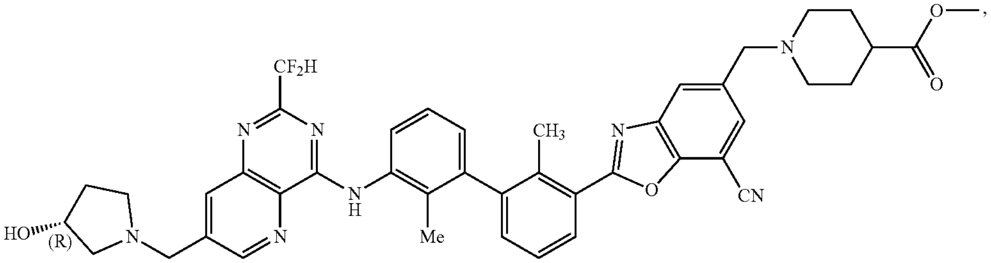

or a salt thereof.

In some embodiments, the compound of formula A-3 or the salt thereof is prepared by a process comprising:

reacting a compound of formula A-1:

(A-1)

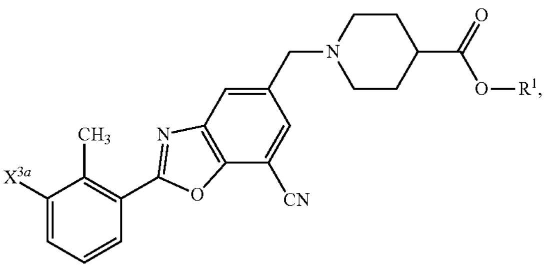

or a salt thereof, with a compound of formula A-2:

(A-2)

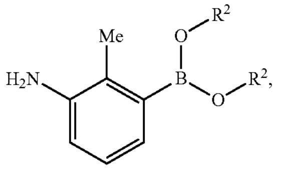

or a salt thereof, in the presence of a Suzuki catalyst and a base, wherein $X^{3a}$ is halo; $R^1$ is $C_{1-6}$ alkyl; and each $R^2$ is independently selected from H and $C_{1-6}$ alkyl; or each $R^2$ together form an $C_{2-3}$ alkylene linker, which is optionally substituted by 1, 2, 3, or 4 independently selected $C_{1-4}$ alkyl groups. In some embodiments, $R^1$ is t-butyl. In some embodiments, $R^1$ is methyl.

In some embodiments, wherein the Suzuki catalyst, present in the reacting of the compound of formula A-1, or the salt thereof, with the compound of formula A-2, or the salt thereof, is a palladium catalyst. In some embodiments, the Suzuki catalyst, present in the reacting of the compound of formula A-1, or the salt thereof, with the compound of formula A-2, or the salt thereof, is selected from CataCXium® Pd G4, $Pd(PPh_3)_4$ $Pd(dppf)_2Cl_2$, dichlorobis[di-tert-butyl(p-dimethylaminophenyl)phosphino]palladium and $PdCl_2$(dtbpf) (Pd-118). In some embodiments, the Suzuki catalyst, present in the reacting of the compound of formula A-1, or the salt thereof, with the compound of formula A-2, or the salt thereof, is $PdCl_2$(dtbpf) (Pd-118).

In some embodiments, the base, present in the reacting of the compound of formula A-1, or the salt thereof, with the compound of formula A-2, or the salt thereof, is an alkali metal base. In some embodiments, the base, present in the reacting of the compound of formula A-1, or the salt thereof, with the compound of formula A-2, or the salt thereof, is an alkali metal phosphate. In some embodiments, the base, present in the reacting of the compound of formula A-1, or the salt thereof, with the compound of formula A-2, or the salt thereof, is potassium phosphate dibasic.

In some embodiments, from about 1 to about 2 molar equivalents of the compound of formula A-2, or the salt thereof, is utilized relative to the compound of formula A-1, or the salt thereof. In some embodiments, from about 1 to about 1.5 molar equivalents of the compound of formula A-2, or the salt thereof, is utilized relative to the compound of formula A-1, or the salt thereof. In some embodiments, about 1 molar equivalent of the compound of formula A-2, or the salt thereof, is utilized relative to the compound of formula A-1, or the salt thereof.

In some embodiments, from about 1 to about 9 molar equivalents of the base is utilized relative to the compound of formula A-1, or the salt thereof. In some embodiments, from about 3 to about 5 molar equivalents of the base is utilized relative to the compound of formula A-1, or the salt thereof. In some embodiments, about 4 molar equivalents of the base is utilized relative to the compound of formula A-1, or the salt thereof.

In some embodiments, from about 0.001 to about 0.1 molar equivalent of the Suzuki catalyst is utilized relative to the compound of formula A-1, or the salt thereof. In some embodiments, about 0.008 molar equivalent of the Suzuki catalyst is utilized relative to the compound of formula A-1, or the salt thereof.

In some embodiments, the reacting of the compound of formula A-1, or the salt thereof, with the compound of formula A-2 or the salt thereof, is carried out at a temperature of about 70° C. to about 100° C. In some embodiments, the reacting of the compound of formula A-1, or the salt thereof, with the compound of formula A-2 or the salt thereof, is carried out at a temperature of about 80° C.

In some embodiments, the reacting of the compound of formula A-1, or the salt thereof, with the compound of formula A-2, or the salt thereof, is carried out in a solvent component. In some embodiments, the reacting of the compound of formula A-1, or the salt thereof, with the compound of formula A-2, or the salt thereof, is carried out in a solvent component comprising a polar protic solvent. In some embodiments, the reacting of the compound of formula A-1, or the salt thereof, with the compound of formula A-2, or the salt thereof, is carried out in a solvent component comprising $C_{1-6}$ alkanol and water. In some embodiments, the reacting of the compound of formula A-1, or the salt thereof, with the compound of formula A-2, or the salt thereof, is carried out in a solvent component comprising water and tert-butanol.

In some embodiments, the compound of formula A-1, or the salt thereof, is a compound of formula A-1a:

(A-1a)

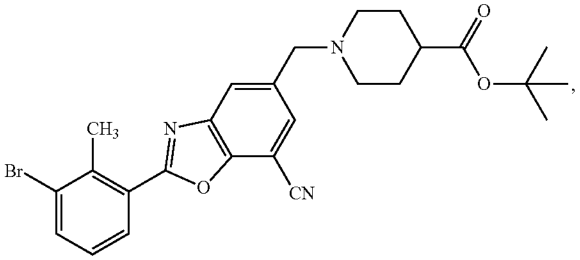

or a salt thereof.

In some embodiments, the compound of formula A-1, or the salt thereof, is a compound of formula A-1a':

(A-1a')

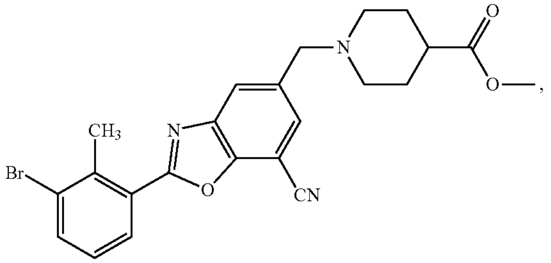

or a salt thereof.

In some embodiments, the compound of formula A-2, or the salt thereof, is a compound of formula A-2a:

(A-2a)

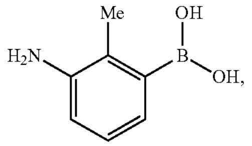

or a salt thereof.

In some embodiments, the process comprises:

reacting a compound of formula A-1a:

(A-1a)

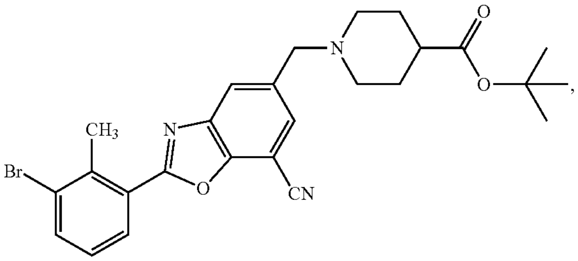

or a salt thereof, with a compound of formula A-2a:

(A-2a)

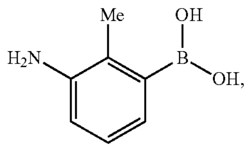

or a salt thereof, in the presence of a Suzuki catalyst and a base.

In some embodiments, the process comprises: reacting a compound of formula A-1a':

(A-1a')

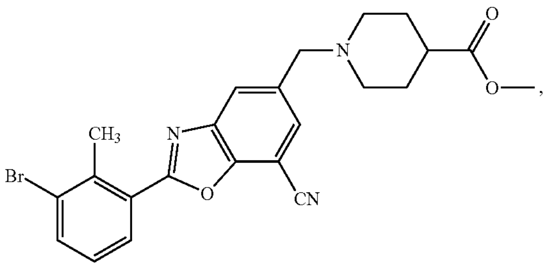

or a salt thereof, with a compound of formula A-2a:

(A-2a)

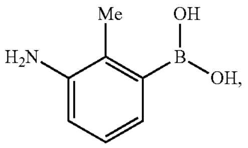

or a salt thereof, in the presence of a Suzuki catalyst and a base.

In some embodiments, the compound of formula 1, or the salt thereof, is prepared by a process comprising: converting a compound of formula A-7:

(A-7)

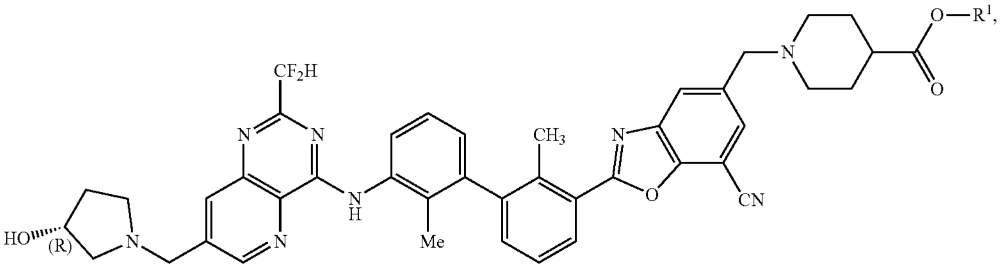

or a salt thereof, to the compound of formula 1:

(1)

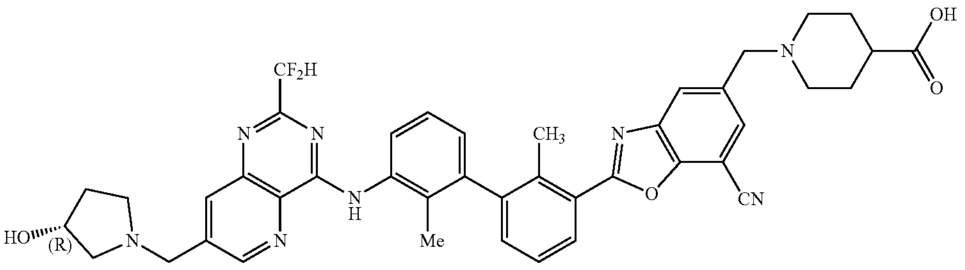

or a salt thereof, wherein $R^1$ is $C_{1-6}$ alkyl. In some embodiments, $R^1$ is t-butyl. In some embodiments, $R^1$ is methyl.

In some embodiments, the converting of the compound of formula A-7, or the salt thereof, to the compound of formula 1, or the salt thereof, comprises treating the compound of formula A-7, or the salt thereof, with a Lewis acid. In some embodiments, the Lewis acid, present in the converting of the compound of formula A-7, or the salt thereof, is iodotrimethylsilane. In some embodiments, from about 1 to about 5 molar equivalents of the Lewis acid is utilized relative to the compound of formula A-7, or the salt thereof. In some embodiments, from about 2 to about 4 molar equivalents of the Lewis acid is utilized relative to the compound of formula A-7, or the salt thereof. In some embodiments, about 3 molar equivalents of the Lewis acid is utilized relative to the compound of formula A-7, or the salt thereof.

In some embodiments, the converting of the compound of formula A-7, or the salt thereof, to the compound of formula 1, or the salt thereof, comprises treating the compound of formula A-7, or the salt thereof, with a base. In some embodiments, the base, present in the converting of the compound of formula A-7, or the salt thereof, is sodium hydroxide. In some embodiments, from about 1 to about 5 molar equivalents of the base is utilized relative to the compound of formula A-7, or the salt thereof. In some embodiments, from about 1 to about 3 molar equivalents of the base is utilized relative to the compound of formula A-7, or the salt thereof. In some embodiments, about 2 molar equivalents of the base is utilized relative to the compound of formula A-7, or the salt thereof.

In some embodiments, the converting of the compound of formula A-7, or the salt thereof, is carried out at a temperature of about room temperature. In some embodiments, the converting of the compound of formula A-7, or the salt thereof, is carried out at a temperature of about 0° C. to about 10° C. In some embodiments, the converting of the compound of formula A-7, or the salt thereof, is carried out at a temperature of about 5° C.

In some embodiments, the converting of the compound of formula A-7, or the salt thereof, is carried out in a solvent component. In some embodiments, the converting of the compound of formula A-7, or the salt thereof, is carried out in a solvent component comprising a polar aprotic solvent. In some embodiments, the converting of the compound of formula A-7, or the salt thereof, is carried out in a solvent component comprising an organohalide. In some embodiments, the converting of the compound of formula A-7, or the salt thereof, is carried out in a solvent component comprising dichloromethane. In some embodiments, the converting of the compound of formula A-7, or the salt thereof, is carried out in a solvent component comprising a di-$C_{1-6}$ alkyl ether, a 4-10 membered heterocycloalkyl ether, a polar protic solvent, or a mixture thereof. In some embodiments, the converting of the compound of formula A-7, or the salt thereof, is carried out in a solvent component comprising tetrahydrofuran and water.

In some embodiments, the compound of A-7, or the salt thereof, is a compound of formula A-7a:

(A-7a)

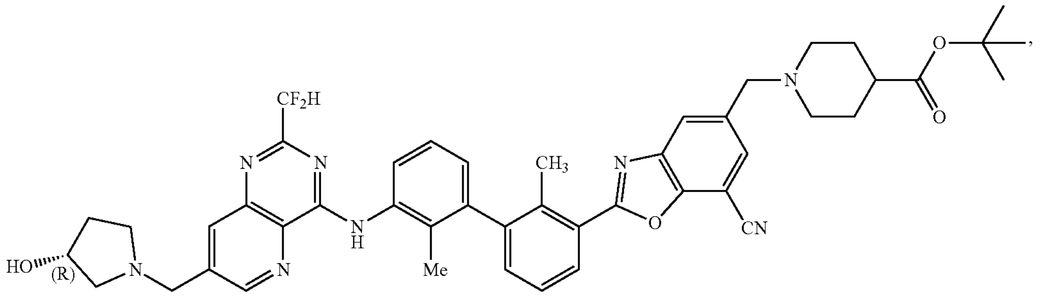

or a salt thereof.

In some embodiments, the compound of A-7, or the salt thereof, is a compound of formula A-7a':

(A-7a')

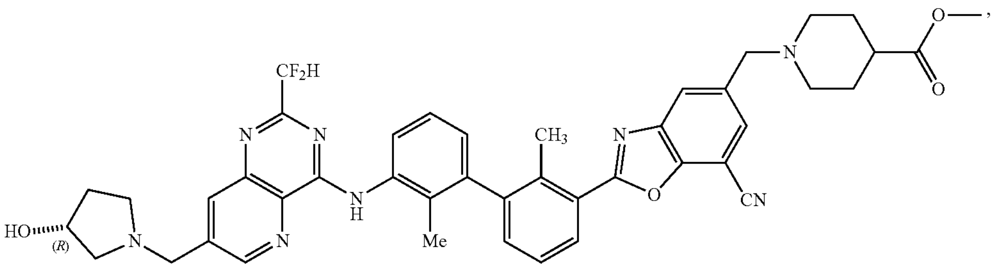

or a salt thereof.

In some embodiments, the compound of formula 1, or the salt thereof, is prepared by a process comprising:

reacting a compound of formula A-7a:

(A-7a)

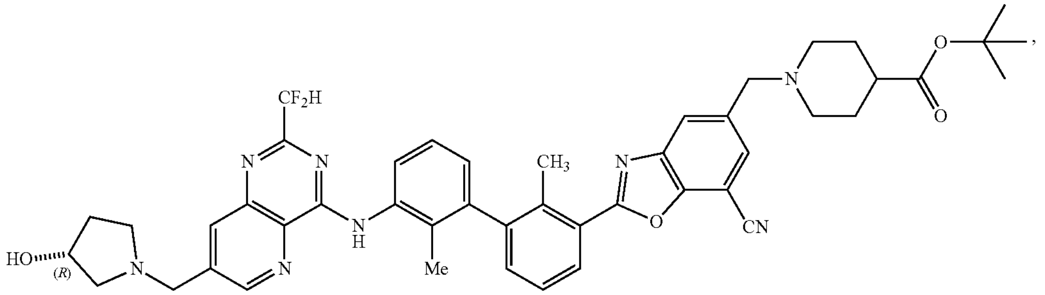

or a salt thereof, with a Lewis acid to form the compound of formula 1:

(1)

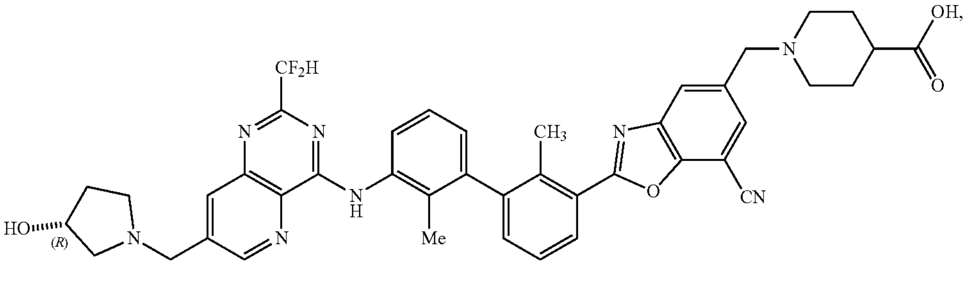

or a salt thereof.

In some embodiments, the compound of formula 1, or the salt thereof, is prepared by a process comprising:

deprotecting a compound of formula A-7a':

(A-7a')

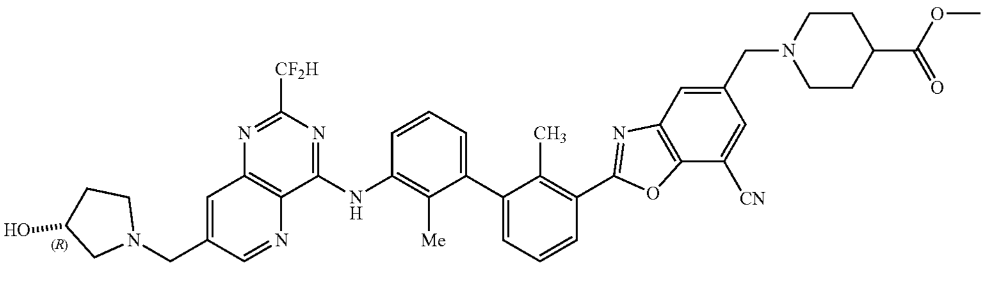

or a salt thereof, in the presence of a base to form the compound of formula 1:

(1)

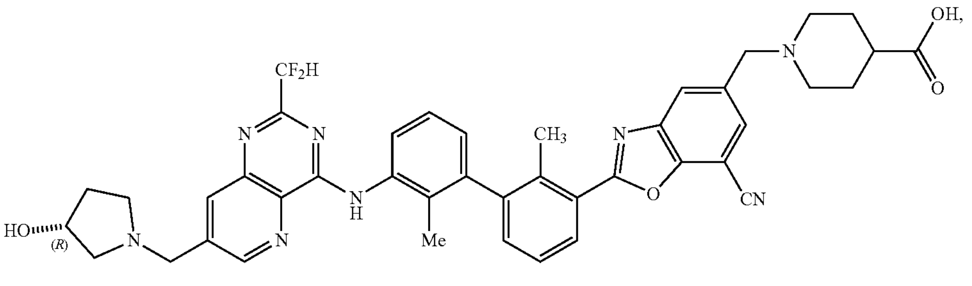

or a salt thereof.

The present disclosure further provides a process of preparing Compound of Formula 1, or a salt thereof, comprising:

a) reacting a compound of formula A-3a:

(A-3a)

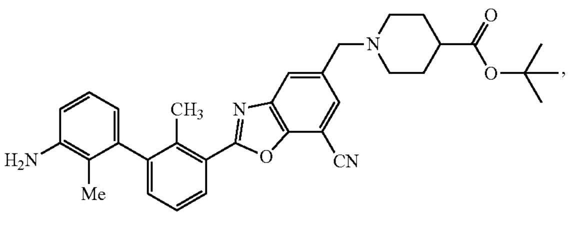

or a salt thereof, with a compound of formula A-4a:
(A-4a)
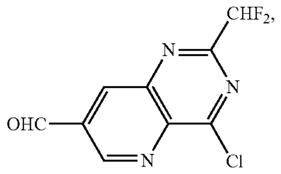
or a salt thereof, in the presence of an alkali metal halide and a base, to form a compound of formula A-5a:
(A-5a)
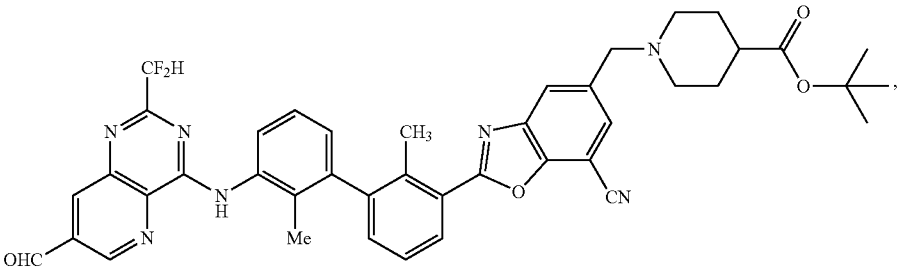
or a salt thereof;
b) reacting the compound of formula A-5a:
(A-5a)
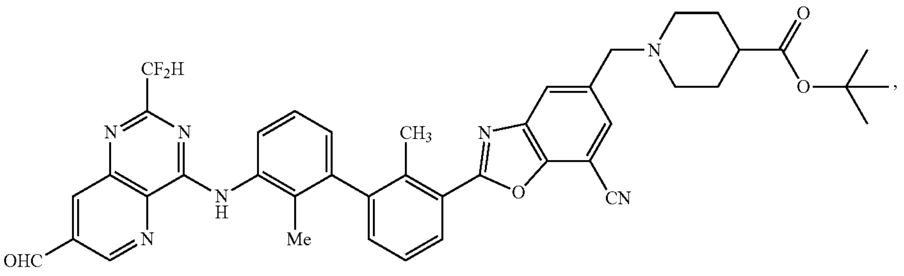
or a salt thereof, with a compound of formula A-6:
(A-6)
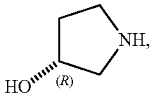
or a salt thereof, in the presence of a reducing agent to form a compound of formula A-7a:

(A-7a)
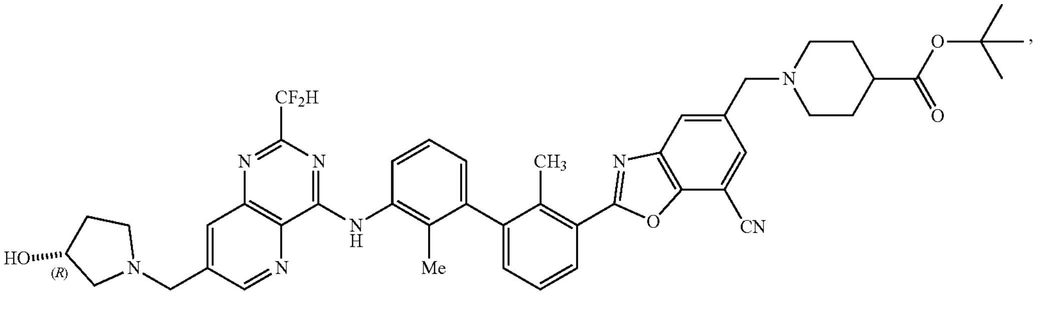
or a salt thereof, and
c) reacting the compound of formula A-7a:
(A-7a)
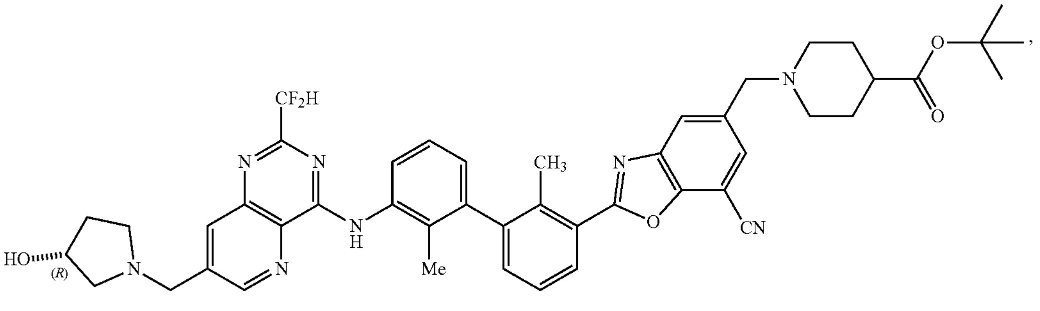
or a salt thereof, with a Lewis acid to form the compound of formula 1:
(1)
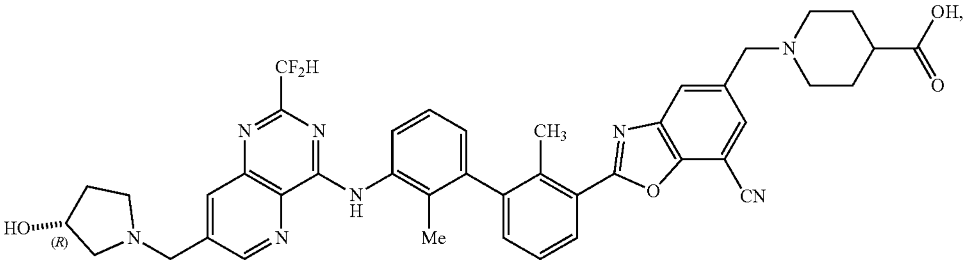
or a salt thereof.
The present disclosure further provides a process of preparing Compound of Formula 1, or a salt thereof, comprising:
a) reacting a compound of formula A-3a:
(A-3a)
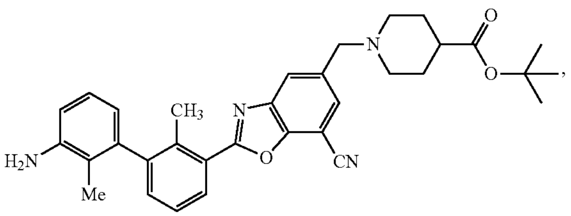

or a salt thereof, with a compound of formula B-1a:
(B-1a)
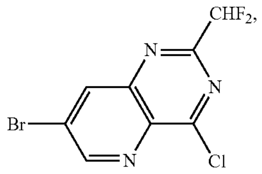
or a salt thereof, in the presence of a base, to form a compound of formula B-2a:
(B-2a)
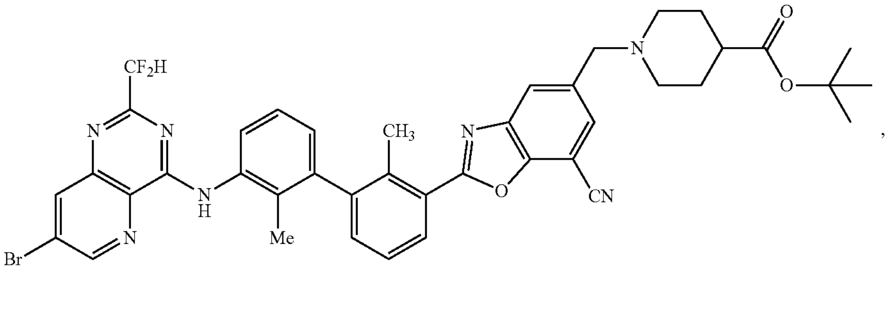
or a salt thereof;
b) reacting the compound of formula B-2a or a salt thereof, with a salt of formula B-3a:
(B-3a)
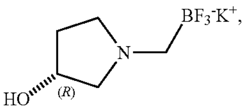
in the presence of a Suzuki catalyst and a base to form a compound of formula A-7a:
(A-7a)
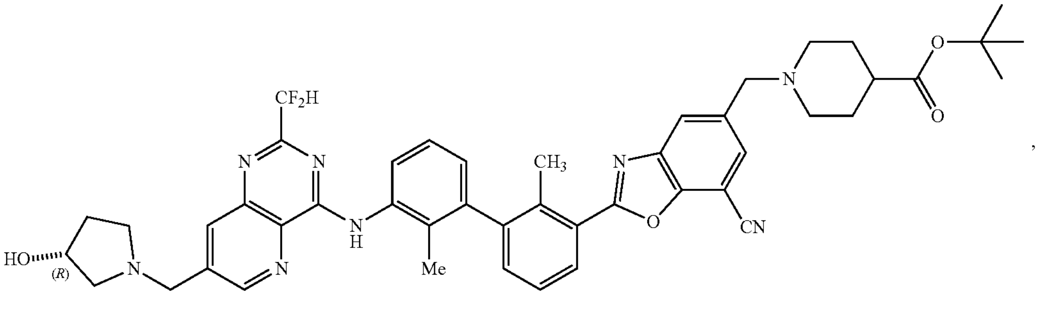
or a salt thereof, and c) reacting the compound of formula A-7a:

(A-7a)

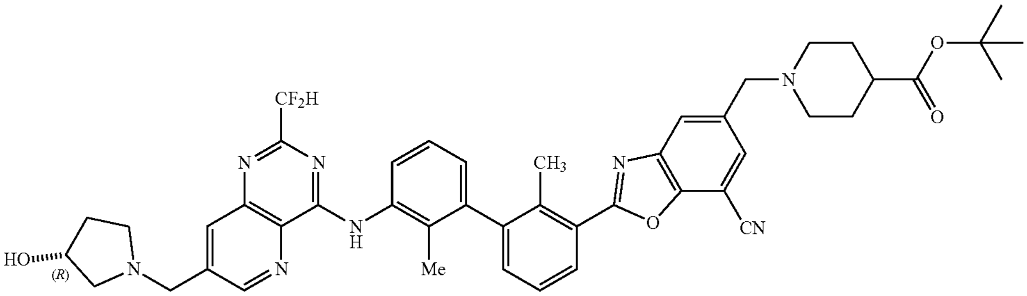

, or a salt thereof, with a Lewis acid to form the compound of formula 1:

(1)

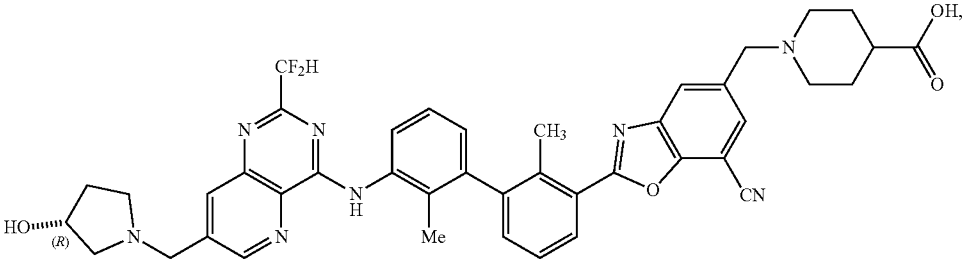

or a salt thereof.

The present disclosure further provides a process of preparing Compound of Formula 1, or a salt thereof, comprising:

a) reacting a compound of formula A-3a':

(A-3a')

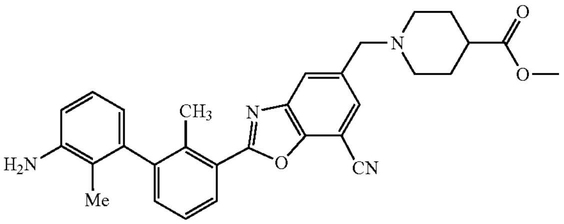

, or a salt thereof, with a compound of formula B-1a:

(B-1a)

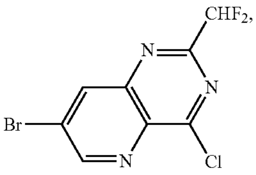

or a salt thereof, in the presence of a base, to form a compound of formula B-2a':

(B-2a')

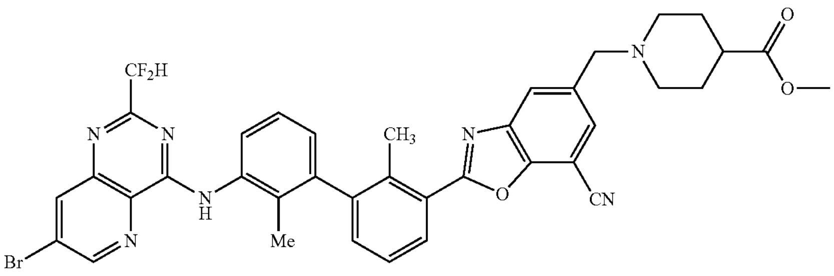

, or a salt thereof;

b) reacting the compound of formula B-2a' or a salt thereof, with a salt of formula B-3a:
(B-3a)
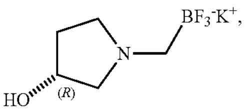
in the presence of a Suzuki catalyst and a base to form a compound of formula A-7a':
(A-7a')
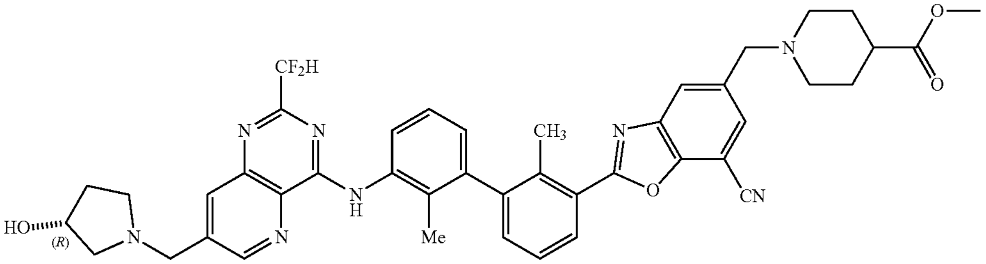
,
or a salt thereof, and
c) deprotecting the compound of formula A-7a':
(A-7a')
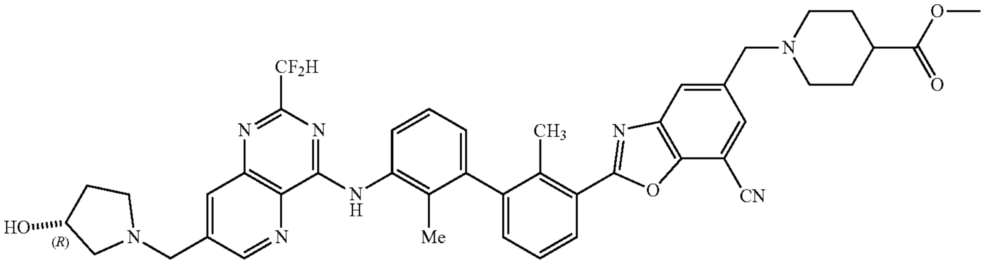
,
or a salt thereof, in the presence of a base to form the compound of formula 1:
(1)
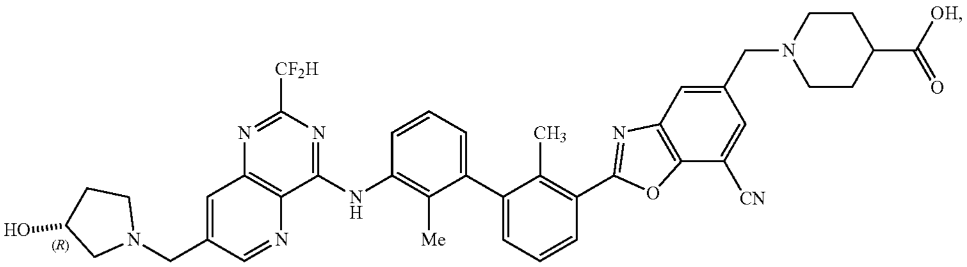
or a salt thereof.

In some embodiments, a process of preparing a compound of formula A-1:

(A-1)

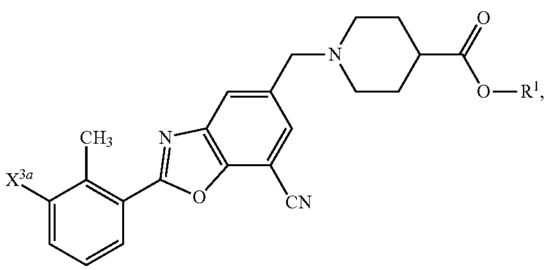

or a salt thereof, comprising: converting a compound of formula 6:

(6)

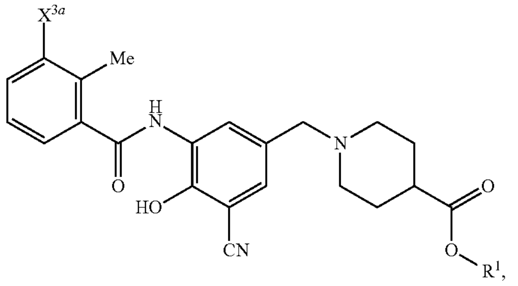

or a salt thereof, under oxidation conditions to form the compound of formula A-1, or the salt thereof, wherein $R^1$ is $C_{1-6}$ alkyl and $X^{3a}$ is halo.

In some embodiments, $R^1$ is t-butyl. In some embodiments, $R^1$ is methyl.

In some embodiments, the compound of formula A-1, or the salt thereof, is prepared by a process comprising:

converting a compound of formula 6:

(6)

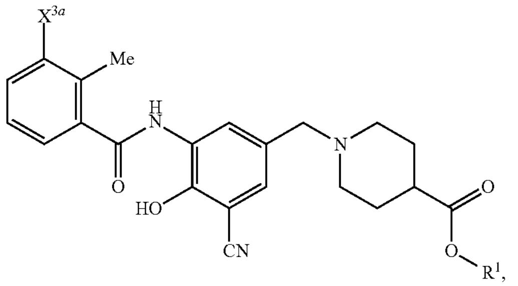

or a salt thereof, under oxidation conditions to the compound of formula A-1, or the salt thereof, wherein $R^1$ is $C_{1-6}$ alkyl and $X^{3a}$ is halo. In some embodiments, $X^{3a}$ is bromo. In some embodiments, $R^1$ is t-butyl. In some embodiments, $R^1$ is methyl.

In some embodiments, the oxidation conditions of converting the compound of formula 6, or the salt thereof, to the compound of formula A-1, or the salt thereof, comprise treating with a free radical initiator and $P(R^3)_3$, wherein $R^2$ is $C_{1-6}$ alkyl, $C_{5-6}$ cyclohexyl, or $C_{6-9}$ aryl. In some embodiments, the $P(R^3)_3$ is triphenylphosphine.

In some embodiments, the free radical initiator is a diazo compound or a peroxide compound. In some embodiments, the free radical initiator is a diazo compound. In some embodiments, the free radical initiator has formula $R^4$—OC(═O)—N═N—C(O)—$OR^{4'}$, wherein $R^4$ and $R^{4'}$ are independently selected from $C_{1-6}$ alkyl and benzyl. In some embodiments, the free radical initiator is diisopropylazodicarboxylate.

In some embodiments, from about 1 to about 2 molar equivalents of $P(R^3)_3$ is utilized relative to the compound of formula 6, or the salt thereof. In some embodiments, about 1.7 molar equivalents of $P(R^2)_3$ is utilized relative to the compound of formula 6, or the salt thereof.

In some embodiments, from about 1 to about 2 molar equivalents of the free radical initiator is utilized relative to the compound of formula 6, or the salt thereof. In some embodiments, about 1.7 molar equivalents of the free radical initiator is utilized relative to the compound of formula 6, or the salt thereof.

In some embodiments, the converting of the compound of formula 6 or the salt thereof to the compound of formula A-1, or the salt thereof, is carried out at a temperature of from about 50° C. to about 80° C. In some embodiments, the converting of the compound of formula 6 or the salt thereof to the compound of formula A-1, or the salt thereof, is carried out at a temperature of about 65° C.

In some embodiments, the converting of compound 6, or the salt thereof, to the compound of formula A-1, or the salt thereof, is carried out in a solvent component. In some embodiments, the converting of compound 6, or the salt thereof, to the compound of formula A-1, or the salt thereof, is carried out in a solvent component comprising a di-$C_{1-6}$ alkyl ether or a 4-10 membered heterocycloalkyl ether. In some embodiments, the converting of compound 6, or the salt thereof, to the compound of formula A-1, or the salt thereof, is carried out in a solvent component comprising tetrahydrofuran.

In some embodiments, the compound of A-1 or the salt thereof is a compound of formula A-1a:

(A-1a)

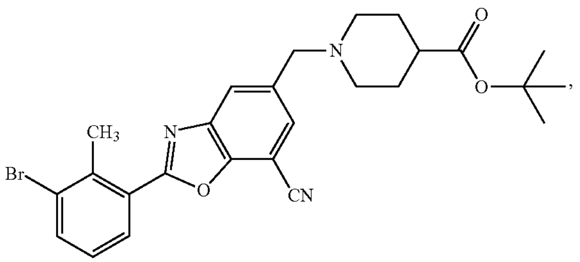

or a salt thereof.

In some embodiments, the compound of formula 6, or the salt thereof, is a compound of formula 6a:

(6a)

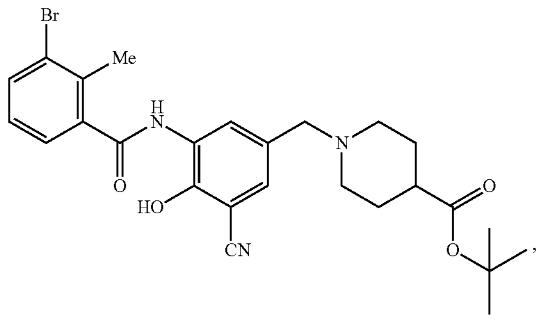

or a salt thereof.

In some embodiments, the compound of formula 6, or the salt thereof, is prepared by a process comprising:

reacting a compound of formula 5:

(5)

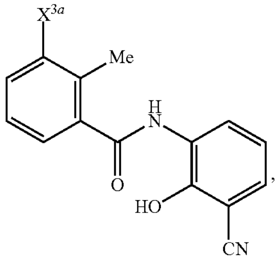

or a salt thereof, with a compound of formula 9:

(9)

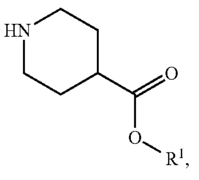

or a salt thereof, wherein $R^1$ is $C_{1-6}$ alkyl, and paraformaldehyde; and $X^{3a}$ is halo.

In some embodiments, $R^1$ is t-butyl. In some embodiments, $R^1$ is methyl.

In some embodiments, wherein $X^{3a}$ is bromo.

In some embodiments, from about 1 to about 1.5 molar equivalents of paraformaldehyde is utilized relative to the compound of formula 5, or the salt thereof. In some embodiments, about 1 molar equivalent of paraformaldehyde is utilized relative to the compound of formula 5, or the salt thereof.

In some embodiments, from about 1 to about 1.5 molar equivalents of the compound of formula 9, or the salt thereof, is utilized relative to the compound of formula 5, or the salt thereof. In some embodiments, wherein about 1 molar equivalent of the compound of formula 9 or the salt thereof is utilized relative to the compound of formula 5, or the salt thereof.

In some embodiments, the reacting of the compound of formula 5, or the salt thereof, with the compound of formula 9, or the salt thereof, and paraformaldehyde, is carried out at a temperature of from about 60° C. to about 80° C. In some embodiments, the reacting of the compound of formula 5, or the salt thereof, with the compound of formula 9, or the salt thereof, and paraformaldehyde, is carried out at a temperature of about 70° C.

In some embodiments, the reacting of the compound of formula 5, or the salt thereof, with the compound of formula 9, or the salt thereof, and paraformaldehyde, is carried out in a solvent component. In some embodiments, the reacting of the compound of formula 5, or the salt thereof, with the compound of formula 9, or the salt thereof, and paraformaldehyde, is carried out in a solvent component comprising a polar aprotic solvent. In some embodiments, the reacting of the compound of formula 5, or the salt thereof, with the compound of formula 9, or the salt thereof, and paraformaldehyde, is carried out in a solvent component comprising acetonitrile.

In some embodiments, the compound of formula 6, or the salt thereof, is a compound of formula 6a:

(6a)

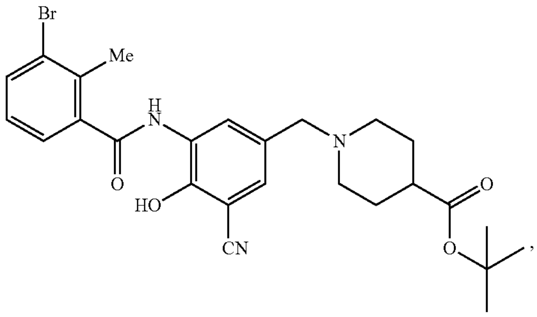

or a salt thereof.

In some embodiments, the compound of formula 9, or the salt thereof, is a compound of formula 9a:

(9a)

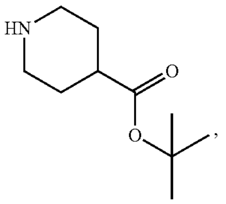

or a salt thereof.

In some embodiments, the compound of formula 5, or the salt thereof, is prepared by a process comprising:

hydrolyzing a compound of formula 4:

(4)

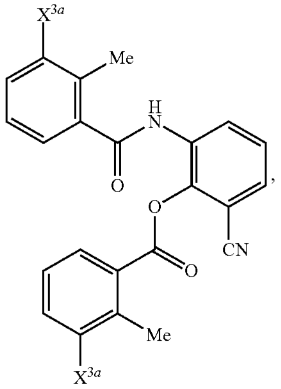

to the compound of formula 5, or a salt thereof, wherein $X^{3a}$ is halo.

In some embodiments, $X^{3a}$ is bromo.

In some embodiments, the hydrolyzing of the compound of formula 4 is conducted in the presence of a base. In some embodiments, the base, present in the hydrolyzing of the compound of formula 4, is an alkali metal base. In some embodiments, the base, present for the hydrolyzing of the compound of formula 4, is an alkali metal hydroxide. In some embodiments, the base, present in the hydrolyzing of the compound of formula 4, is selected from lithium hydroxide, sodium hydroxide, potassium hydroxide, rubidium hydroxide, and cesium hydroxide. In some embodiments, the base, present in the hydrolyzing of the compound of formula 4, is sodium hydroxide.

In some embodiments, the hydrolyzing of the compound of formula 4 is carried out at a temperature of about room temperature.

In some embodiments, the hydrolyzing of the compound of formula 4 is carried out in a solvent component. In some embodiments, the hydrolyzing of the compound of formula 4 is carried out in a solvent component comprising a di-$C_{1-6}$ alkyl ether or a 4-10 membered heterocycloalkyl ether, and water. In some embodiments, the hydrolyzing of the compound of formula 4 is carried out in a solvent component comprising tetrahydrofuran and water.

In some embodiments, the compound of formula 4 is prepared by a process comprising:

reacting a compound of formula 3:

(3)

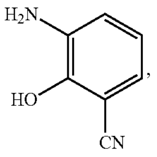

or a salt thereof, with a compound of formula 8A:

(8A)

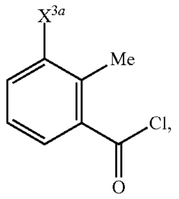

in the presence of a base, wherein $X^{3a}$ is halo.

In some embodiments, $X^{3a}$ is bromo.

In some embodiments, the base is an amine base. In some embodiments, the base, present in the reacting of the compound of formula 3, or the salt thereof, with the compound of formula 8A, is selected from N,N-diisopropylamine, methylamine, dimethylamine, trimethylamine, and ethylamine. In some embodiments, the base, present in the reacting of the compound of formula 3, or the salt thereof, with the compound of formula 8A, is trimethylamine.

In some embodiments, wherein from about 1 to about 3 molar equivalents of the compound of formula 8A is utilized relative to the compound of formula 3, or the salt thereof. In some embodiments, from about 1.5 to about 2.5 molar equivalents of the compound of formula 8A is utilized relative to the compound of formula 3, or the salt thereof. In some embodiments, from about 2 to about 3 molar equivalents of the compound of formula 8A is utilized relative to the compound of formula 3, or the salt thereof. In some embodiments, from about 2 to about 2.5 molar equivalents of the compound of formula 8A is utilized relative to the compound of formula 3, or the salt thereof. In some embodiments, about 2 molar equivalents of the compound of formula 8A is utilized relative to the compound of formula 3, or the salt thereof.

In some embodiments, from about 2 to about 4 molar equivalents of the base is utilized relative to the compound of formula 3, or the salt thereof. In some embodiments, about 3 molar equivalents of the base is utilized relative to the compound of formula 3, or the salt thereof.

In some embodiments, the reacting of the compound of formula 3, or the salt thereof, with the compound of formula 8A, is carried out at room temperature. In some embodiments, the reacting of the compound of formula 3, or the salt thereof, with the compound of formula 8A, is carried out at a temperature of from about 20° C. to about 30° C.

In some embodiments, the reacting of the compound of formula 3, or the salt thereof, and the compound of formula 8A is carried out in a solvent component S10. In some embodiments, the reacting of the compound of formula 3, or the salt thereof, and the compound of formula 8A is carried out in a solvent component comprising a di-$C_{1-6}$ alkyl ether or a 4-10 membered heterocycloalkyl ether. In some embodiments, the reacting of the compound of formula 3, or the salt thereof, and the compound of formula 8A is carried out in a solvent component comprising tetrahydrofuran.

In some embodiments, the compound of formula 8A is prepared by a process comprising:

reacting a compound of formula 8:

(8)

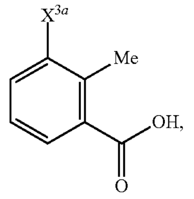

or a salt thereof, with a chlorinating agent, wherein $X^{3a}$ is halo.

In some embodiments, $X^{3a}$ is bromo.

In some embodiments, the chlorinating agent is selected from oxalyl chloride, phosphorus oxychloride, diphosgene, thionyl chloride, sulfuryl chloride and phosphorus pentachloride. In some embodiments, the chlorinating agent is oxalyl chloride. In some embodiments, the reacting of the compound of formula 8, or the salt thereof, with the chlorinating agent is conducted in the presence of a catalyst. In some embodiments, the catalyst is dimethylformamide.

In some embodiments, from about 1 to about 1.5 molar equivalents of the chlorinating agent is utilized relative to the compound of formula 8, or the salt thereof. In some embodiments, about 1 molar equivalent of the chlorinating agent is utilized relative to the compound of formula 8, or the salt thereof. In some embodiments, the reacting of the compound of formula 8, or the salt thereof, with the chlorinating agent is carried out at a temperature of from about 20° C. to about 30° C.

In some embodiments, the reacting of the compound of formula 8, or the salt thereof, with the chlorinating agent is carried out in a solvent component. In some embodiments, the reacting of the compound of formula 8, or the salt thereof, with the chlorinating agent is carried out in a solvent component comprising a di-$C_{1-6}$ alkyl ether or a 4-10 membered heterocycloalkyl ether. In some embodiments, the reacting of the compound of formula 8, or the salt thereof, with the chlorinating agent is carried out in a solvent component comprising tetrahydrofuran. In some embodiments, the reacting of the compound of formula 8, or the salt thereof, with the chlorinating agent is carried out in a solvent component comprising dimethylformamide.

In some embodiments, the compound of formula 3, or the salt thereof, is prepared by a process comprising:

reacting a compound of formula 2:

(2)

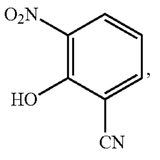

or a salt thereof, with a reducing agent.

In some embodiments, the reducing agent, present in the reacting with the compound of formula 2, or the salt thereof, is sodium hydrosulfite. In some embodiments, the reacting of the compound of formula 2, or the salt thereof, is carried out at a temperature of about room temperature.

In some embodiments, the reacting of the compound of formula 2, or the salt thereof, with the reducing agent, is carried out in a solvent component. In some embodiments, the reacting of the compound of formula 2, or the salt thereof, with the reducing agent, is carried out in a solvent component comprising a di-$C_{1-6}$ alkyl ether or a 4-10 membered heterocycloalkyl ether, and water. In some embodiments, the reacting of the compound of formula 2, or the salt thereof, with the reducing agent, is carried out in a solvent component comprising tetrahydrofuran and water.

In some embodiments, the compound of formula B-1, or the salt thereof, is prepared by a process comprising:

reacting a compound of formula 12:

(12)

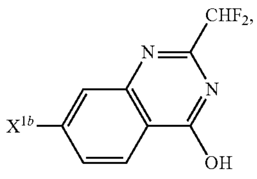

or a salt thereof, with a halogenating agent, wherein $X^{1b}$ is halo.

In some embodiments, $X^{1b}$ is bromo.

In some embodiments, the compound of formula B-1 has formula B-1a.

In some embodiments, the reacting of the compound of formula 12 with the halogenating agent is conducted in the presence of a base and a catalyst. In some embodiments, the base, present for the reacting of the compound of formula 12 with the halogenating agent, is an amine base. In some embodiments, the base, present in the reacting of the compound of formula 12 with the halogenating agent, is selected from N,N-diethylaniline, N,N-diisopropylamine, methylamine, dimethylamine, trimethylamine, and ethylamine. In some embodiments, the base, present in the reacting of the compound of formula 12 with the halogenating agent, is N,N-diethylaniline.

In some embodiments, the halogenating agent is a chlorinating agent. In some embodiments, the halogenating agent is selected from oxalyl chloride, phosphorus oxychloride, triphosgene, thionyl chloride, sulfuryl chloride and phosphorus pentachloride. In some embodiments, the halogenating agent is phosphorus oxychloride.

In some embodiments, the catalyst, present in the reacting of the compound of formula 12 with the halogenating agent, is benzyltriethylammonium chloride.

In some embodiments, from about 1 to about 2 molar equivalents of the base is utilized relative to the compound of formula 12, or the salt thereof. In some embodiments, about 1.5 molar equivalents of the base is utilized relative to the compound of formula 12, or the salt thereof.

In some embodiments, from about 2 to about 4 molar equivalents of the halogenating agent is utilized relative to the compound of formula 12, or the salt thereof. In some embodiments, from about 2.5 to about 3.5 molar equivalents of the halogenating agent is utilized relative to the compound of formula 12, or the salt thereof. In some embodiments, about 3 molar equivalents of the halogenating agent is utilized relative to the compound of formula 12, or the salt thereof.

In some embodiments, from about 1 to about 3 molar equivalents of the catalyst is utilized relative to the compound of formula 12, or the salt thereof. In some embodiments, about 2 molar equivalents of the catalyst is utilized relative to the compound of formula 12, or the salt thereof.

In some embodiments, the reacting of the compound of formula 12, or the salt thereof, with the halogenating agent is carried out at a temperature of from about 70° C. to about 80° C. In some embodiments, reacting of the compound of formula 12, or the salt thereof, with the halogenating agent is carried out at a temperature of about 75° C.

In some embodiments, the reacting of the compound of formula 12, or the salt thereof, with the halogenating agent is carried out in a solvent component. In some embodiments, the reacting of the compound of formula 12, or the salt thereof, with the halogenating agent is carried out in a solvent component comprising a polar aprotic solvent. In some embodiments, the reacting of the compound of formula 12, or the salt thereof, with the halogenating agent is carried out in a solvent component comprising acetonitrile.

In some embodiments, the compound of formula A-4, or the salt thereof, is prepared by a process comprising:

oxidizing a compound of formula 14:

(14)

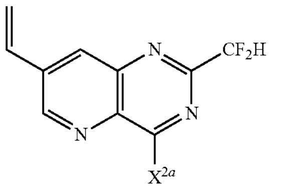

or a salt thereof, to form the compound of formula A-4, wherein $X^{2a}$ is halo.

In some embodiments, $X^{2a}$ is chloro.

In some embodiments, the compound of formula A-4, or a salt thereof, is a compound of formula A-4a, (A-4a)

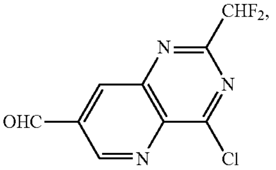

or a salt thereof.

In some embodiments, the oxidizing of the compound of formula 14, or the salt thereof, is carried out in the presence of a catalyst. In some embodiments, the catalyst, present in the oxidizing of the compound of formula 14, or the salt thereof, is osmium tetroxide.

In some embodiments, the oxidizing of the compound of formula 14, or the salt thereof, is carried out in the presence of an oxidizing agent. In some embodiments, the oxidizing agent, present in the oxidizing of the compound of formula 14, or the salt thereof, is sodium periodate.

In some embodiments, the oxidizing of the compound of formula 14, or the salt thereof, is carried out in the presence of a base. In some embodiments, the base, present in the oxidizing of the compound of formula 14, or the salt thereof, is an aromatic base. In some embodiments, the base, present in the oxidizing of the compound of formula 14, or the salt thereof, is 2,6-dimethylpyridine.

In some embodiments, from about 0.001 to about 0.1 molar equivalent of the catalyst is utilized relative to the compound of formula 14, or the salt thereof. In some embodiments, from about 0.01 molar equivalent of the catalyst is utilized relative to the compound of formula 14, or the salt thereof.

In some embodiments, from about 3 to about 5 molar equivalents of the oxidizing agent is utilized relative to the compound of formula 14, or the salt thereof. In some embodiments, from about 4 molar equivalents of the oxidizing agent is utilized relative to the compound of formula 14, or the salt thereof.

In some embodiments, from about 1 to about 3 molar equivalents of the base is utilized relative to the compound of formula 14, or the salt thereof. In some embodiments, from about 2 molar equivalents of the base is utilized relative to the compound of formula 14, or the salt thereof.

In some embodiments, the oxidizing of the compound of formula 14, or the salt thereof, is carried out at a temperature of from about 10° C. to about 15° C.

In some embodiments, the oxidizing of the compound of formula 14, or the salt thereof, is carried out in a solvent component. In some embodiments, the oxidizing of the compound of formula 14, or the salt thereof is carried out in a solvent component comprising a di-$C_{1-6}$ alkyl ether, a 4-10 membered heterocycloalkyl ether, a polar protic solvent, or a mixture thereof. In some embodiments, the oxidizing of the compound of formula 14, or the salt thereof is carried out in a solvent component comprising tetrahydrofuran and water.

In some embodiments, the compound of formula 14, or the salt thereof, is prepared by a process comprising:

reacting a compound of formula 13:

(13)

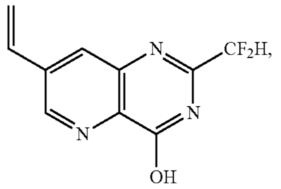

or a salt thereof, with a halogenating agent to form the compound of formula 14, or the salt thereof.

In some embodiments, the reacting of the compound of formula 13, or the salt thereof, with the halogenating agent is conducted in the presence of a base. In some embodiments, the base, present in the reacting of the compound of formula 13, or the salt thereof, with the halogenating agent, is an amine base. In some embodiments, the base, present in the reacting of the compound of formula 13, or the salt thereof, with the halogenating agent, is selected from N,N-diethylaniline, N,N-diisopropylamine, methylamine, dimethylamine, trimethylamine, and ethylamine. In some embodiments, the base, present in the reacting of the compound of formula 13, or the salt thereof, with the halogenating agent, is N,N-diethylaniline.

In some embodiments, the halogenating agent, utilized in the reacting with the compound of formula 13, or the salt thereof, is a chlorinating agent. In some embodiments, the halogenating agent, utilized in the reacting with the compound of formula 13, or the salt thereof, is selected from oxalyl chloride, phosphorus oxychloride, triphosgene, thionyl chloride, sulfuryl chloride and phosphorus pentachloride. In some embodiments, the halogenating agent, utilized in the reacting with the compound of formula 13, or the salt thereof, is phosphorus oxychloride.

In some embodiments, from about 1 to about 2 molar equivalents of the base is utilized relative to the compound of formula 13, or the salt thereof. In some embodiments, about 1 molar equivalent of the base is utilized relative to the compound of formula 13, or the salt thereof.

In some embodiments, from about 1 to about 2 molar equivalents of the halogenating agent is utilized relative to the compound of formula 13, or the salt thereof. In some embodiments, about 1 molar equivalent of the halogenating agent is utilized relative to the compound of formula 13, or the salt thereof.

In some embodiments, the reacting of the compound of formula 13, or the salt thereof, with the halogenating agent, is carried out at a temperature of from about 100° C. to about 150° C. In some embodiments, the reacting of the compound of formula 13, or the salt thereof, with the halogenating agent, is carried out at a temperature of about 130° C.

In some embodiments, the reacting of the compound of formula 13, or the salt thereof, with the halogenating agent, is carried out in a solvent component. In some embodiments, the reacting of the compound of formula 13, or the salt thereof, with the halogenating agent is carried out in a solvent component comprising an aromatic hydrocarbon. In some embodiments, the reacting of the compound of formula 13, or the salt thereof, with the halogenating agent is carried out in a solvent component comprising toluene.

In some embodiments, the compound of formula 13, or the salt thereof, is prepared by a process comprising:

reacting a compound of formula 12:

(12)

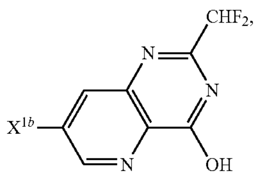

or a salt thereof, with 4,4,5,5-tetramethyl-2-vinyl-1,3,2-dioxaborolane in the presence of a Suzuki catalyst and a base to form the compound of formula 13, or the salt thereof, wherein $X^{1b}$ is halo.

In some embodiments, $X^{1b}$ is bromo.

In some embodiments, the Suzuki catalyst, present in the reacting of the compound of formula 12, or the salt thereof, with 4,4,5,5-tetramethyl-2-vinyl-1,3,2-dioxaborolane, is a palladium catalyst. In some embodiments, the Suzuki catalyst, present in the reacting of the compound of formula 12, or the salt thereof, with 4,4,5,5-tetramethyl-2-vinyl-1,3,2-dioxaborolane, is selected from RuPhos Pd G4, CataCXium® Pd G4, $Pd(PPh_3)_4$, $Pd(dppf)_2Cl_2$, dichlorobis[di-tert-butyl(p-dimethylaminophenyl)phosphino]palladium and $PdCl_2(dtbpf)$ (Pd-118). In some embodiments, the Suzuki catalyst, present in the reacting of the compound of formula 12, or the salt thereof, with 4,4,5,5-tetramethyl-2-vinyl-1,3,2-dioxaborolane, is $Pd(dppf)_2Cl_2$.

In some embodiments, the base, present in the reacting of the compound of formula 12, or the salt thereof, with the 4,4,5,5-tetramethyl-2-vinyl-1,3,2-dioxaborolane, is an alkali metal base. In some embodiments, the base, present in the reacting of the compound of formula 12, or the salt thereof, with the 4,4,5,5-tetramethyl-2-vinyl-1,3,2-dioxaborolane, is an alkali metal carbonate. In some embodiments, the base, present in the reacting of the compound of formula 12, or the salt thereof, with the 4,4,5,5-tetramethyl-2-vinyl-1,3,2-dioxaborolane, is selected from cesium carbonate, lithium carbonate, sodium carbonate and potassium carbonate. In some embodiments, the base, present in the reacting of the compound of formula 12, or the salt thereof, with the 4,4,5,5-tetramethyl-2-vinyl-1,3,2-dioxaborolane, is potassium carbonate.

In some embodiments, from about 1 to about 2 molar equivalents of the 4,4,5,5-tetramethyl-2-vinyl-1,3,2-dioxaborolane is utilized relative to the compound of formula 12, or the salt thereof. In some embodiments, from about 1.5 molar equivalents of the 4,4,5,5-tetramethyl-2-vinyl-1,3,2-dioxaborolane is utilized relative to the compound of formula 12, or the salt thereof.

In some embodiments, from about 1 to about 5 molar equivalents of the base is utilized relative to the compound of formula 12, or the salt thereof. In some embodiments, from about 2 to about 4 molar equivalents of the base is utilized relative to the compound of formula 12, or the salt thereof. In some embodiments, about 3 molar equivalents of the base is utilized relative to the compound of formula 12, or the salt thereof.

In some embodiments, from about 0.01 to about 0.1 molar equivalent of the Suzuki catalyst is utilized relative to the compound of formula 12, or the salt thereof. In some embodiments, about 0.04 molar equivalent of the Suzuki catalyst is utilized relative to the compound of formula 12, or the salt thereof.

In some embodiments, the reacting of the compound of formula 12, or the salt thereof, with the 4,4,5,5-tetramethyl-2-vinyl-1,3,2-dioxaborolane is carried out at a temperature of from about 80° C. to about 85° C. In some embodiments, the reacting of the compound of formula 12, or the salt thereof, with the 4,4,5,5-tetramethyl-2-vinyl-1,3,2-dioxaborolane is carried out in a solvent component. In some embodiments, the reacting of the compound of formula 12, or the salt thereof, with the 4,4,5,5-tetramethyl-2-vinyl-1,3,2-dioxaborolane is carried out in a solvent component comprising a polar protic solvent, a $C_{1-6}$ alkanol, or a mixture thereof. In some embodiments, the reacting of the compound of formula 12, or the salt thereof, with the 4,4,5,5-tetramethyl-2-vinyl-1,3,2-dioxaborolane is carried out in a solvent component comprising water and ethanol.

In some embodiments, the compound of formula 12, or the salt thereof, is prepared by a process comprising:

reacting a compound of formula 11:

(11)

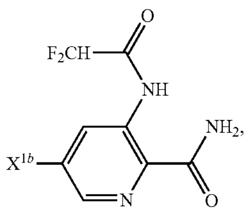

or a salt thereof, with a base, wherein $X^{1b}$ is halo.

In some embodiments, $X^{1b}$ is bromo.

In some embodiments, the base, utilized in the reacting with the compound of formula 11, or the salt thereof, is an alkali metal base. In some embodiments, the base, utilized in the reacting with the compound of formula 11, or the salt thereof, is an alkali metal hydroxide. In some embodiments, the base, utilized in the reacting with the compound of formula 11, or the salt thereof, is selected from lithium hydroxide, sodium hydroxide, potassium hydroxide, rubidium hydroxide, and cesium hydroxide. In some embodiments, the base, utilized in the reacting with the compound of formula 11, or the salt thereof, is sodium hydroxide. In some embodiments, from about 1 to about 3 molar equivalents of the base is utilized relative to the compound of formula 11, or the salt thereof. In some embodiments, about 2 molar equivalents of the base is utilized relative to the compound of formula 11, or the salt thereof.

In some embodiments, the reacting of the compound of formula 11, or the salt thereof, with the base, is carried out at a temperature of from about 80° C. to about 90° C. In some embodiments, the reacting of the compound of formula 11, or the salt thereof, with the base, is carried out at a temperature of about 85° C.

In some embodiments, the reacting of the compound of formula 11, or the salt thereof, with the base, is carried out in a solvent component. In some embodiments, the solvent component comprises a protic solvent. In some embodiments, the reacting of the compound of formula 11, or the salt thereof, with the base, is carried out in a solvent component comprising a $C_{1-6}$ alkanol. In some embodiments, the reacting of the compound of formula 11, or the salt thereof, with the base, is carried out in a solvent component comprising ethanol.

In some embodiments, the compound of formula 11, or the salt thereof, is prepared by a process comprising:

reacting a compound of formula 10:

(10)

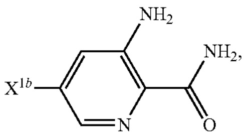

or a salt thereof, with 2,2-difluoroacetic anhydride, wherein $X^{1b}$ is halo.

In some embodiments, $X^{1b}$ is bromo.

In some embodiments, from about 1 to about 2 molar equivalents of the 2,2-difluoroacetic anhydride is utilized relative to the compound of formula 10, or the salt thereof. In some embodiments, about 1.5 molar equivalents of the 2,2-difluoroacetic anhydride is utilized relative to the compound of formula 10, or the salt thereof. In some embodiments, the reacting of the compound of formula 10, or the salt thereof, with the 2,2-difluoroacetic anhydride, is carried out at a temperature of about 50° C. to about 70° C. In some embodiments, the reacting of the compound of formula 10, or the salt thereof, with the 2,2-difluoroacetic anhydride, is carried out at a temperature of about 60° C.

In some embodiments, the reacting of the compound of formula 10, or the salt thereof, with the 2,2-difluoroacetic anhydride, is carried out in a solvent component. In some embodiments, the reacting of the compound of formula 10, or the salt thereof, with the 2,2-difluoroacetic anhydride, is carried out in a solvent component comprising a di-$C_{1-6}$ alkyl ether or a 4-10 membered heterocycloalkyl ether. In some embodiments, the reacting of the compound of formula 10, or the salt thereof, with the 2,2-difluoroacetic anhydride, is carried out in a solvent component comprising 1,4-dioxane.

The present disclosure is further directed to a process of preparing (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidine-4-carboxylic acid (compound of formula 1), or a salt thereof, comprising:

a) reacting a compound of formula A-3a':

A-3a'

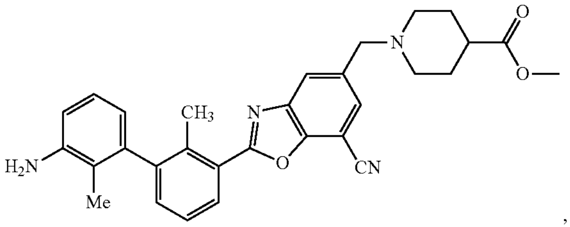

, or a salt thereof, with a compound of formula B-1a:

B-1a

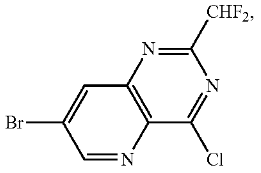

or a salt thereof, in the presence of a base, to form a compound of formula B-2a':

B-2a'

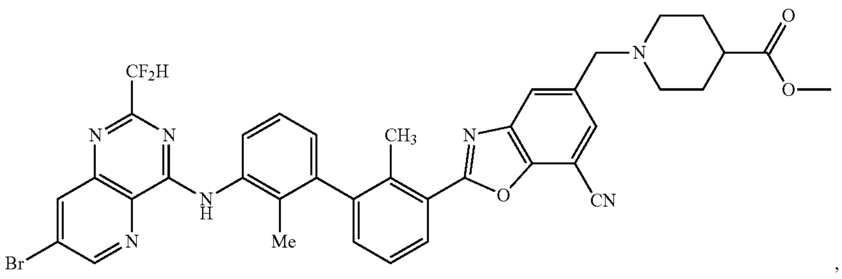

, or a salt thereof;

b) reacting the compound of formula B-2a' or a salt thereof, with a salt of formula B-3a:

B-3a
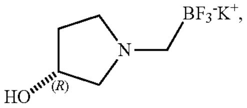
in the presence of a Suzuki catalyst and a base to form a compound of formula A-7a':
A-7a'
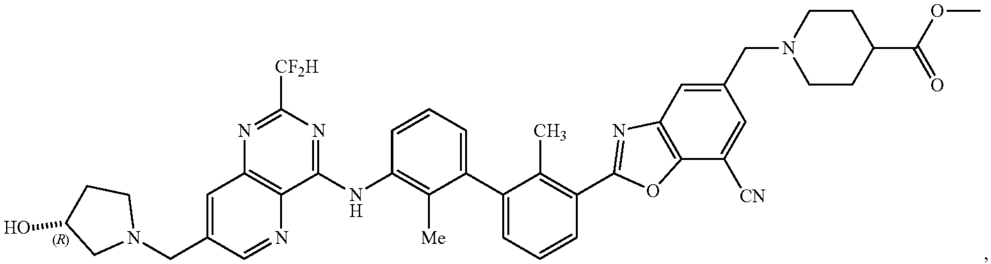
,
or a salt thereof, and
c) deprotecting the compound of formula A-7a':
A-7a'
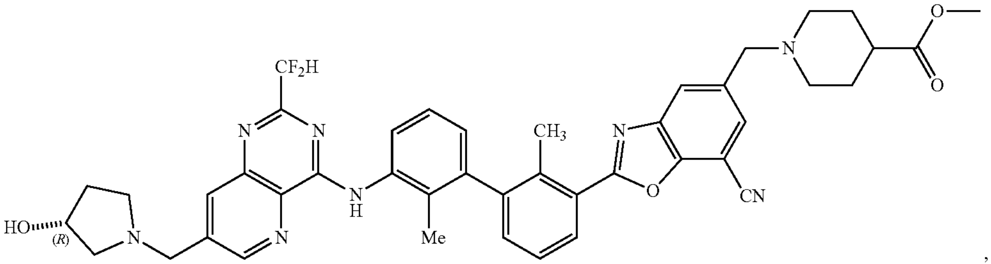
,
or a salt thereof, in the presence of a base to form the compound of formula 1:
1
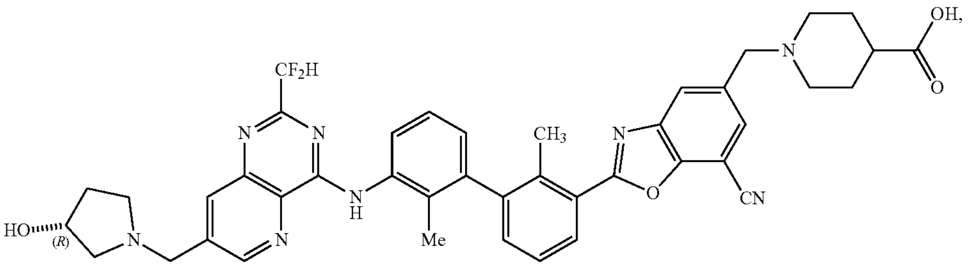
or a salt thereof.

The present disclosure also provides a process of preparing (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidine-4-carboxylic acid, or a salt thereof, comprising:

(a) reacting a compound of formula A-1a':

A-1a'

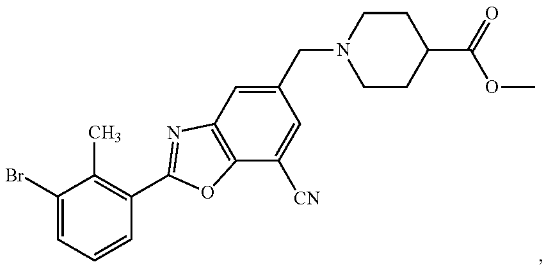

, or a salt thereof, with a compound of formula A-2a:

A-2a

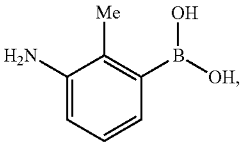

or a salt thereof, in the presence of a Suzuki catalyst and a base to form a compound of formula 3a':

A-3a'

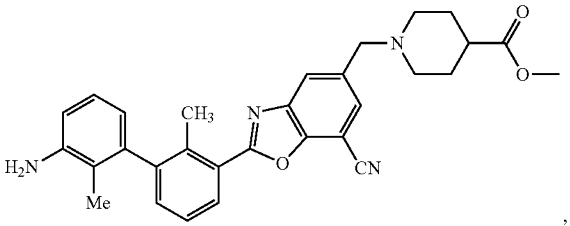

, or a salt thereof;

(b) reacting the compound of formula A-3a', or the salt thereof with a compound of formula B-1a:

B-1a

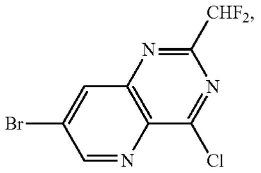

or a salt thereof, in the presence of a base, to form a compound of formula B-2a':

B-2a'

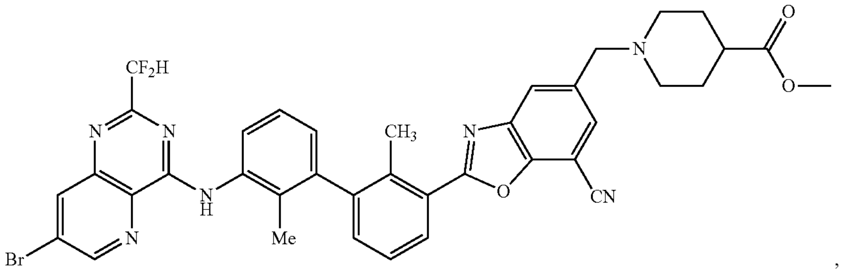

, or a salt thereof;

(c) reacting the compound of formula B-2a', or the salt thereof, with a salt of formula B-3a:

B-3a

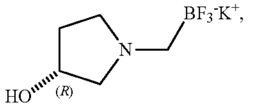

in the presence of a Suzuki catalyst and a base to form a compound of formula A-7a':

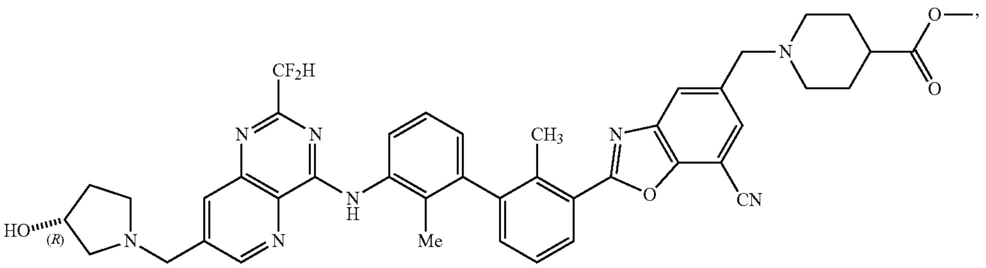

A-7a', or a salt thereof, and (d) deprotecting the compound of formula A-7a', or the salt thereof, in the presence of a base to form the (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl) piperidine-4-carboxylic acid, or the salt thereof.

In some embodiments, the compound of formula A-2a, or the salt thereof, is a hydrochloric acid salt of formula A-2a.

In some embodiments, wherein the Suzuki catalyst, present in the reacting of the compound of formula A-1a', or the salt thereof, with the compound of formula A-2a, or the salt thereof, is a palladium catalyst. In some embodiments, the Suzuki catalyst, present in the reacting of the compound of formula A-1a', or the salt thereof, with the compound of formula A-2a, or the salt thereof, is selected from CataCXium® Pd G4, $Pd(PPh_3)_4$ $Pd(dppf)_2Cl_2$, dichlorobis[di-tert-butyl(p-dimethylaminophenyl)phosphino]palladium and $PdCl_2(dtbpf)$ (Pd-118). In some embodiments, the Suzuki catalyst, present in the reacting of the compound of formula A-1a', or the salt thereof, with the compound of formula A-2a, or the salt thereof, is $PdCl_2(dtbpf)$ (Pd-118).

In some embodiments, the base, present in the reacting of the compound of formula A-1a', or the salt thereof, with the compound of formula A-2a, or the salt thereof, is a phosphate or a carbonate base. In some embodiments, the base, present in the reacting of the compound of formula A-1a', or the salt thereof, with the compound of formula A-2a, or the salt thereof, is a phosphate base. In some embodiments, the base, present in the reacting of the compound of formula A-1a', or the salt thereof, with the compound of formula A-2a, or the salt thereof, is an alkali metal phosphate. In some embodiments, the base, present in the reacting of the compound of formula A-1a', or the salt thereof, with the compound of formula A-2a, or the salt thereof, is potassium phosphate dibasic.

In some embodiments, from about 1 to about 2 molar equivalents of the compound of formula A-2a, or the salt thereof, is utilized relative to the compound of formula A-1a', or the salt thereof. In some embodiments, from about 1 to about 1.5 molar equivalents of the compound of formula A-2a, or the salt thereof, is utilized relative to the compound of formula A-1a', or the salt thereof. In some embodiments, from about 1 to about 1.2 molar equivalent of the compound of formula A-2a, or the salt thereof, is utilized relative to the compound of formula A-1a', or the salt thereof. In some embodiments, about 1.1 molar equivalent of the compound of formula A-2a, or the salt thereof, is utilized relative to the compound of formula A-1a', or the salt thereof.

In some embodiments, from about 0.001 to about 0.1 molar equivalent of the Suzuki catalyst is utilized relative to the compound of formula A-1a', or the salt thereof. In some embodiments, from about 0.001 to about 0.01 molar equivalent of the Suzuki catalyst is utilized relative to the compound of formula A-1a', or the salt thereof. In some embodiments, about 0.008 molar equivalent of the Suzuki catalyst is utilized relative to the compound of formula A-1a', or the salt thereof.

In some embodiments, the reacting of the compound of formula A-1a', or the salt thereof, with the compound of formula A-2a or the salt thereof, is carried out at a temperature of about 70° C. to about 100° C. In some embodiments, the reacting of the compound of formula A-1a', or the salt thereof, with the compound of formula A-2a or the salt thereof, is carried out at a temperature of about 80° C.

In some embodiments, the reacting of the compound of formula A-1a', or the salt thereof, with the compound of formula A-2a, or the salt thereof, is carried out in a solvent component. In some embodiments, the reacting of the compound of formula A-1a', or the salt thereof, with the compound of formula A-2a, or the salt thereof, is carried out in a solvent component comprising a polar protic solvent. In some embodiments, the reacting of the compound of formula A-1a', or the salt thereof, with the compound of formula A-2a, or the salt thereof, is carried out in a solvent component comprising $C_{1-6}$ alkanol and water. In some embodiments, the reacting of the compound of formula A-1a', or the salt thereof, with the compound of formula A-2a, or the salt thereof, is carried out in a solvent component comprising water and tert-butanol.

In some embodiments, the base, present in the reacting of the compound of formula A-3a', or the salt thereof, with the compound of formula B-1a, or the salt thereof, is an alkali metal base. In some embodiments, the base, present in the reacting of the compound of formula A-3a', or the salt thereof, with the compound of formula B-1a, or the salt thereof, is an alkali metal carbonate. In some embodiments, the base, present in the reacting of the compound of formula A-3a', or the salt thereof, with the compound of formula B-1a, or the salt thereof, is selected from cesium carbonate, lithium carbonate, sodium carbonate, and potassium carbonate. In some embodiments, the base, present in the reacting of the compound of formula A-3a', or the salt thereof, with the compound of formula B-1a, or the salt thereof, is potassium carbonate.

In some embodiments, from about 1 to about 1.5 molar equivalents of the compound of formula B-1a, or the salt thereof, is utilized relative to the compound of formula A-3a', or the salt thereof. In some embodiments, about 1.1 molar equivalents of the compound of formula B-1a, or the salt thereof, is utilized relative to the compound of formula A-3a', or the salt thereof. In some embodiments, about 1 molar equivalent of the compound of formula B-1a, or the salt thereof, is utilized relative to the compound of formula A-3a', or the salt thereof.

In some embodiments, from about 1 to about 4 molar equivalents of the base is utilized relative to the compound of formula A-3a', or the salt thereof. In some embodiments, from about 1 to about 2 molar equivalents of the base is utilized relative to the compound of formula A-3a', or the salt thereof. In some embodiments, from about 1 to about 1.1 molar equivalents of the base is utilized relative to the compound of formula A-3a', or the salt thereof.

In some embodiments, the reacting of the compound of formula A-3a', or the salt thereof, with the compound of formula B-1a, or the salt thereof, is carried out at a temperature of about 40° C. to about 60° C. In some embodiments, the reacting of the compound of formula A-3a', or the salt thereof, with the compound of formula B-1a, or the salt thereof, is carried out at a temperature of about 50° C.

In some embodiments, the reacting of the compound of formula A-3a', or the salt thereof, with the compound of formula B-1a, or the salt thereof, is carried out in a solvent component. In some embodiments, the solvent component comprises an organic ether. In some embodiments, the solvent component comprises tetrahydrofuran.

In some embodiments, the base, present in the reacting of the compound of formula B-2a', or the salt thereof, with the salt of formula B-3a, is a carbonate base. In some embodiments, wherein the base, present in the reacting of the compound of formula B-2a', or the salt thereof, with the salt of formula B-3a, is an alkali metal carbonate. In some embodiments, the base, present in the reacting of the compound of formula B-2a', or the salt thereof, with the salt of formula B-3a, is selected from cesium carbonate, lithium carbonate, sodium carbonate, and potassium carbonate. In some embodiments, the base, present in the reacting of the compound of formula B-2a', or the salt thereof, with the salt of formula B-3a, is cesium carbonate.

In some embodiments, from about 1 to about 4 molar equivalents of the salt of formula B-3a is utilized relative to the compound of formula B-2a', or the salt thereof. In some embodiments, from about 1.5 to about 2.5 molar equivalents of the salt of formula B-3a is utilized relative to the compound of formula B-2a', or the salt thereof. In some embodiments, from about 1 to about 2 molar equivalents of the salt of formula B-3a is utilized relative to the compound of formula B-2a', or the salt thereof. In some embodiments, about 1.6 molar equivalents of the salt of formula B-3a is utilized relative to the compound of formula B-2a', or the salt thereof.

In some embodiments, from about 3 to about 9 molar equivalents of the base is utilized relative to the compound of formula B-2a', or the salt thereof. In some embodiments, from about 5 to about 7 molar equivalents of the base is utilized relative to the compound of formula B-2a', or the salt thereof. In some embodiments, about 6 molar equivalents of the base is utilized relative to the compound of formula B-2a', or the salt thereof.

In some embodiments, from about 0.01 to about 0.5 molar equivalent of the Suzuki catalyst is utilized relative to the compound of formula B-2a', or the salt thereof. In some embodiments, from about 0.01 to about 0.1 molar equivalent of the Suzuki catalyst is utilized relative to the compound of formula B-2a', or the salt thereof. In some embodiments, from about 0.03 to about 0.05 molar equivalent of the Suzuki catalyst is utilized relative to the compound of formula B-2a', or the salt thereof. In some embodiments, about 0.04 molar equivalent of the Suzuki catalyst is utilized relative to the compound of formula B-2a', or the salt thereof.

In some embodiments, wherein the reacting the compound of formula B-2a', or the salt thereof, with the salt of formula B-3a, is carried out at reflux temperature. In some embodiments, wherein the reacting the compound of formula B-2a', or the salt thereof, with the salt of formula B-3a, is carried out at a temperature of about 80° C. to about 120° C. In some embodiments, the reacting of the compound of formula B-2a', or the salt thereof, with the salt of formula B-3a, is carried out at a temperature of about 100° C. In some embodiments, the reacting of the compound of formula B-2a', or the salt thereof, with the salt of formula B-3a, is carried out at a temperature of about 90° C.

In some embodiments, the reacting of the compound of B-2a', or the salt thereof, with the salt of formula B-3a, is carried out in a solvent component. In some embodiments, the reacting of the compound of B-2a', or the salt thereof, with the salt of formula B-3a, is carried out in a solvent component comprising a non-protic organic solvent. In some embodiments, the reacting of the compound of B-2a', or the salt thereof, with the salt of formula B-3a, is carried out in a solvent component comprising a di-$C_{1-6}$ alkyl ether or a 4-10 membered heterocycloalkyl ether. In some embodiments, the solvent component comprises dioxane.

In some embodiments, the Suzuki catalyst, present for the reacting of the compound of formula B-2a', or the salt thereof, with the compound of formula B-3a, or the salt thereof, is a palladium catalyst. In some embodiments, the Suzuki catalyst, present for the reacting of the compound of formula B-2a', or the salt thereof, with the compound of formula B-3a, or the salt thereof, is selected from CataCXium® Pd G4, $Pd(PPh_3)_4$, $Pd(dppf)_2Cl_2$, dichlorobis[di-tert-butyl(p-dimethylaminophenyl)phosphino]palladium and $PdCl_2(dtbpf)$ (Pd-118). In some embodiments, the Suzuki catalyst is CataCXium® Pd G4. In some embodiments, the Suzuki catalyst, present for the reacting of the compound of formula B-2a', or the salt thereof, with the compound of formula B-3a, or the salt thereof, is selected from CataCXium® Pd G4 ((2'-(methylamino)-[1,1'-biphenyl]-2-yl)((methylsulfonyl)oxy)palladium di(1-adamantyl)-n-butylphosphine complex), CataCXium® $[Pd(allyl)Cl]_2$, $Pd(PPh_3)_4$, $Pd(dppf)_2Cl_2$, dichlorobis[di-tert-butyl(p-dimethylaminophenyl)phosphino]palladium and $PdCl_2(dtbpf)$ (Pd-118). In some embodiments, wherein the Suzuki catalyst, present for the reacting of the compound of formula B-2a', or the salt thereof, with the compound of formula B-3a, or the salt thereof, is CataCXium® $[Pd(allyl)Cl]_2$.

In some embodiments, the reacting of the compound of formula B-2a', or the salt thereof, with the salt of formula B-3a forms a compound of formula A-7a'. In some embodiments, after the reacting of the compound of formula B-2a', or the salt thereof, with the salt of formula B-3a, the compound of formula A-7a' is reacted with at least 3 equivalents of glycolic acid to form a triglycolate salt of the compound of formula A-7a'.

In some embodiments, the reacting of the compound of formula A-7a', or the salt thereof, with glycolic acid, is carried out in a solvent component. In some embodiments, the solvent component comprises an organic ether. In some embodiments, the solvent component comprises tetrahydrofuran.

In some embodiments, the trigylcolate salt of the compound of formula A-7a' is dissolved in water and washed with 2-methyl-THF. In some embodiments, the washing with 2-methyl-THF is carried out at an elevated temperature. In some embodiments, the elevated temperature is from about 30° C. to about 50° C. In some embodiments, the elevated temperature is about 40° C.

In some embodiments, the trigylcolate salt of the compound of formula A-7a' is then reacted with a base to give the compound of formula A-7a'. In some embodiments, the base is a phosphate or carbonate base. In some embodiments, the base is an alkali metal phosphate. In some embodiments, the base is potassium phosphate or sodium phosphate. In some embodiments, the base is potassium phosphate. In some embodiments, the reacting of the trigylcolate salt of the compound of formula A-7a', with the base, is carried out in a solvent component. In some embodiments, the solvent component comprises a polar protic solvent. In some embodiments, the solvent component comprises water.

In some embodiments, the deprotecting of the compound of formula A-7a', or the salt thereof, comprises treating the compound of formula A-7a', or the salt thereof, with a base. In some embodiments, the base, present in the deprotecting of the compound of formula A-7a', or the salt thereof, is sodium hydroxide. In some embodiments, from about 1 to about 5 molar equivalents of the base is utilized relative to the compound of formula A-7a', or the salt thereof. In some embodiments, from about 1 to about 3 molar equivalents of the base is utilized relative to the compound of formula A-7a', or the salt thereof. In some embodiments, about 2 molar equivalents of the base is utilized relative to the compound of formula A-7a', or the salt thereof.

In some embodiments, the deprotecting of the compound of formula A-7a', or the salt thereof, is carried out at a temperature of about 0° C. to about 10° C. In some embodiments, the deprotecting of the compound of formula A-7a', or the salt thereof, is carried out at a temperature of about 5° C.

In some embodiments, the deprotecting of the compound of formula A-7a', or the salt thereof, is carried out in a solvent component. In some embodiments, the deprotecting of the compound of formula A-7a', or the salt thereof, is carried out in a solvent component comprising a polar aprotic solvent. In some embodiments, the deprotecting of the compound of formula A-7a', or the salt thereof, is carried out in a solvent component comprising a di-$C_{1-6}$ alkyl ether, a 4-10 membered heterocycloalkyl ether, a polar protic solvent, or a mixture thereof. In some embodiments, the deprotecting of the compound of formula A-7a', or the salt thereof, is carried out in a solvent component comprising tetrahydrofuran and water.

In some embodiments, provided herein is a compound of formula A-1:

(A-1)

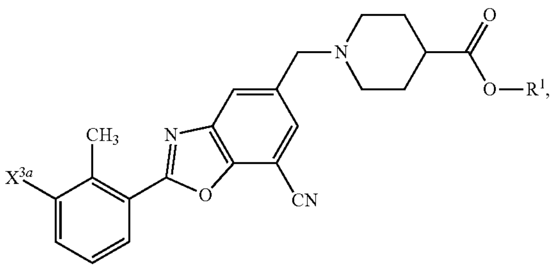

or a salt thereof, wherein $R^1$ is $C_{1-6}$ alkyl; and $X^{3a}$ is halo. In some embodiments, $R^1$ is t-butyl. In some embodiments, $R^1$ is methyl.

In some embodiments, the compound of formula A-1 is a compound of formula A-1a:

(A-1a)

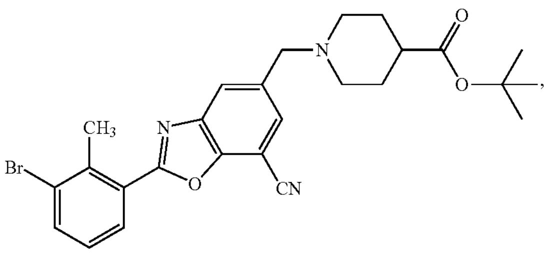

or a salt thereof.

In some embodiments, the compound of formula A-1 is a compound of formula A-1a':

(A-1a')

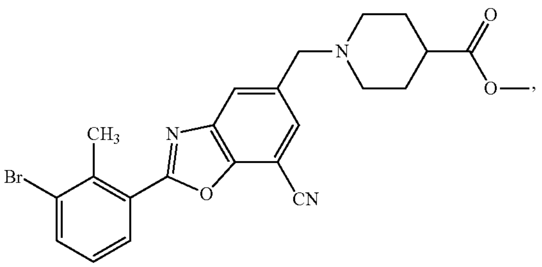

or a salt thereof.

In some embodiments, provided herein is a compound of formula A-3:

(A-3)

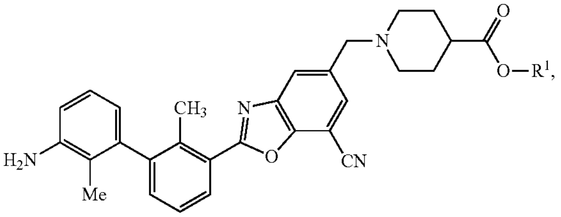

or a salt thereof, wherein $R^1$ is $C_{1-6}$ alkyl. In some embodiments, $R^1$ is t-butyl. In some embodiments, $R^1$ is methyl.

In some embodiments, the compound of formula A-3 is a compound of formula A-3a:

(A-3a)

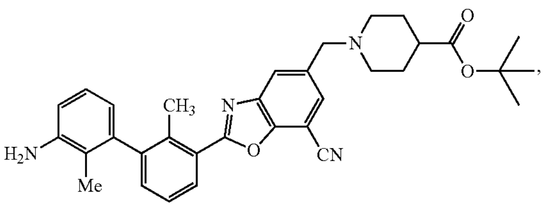

or a salt thereof.

In some embodiments, the compound of formula A-3 is a compound of formula A-3a':

(A-3a')

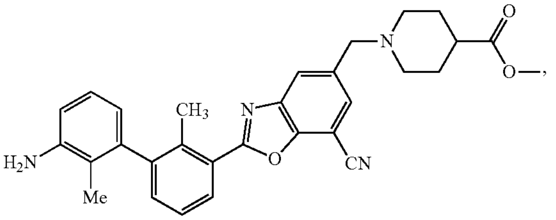

or a salt thereof.

In some embodiments, provided herein is a compound of formula A-4:

(A-4)

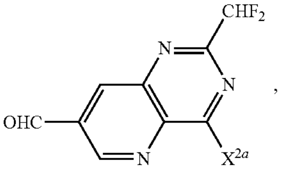

or a salt thereof, wherein $X^{2a}$ is halo.

In some embodiments, the compound of formula A-4 is a compound of formula A-4a:

(A-4a)

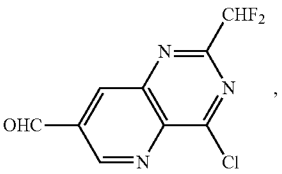

or a salt thereof.

In some embodiments, provided herein is a compound of formula A-5:

(A-5)

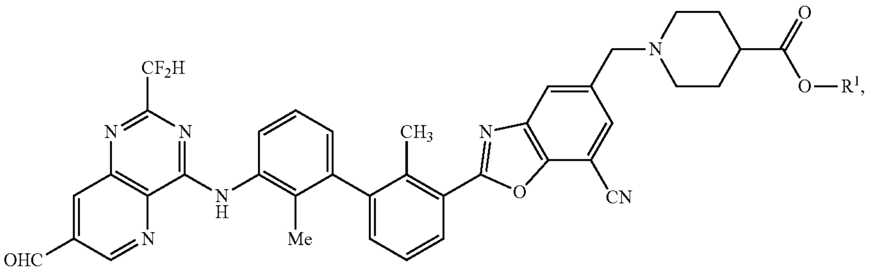

or a salt thereof, wherein $R^1$ is $C_{1-6}$ alkyl. In some embodiments, $R^1$ is t-butyl. In some embodiments, $R^1$ is methyl.

In some embodiments, the compound of formula A-5 is a compound of formula A-5a:

(A-5a)

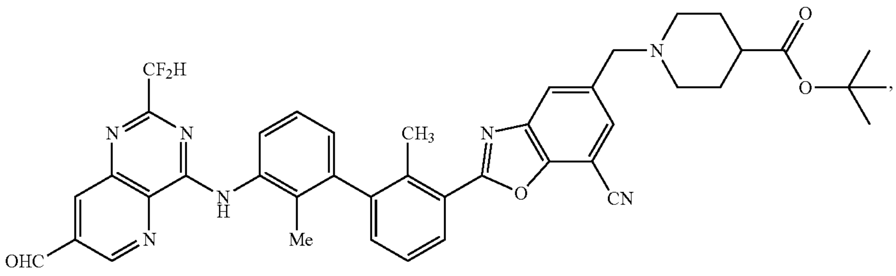

or a salt thereof.

In some embodiments, provided herein is a compound of formula A-7:

(A-7)

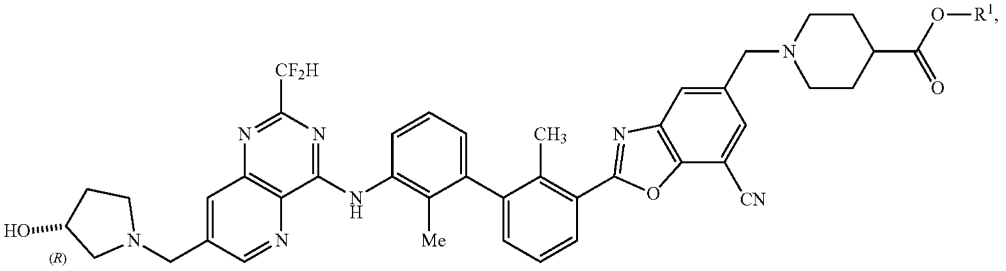

or a salt thereof, wherein $R^1$ is $C_{1-6}$ alkyl. In some embodiments, $R^1$ is t-butyl. In some embodiments, $R^1$ is methyl.

In some embodiments, the compound of formula A-7 is a compound of formula A-7a:

(A-7a)

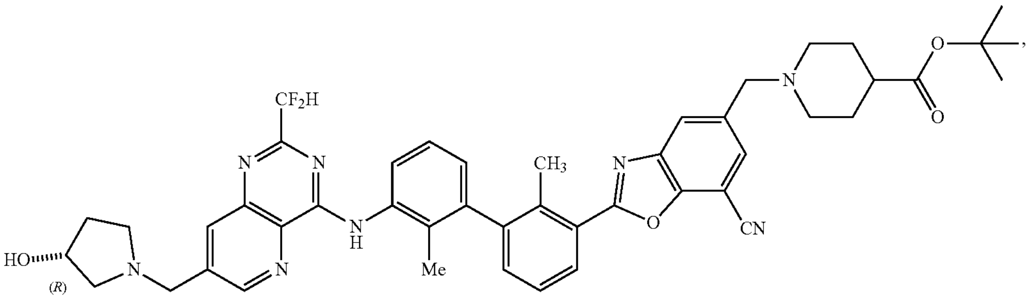

or a salt thereof.

In some embodiments, the compound of formula A-7 is a compound of formula A-7a':

(A-7a')

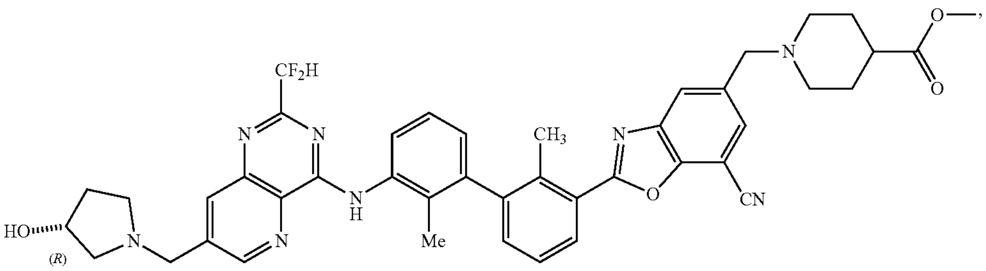

or a salt thereof.

In some embodiments, provided herein is a compound of formula B-2:

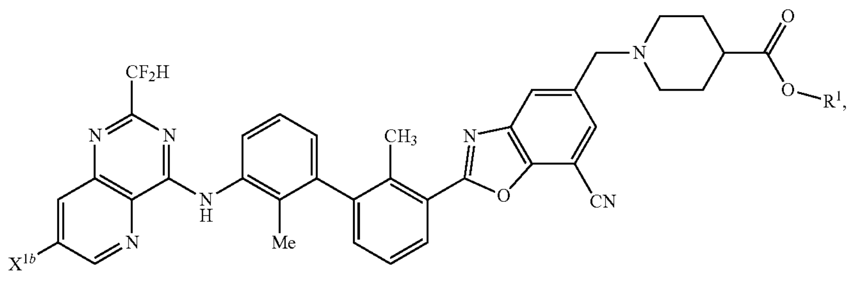

(B-2)

or a salt thereof, wherein $R^1$ is $C_{1-6}$ alkyl, wherein $X^{1b}$ is halo. In some embodiments, $R^1$ is t-butyl. In some embodiments, $R^1$ is methyl.

In some embodiments, the compound of formula B-2 is a compound of formula B-2a:

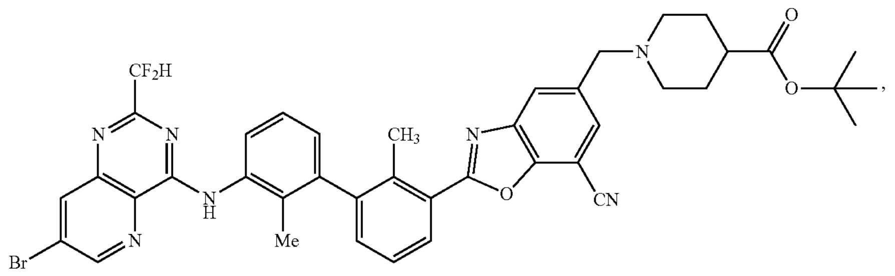

(B-2a)

or a salt thereof.

In some embodiments, the compound of formula B-2 is a compound of formula B-2a':

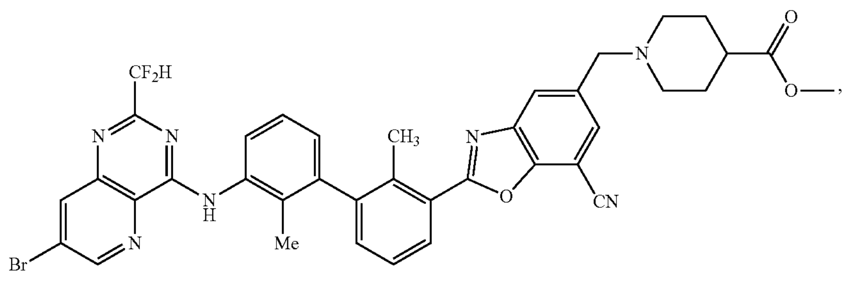

(B-2a')

or a salt thereof.

In some embodiments, provided herein is a compound selected from a compound of formula 4, a compound of formula 5, and a compound of formula 6:

(4)

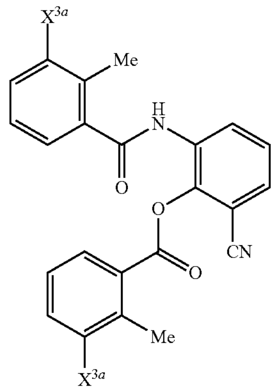

(5)

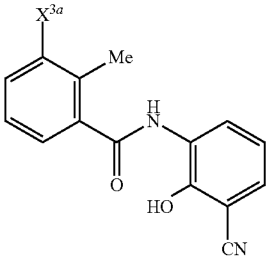

(6)

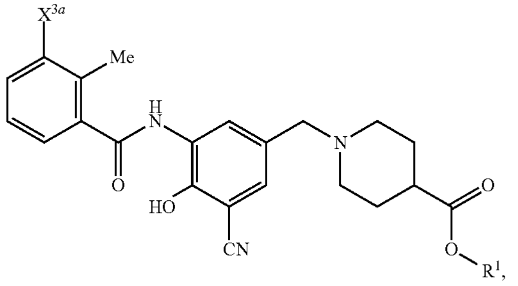

or a salt thereof, wherein each $X^{3a}$ is independently halo; and $R^1$ is $C_{1-6}$ alkyl. In some embodiments, $R^1$ is t-butyl. In some embodiments, $R^1$ is methyl.

In some embodiments, the compound of formula 4 is a compound of formula 4a:

(4a)

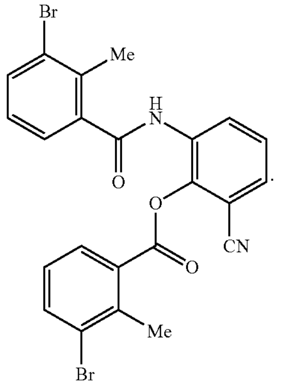

In some embodiments, the compound of formula 5 is a compound of formula 5a:

(5a)

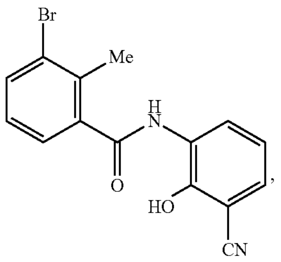

or a salt thereof.

In some embodiments, the compound of formula 6 is a compound of formula 6a:

(6a)

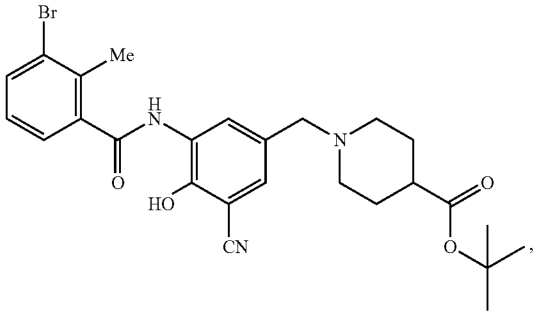

or a salt thereof.

In some embodiments, provided herein is a compound of formula 11:

(11)

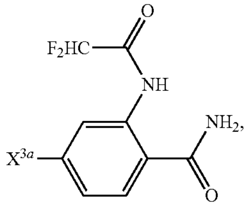

or a salt thereof, wherein $X^{3a}$ is halo.

In some embodiments, the compound of formula 11 is a compound of formula 11a:

(11a)

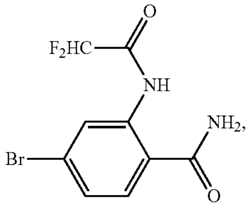

or a salt thereof.

The compound of Formula 1 can be synthesized using a process shown in Scheme 1. Palladium-catalyzed cross-coupling reaction of halo-substituted compound A-1a with a boronic ester of formula A-2a under standard conditions (such as Suzuki coupling reaction, e.g., in the presence of a palladium catalyst and a suitable base) can produce a compound of formula A-3a. The reaction of amine A-3a with aldehyde compound A-4a (e.g., using lithium bromide and N,N-diisopropylamine) can generate a compound of formula A-5a. The reaction of amine A-6 with aldehyde compound A-5a under reductive amination conditions (e.g., sodium triacetoxyborohydride or sodium cyanoborohydride as the reducing reagent) can generate a compound of formula A-7a. Then ester A-7a can be deprotected (e.g., using TMSI) to provide the desired Compound of Formula 1.

Scheme 1

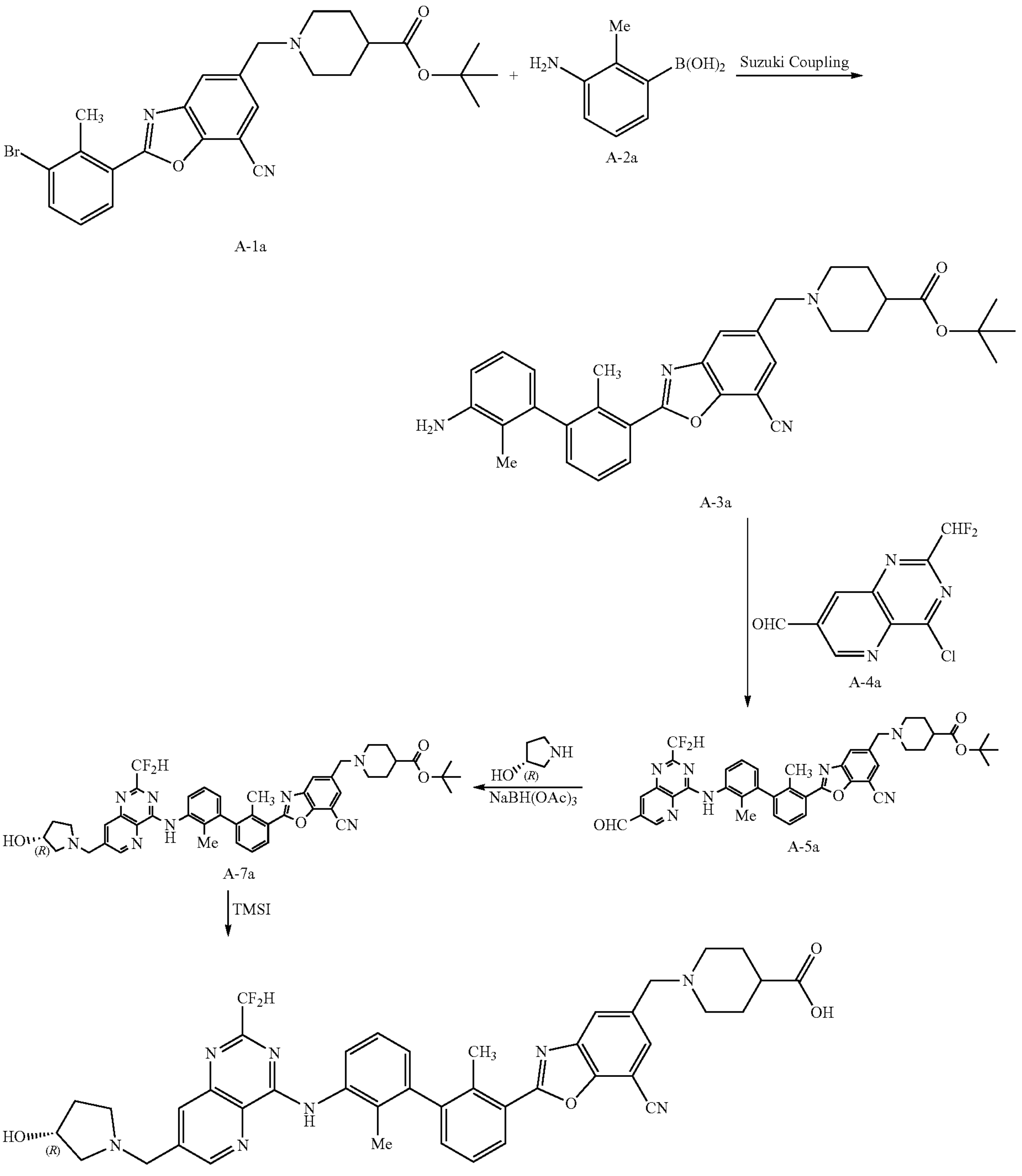

A-1a

A-2a

A-3a

A-4a

A-5a

A-7a

Compound of Formula 1

The compound of Formula 1 can be synthesized using a process shown in Scheme 2. Palladium-catalyzed cross-coupling reaction of halo-substituted compound A-1a with a boronic ester of formula A-2a under standard conditions (such as Suzuki coupling reaction, e.g., in the presence of a palladium catalyst and a suitable base) can produce a compound of formula A-3a. The reaction of amine A-3a with halo-substituted compound B-1a under basic conditions (e.g., using potassium carbonate) can generate a compound of formula B-2a. The reaction of halo-substituted compound B-2a with borate salt compound B-3a (e.g., using an in-situ generated Palladium catalyst) can generate a compound of formula A-7a. Then ester A-7a can be deprotected (e.g., using TMSI) to provide the desired compound of Formula 1.

Scheme 2

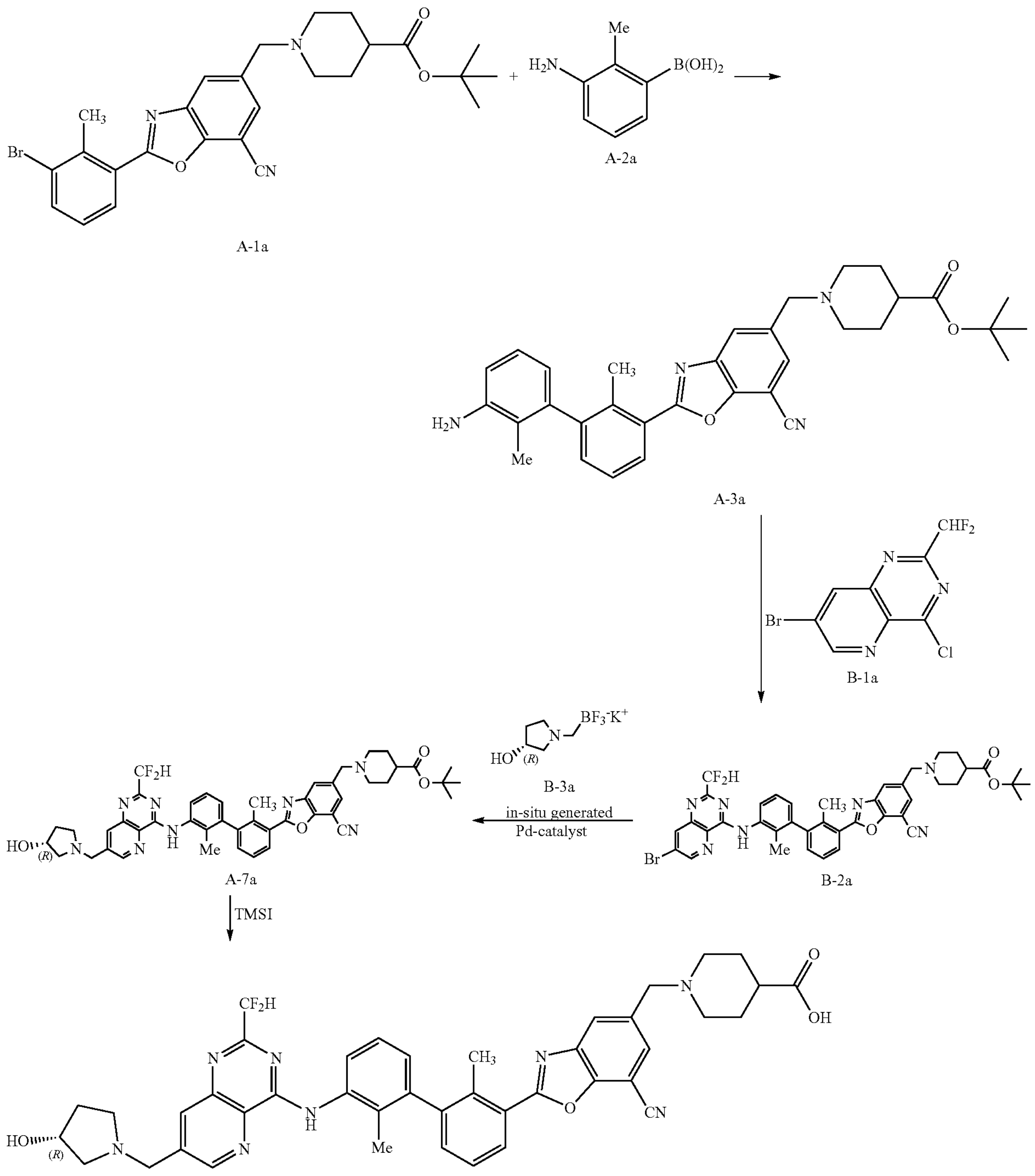

Compound of Formula 1

A compound of formula A-1a can be prepared according to Scheme 3. Nitro-substituted compound 2 can be reduced to the amine-substituted compound 3 using a reducing agent (e.g., $Na_2S_2O_4$). Alcohol 5a can be prepared by reacting amine 3 with acid chloride 8A' (e.g., generated in situ using carboxylic acid 8' and oxalyl chloride) via intermediate ester 4a cleaved under basic conditions. Alcohol 5a may be coupled with cyclic amine 9a to generate compound 6a. The ester amine and adjacent alcohol of compound 6a may be reductively cyclized (e.g., using a free radical initiator such as diisopropylazodicarboxylate (DIAD)) to the compound of formula A-1a.

Scheme 3

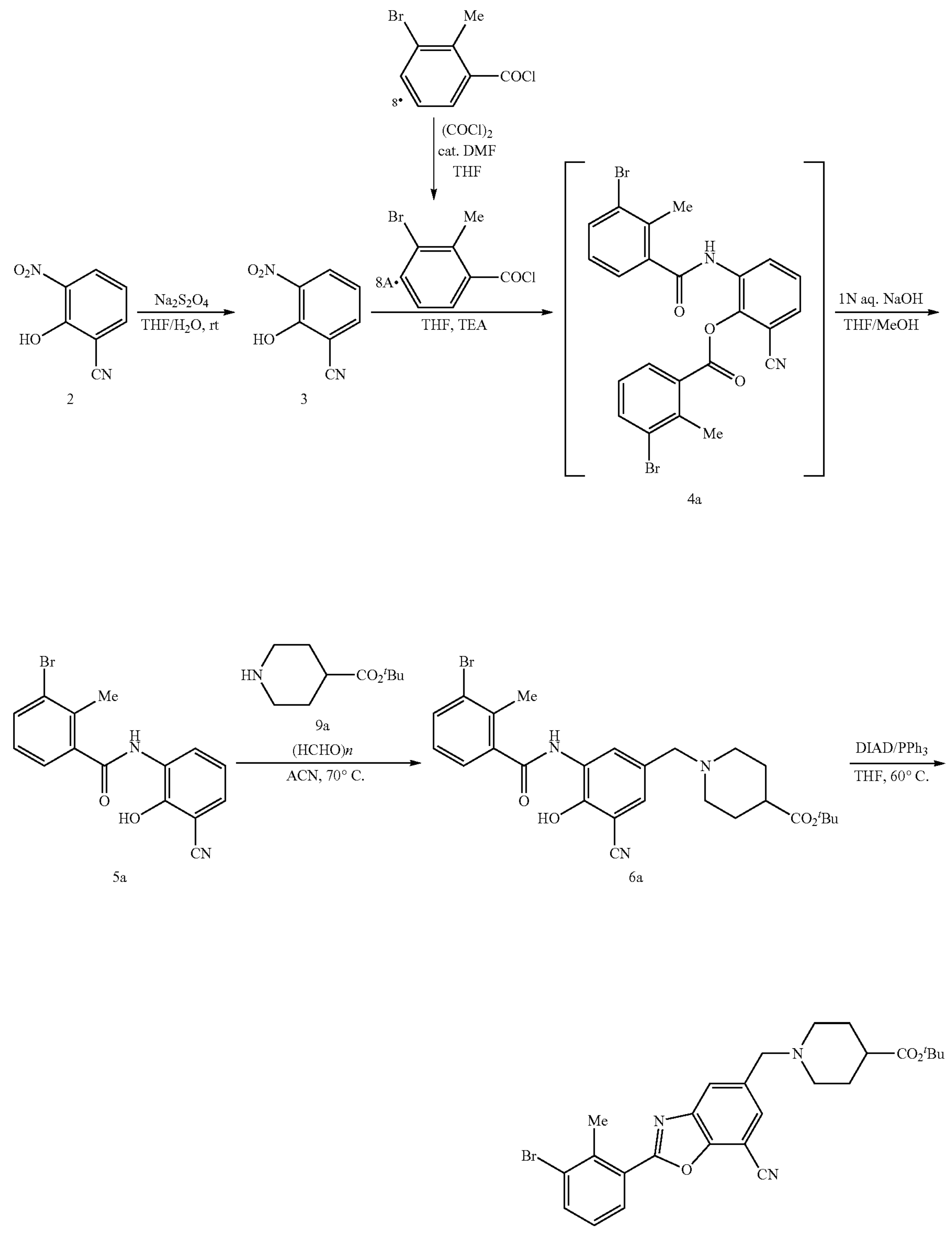

A-1a

The compound of formula B-1a can be prepared according to Scheme 4. Amine 10a can be converted to ester amine 11a in the presence of 2,2-difluoroacetic anhydride. The ester amine 11a can be reductively cyclized to alcohol 12a. Alcohol 12a can be converted to halo-substituted compound B-1a (e.g., using phosphorus oxychloride).

Scheme 4

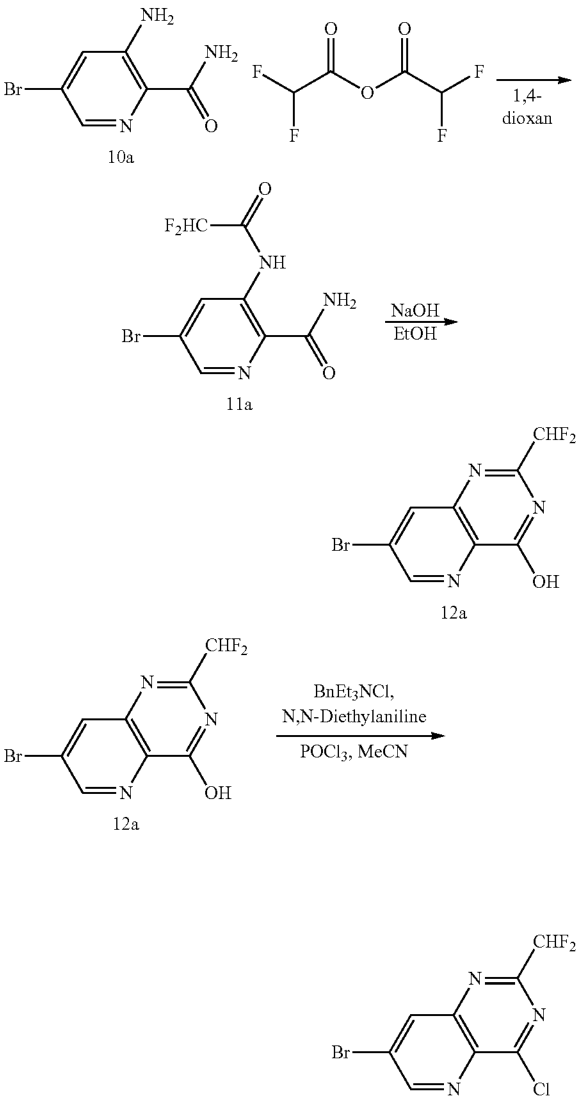

10a

11a

12a

12a

B-1a

The compound of formula A-4a can be prepared according to Scheme 5. Palladium-catalyzed cross-coupling reaction of halo-substituted compound of formula 12a with a boronic ester of formula 15a under standard conditions (such as Suzuki coupling reaction, e.g., in the presence of a palladium catalyst and a suitable base) can produce alcohol of formula 13. The alcohol of formula 13 can be converted to halo-substituted compound of formula 14a (e.g., using phosphorus oxychloride). The alkene of halo-substituted compound of formula 14a can be oxidatively cleaved (e.g., using sodium periodate and osmium tetroxide) to produce the aldehyde of formula A-4a.

Scheme 5

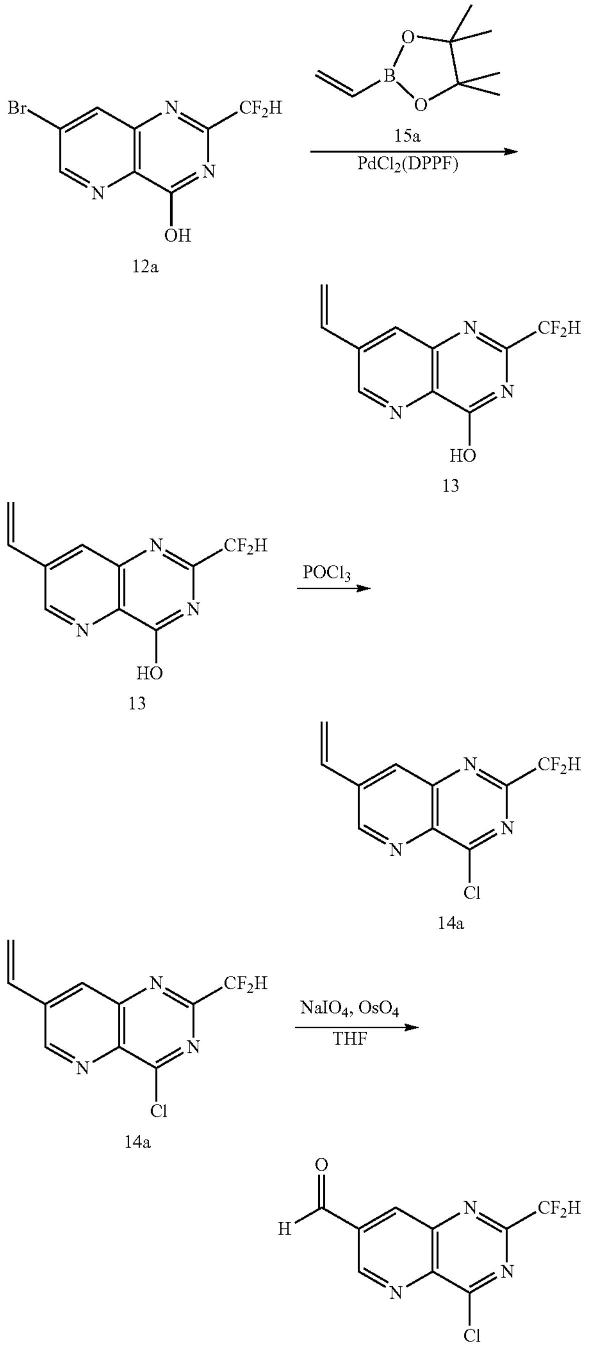

12a

13

13

14a

14a

A-4a

The compound of Formula 1 can be synthesized using a process shown in Scheme 6. Palladium-catalyzed cross-coupling reaction of halo-substituted compound A-1a' with a boronic ester of formula A-2a HCl under standard conditions (such as Suzuki coupling reaction, e.g., in the presence of a palladium catalyst and a suitable base) can produce a compound of formula A-3a'. The reaction of amine A-3a' with halo-substituted compound B-1a under basic conditions (e.g., using potassium carbonate) can generate a compound of formula B-2a'. The reaction of halo-substituted compound B-2a' with borate salt compound B-3a (e.g., using an in-situ generated Palladium catalyst) can generate a compound of formula A-7a'. Then ester A-7a' can be deprotected (e.g., under basic conditions) to provide the desired compound of Formula 1.

Scheme 6
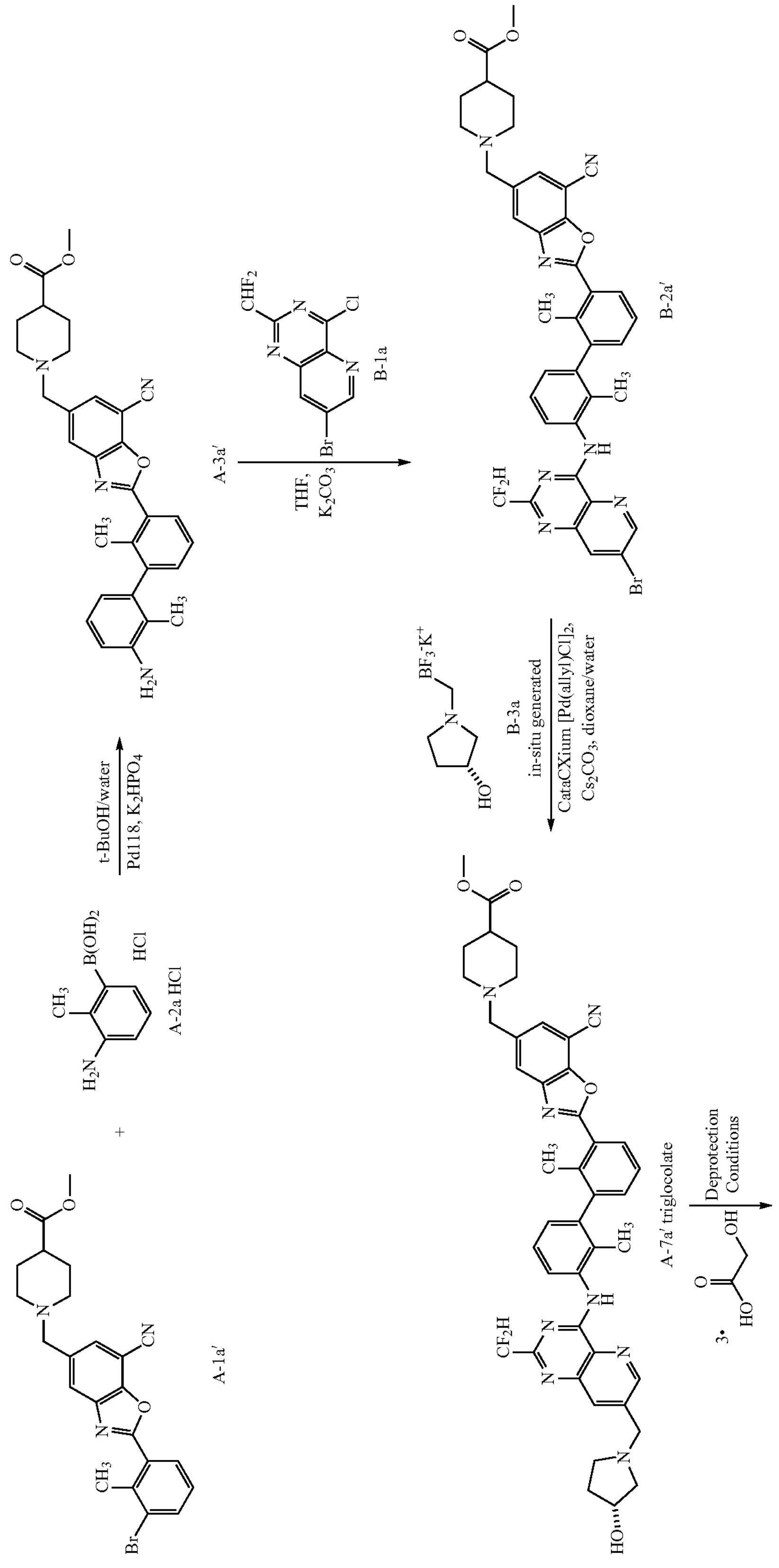
A-1a′
A-2a HCl
A-3a′
B-1a
B-2a′
B-3a
A-7a′ triglocolate

-continued
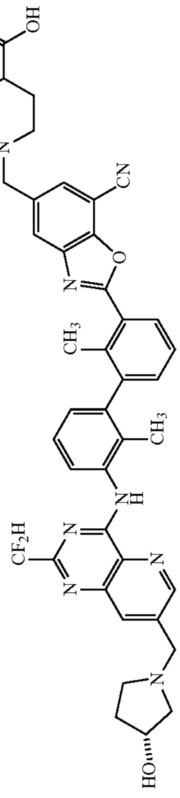
Compound of Formula 1
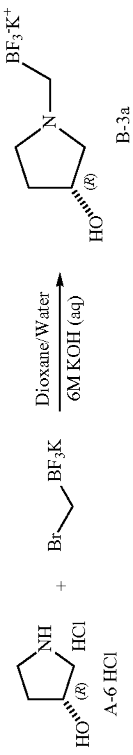
A-6 HCl
B-3a

Solid Forms and Salts

The present disclosure is further directed to, inter alia, a solid form or salt form of (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidine-4-carboxylic acid (Compound of Formula 1):

Compound of Formula 1

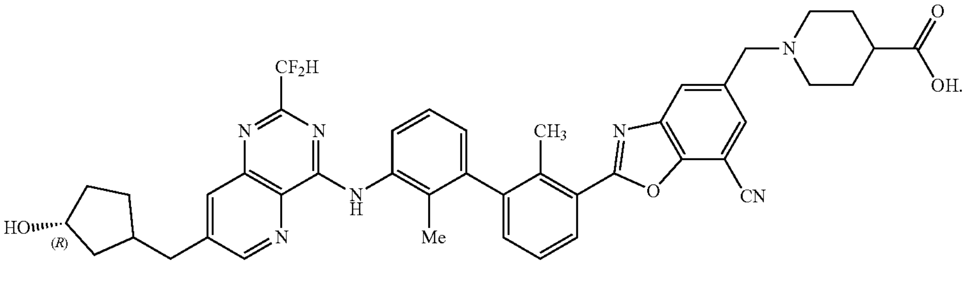

The compound of Formula 1 is disclosed in U.S. Patent Publication No. 2019/0300524, which is incorporated herein by reference.

In some embodiments, the solid form is a crystalline free base of (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidine-4-carboxylic acid (Compound of Formula 1 crystalline free base).

In some embodiments, the solid form is a crystalline free base of Form I of (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidine-4-carboxylic acid (Form I of Compound of Formula 1 crystalline free base).

In some embodiments, the solid form is a crystalline free base of Form II of (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidine-4-carboxylic acid (Form II of Compound of Formula 1 crystalline free base).

In some embodiments, the present disclosure provides salts of Compound of Formula 1:

Compound of Formula 1

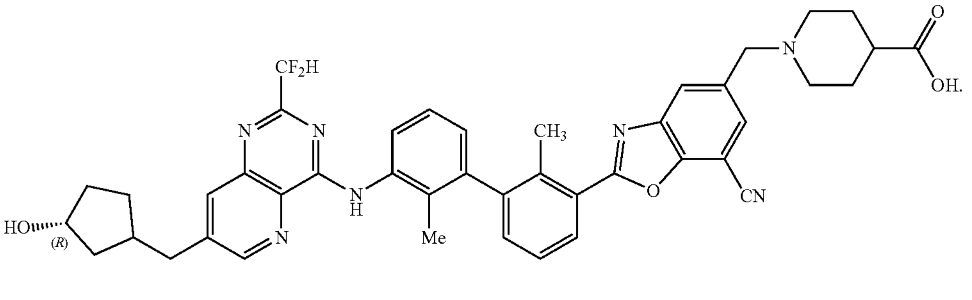

In some embodiments, the salt is (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidine-4-carboxylic acid methanesulfonic acid salt (compound of Formula 1 methanesulfonic acid salt).

Different forms of the same substance have different bulk properties relating to, for example, hygroscopicity, solubility, stability, and the like. Forms with high melting points often have good thermodynamic stability which is advantageous in prolonging shelf-life drug formulations comprising the solid form. Forms with lower melting points often are less thermodynamically stable, but are advantageous in that they have increased water solubility, translating to increased drug bioavailability. Forms that are weakly hygroscopic are desirable for their stability to heat and humidity and are resistant to degradation during long storage.

Crystalline Free Base

In some embodiments, the solid form of the compound of Formula 1 is a crystalline free base of Form I. In some embodiments, the solid form of the compound of Formula 1 is a crystalline free base of Form II.

In some embodiments, the crystalline free base of Form I is a hydrate. In some embodiments, the crystalline free base of Form I is a sesquihydrate.

In some embodiments, the crystalline free base of Form I can be characterized by the X-ray powder diffraction (XRPD) pattern substantially as shown in FIG. 1.

In some embodiments, the crystalline free base of Form I has at least one X-ray powder diffraction (XRPD) peak, in terms of 2-theta (±0.2 degrees), selected from 7.0, 8.5, 10.0, 10.6, 14.6, 15.2, 15.8, 17.2, 20.1, 21.1, 23.9, 24.8, 26.1, 28.1, 29.6, and 30.2 degrees. In some embodiments, the crystalline free base of Form I has at least two X-ray powder diffraction (XRPD) peaks, in terms of 2-theta (±0.2 degrees), selected from 7.0, 8.5, 10.0, 10.6, 14.6, 15.2, 15.8, 17.2, 20.1, 21.1, 23.9, 24.8, 26.1, 28.1, 29.6, and 30.2 degrees. In some embodiments, the crystalline free base of Form I has at least three X-ray powder diffraction (XRPD) peaks, in terms of 2-theta (±0.2 degrees), selected from 7.0, 8.5, 10.0, 10.6, 14.6, 15.2, 15.8, 17.2, 20.1, 21.1, 23.9, 24.8, 26.1, 28.1, 29.6, and 30.2 degrees. In some embodiments, the crystalline free base of Form I has at least four X-ray powder diffraction (XRPD) peaks, in terms of 2-theta (0.2 degrees), selected from 7.0, 8.5, 10.0, 10.6, 14.6, 15.2, 15.8, 17.2, 20.1, 21.1, 23.9, 24.8, 26.1, 28.1, 29.6, and 30.2 degrees. In some embodiments, the crystalline free base of Form I has characteristic X-ray powder diffraction (XRPD) peaks, in terms of 2-theta (±0.2 degrees), at 7.0, 8.5, 10.0, 10.6, 14.6, 15.2, 15.8, 17.2, 20.1, 21.1, 23.9, 24.8, 26.1, 28.1, 29.6, and 30.2 degrees.

Figure 2:
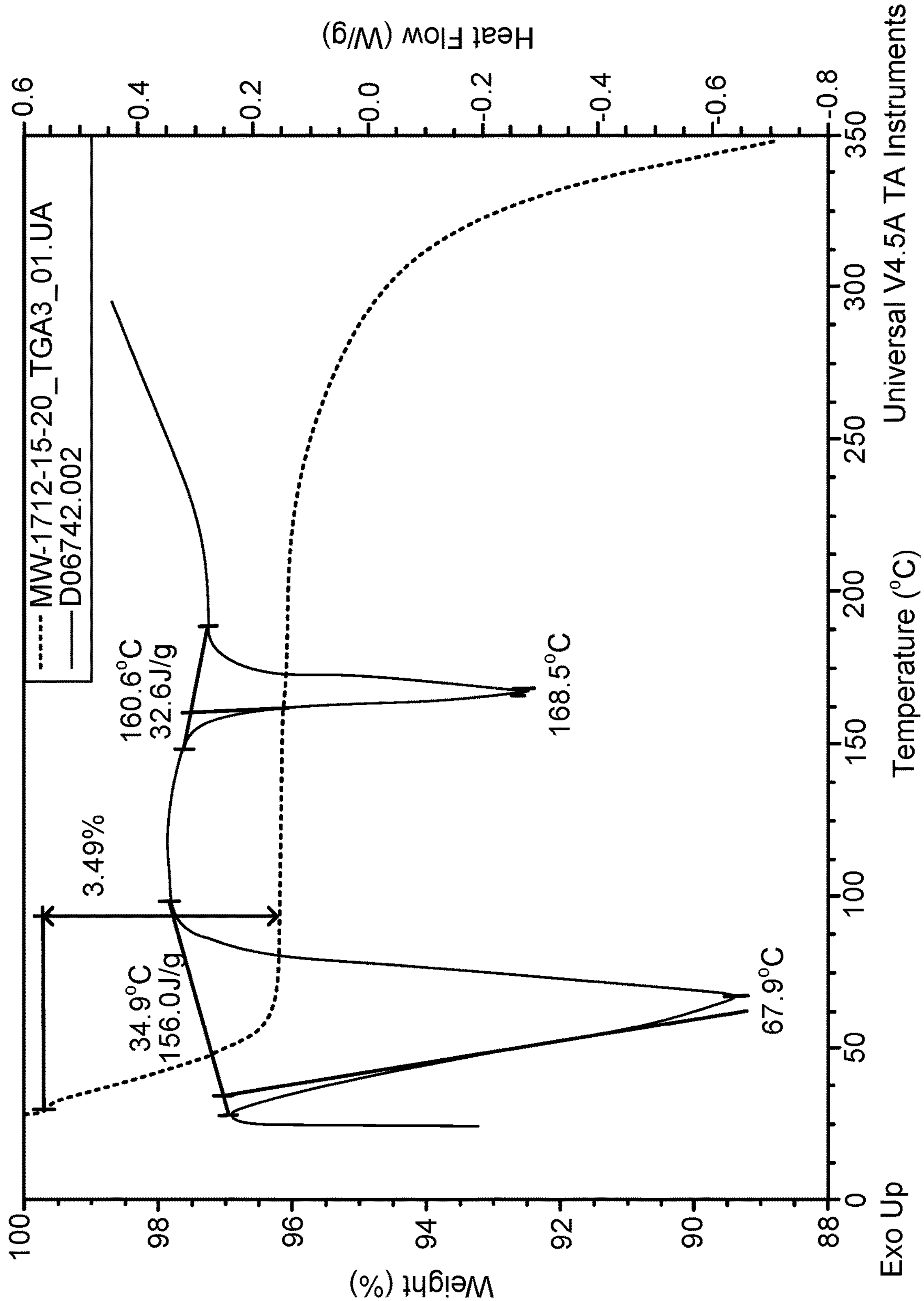
FIG. 2 shows a DSC thermogram and a TGA thermogram of Form I of the compound of Formula 1 crystalline free base.

In some embodiments, the crystalline free base of Form I exhibits a DSC thermogram having a first endothermic peak with an onset temperature (±3° C.) at 35° C. and a maximum temperature (±3° C.) at 68° C. and a second endothermic peak with an onset temperature (±3° C.) at 161° C. and a maximum temperature (±3° C.) at 169° C. In some embodiments, the crystalline free base of Form I has a DSC thermogram substantially as depicted in FIG. 2. In some embodiments, the crystalline free base of Form I has a TGA thermogram substantially as depicted in FIG. 2.

In some embodiments, the crystalline free base of Form I can be produced by a process comprising precipitating the Form I from a solvent, following adding seeds of the crystalline free base of Form I in the solvent. In some embodiments, the solvent is tetrahydrofuran.

For example, the crystalline free base of Form I can be prepared by a process comprising:

a) preparing a suspension of the compound of Formula 1 in a solvent (e.g., tetrahydrofuran);
b) heating the suspension of a) to above room temperature (e.g., to 40° C.) to form a solution;
c) cool the solution of b) (e.g., to 30° C.);
d) adding seeds of Form I to the solution of c);
e) adding a solvent or solvent mixture (e.g., MEK:$H_2O$ (11:2, 1 vol)) to the suspension of d);
f) cooling the solution of e) to below room temperature (e.g., about 5° C. at a rate of 0.1° C./min) to form a suspension; and
g) filtering the crystalline free base of Form I from the suspension of f).

For example, the crystalline free base of Form I can be prepared by a process comprising:

a) preparing a suspension of the compound of Formula 1 in a solvent (e.g., tetrahydrofuran);
b) heating the suspension of a) to above room temperature (e.g., 40° C.) to form a solution;
c) adding a solvent (e.g., MEK:H2O (11:2, 0.7 vol)) to the solution of b)
d) adding seeds of the crystalline free base of Form I to the solution of c);
e) adding a solvent or solvent mixture (e.g., MEK:$H_2O$ (11:2, 0.3 vol)) to the suspension of d);
f) cooling the solution of e) to below room temperature (e.g., about 5° C. at a rate of 0.1° C./min) to form a suspension; and
g) filtering the crystalline free base of Form I from the suspension of f).

Figure 3:
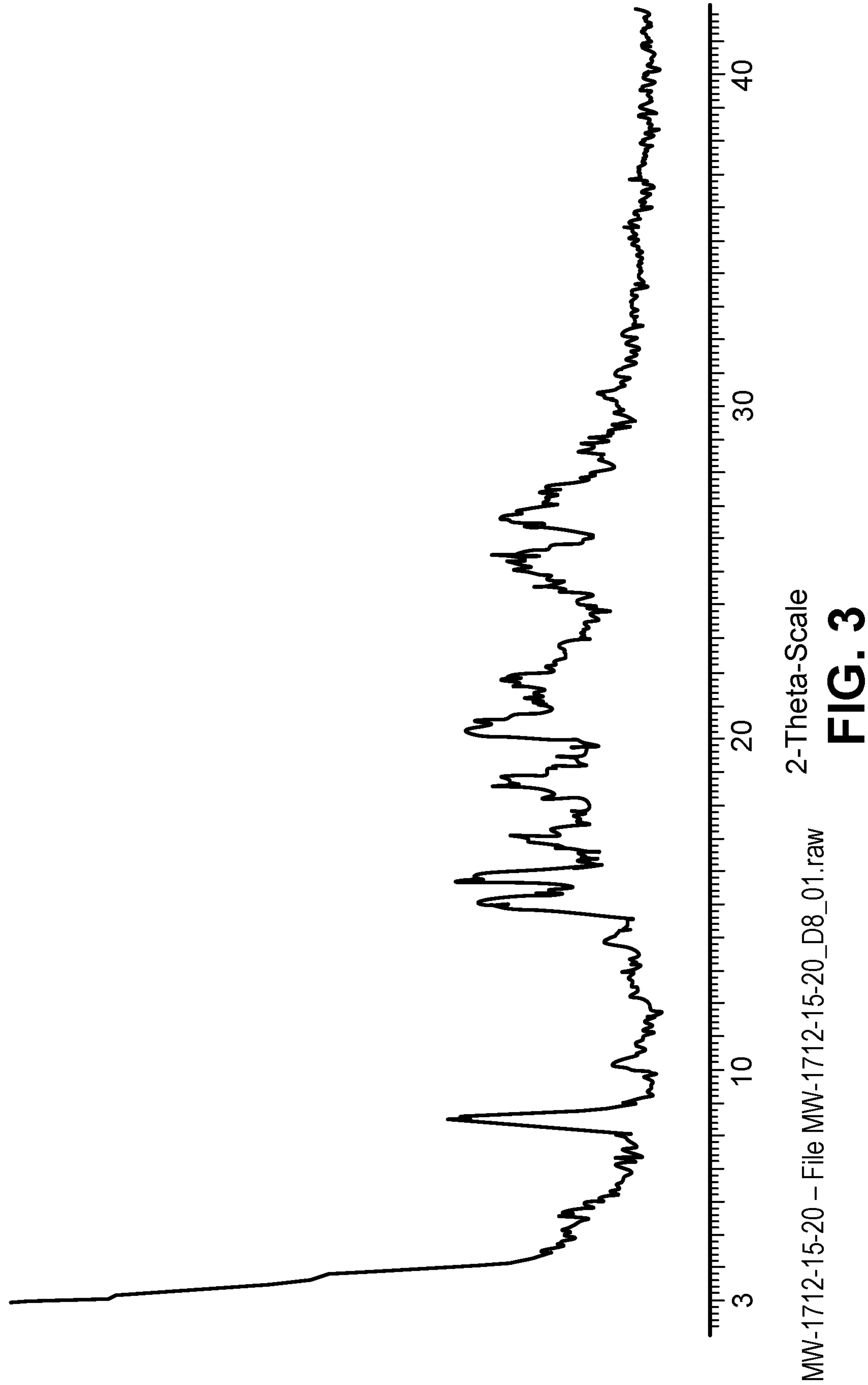
FIG. 3 shows an XRPD pattern of Form II of the compound of Formula 1 crystalline free base.

In some embodiments, the compound of Formula 1 crystalline free base of Form II can be characterized by the X-ray powder diffraction (XRPD) pattern substantially as shown in FIG. 3.

In some embodiments, the crystalline free base of Form II is a hydrate. In some embodiments, the crystalline free base of Form II is a dihydrate.

In some embodiments, the crystalline free base of Form II has at least one X-ray powder diffraction (XRPD) peak, in terms of 2-theta (±0.2 degrees), selected from 8.5, 15.0, 15.7, 17.0, 18.6, 20.2, 20.5, 21.7, 25.5, and 26.7 degrees. In some embodiments, the crystalline free base of Form II has at least two X-ray powder diffraction (XRPD) peaks, in terms of 2-theta (±0.2 degrees), selected from 8.5, 15.0, 15.7, 17.0, 18.6, 20.2, 20.5, 21.7, 25.5, and 26.7 degrees. In some embodiments, the crystalline free base of Form II has at least three X-ray powder diffraction (XRPD) peaks, in terms of 2-theta (±0.2 degrees), selected from 8.5, 15.0, 15.7, 17.0, 18.6, 20.2, 20.5, 21.7, 25.5, and 26.7 degrees. In some embodiments, the crystalline free base of Form II has at least four X-ray powder diffraction (XRPD) peaks, in terms of 2-theta (±0.2 degrees), selected from 8.5, 15.0, 15.7, 17.0, 18.6, 20.2, 20.5, 21.7, 25.5, and 26.7 degrees. In some embodiments, the crystalline free base of Form II has characteristic X-ray powder diffraction (XRPD) peaks, in terms of 2-theta (±0.2 degrees), at 8.5, 15.0, 15.7, 17.0, 18.6, 20.2, 20.5, 21.7, 25.5, and 26.7 degrees.

Figure 4:
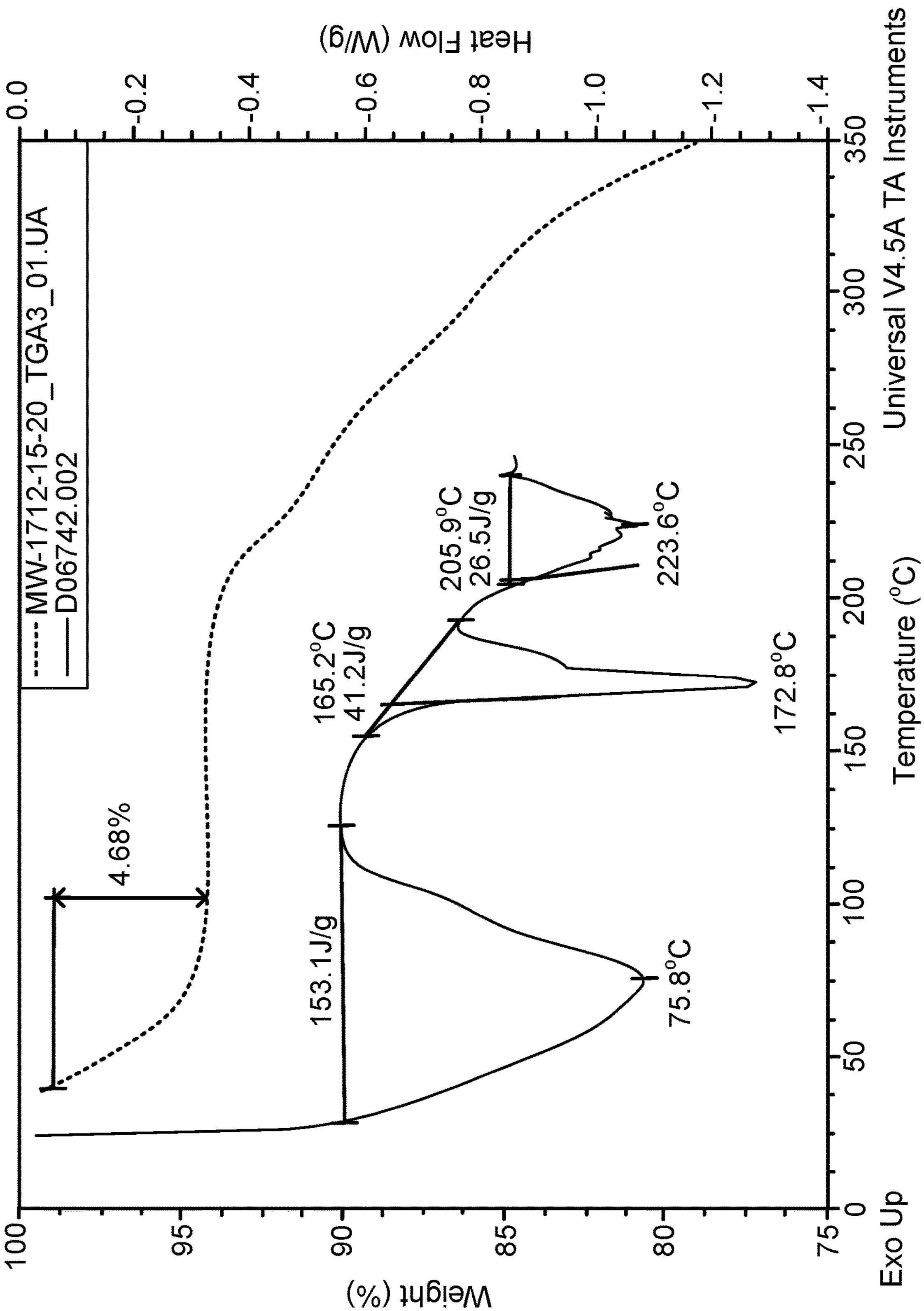
FIG. 4 shows a DSC thermogram and a TGA thermogram of Form II of the compound of Formula 1 crystalline free base.

In some embodiments, the crystalline free base of Form II exhibits a DSC thermogram having a first endothermic peak with a maximum temperature (±3° C.) at 76° C., a second endothermic peak with an onset temperature (±3° C.) at 165° C. and a maximum temperature (±3° C.) at 173° C., and a third endothermic peak with an onset temperature (±3° C.) at 206° C. and a maximum temperature (±3° C.) at 224° C. In some embodiments, the crystalline free base of Form II has a DSC thermogram substantially as depicted in FIG. 4. In some embodiments, the crystalline free base of Form II has a TGA thermogram substantially as depicted in FIG. 4.

In some embodiments, the crystalline free base of Form II can be produced by a process comprising precipitating the crystalline free base of Form II from a solvent, following reacting of the compound of Formula 1 with L-arginine (e.g., about 1.0 molar eq. or more) in the solvent. In some embodiments, the solvent is methyl ethyl ketone or a mixture thereof.

For example, the crystalline free base of Form II can be prepared by a process comprising:

a) preparing a suspension of the compound of Formula 1 in a solvent comprising methyl ethyl ketone
b) heating the suspension of a) to above room temperature to form a solution;
c) add at least 1 equivalent of L-arginine to the solution of b);
d) cooling the solution of c) to below room temperature to form a suspension; and
e) filtering the crystalline free base of Form II from the suspension of d).

For example, the crystalline free base of Form II can be prepared by a process comprising:

a) preparing a suspension of the compound of Formula 1 in a solvent comprising methyl ethyl ketone
b) heating the suspension of a) to about 50° C. to form a solution;
c) add at least 1.0 to 1.2 equivalent of L-arginine to the solution of b);
d) cooling the solution of c) to about 5° C. at a rate of 0.1° C./min to form a suspension; and
e) filtering the crystalline free base of Form II from the suspension of d) using a filter under an inert atmosphere.

Methanesulfonic Acid Salts

In some embodiments, the salt of the compound of Formula 1 is (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidine-4-carboxylic acid methanesulfonic acid salt (compound of Formula 1 methanesulfonic acid salt).

In some embodiments, the methanesulfonic acid salt is a hydrate. In some embodiments, the methanesulfonic acid salt is a dihydrate.

The methanesulfonic acid salt can be prepared by any suitable method for preparation of methanesulfonic acid addition salts. For example, the compound of Formula 1 can be reacted with methanesulfonic acid (e.g., about 1.0 molar eq. or more) in a solvent and the resulting salt can be isolated by decanting off the solvent. In certain embodiments, the compound of Formula 1 is reacted with about 1 to about 2 molar equivalents of methanesulfonic acid. In certain embodiments, the compound of Formula 1 is reacted with about 1 to about 1.5 molar equivalents of methanesulfonic acid. In certain embodiments, the compound of Formula 1 is reacted with about 1.2 molar equivalents of methanesulfonic acid. In certain embodiments, the compound of Formula 1 is reacted with about 1 molar equivalents of methanesulfonic acid.

The solvent can comprise any solvent or mixture of solvents capable of at least partially dissolving the compound of Formula 1. In some embodiments, the solvent comprises an alcohol. Suitable alcohols include methanol, ethanol, 2-nitroethanol, 2-fluoroethanol, 2,2,2-trifluoroethanol, ethylene glycol, 1-propanol, isopropanol (isopropyl alcohol, 2-propanol), 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol. In some embodiments, the solvent comprises dioxane, dimethylsulfoxide, acetone, tetrahydrofuran, dichloromethane, methanol, ethanol, 1-propanol, or isopropanol. In some embodiments, the solvent comprises acetone or methyl ethyl ketone. In some embodiments, the solvent comprises methyl ethyl ketone.

In some embodiments, the solvent is a mixture of acetone and water.

In some embodiments, the solvent is about room temperature. In some embodiments, the solvent is heated to a temperature of about 50° C. In some embodiments, the temperature is from about 40° C. to about 80° C. In some embodiments, the temperature is from about 40° C. to about 60° C. In some embodiments, the temperature is from about 50° C. to about 55° C. In some embodiments, the temperature is about 45° C., about 50° C., about 55° C., about 60° C., about 65° C., about 70° C., about 75° C., or about 80° C.

In some embodiments, precipitation is induced by cooling the heated reaction over a period of time. In some embodiments, precipitation is induced by cooling the heated reaction to below ambient temperature (e.g., about 0° C. to about 20° C., about 0° C. to about 10° C., or about 5° C.) at a rate of about 0.1° C./min.

The precipitation of the methanesulfonic acid salt, in some embodiments, is carried out by filtering the salt from solution.

In some embodiments, the methanesulfonic acid salt is amorphous. In some embodiments, the methanesulfonic acid salt is crystalline. In some embodiments, the methanesulfonic salt is a mixture comprising crystalline and amorphous forms.

In some embodiments, the methanesulfonic acid salt has Form III.

In some embodiments, the methanesulfonic acid salt of Form III can be produced by a process comprising precipitating the methanesulfonic acid salt of Form III from a solvent, following reacting of the compound of Formula 1 with methanesulfonic acid (e.g., about 1.0 molar eq. or more) in the solvent. In some embodiments, the solvent is acetone, water, or a mixture thereof.

For example, the methanesulfonic acid salt of Form III can be prepared by a process comprising:

a) preparing a suspension of the compound of Formula 1 and at least 1 equivalent of methanesulfonic acid in a solvent comprising methyl ethyl ketone;
b) heating the suspension of a) to above room temperature;
c) cooling the solution of b) to below room temperature; and
d) decanting off any liquids from the solution of c).

For example, the methanesulfonic acid salt of Form III can be prepared by a process comprising:

a) preparing a suspension of the compound of Formula 1 and at least 1 equivalent (e.g., about 1.2 equivalents) of methanesulfonic acid in a solvent comprising methyl ethyl ketone;
b) heating the suspension of a) to about 50° C.;
c) cooling the solution of b) to about 5° C.;
d) decanting off any liquids from the solution of c); and
e) treating the remaining solids from d) with a solvent (e.g., 2-propanol, ethyl acetate, and tert-butyl methyl ether) and maturing for about 3 days to improve crystallinity.

Figure 5:
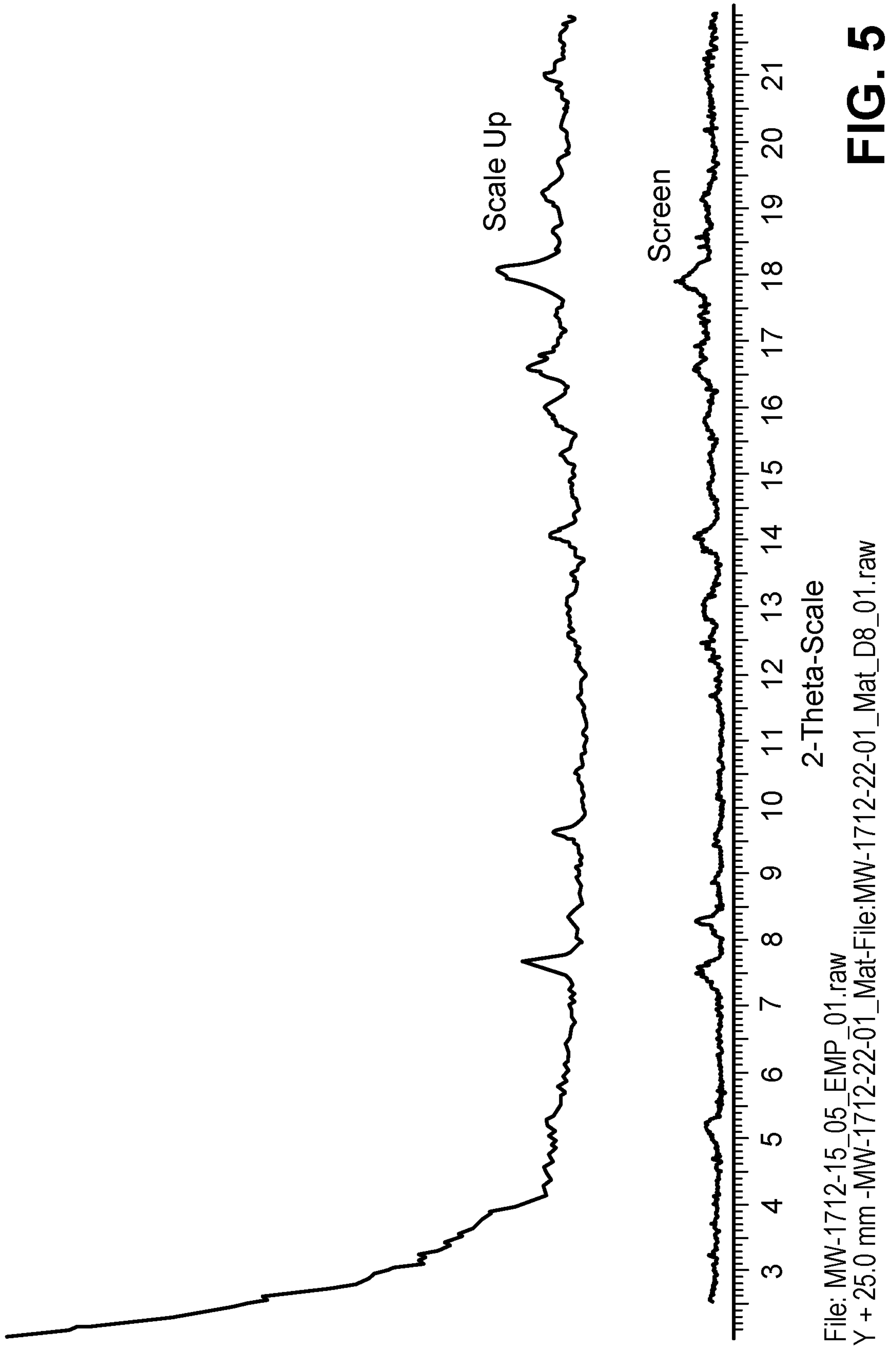
FIG. 5 shows an XRPD pattern of Form III of the methanesulfonic acid salt of the compound of Formula 1.

In some embodiments, the methanesulfonic acid salt of Form III can be characterized by the X-ray powder diffraction (XRPD) pattern substantially as shown in FIG. 5.

In some embodiments, the methanesulfonic acid salt of Form III has at least one X-ray powder diffraction (XRPD) peak, in terms of 2-theta (±0.2 degrees), selected from 5.2, 7.5, 8.2, 8.8, 9.4, 11.6, 12.4, 13.0, 14.0, 14.8, 15.8, 16.6, 16.9, 17.3, 17.9, 19.2, 23.6, 24.5, 25.5, and 26.6 degrees. In some embodiments, the methanesulfonic acid salt of Form III has at least two X-ray powder diffraction (XRPD) peaks, in terms of 2-theta (±0.2 degrees), selected from 5.2, 7.5, 8.2, 8.8, 9.4, 11.6, 12.4, 13.0, 14.0, 14.8, 15.8, 16.6, 16.9, 17.3, 17.9, 19.2, 23.6, 24.5, 25.5, and 26.6 degrees. In some embodiments, the methanesulfonic acid salt of Form III has at least three X-ray powder diffraction (XRPD) peaks, in terms of 2-theta (±0.2 degrees), selected from 5.2, 7.5, 8.2, 8.8, 9.4, 11.6, 12.4, 13.0, 14.0, 14.8, 15.8, 16.6, 16.9, 17.3, 17.9, 19.2, 23.6, 24.5, 25.5, and 26.6 degrees. In some embodiments, the methanesulfonic acid salt of Form III has at least four X-ray powder diffraction (XRPD) peaks, in terms of 2-theta (±0.2 degrees), selected from 5.2, 7.5, 8.2, 8.8, 9.4, 11.6, 12.4, 13.0, 14.0, 14.8, 15.8, 16.6, 16.9, 17.3, 17.9, 19.2, 23.6, 24.5, 25.5, and 26.6 degrees. In some embodiments, the methanesulfonic acid salt of Form III has characteristic X-ray powder diffraction (XRPD) peaks, in terms of 2-theta (±0.2 degrees), at 5.2, 7.5, 8.2, 8.8, 9.4, 11.6, 12.4, 13.0, 14.0, 14.8, 15.8, 16.6, 16.9, 17.3, 17.9, 19.2, 23.6, 24.5, 25.5, and 26.6 degrees.

Figure 6:
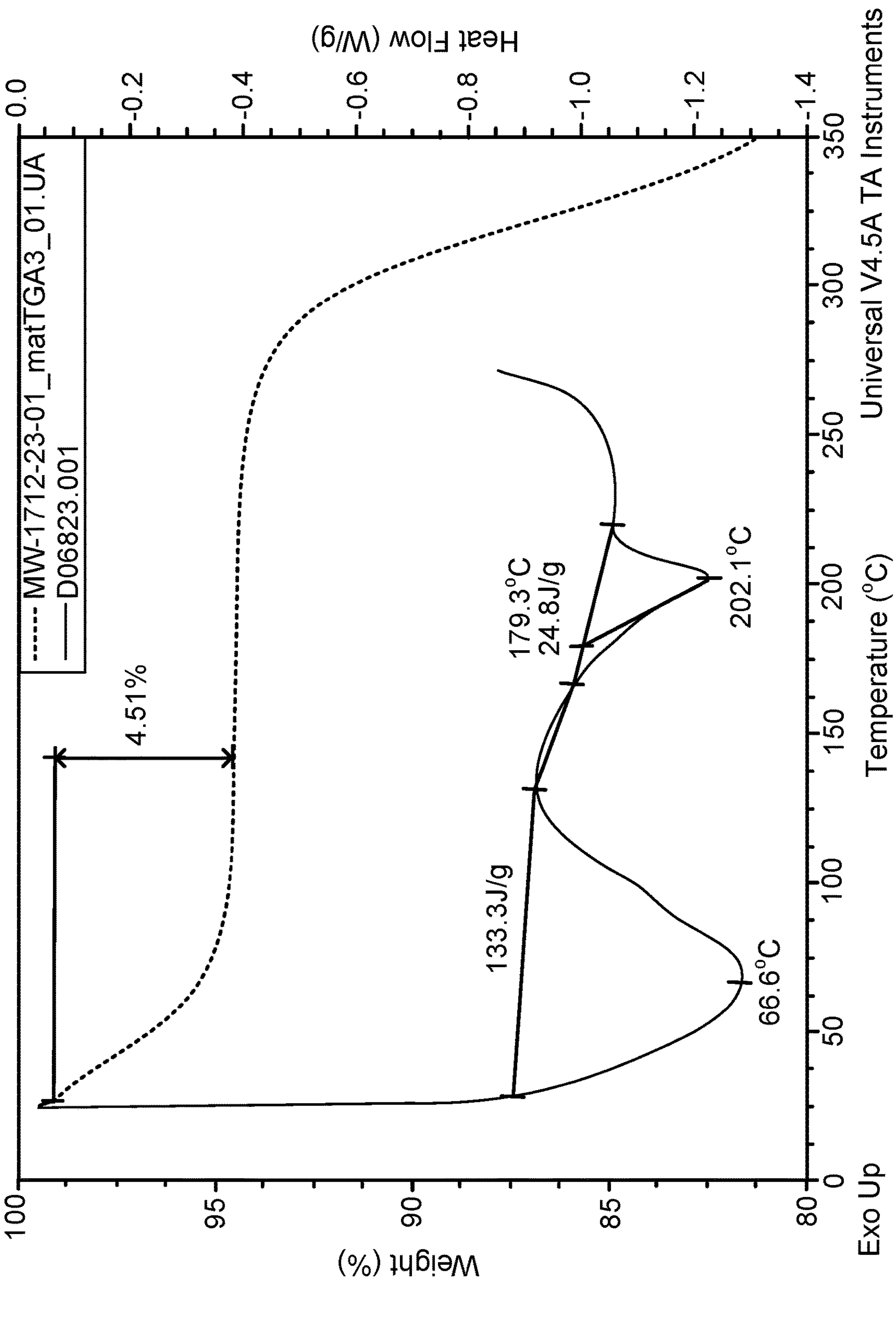
FIG. 6 shows a DSC thermogram and a TGA thermogram of Form III of the methanesulfonic acid salt of the Compound of Formula 1.

In some embodiments, the methanesulfonic acid salt of Form III can be characterized by the DSC thermogram substantially as depicted in FIG. 6.

In some embodiments, the methanesulfonic acid salt of Form III exhibits a DSC thermogram having a first endothermic peak with an onset temperature (±3° C.) at 30° C. and a maximum (±3° C.) at 67° C., and a second endothermic peak with an onset temperature (±3° C.) at 179° C. and a maximum at (±3° C.) 202° C. In some embodiments, the methanesulfonic acid salt of Form III has a DSC thermogram substantially as depicted in FIG. 6. In some embodiments, the methanesulfonic acid salt of Form III has a TGA thermogram substantially as depicted in FIG. 6.

The different solid forms and salt forms thereof can be identified by solid state characterization methods such as by X-ray powder diffraction (XRPD). Other characterization methods such as differential scanning calorimetry (DSC), thermogravimetric analysis (TGA), dynamic vapor sorption (DVS), solid state NMR, and the like further help identify the form as well as help determine stability and solvent/water content.

An XRPD pattern of reflections (peaks) is typically considered a fingerprint of a particular crystalline form. It is well known that the relative intensities of the XRPD peaks can widely vary depending on, inter alia, the sample preparation technique, crystal size distribution, various filters used, the sample mounting procedure, and the particular instrument employed. In some instances, new peaks may be observed or existing peaks may disappear, depending on the type of the instrument or the settings. As used herein, the term "peak" refers to a reflection having a relative height/intensity of at least about 4% of the maximum peak height/intensity. Moreover, instrument variation and other factors can affect the 2-theta values. Thus, peak assignments, such as those reported herein, can vary by plus or minus about 0.2° (2-theta), and the term "substantially" and "about" as used in the context of XRPD herein is meant to encompass the above-mentioned variations.

In the same way, temperature readings in connection with DSC, TGA, or other thermal experiments can vary about +3° C. depending on the instrument, particular settings, sample preparation, etc. Accordingly, a crystalline form reported herein having a DSC thermogram "substantially" as shown in any of the Figures or the term "about" is understood to accommodate such variation.

In some embodiments, the compounds, solid forms and salt forms are substantially isolated. By "substantially isolated" is meant that the compounds, solid form, salt form or crystalline form thereof is at least partially or substantially separated from the environment in which it was formed or detected. Partial separation can include, for example, a composition enriched in the solid forms and salt forms. Substantial separation can include compositions containing at least about 50%, at least about 60%, at least about 70%, at least about 80%, at least about 90%, at least about 95%, at least about 97%, or at least about 99% by weight of the solid forms and salt forms. As used herein, "crystalline" or "crystalline form" is meant to refer to a certain lattice configuration of a crystalline substance. Different crystalline forms of the same substance typically have different crystalline lattices (e.g., unit cells) which are attributed to different physical properties that are characteristic of each of the crystalline forms. In some instances, different lattice configurations have different water or solvent content.

In some embodiments, the compounds, solid forms and salt forms described herein can be found together with other substances such as water and solvents (e.g., hydrates and solvates) or can be isolated. As used herein, "hydrate" is meant to refer to a compound (e.g., a crystalline compound), in which water molecules are chemically bound to another compound or an element.

The phrase "pharmaceutically acceptable" is employed herein to refer to those salts, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Generally, the term "about" means ±10%. In some embodiments, the term "about" means ±5%.

The reactions described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures).

The reactions for preparing the compounds (e.g., the Compound of Formula I), solid forms and salts thereof, can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of the compounds (e.g., the Compound of Formula I), solid forms and salts thereof, can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry: Reactions, Mechanisms, and Structure*, $6^{th}$ Ed. (Wiley, 2007); Petursson et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^{1}H$ or $^{13}C$), infrared spectroscopy, spectrophotometry (e.g., UV-visible), mass spectrometry or by chromatographic methods such as high performance liquid chromatography (HPLC) or thin layer chromatography (TLC).

Suitable protic solvents can include, by way of example and without limitation, water, $C_1$. 6 alkanol, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, iso-butyl alcohol, tert-butyl alcohol, 2-ethoxyethanol, diethylene glycol, 1-, 2-, or 3-pentanol, neo-pentyl alcohol, tert-pentyl alcohol, diethylene glycol monomethyl ether, diethylene glycol monoethyl ether, cyclohexanol, benzyl alcohol, phenol, or glycerol.

Suitable aprotic solvents or non-protic organic solvents can include, by way of example and without limitation, di-$C_{1-6}$ alkyl ether, a 4-10 membered heterocycloalkyl ether, tetrahydrofuran (THF), acetonitrile, N,N-dimethylformamide (DMF), N,N-dimethylacetamide (DMA), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, dichloromethane, or hexamethylphosphoramide.

The expressions, "ambient temperature" and "room temperature" or "rt" as used herein, are understood in the art, and refer generally to a temperature, e.g., a reaction temperature, that is about the temperature of the room in which the salt forming reaction is carried out, for example, a temperature from about 20° C. to about 30° C.

The salt forming reactions described herein can be carried out in air or under an inert atmosphere. Typically, reactions containing reagents or products that are substantially reactive with air can be carried out using air-sensitive synthetic techniques that are well known to the skilled artisan.

Example acids can be inorganic or organic acids. Inorganic acids include hydrochloric acid, hydrobromic acid, sulfuric acid, phosphoric acid, and nitric acid. Organic acids include formic acid, acetic acid, propionic acid, butanoic acid, benzoic acid, 4-nitrobenzoic acid, methanesulfonic acid, p-toluenesulfonic acid, benzenesulfonic acid, tartaric acid, trifluoroacetic acid, propiolic acid, butyric acid, 2-butynoic acid, vinyl acetic acid, pentanoic acid, hexanoic acid, heptanoic acid, octanoic acid, nonanoic acid and decanoic acid.

Example bases include alkali metal bases such as alkali metal hydroxides (e.g., cesium acetate, lithium acetate, sodium acetate, and potassium acetate), alkali metal carbonate (e.g., lithium carbonate, sodium carbonate, and potassium carbonate), alkali metal phosphates (e.g., cesium phosphate, lithium phosphate, sodium phosphate, potassium phosphate, and potassium phosphate dibasic), and alkali metal acetate (e.g., cesium acetate, lithium acetate, sodium acetate, and potassium acetate). Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include sodium and potassium salts of methyl, ethyl, n-propyl, i-propyl, n-butyl, t-butyl, trimethylsilyl and cyclohexyl substituted amides.

As used herein, the term "alkyl", employed alone or in combination with other terms, refers to a saturated hydrocarbon group that may be straight-chain or branched. In some embodiments, the alkyl group contains 1 to 12, 1 to 8, or 1 to 6 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, n-heptyl, n-octyl, and the like. In some embodiments, the alkyl moiety is methyl, ethyl, n-propyl, isopropyl, n-butyl, isobutyl, tert-butyl, n-pentyl, isopentyl, neopentyl, n-hexyl, or 2,4,4-trimethylpentyl. In some embodiments, the alkyl moiety is methyl.

As used herein, "alkylene" refers to a divalent alkyl group.

As used herein, the term "haloalkyl", employed alone or in combination with other terms, refers to an alkyl group having from one halogen atom to 2n+1 halogen atoms which may be the same or different, where "n" is the number of carbon atoms in the alkyl group.

As used herein, the term "4-10 membered heterocycloalkyl ether" refers to a non-aromatic ring or ring system, which optionally contain one or more alkenylene groups as part of the ring structure, which has at least one oxygen heteroatom ring member and 4-10 ring members. Included within the term "heterocycloalkyl" are monocyclic 4-, 5-, 6- and 7-membered heterocycloalkyl groups. Examples of 4-10 membered heterocycloalkyl ether include tetrahydrofuran, tetrahydropyran, dioxane, and the like.

The term "$C_{1-6}$ alkanol" as used herein, refers to an alkyl group having 1 to 6 carbon atoms including one or more hydroxyl (OH) substituents. Examples of $C_{1-6}$ alcohol include, but are not limited to, methanol, ethanol, n-propanol, isopropanol, n-butanol and the like.

As used herein, the term "di-$C_{1-6}$ alkyl ether" refers to two saturated hydrocarbon groups that may be straight-chain or branched, which has at least one oxygen heteroatom (e.g., $C_{1-6}$ alkyl-O—$C_{1-6}$ alkyl, wherein each $C_{1-6}$ alkyl is independently selected; or $C_{1-6}$ alkyl-(O—$C_{1-6}$ alkylene)$_n$-O—$C_{1-6}$ alkyl, wherein n is 1-6 and wherein each $C_{1-6}$ alkyl and $C_{1-6}$ alkylene are independently selected). Example of di-$C_{1-6}$ alkyl ether includes diethyl ether, diglyme and the like.

As used herein, the terms "halo" and "halogen", employed alone or in combination with other terms, refer to fluoro, chloro, bromo, and iodo.

The term "Lewis acid" as used herein refers to a compound that is capable of accepting an electron pair from a Lewis base to form a Lewis adduct. Examples of Lewis acid includes trimethylsilyl triflate, scandium triflate, trimethylsilyl iodide, trimethyl borate, iodotrimethylsilane, and boron trifluoride etherate.

As used herein, the term "organic ether" as used herein, refers to an oxygen atom connected to two alkyl or aryl groups (e.g., $C_{1-6}$ alkyl-O—$C_{1-6}$ alkyl, wherein each $C_{1-6}$ alkyl is independently selected; $C_{1-6}$ alkyl-(O—$C_{1-6}$ alkylene)$_n$-O—$C_{1-6}$ alkyl, wherein n is 1-6 and wherein each $C_{1-6}$ alkyl and $C_{1-6}$ alkylene are independently selected; or R—O—R', wherein R and R' are each taken together to form a 5-6 membered heterocyclic ring which is optionally substituted by 1-4 independently selected $C_{1-4}$ alkyl substituents). Examples of an organic ether include tetrahydrofuran, dimethyl ether, diethyl ether, diglyme and the like.

As used herein, the term "organohalide" as used herein, refers to organic compounds containing a halogen atom (e.g., Cl, Br, I, F, etc.) bonded to a carbon atom (e.g., $C_{1-6}$ haloalkyl). Examples of an organohalide include dichloromethane, chloroform, and the like.

As used herein, the term "organonitrile" as used herein, refers to any organic compound that has a —C≡N functional group (e.g., $C_{1-6}$ alkyl-CN). Examples of an organonitrile include acetonitrile and the like.

The term "oxidizing agent" as used herein refers to a compound or element that accepts an electron from an electron donor in a redox chemical reaction. Examples of oxidizing agent include Dess-Martin periodinane, sodium periodate, aluminium nitrate, ammonium cerium(IV) sulfate, chlorates (ammonium, sodium), ammonium dichromate, nitrates (ammonium, chlorine, copper (II), magnesium, nickel, sodium), nitrites (ammonium, calcium, sodium), ammonium perchlorate, permanganates (ammonium, calcium, sodium), persulfates (ammonium, sodium), antimony pentachloride, Benedict's reagent, 1,4-benzoquinone, bis(trimethylsilyl) peroxide, bromic acid, bromine, bromine monochloride, bromine pentafluoride, bromine trifluoride, bromous acid, tert-Butyl hydroperoxide, calcium bromate, calcium chlorate, calcium hypochlorite, calcium iodate, calcium permanganate, calcium peroxide, chloranil, chloric acid, chlorine, chlorine monofluoride, chlorine pentafluoride, chlorine trifluoride, meta-Chloroperoxybenzoic acid, N-chlorosuccinimide, chlorous acid, cobalt(II) chlorate, cobalt(II) nitrate, Collins reagent, copper(II) acetate, copper(II) hydroxide, Cornforth reagent, (Diacetoxyiodo)benzene, dichlorine heptoxide, 2,3-dichloro-5,6-dicyano-1,4-benzoquinone, dimethyldioxirane, dinitrogen tetroxide, dioxygen difluoride, Fehling's solution, Fenton's reaction, Fenton's reagent, ferrate(VI), ferrocenium tetrafluoroborate, fluorine, fluorine perchlorate, Frémy's salt, Haber-Weiss reaction, high-valent iron, Hill reagent, hydrazine nitrate, hydrogen peroxide, hydrogen peroxide—urea, hypobromous acid, hypochlorous acid, hypoiodous acid, iodane, iodic acid, iodine, iodine heptafluoride, iodine monochloride, iodine pentafluoride, iodine pentoxide, iodine trichloride, iodobenzene dichloride, 2-iodoxybenzoic acid, iron (III) chromate, iron(III) nitrate, Jones reagent, lithium chlorate, lithium hypochlorite, lithium nitrate, lithium nitrite, lithium perchlorate, lithium peroxide, magnesium monoperoxyphthalate, manganese(III) acetate, monosodium xenate, nitronium perchlorate, nitrosyl-O-hydroxide, nitrous acid, osmium tetroxide, oxygen, oxygen difluoride, ozone, palladium(II) nitrate, perbromic acid, perchlorate, perchloric acid, performic acid, periodatonickelates, periodic acid, periodinane, permanganic acid, peroxy acid, peroxymonosulfuric acid, potassium bromate, potassium chlorochromate, potassium chromate, potassium dichromate, potassium ferrate, potassium ferricyanide, potassium hypochlorite, potassium iodate, potassium nitrite, potassium periodate, potassium permanganate, potassium peroxide, potassium peroxymonosulfate, potassium persulfate, potassium superoxide, potassium tetraperoxochromate(V), pyridine-N-oxide, pyridinium chlorochromate, pyridinium perbromide, reoxidant, Rozen's reagent, selenic acid, selenium hexasulfide, selenium trioxide, selenous acid, silver bromate, silver chlorate, silver chromate, silver dichromate, silver iodate, silver nitrate, silver perchlorate, silver tetrafluoroborate, singlet oxygen, sodium bromate, sodium chlorite, sodium chromate, sodium dichromate, sodium hypochlorite, sodium iodate, sodium nitrite, sodium perborate, sodium percarbonate, sodium peroxide, sodium peroxycarbonate, sodium persulfate, sodium superoxide, strontium bromate, strontium nitrate, strontium peroxide, sulfuric acid, super-oxidized solution, superoxidant, telluric acid, tetrapropylammonium perruthenate, Tollens' reagent, trimethylamine N-oxide, trinitroethylorthocarbonate, trinitroethylorthoformate, tris(4-bromophenyl)ammoniumyl hexachloroantimonate, vanadium(V) oxide, zinc peroxide, and the like.

Examples of reducing agent include borohydride reducing agents (e.g., $NaBH_4$, $LiBH_4$, $NaBH_3CN$, $NaBH(OAc)_3$, diborane, $BH_3$, 9-borabicyclo[3.3.1]nonane (9-BBN), acyloxyborone, and the like), sodium hydrosulfite, diisobutyl aluminum hydride (DIBAH), diisobutylaluminiumhydride, and the like.

The Suzuki coupling reactions can be initiated using a number of palladium(0) and palladium(II) catalysts and performed under conditions known in the art (see, e.g., Miyaura and Suzuki, *Chem. Rev.* 1995, 95, 2457-2483, which is hereby incorporated in its entirety). In some embodiments, the Suzuki catalyst is a catalyst selected from RuPhos Pd G4, CataCXium® Pd G4, $Pd(PPh_3)_4$, $Pd(dppf)_2Cl_2$, dichlorobis[di-tert-butyl(p-dimethylaminophenyl)phosphino]palladium, $PdCl_2(dtbpf)$ (Pd-118), and tetrakis(tri(o-tolyl)phosphine)palladium(0). In some embodiments, the Suzuki catalyst is a catalyst selected from CataCXium® Pd G4 ((2'-(methylamino)-[1,1'-biphenyl]-2-yl)((methylsulfonyl)oxy)palladium di(1-adamantyl)-n-butylphosphine complex), CataCXium® [Pd(allyl)Cl]2, $Pd(PPh_3)_4$, $Pd(dppf)_2Cl_2$, dichlorobis[di-tert-butyl(p-dimethylaminophenyl)phosphino]palladium and $PdCl_2(dtbpf)$ (Pd-118).

The Suzuki catalyst can be purchased commercially: RuPhos Pd G4 (Sigma-Aldrich, cat. #804290), CataCXium® Pd G4 (Sigma-Aldrich, cat. #900349; ((2'-(methylamino)-[1,1'-biphenyl]-2-yl)((methylsulfonyl)oxy)palladium di(1-adamantyl)-n-butylphosphine complex), and $Pd(PPh_3)_4$ (Sigma-Aldrich, cat. #697265), $Pd(dppf)_2Cl_2$ (Sigma-Aldrich, cat. #697230). Structures of exemplary catalyst are also shown below:

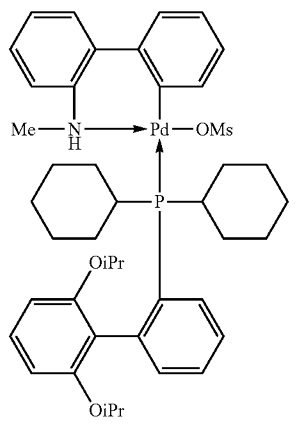

RuPhos Pd G4

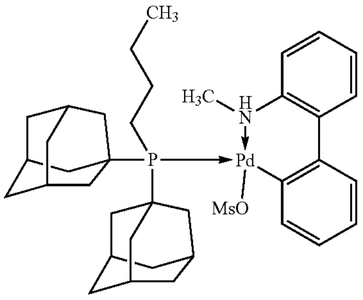

CataCXium® Pd G4

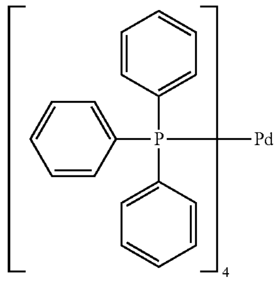

$Pd(PPh_3)_4$

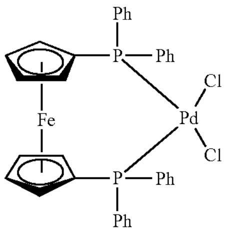

$Pd(dppf)_2Cl_2$

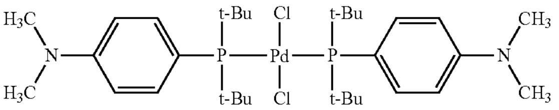

dichlorobis[di-tert-butyl(p-dimethylaminophenyl)phosphino]palladium

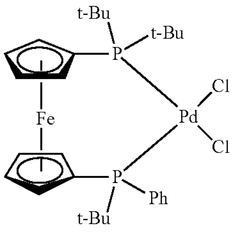

$PdCl_2(dtbpf)$ (Pd-118)

A chlorinating agent can be, for example, oxalyl chloride, phosphorus oxychloride, diphosgene, thionyl chloride, sulfuryl chloride, or phosphorus pentachloride.

Methods of Use

Solid forms and salt forms described of the present disclosure can inhibit the activity of PD-1/PD-L1 protein/protein interaction and, thus, are useful in treating diseases and disorders associated with activity of PD-1 and the diseases and disorders associated with PD-L1 including its interaction with other proteins such as PD-1 and B7-1 (CD80). In certain embodiments, the solid forms and salt forms described of the present disclosure are useful for therapeutic administration to enhance, stimulate and/or increase immunity in cancer, chronic infection or sepsis, including enhancement of response to vaccination. In some embodiments, the present disclosure provides a method for inhibiting the PD-1/PD-L1 protein/protein interaction. The method includes administering to an individual or a patient a solid form, salt form or crystalline form thereof of Compound of Formula 1. The solid forms and salt forms described of the present disclosure can be used alone, in combination with other agents or therapies or as an adjuvant or neoadjuvant for the treatment of diseases or disorders, including cancer or infection diseases. For the uses described herein, any of the solid forms and salt forms described of the disclosure, including any of the embodiments or claims thereof, may be used.

The solid forms and salt forms described of the present disclosure inhibit the PD-1/PD-L1 protein/protein interaction, resulting in a PD-1 pathway blockade. The blockade of PD-1 can enhance the immune response to cancerous cells and infectious diseases in mammals, including humans. In some embodiments, the present disclosure provides treatment of an individual or a patient in vivo using a solid form, salt form or crystalline form thereof of Compound of Formula 1 such that growth of cancerous tumors is inhibited. A solid form, salt form or crystalline form thereof of Compound of Formula 1, can be used to inhibit the growth of cancerous tumors. Alternatively, a solid form, salt form or crystalline form thereof of Compound of Formula 1, can be used in conjunction with other agents or standard cancer treatments, as described below. In one embodiment, the present disclosure provides a method for inhibiting growth of tumor cells in vitro. The method includes contacting the tumor cells in vitro with a solid form, salt form or crystalline form thereof of Compound of Formula 1. In another embodiment, the present disclosure provides a method for inhibiting growth of tumor cells in an individual or a patient. The method includes administering to the individual or patient in need thereof a therapeutically effective amount of a solid form, salt form or crystalline form thereof of Compound of Formula 1.

In some embodiments, provided herein is a method for treating cancer. The method includes administering to a patient in need thereof, a therapeutically effective amount of a solid form, salt form or crystalline form thereof of Compound of Formula 1. Examples of cancers include those whose growth may be inhibited using salts of the disclosure and cancers typically responsive to immunotherapy.

In some embodiments, the present disclosure provides a method of enhancing, stimulating and/or increasing the immune response in a patient. The method includes administering to the patient in need thereof a therapeutically effective amount of a solid form, salt form or crystalline form thereof of Compound of Formula 1.

Examples of cancers that are treatable using the solid forms and salt forms described of the present disclosure include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The solid forms and salt forms described of the present disclosure are also useful for the treatment of metastatic cancers, especially metastatic cancers that express PD-L1.

In some embodiments, cancers treatable with solid forms and salt forms described of the present disclosure include melanoma (e.g., metastatic malignant melanoma, cutaneous melanoma), renal cancer (e.g., clear cell carcinoma), prostate cancer (e.g., hormone refractory prostate adenocarcinoma), breast cancer (e.g., breast invasive carcinoma), colon cancer, lung cancer (e.g., non-small cell lung cancer and small cell lung cancer), squamous cell head and neck cancer (e.g., squamous cell carcinoma of the head and neck), urothelial cancer (e.g., bladder cancer, nonmuscle invasive bladder cancer (NMIBC)) and cancers with high microsatellite instability ($MSI^{high}$). Additionally, the disclosure includes refractory or recurrent malignancies whose growth may be inhibited using the salts of the disclosure.

In some embodiments, cancers that are treatable using the solid forms and salt forms described of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CMIL), DLBCL, mantle cell lymphoma, Non-Hodgkin lymphoma (including relapsed or refractory NHL and recurrent follicular), Hodgkin lymphoma or multiple myeloma) and combinations of said cancers.

In some embodiments, cancers that are treatable using the solid forms and salt forms described of the present disclosure include, but are not limited to, cholangiocarcinoma, bile duct cancer, biliary tract cancer, triple negative breast cancer, rhabdomyosarcoma, small cell lung cancer, leiomyosarcoma, hepatocellular carcinoma, Ewing's sarcoma, brain cancer, brain tumor, astrocytoma, neuroblastoma, neurofibroma, basal cell carcinoma, chondrosarcoma, epithelioid sarcoma, eye cancer, Fallopian tube cancer, gastrointestinal cancer, gastrointestinal stromal tumors, hairy cell leukemia, intestinal cancer, islet cell cancer, oral cancer, mouth cancer, throat cancer, laryngeal cancer, lip cancer, mesothelioma, neck cancer, nasal cavity cancer, ocular cancer, ocular melanoma, pelvic cancer, rectal cancer, renal cell carcinoma, salivary gland cancer, sinus cancer, spinal cancer, tongue cancer, tubular carcinoma, urethral cancer, and ureteral cancer.

In some embodiments, the solid forms and salt forms described of the present disclosure can be used to treat sickle cell disease and sickle cell anemia.

In some embodiments, diseases and indications that are treatable using the solid forms and salt forms described of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), and essential thrombocytosis (ET)), myelodysplasia syndrome (MDS), T-cell acute lymphoblastic lymphoma (T-ALL) and multiple myeloma (MM).

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, hamartoma, and teratoma.

Exemplary lung cancers include non-small cell lung cancer (NSCLC) (e.g., squamous cell NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Exemplary gastrointestinal cancers include cancers of the esophagus (carcinoma, squamous cell carcinoma, adenocarcinoma, leiomyosarcoma, lymphoma), stomach (carcinoma, lymphoma, leiomyosarcoma, adenocarcinoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer (e.g., colorectal adenocarcinoma).

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma). In some embodiments, the cancer is a urological cancer (e.g., papillary kidney carcinoma, testicular germ cell cancer, chromophobe renal cell carcinoma, clear cell renal carcinoma, or prostate adenocarcinoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors.

Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, serous adenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma (e.g., cutaneous squamous cell carcinoma), Kaposi's sarcoma, moles dysplastic nevi, lipoma, angioma, dermatofibroma, and keloids. In some embodiments, diseases and indications that are treatable using the salts of the present disclosure include, but are not limited to, sickle cell disease (e.g., sickle cell anemia), triple-negative breast cancer (TNBC), myelodysplastic syndromes, testicular cancer, bile duct cancer, esophageal cancer, and urothelial carcinoma.

PD-1 pathway blockade with solid forms and salt forms described of the present disclosure can also be used for treating infections such as viral, bacteria, fungus and parasite infections. The present disclosure provides a method for treating infections such as viral infections. The method includes administering to a patient in need thereof, a therapeutically effective amount of a solid form, salt form or crystalline form thereof of Compound of Formula 1. Examples of viruses causing infections treatable by methods of the present disclosure include, but are not limited to, human immunodeficiency virus, human papillomavirus, influenza, hepatitis A, B, C or D viruses, adenovirus, poxvirus, herpes simplex viruses, human cytomegalovirus, severe acute respiratory syndrome virus, ebola virus, and measles virus. In some embodiments, viruses causing infections treatable by methods of the present disclosure include, but are not limited to, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus, tuberculosis and arboviral encephalitis virus.

The present disclosure provides a method for treating bacterial infections. The method includes administering to a patient in need thereof, a therapeutically effective amount of a solid form, salt form or crystalline form thereof of Compound of Formula 1. Non-limiting examples of pathogenic bacteria causing infections treatable by methods of the disclosure include chlamydia, rickettsial bacteria, mycobacteria, staphylococci, streptococci, pneumococci, meningococci and conococci, *Klebsiella, Proteus, Serratia,*

*Pseudomonas, Legionella*, diphtheria, *Salmonella*, bacilli, cholera, *tetanus*, botulism, *anthrax*, plague, leptospirosis, and Lyme's disease bacteria.

The present disclosure provides a method for treating fungus infections. The method includes administering to a patient in need thereof, a therapeutically effective amount of a solid form, salt form or crystalline form thereof of Compound of Formula 1. Non-limiting examples of pathogenic fungi causing infections treatable by methods of the disclosure include *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum.*

The present disclosure provides a method for treating parasite infections. The method includes administering to a patient in need thereof, a therapeutically effective amount of a solid form, salt form or crystalline form thereof of Compound of Formula 1. Non-limiting examples of pathogenic parasites causing infections treatable by methods of the disclosure include *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis.*

The present disclosure provides a method for treating neurodegenerative diseases or disorders. The method includes administering to a patient in need thereof, a therapeutically effective amount of a solid form, salt form or crystalline form thereof of Compound of Formula 1. Non-limiting examples of neurodegenerative diseases or disorders include Alzheimer's disease, Parkinson's disease, Huntington's disease, prion disease, Motor neurone diseases, Spinocerebellar ataxia and Spinal muscular atrophy.

It is believed that solid forms and salt forms, may possess satisfactory pharmacological profile and promising biopharmaceutical properties, such as toxicological profile, metabolism and pharmacokinetic properties, solubility, and permeability. It will be understood that determination of appropriate biopharmaceutical properties is within the knowledge of a person skilled in the art, e.g., determination of cytotoxicity in cells or inhibition of certain targets or channels to determine potential toxicity.

The terms "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active solid form, salt form or crystalline form thereof that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the solid forms and salt forms are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

Combination Therapies

Immune-Checkpoint Therapies

Solid forms and salt forms described of the present disclosure can be used in combination with one or more immune checkpoint inhibitors for the treatment of diseases, such as cancer or infections. Exemplary immune checkpoint inhibitors include inhibitors against immune checkpoint molecules such as CBL-B, CD20, CD122, CD96, CD73, CD47, CSF1R, JAK, PI3K delta, PI3K gamma, TAM, arginase, HPK1, A2AR, B7-H3, B7-H4, BTLA, CTLA-4, LAG3, TIM3, TIGIT, CD112R, VISTA, PD-1, PD-L1 and PD-L2. In some embodiments, the immune checkpoint molecule is a stimulatory checkpoint molecule selected from CD27, CD28, CD40, ICOS, OX40, GITR and CD137 (4-1BB). In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT, and VISTA. In some embodiments, the solid forms and salt forms described herein provided herein can be used in combination with one or more agents selected from KIR inhibitors, TIGIT inhibitors, LAIR1 inhibitors, CD160 inhibitors, 2B4 inhibitors and TGF beta inhibitors.

In some embodiments, the solid forms and salt forms provided herein can be used in combination with one or more agonists of immune checkpoint molecules, e.g., OX40, CD27, GITR, and CD137 (also known as 4-1BB).

In some embodiments, the agonist of an immune checkpoint molecule is an agonist of OX40, CD27, CD28, GITR, ICOS, CD40, TLR7/8, and CD137 (also known as 4-1B).

In some embodiments, the agonist of CD137 is urelumab. In some embodiments, the agonist of CD137 is utomilumab.

In some embodiments, the agonist of an immune checkpoint molecule is an agonist of CD40. In some embodiments, the agonist of CD40 is CP-870893, ADC-1013, CDX-1140, SEA-CD40, RO7009789, JNJ-64457107, APX-005M, or Chi Lob 7/4.

In some embodiments, the agonist of an immune checkpoint molecule is an agonist of ICOS. In some embodiments, the agonist of ICOS is GSK-3359609, JTX-2011, or MEDI-570.

In some embodiments, the agonist of an immune checkpoint molecule is an agonist of CD28. In some embodiments, the agonist of CD28 is theralizumab.

In some embodiments, the agonist of an immune checkpoint molecule is an agonist of CD27. In some embodiments, the agonist of CD27 is varlilumab.

In some embodiments, the agonist of an immune checkpoint molecule is an agonist of TLR7/8. In some embodiments, the agonist of TLR7/8 is MEDI9197.

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, cemiplimab, spartalizumab, camrelizumab, cetrelimab, toripalimab, sintilimab, SHR-1210, PDR001, MGA012, PDR001, AB122, AMP-224, JTX-4014, BGB-108, BCD-100, BAT1306, LZM009, AK105, HLX10, or TSR-042. In some embodiments, the anti-PD-1 monoclonal antibody is nivolumab or pembrolizumab. In some embodiments, the anti-PD1 antibody is pembrolizumab. In some embodiments, the anti-PD-1 monoclonal antibody is MGA012. In some embodiments, the anti-PD1 antibody is SHR-1210. Other anti-cancer agent (s) include antibody therapeutics such as 4-1BB (e.g. urelumab, utomilumab).

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), durvalumab (Imfinzi®), atezolizumab (Tecentriq®), Avelumab (Bavencio®), MSB0010718C, tislelizumab, FAZ053, KN035, CS1001, SHR-1316, CBT-502, A167, STI-A101, CK-301, BGB-A333, MSB-2311, HLX20, or LY3300054. In some embodiments, the anti-PD-L1 monoclonal antibody is MPDL3280A or MEDI4736.

In some embodiments, the inhibitor of an immune checkpoint molecule is an inhibitor of PD-1 and PD-L1, e.g., an anti-PD-1/PD-L1 bispecific antibody. In some embodiments, the anti-PD-1/PD-L1 bispecific antibody is MCLA-136.

In some embodiments, the inhibitor is MCLA-145.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of PD-1 and CTLA-4, e.g., an anti-PD-1/CTLA-4 bispecific antibody. In some embodiments, the anti-PD-1/CTLA-4 antibody is AK104.

In some embodiments, the inhibitor of an immune checkpoint molecule is an inhibitor of LAG3, e.g., an anti-LAG3 antibody. In some embodiments, the anti-LAG3 antibody is BMS-986016, LAG525, INCAGN2385, or eftilagimod alpha (IMP321).

In some embodiments, the inhibitor of an immune checkpoint molecule is an inhibitor of CD73. In some embodiments, the inhibitor of CD73 is oleclumab. In some embodiments, the inhibitor of CD73 is MEDI9447.

In some embodiments, the inhibitor of an immune checkpoint molecule is an inhibitor of TIGIT. In some embodiments, the inhibitor of TIGIT is OMP-31M32.

In some embodiments, the inhibitor of an immune checkpoint molecule is an inhibitor of VISTA. In some embodiments, the inhibitor of VISTA is JNJ-61610588 or CA-170.

In some embodiments, the inhibitor of an immune checkpoint molecule is an inhibitor of B7-H3. In some embodiments, the inhibitor of B7-H3 is enoblituzumab, MGD009, or 8H9.

In some embodiments, the inhibitor of an immune checkpoint molecule is an inhibitor of KIR. In some embodiments, the inhibitor of KIR is lirilumab or IPH4102.

In some embodiments, the inhibitor of an immune checkpoint molecule is an inhibitor of A2aR. In some embodiments, the inhibitor of A2aR is CPI-444.

In some embodiments, the inhibitor of an immune checkpoint molecule is an inhibitor of TGF-beta. In some embodiments, the inhibitor of TGF-beta is trabedersen, galusertinib, or M7824.

In some embodiments, the inhibitor of an immune checkpoint molecule is an inhibitor of PI3K-gamma. In some embodiments, the inhibitor of PI3K-gamma is IPI-549.

In some embodiments, the inhibitor of an immune checkpoint molecule is an inhibitor of CD47. In some embodiments, the inhibitor of CD47 is Hu5F9-G4 or TTI-621.

In some embodiments, the inhibitor of an immune checkpoint molecule is an inhibitor of CD70. In some embodiments, the inhibitor of CD70 is cusatuzumab or BMS-936561.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the agonist of an immune checkpoint molecule is an agonist of GITR, e.g., an anti-GITR antibody. In some embodiments, the agonist is TRX518, MK-4166, INCAGN1876, MK-1248, AMG228, BMS-986156, GWN323, MEDI1873, or MEDI6469.

In some embodiments, the agonist of an immune checkpoint molecule is an agonist of OX40, e.g., OX40 agonist antibody or OX40L fusion protein. In some embodiments, the anti-OX40 antibody is MEDI0562, MOXR-0916, PF-04518600, GSK3174998, BMS-986178, or 9B12. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The solid forms and salt forms of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor. In some embodiments, the bispecific antibody binds to PD-1 and PD-L1. In some embodiments, the bispecific antibody that binds to PD-1 and PD-L1 is MCLA-136. In some embodiments, the bispecific antibody binds to PD-L1 and CTLA-4. In some embodiments, the bispecific antibody that binds to PD-L1 and CTLA-4 is AK104.

In some embodiments, the solid forms and salt forms of the disclosure can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196.

As provided throughout, the additional compounds, inhibitors, agents, etc. can be combined with the present solid form, salt form or crystalline form thereof in a single or continuous dosage form, or they can be administered simultaneously or sequentially as separate dosage forms.

Cancer Therapies

Cancer cell growth and survival can be impacted by dysfunction in multiple biological pathways. Thus, it may be useful to combine inhibitors of different mechanisms, such as enzyme inhibitors, signal transduction inhibitors, inhibitors of chromatin dynamics or modulators of immune responses, to treat such conditions. Targeting more than one signaling pathway (or more than one biological molecule involved in a given signaling pathway) may reduce the likelihood of drug-resistance arising in a cell population, or reduce the toxicity of treatment.

The solid forms and salt forms of the present disclosure can be used in combination with one or more other therapies for the treatment of diseases, such as cancer or infections. Examples of diseases and indications treatable with combination therapies include those as described herein. Examples of cancers include solid tumors and non-solid tumors, such as liquid tumors, blood cancers. Examples of infections include viral infections, bacterial infections, fungus infections or parasite infections. For example, the solid forms and salt forms of the present disclosure can be combined with one or more inhibitors of the following kinases for the treatment of cancer: Akt1, Akt2, Akt3, BCL2, CDK, TGF-□R, PKA, PKG, PKC, CaM-kinase, phosphorylase kinase, MEKK, ERK, MAPK, mTOR, EGFR, HER2, HER3, HER4, INS-R, IDH2, IGF-1R, IR-R, PDGFDR, PDGFDR, PI3K (alpha, beta, gamma, delta, and multiple or selective), CSF1R, KIT, FLK-II, KDR/FLK-1, FLK-4, fit-1, FGFR1, FGFR2, FGFR3, FGFR4, c-Met, PARP, Ron, Sea, TRKA, TRKB, TRKC, TAM kinases (Axl, Mer, Tyro3), FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. In some embodiments, the solid forms and salt forms of the present disclosure can be combined with one or more of the following inhibitors for the treatment of cancer or infections. Non-limiting examples of inhibitors that can be combined with the solid forms and salt forms of the present disclosure for treatment of cancer and infections include an FGFR inhibitor (FGFR1, FGFR2, FGFR3 or FGFR4, e.g., pemigatinib (INCY54828), INCB62079), an EGFR (also known as ErB-1 or HER-1) inhibitor (e.g., erlotinib, gefitinib, vandetanib, orsimertinib, cetuximab, necitumumab, or panitumumab), a VEGFR inhibitor or pathway blocker (e.g., bevacizumab, pazopanib, sunitinib, sorafenib, axitinib, regorafenib, ponatinib, cabozantinib, vandetanib, ramucirumab, lenvatinib, ziv-aflibercept), a PARP inhibitor (e.g., olaparib, rucaparib, veliparib or niraparib), a JAK inhibitor (JAK1 and/or JAK2, e.g., ruxolitinib, baricitinib or itacitinib (INCB39110)), an IDO inhibitor (e.g., epacadostat, NLG919, or BMS-986205, MK7162), an LSD1 inhibitor (e.g., INCB59872 and INCB60003), a TDO inhibitor, a PI3K-delta inhibitor (e.g., Parsaclisib (INCB50465) and INCB50797), a PI3K-gamma inhibitor such as PI3K-gamma selective inhibitor, a Pim inhibitor (e.g., INCB53914), an EGFR inhibitor (also known as ErB-1 or HER-1; e.g., erlotinib, gefitinib, vandetanib, orsimertinib, cetuximab, necitumumab, or panitumumab), a VEGFR inhibitor or pathway blocker (e.g., bevacizumab, pazopanib, sunitinib, sorafenib, axitinib, regorafenib, ponatinib, cabozantinib, vandetanib, ramucirumab, lenvatinib, ziv-aflibercept), a PARP inhibitor (e.g., olaparib, rucaparib, veliparib, talazoparib, or niraparib), a CSF1R inhibitor, a TAM receptor tyrosine kinase (Tyro-3, Axl, and Mer), an adenosine receptor antagonist (e.g., A2a/A2b receptor antagonist), an HPK1 inhibitor, a chemokine receptor inhibitor (e.g., CCR2 or CCR5 inhibitor), a SHP1/2 phosphatase inhibitor, a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643), an arginase inhibitor (INCB001158), a PARP inhibitor (such as rucaparib or olaparib), sitravatinib, a B-Raf inhibitor-MEK inhibitor combination (such as encorafenib plus binimetinib, dabrafenib plus trametinib, or cobimetinib plus vemurafenib), and an adenosine receptor antagonist or combinations thereof.

In some embodiments, the solid forms and salt forms of the present disclosure can be combined with a TLR7 agonist (e.g., imiquimod).

The solid forms and salt forms of the present disclosure can further be used in combination with other methods of treating cancers, for example by chemotherapy, irradiation therapy, tumor-targeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, bispecific or multi-specific antibody, antibody drug conjugate, adoptive T cell transfer, Toll receptor agonists, STING agonists, RIG-I agonists, oncolytic virotherapy and immunomodulating small molecules, including thalidomide or JAK1/2 inhibitor, PI3Kδ inhibitor and the like. The solid forms and salt forms can be administered in combination with one or more anti-cancer drugs, such as a chemotherapeutic agent. Examples of chemotherapeutics include any of abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat and zoledronate.

Other anti-cancer agent(s) include antibody therapeutics such as trastuzumab (Herceptin), antibodies to costimulatory molecules such as CTLA-4 (e.g., ipilimumab), 4-1BB (e.g., urelumab, utomilumab), antibodies to PD-1 and PD-L1, or antibodies to cytokines (IL-10, TGF-β, etc.). Examples of antibodies to PD-1 and/or PD-L1 that can be combined with salts of the present disclosure for the treatment of cancer or infections such as viral, bacteria, fungus and parasite infections include, but are not limited to nivolumab, pembrolizumab, atezolizumab, durvalumab, avelumab and SHR-1210.

The solid forms and salt forms of the present disclosure can further be used in combination with one or more anti-inflammatory agents, steroids, immunosuppressants or therapeutic antibodies.

The solid forms and salt forms, can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The solid forms and salt forms, can be used in combination with a vaccination protocol for the treatment of cancer.

In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the solid forms and salt forms of the present disclosure can be used in combination with tumor specific antigen such as heat shock proteins isolated from tumor tissue itself. In some embodiments, the solid forms and salt forms, can be combined with dendritic cells immunization to activate potent anti-tumor responses.

The solid forms and salt forms of the present disclosure can be used in combination with bispecific macrocyclic peptides that target Fe alpha or Fe gamma receptor-expressing effectors cells to tumor cells. The solid forms and salt forms of the present disclosure can also be combined with macrocyclic peptides that activate host immune responsiveness.

The solid forms and salt forms of the present disclosure can be used in combination with bone marrow transplant for the treatment of a variety of tumors of hematopoietic origin.

The solid forms and salt forms, can be used in combination with vaccines, to stimulate the immune response to pathogens, toxins, and self antigens. Examples of pathogens for which this therapeutic approach may be particularly useful, include pathogens for which there is currently no effective vaccine, or pathogens for which conventional vaccines are less than completely effective. These include, but are not limited to, HIV, Hepatitis (A, B, & C), Influenza, Herpes, *Giardia*, Malaria, *Leishmania, Staphylococcus aureus, Pseudomonas Aeruginosa.*

Viruses causing infections treatable by methods of the present disclosure include, but are not limited to human papillomavirus, influenza, hepatitis A, B, C or D viruses, adenovirus, poxvirus, herpes simplex viruses, human cytomegalovirus, severe acute respiratory syndrome virus, ebola virus, measles virus, herpes virus (e.g., VZV, HSV-1, HAV-6, HSV-II, and CMV, Epstein Barr virus), flaviviruses, echovirus, rhinovirus, coxsackie virus, coronavirus, respiratory syncytial virus, mumpsvirus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Pathogenic bacteria causing infections treatable by methods of the disclosure include, but are not limited to, chlamydia, rickettsial bacteria, mycobacteria, staphylococci, streptococci, pneumococci, meningococci and conococci, *Klebsiella, Proteus, Serratia, Pseudomonas, Legionella*, diphtheria, *Salmonella*, bacilli, cholera, *tetanus*, botulism, *anthrax*, plague, leptospirosis, and Lyme's disease bacteria.

Pathogenic fungi causing infections treatable by methods of the disclosure include, but are not limited to, *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum.*

Pathogenic parasites causing infections treatable by methods of the disclosure include, but are not limited to, *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis.*

When more than one pharmaceutical agent is administered to a patient, they can be administered simultaneously, separately, sequentially, or in combination (e.g., for more than two agents).

Formulation, Dosage Forms and Administration

When employed as pharmaceuticals, the solid forms and salt forms of the present disclosure can be administered in the form of pharmaceutical compositions. Thus the present disclosure provides a composition comprising a solid form, salt form or crystalline form thereof of Compound of Formula 1, and at least one pharmaceutically acceptable carrier or excipient. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which comprise, as the active ingredient, the solid form, salt form or crystalline form thereof of the present disclosure, in combination with one or more pharmaceutically acceptable carriers or excipients. In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active salt, soft and hard gelatin capsules, suppositories, sterile injectable solutions and sterile packaged powders.

In preparing a formulation, the active solid form, salt form or crystalline form thereof can be milled to provide the appropriate particle size prior to combining with the other ingredients. If the active salt is substantially insoluble, it can be milled to a particle size of less than 200 mesh. If the active solid form, salt form or crystalline form thereof is substantially water soluble, the particle size can be adjusted by milling to provide a substantially uniform distribution in the formulation, e.g., about 40 mesh.

The solid forms and salt forms of the present disclosure may be milled using known milling procedures such as wet milling to obtain a particle size appropriate for tablet formation and for other formulation types. Finely divided (nanoparticulate) preparations of the solid forms and salt forms of the present disclosure can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one solid form, salt form or crystalline form thereof of Compound of Formula 1. In some embodiments, the silicified microcrystalline cellulose comprises about 98% microcrystalline cellulose and about 2% silicon dioxide w/w.

In some embodiments, the composition is a sustained release composition comprising at least one solid form, salt form or crystalline form thereof of Compound of Formula 1, and at least one pharmaceutically acceptable carrier or excipient. In some embodiments, the composition comprises at least one solid form, salt form or crystalline form thereof of Compound of Formula 1, and at least one component selected from microcrystalline cellulose, lactose monohydrate, hydroxypropyl methylcellulose and polyethylene oxide. In some embodiments, the composition comprises at least one solid form, salt form or crystalline form thereof of Compound of Formula 1, and microcrystalline cellulose, lactose monohydrate and hydroxypropyl methylcellulose. In some embodiments, the composition comprises at least one solid form, salt form or crystalline form thereof of Compound of Formula 1, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active solid form, salt form or crystalline form thereof may be effective over a wide dosage range and is generally administered in a therapeutically effective amount. It will be understood, however, that the amount of the solid form, salt form or crystalline form thereof actually administered will usually be determined by a physician, according to the relevant circumstances, including the condition to be treated, the chosen route of administration, the actual solid form, salt form or crystalline form thereof administered, the age, weight, and response of the individual patient, the severity of the patient's symptoms and the like.

The therapeutic dosage of a solid form, salt form or crystalline form thereof of the present invention can vary according to, e.g., the particular use for which the treatment is made, the manner of administration of the solid form, salt form or crystalline form thereof, the health and condition of the patient, and the judgment of the prescribing physician. The proportion or concentration of a solid form, salt form or crystalline form thereof of the invention in a pharmaceutical composition can vary depending upon a number of factors including dosage, chemical characteristics (e.g., hydrophobicity), and the route of administration. For example, the solid forms and salt forms of the present disclosure can be provided in an aqueous physiological buffer solution containing about 0.1 to about 10% w/v of the salt for parenteral administration. Some typical dose ranges are from about 1 □g/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the solid form, salt form or crystalline form thereof selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid preformulation composition containing a homogeneous mixture of a solid form, salt form or crystalline form thereof of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the solid form, salt form or crystalline form thereof and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2 or at least about 5 wt % of the salt of the invention. The topical formulations can be suitably packaged in tubes of, e.g., 100 g which are optionally associated with instructions for the treatment of the select indication, e.g., psoriasis or other skin condition.

The amount of solid form, salt form or crystalline form thereof or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the preparations typically will be between 3 and 11, more preferably from 5 to 9 and most preferably from 7 to 8.

The therapeutic dosage of a solid form, salt form or crystalline form thereof of the present invention can vary according to, e.g., the particular use for which the treatment is made, the manner of administration of the solid form, salt form or crystalline form thereof, the health and condition of the patient, and the judgment of the prescribing physician. The proportion or concentration of a solid form, salt form or crystalline form thereof of the invention in a pharmaceutical composition can vary depending upon a number of factors including dosage, chemical characteristics (e.g., hydrophobicity), and the route of administration. For example, the solid forms and salt forms of the present disclosure can be provided in an aqueous physiological buffer solution containing about 0.1 to about 10% w/v of the salt for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the salt selected, formulation of the excipient, and its route of administration. Effective doses can be extrapolated from dose-response curves derived from in vitro or animal model test systems.

Labeled Compounds and Assay Methods

The solid forms and salt forms of the present disclosure can further be useful in investigations of biological processes in normal and abnormal tissues. Thus, another aspect of the present invention relates to labeled solid forms and salt forms of the present disclosure (radio-labeled, fluorescent-labeled, etc.) that would be useful not only in imaging techniques but also in assays, both in vitro and in vivo, for localizing and quantitating PD-1 or PD-L1 protein in tissue samples, including human, and for identifying PD-L1 ligands by inhibition binding of a labeled compound. Accordingly, the present invention includes PD-1/PD-L1 binding assays that contain such labeled salts.

The present invention further includes isotopically-substituted solid forms and salt forms of the present disclosure. An "isotopically-substituted" solid form, salt form or crystalline form thereof is a solid form, salt form or crystalline form thereof of the invention where one or more atoms are replaced or substituted by an atom having the same atomic number but a different atomic mass or mass number, e.g., a different atomic mass or mass number from the atomic mass or mass number typically found in nature (i.e., naturally occurring). It is to be understood that a "radio-labeled" solid form, salt form or crystalline form thereof is a solid form, salt form or crystalline form thereof that has incorporated at least one isotope that is radioactive (e.g., radionuclide). Suitable radionuclides that may be incorporated in salts of the present invention include but are not limited to $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled salts will depend on the specific application of that radio-labeled solid form, salt form or crystalline form thereof. For example, for in vitro PD-L1 protein labeling and competition assays, solid form, salt form or crystalline form thereof that incorporate $^{3}H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

In some embodiments, the radionuclide is selected from the group consisting of $^{3}H$, $^{14}C$, $^{125}I$, $^{35}S$ and $^{82}Br$. Synthetic methods for incorporating radio-isotopes into organic compounds and salts are known in the art.

Specifically, a labeled solid form, salt form or crystalline form thereof of the invention can be used in a screening assay to identify and/or evaluate compounds. For example, a newly synthesized or identified solid form, salt form or crystalline form thereof (i.e., test solid form, salt form or crystalline form thereof) which is labeled can be evaluated for its ability to bind a PD-L1 protein by monitoring its concentration variation when contacting with the PD-L1 protein, through tracking of the labeling. For example, a test solid form, salt form or crystalline form thereof (labeled) can be evaluated for its ability to reduce binding of another compound which is known to bind to a PD-L1 protein (i.e., standard compound). Accordingly, the ability of a test solid form, salt form or crystalline form thereof to compete with the standard compound for binding to the PD-L1 protein directly correlates to its binding affinity. Conversely, in some other screening assays, the standard compound is labeled and test solid form, salt form or crystalline form thereof are unlabeled. Accordingly, the concentration of the labeled standard compound is monitored in order to evaluate the competition between the standard compound and the test solid form, salt form or crystalline form thereof, and the relative binding affinity of the test solid form, salt form or crystalline form thereof is thus ascertained.

Kits

The present disclosure also includes pharmaceutical kits useful, e.g., in the treatment or prevention of diseases or disorders associated with the activity of PD-L1 including its interaction with other proteins such as PD-1 and B7-1 (CD80), such as cancer or infections, which include one or more containers containing a pharmaceutical composition comprising a therapeutically effective amount of a solid form, salt form or crystalline form thereof of Compound of Formula 1, or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The following abbreviations may be used herein: aq. (aqueous); br (broad); d (doublet); dd (doublet of doublets); DCM (dichloromethane); DMF (N,N-dimethylformamide); DMSO (dimethylsulfoxide); Et (ethyl); EtOAc (ethyl acetate); EtOH (ethanol); g (gram(s)); h (hour(s)); HPLC (high performance liquid chromatography); Hz (hertz); IPAc (isopropyl acetate); J (coupling constant); LCMS (liquid chromatography-mass spectrometry); m (multiplet); M (molar); MS (Mass spectrometry); Me (methyl); MeCN (acetonitrile); MeOH (methanol); mg (milligram(s)); MIBK (methyl isobutyl ketone); min. (minutes(s)); mL (milliliter (s)); mmol (millimole(s)); MTBE (tert-butyl methyl ether); nM (nanomolar); NMR (nuclear magnetic resonance spectroscopy); Ph (phenyl); r.t. (room temperature), s (singlet); t (triplet or tertiary); TBS (tert-butyldimethylsilyl); tert (tertiary); tt (triplet of triplets); TFA (trifluoroacetic acid); THF (tetrahydrofuran); μg (microgram(s)); μL (microliter(s)); μM (micromolar); wt % (weight percent).

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The solid forms and salt forms of the present disclosure of the Examples have been found to inhibit the activity of PD-1/PD-L1 protein/protein interaction according to at least one assay described herein.

Embodiments

1. A crystalline form of the compound of formula 1 or a pharmaceutically acceptable salt thereof:

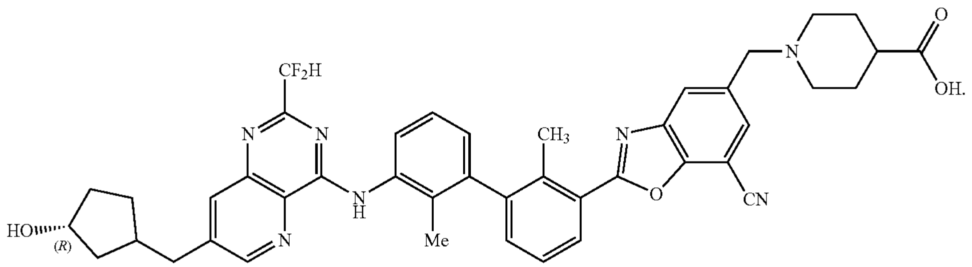

2. The crystalline form of embodiment 1, wherein the compound of formula 1, or the pharmaceutically acceptable salt thereof, is the free base of the compound of formula 1.

3. The crystalline form of embodiment 2, wherein the free base of the compound of formula 1 is a sesquihydrate.

4. The crystalline form of embodiment 2 or 3, having Form I.

5. The crystalline form of embodiment 4, having an X-ray powder diffraction (XRPD) pattern substantially as shown in FIG. 1.

6. The crystalline form of embodiment 4 or 5, having a differential scanning calorimetry (DSC) thermogram substantially as depicted in FIG. 2.

7. The crystalline form of any one of embodiments 4-6, having a thermogravimetric analysis (TGA) thermogram substantially as depicted in FIG. 2.

8. The crystalline form of any one of embodiments 4-6, having at least one XRPD peak, in terms of 2-theta (0.2 degrees), selected from 7.0, 8.5, 10.0, 10.6, 14.6, 15.2, 15.8, 17.2, 20.1, 21.1, 23.9, 24.8, 26.1, 28.1, 29.6, and 30.2 degrees.

9. The crystalline form of any one of embodiments 4-6, having at least two XRPD peaks, in terms of 2-theta (±0.2 degrees), selected from 7.0, 8.5, 10.0, 10.6, 14.6, 15.2, 15.8, 17.2, 20.1, 21.1, 23.9, 24.8, 26.1, 28.1, 29.6, and 30.2 degrees.

10. The crystalline form of any one of embodiments 4-6, having at least three XRPD peaks, in terms of 2-theta (±0.2 degrees), selected from 7.0, 8.5, 10.0, 10.6, 14.6, 15.2, 15.8, 17.2, 20.1, 21.1, 23.9, 24.8, 26.1, 28.1, 29.6, and 30.2 degrees.

11. The crystalline form of any one of embodiments 4-6, having at least four XRPD peaks, in terms of 2-theta (±0.2 degrees), selected from 7.0, 8.5, 10.0, 10.6, 14.6, 15.2, 15.8, 17.2, 20.1, 21.1, 23.9, 24.8, 26.1, 28.1, 29.6, and 30.2 degrees.

12. The crystalline form of any one of embodiments 4-6, having characteristic XRPD peaks, in terms of 2-theta (0.2 degrees), at 7.0, 8.5, 10.0, 10.6, 14.6, 15.2, 15.8, 17.2, 20.1, 21.1, 23.9, 24.8, 26.1, 28.1, 29.6, and 30.2 degrees.

13. The crystalline form of any one of embodiments 4-12, having two endothermic peaks with an onset temperature (±3° C.) at 35° C. and a maximum temperature (±3° C.) at 68° C., and an onset temperature (±3° C.) at 161° C. and a maximum temperature (±3° C.) at 169° C. in a DSC thermogram.

14. The crystalline form of embodiment 2, having Form II.

15. The crystalline form of embodiment 14, having an XRPD pattern as substantially shown in FIG. 3.

16. The crystalline form of embodiment 14 or 15, having a DSC thermogram substantially as depicted in FIG. 4.

17. The crystalline form of any one of embodiments 14-16, having a TGA thermogram substantially as depicted in FIG. 4.

18. The crystalline form of any one of embodiments 14-17, having at least one XRPD peak, in terms of 2-theta (±0.2 degrees), selected from 8.5, 15.0, 15.7, 17.0, 18.6, 20.2, 20.5, 21.7, 25.5, and 26.7 degrees.

19. The crystalline form of any one of embodiments 14-17, having at least two XRPD peaks, in terms of 2-theta (±0.2 degrees), selected from 8.5, 15.0, 15.7, 17.0, 18.6, 20.2, 20.5, 21.7, 25.5, and 26.7 degrees.

20. The crystalline form of any one of embodiments 14-17, having at least three XRPD peaks, in terms of 2-theta (±0.2 degrees), selected from 8.5, 15.0, 15.7, 17.0, 18.6, 20.2, 20.5, 21.7, 25.5, and 26.7 degrees.

21. The crystalline form of any one of embodiments 14-17, having at least four XRPD peaks, in terms of 2-theta (±0.2 degrees), selected from 8.5, 15.0, 15.7, 17.0, 18.6, 20.2, 20.5, 21.7, 25.5, and 26.7 degrees.

22. The crystalline form of any one of embodiments 14-17, having characteristic XRPD peaks, in terms of 2-theta (±0.2 degrees), at 8.5, 15.0, 15.7, 17.0, 18.6, 20.2, 20.5, 21.7, 25.5, and 26.7 degrees.

23. The crystalline form of any one of embodiments 14-22, having three endothermic peaks with a maximum temperature (±3° C.) at 76° C., an onset temperature (±3° C.) at 165° C. and a maximum temperature (±3° C.) at 173° C., an onset temperature (±3° C.) at 206° C. and a maximum temperature (±3° C.) at 224° C. in a DSC thermogram.

24. The crystalline form of embodiment 1, wherein the compound of formula 1, or the pharmaceutically acceptable salt thereof, is a methanesulfonic acid salt.

25. The crystalline form of embodiment 24, having Form III.

26. The crystalline form of embodiment 24 or 25, having an XRPD pattern as substantially shown in FIG. 5.

27. The crystalline form of any one of embodiments 24-26, having a DSC thermogram substantially as depicted in FIG. 6.

28. The crystalline form of any one of embodiments 24-27, having a TGA thermogram substantially as depicted in FIG. 6.

29. The crystalline form of any one of embodiments 24-28, having at least one XRPD peak, in terms of 2-theta (±0.2 degrees), selected from 5.2, 7.5, 8.2, 8.8, 9.4, 11.6, 12.4, 13.0, 14.0, 14.8, 15.8, 16.6, 16.9, 17.3, 17.9, 19.2, 23.6, 24.5, 25.5, and 26.6 degrees.

30. The crystalline form of any one of embodiments 24-28, having at least two XRPD peaks, in terms of 2-theta (0.2 degrees), selected from 5.2, 7.5, 8.2, 8.8, 9.4, 11.6, 12.4, 13.0, 14.0, 14.8, 15.8, 16.6, 16.9, 17.3, 17.9, 19.2, 23.6, 24.5, 25.5, and 26.6 degrees.

31. The crystalline form of any one of embodiments 24-28, having at least three XRPD peaks, in terms of 2-theta (0.2 degrees), selected from 5.2, 7.5, 8.2, 8.8, 9.4, 11.6, 12.4, 13.0, 14.0, 14.8, 15.8, 16.6, 16.9, 17.3, 17.9, 19.2, 23.6, 24.5, 25.5, and 26.6 degrees.

32. The crystalline form of any one of embodiments 24-28, having at least four XRPD peaks, in terms of 2-theta (0.2 degrees), selected from 5.2, 7.5, 8.2, 8.8, 9.4, 11.6, 12.4, 13.0, 14.0, 14.8, 15.8, 16.6, 16.9, 17.3, 17.9, 19.2, 23.6, 24.5, 25.5, and 26.6 degrees.

33. The crystalline form of any one of embodiments 24-28, having characteristic XRPD peaks, in terms of 2-theta (0.2 degrees), at 5.2, 7.5, 8.2, 8.8, 9.4, 11.6, 12.4, 13.0, 14.0, 14.8, 15.8, 16.6, 16.9, 17.3, 17.9, 19.2, 23.6, 24.5, 25.5, and 26.6 degrees.

34. The crystalline form of any one of embodiments 24-33, having two endothermic peaks with an onset temperature (±3° C.) at 30° C. and a maximum temperature (±3° C.) at 67° C., an onset temperature (±3° C.) at 179° C. and a maximum temperature (±3° C.) at 202° C. in a DSC thermogram.

35. A process of preparing (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidine-4-carboxylic acid (compound of formula 1), or a salt thereof, comprising:

reacting a compound of formula A-3:

A-3

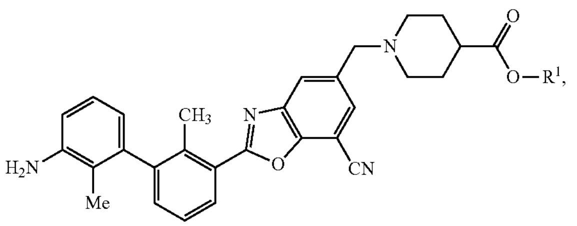

or a salt thereof, with a compound of formula A-4:

A-4

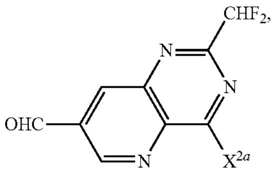

or a salt thereof, to form a compound of formula A-5:

A-5

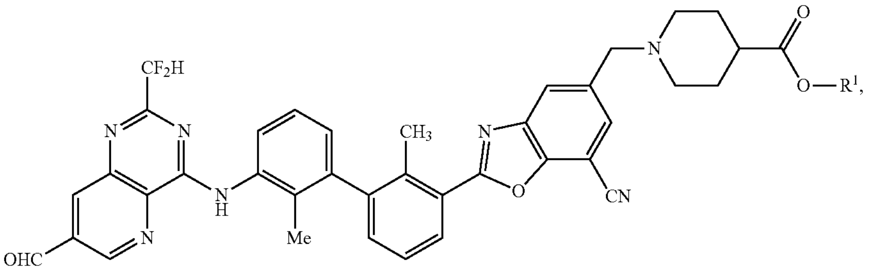

or a salt thereof, wherein $R^1$ is $C_{1-6}$ alkyl; and $X^{2a}$ is halo.

36. The process of embodiment 35, wherein the reacting of the compound of formula A-3, or the salt thereof, with the compound of formula A-4, or the salt thereof, is conducted in the presence of an alkali metal halide and a base.

37. The process of embodiment 36, wherein the alkali metal halide is an alkali metal bromide.

38. The process of embodiment 36 or 37, wherein the alkali metal halide is LiBr.

39. The process of any one of embodiments 36-38, wherein the base is a tertiary amine.

40. The process of any one of embodiments 36-39, wherein the base is selected from N,N-diisopropylamine, methylamine, dimethylamine, trimethylamine, and ethylamine.

41. The process of any one of embodiments 36-40, wherein the base is N,N-diisopropylamine.

42. The process of any one of embodiments 35-41, wherein from about 1 to about 1.5 molar equivalents of the compound of formula A-4, or the salt thereof, is utilized relative to the compound of formula A-3, or the salt thereof.

43. The process of any one of embodiments 35-41, wherein about 1 molar equivalent of the compound of formula A-4, or the salt thereof, is utilized relative to the compound of formula A-3, or the salt thereof.

44. The process of any one of embodiments 36-43, wherein from about 3 to about 5 molar equivalents of the base is utilized relative to the compound of formula A-3, or the salt thereof.

45. The process of any one of embodiments 36-43, wherein about 4 molar equivalents of the base is utilized relative to the compound of formula A-3, or the salt thereof.

46. The process of any one of embodiments 36-43, wherein from about 0.1 to about 1 molar equivalent of alkali metal halide is utilized relative to the compound of formula A-3, or the salt thereof.

47. The process of any one of embodiments 36-43, wherein from about 0.4 to about 0.6 molar equivalent of alkali metal halide is utilized relative to the compound of formula A-3, or the salt thereof.

48. The process of any one of embodiments 36-43, wherein about 0.5 molar equivalent of alkali metal halide is utilized relative to the compound of formula A-3, or the salt thereof.

49. The process of any one of embodiments 36-48, wherein the reacting of the compound of formula A-3, or the salt thereof, with the compound of formula A-4, or the salt thereof, is carried out at a temperature of from about 40° C. to about 50° C.

50. The process of any one of embodiments 35-49, wherein the reacting of the compound of formula A-3, or the salt thereof, with the compound of formula A-4, or the salt thereof, is carried out in a solvent component.

51. The process of embodiment 50, wherein the solvent component comprises a di-$C_{1-6}$ alkyl ether or a 4-10 membered heterocycloalkyl ether.

52. The process of any one of embodiments 50 or 51, wherein the solvent component comprises tetrahydrofuran.

53. The process of any one of embodiments 35-52, wherein the compound of formula A-3, or the salt thereof, is a compound of formula A-3a:

A-3a

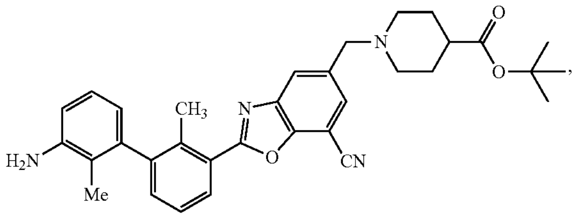

or a salt thereof.

54. The process of any one of embodiments 35-53, wherein the compound of formula A-4, or the salt thereof, is a compound of formula A-4a:

A-4a

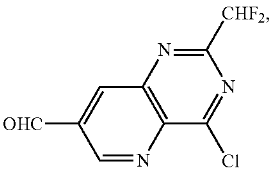

or a salt thereof.

55. The process of any one of embodiments 35-54, wherein the compound of formula A-5, or the salt thereof, is a compound of formula A-5a:

A-5a

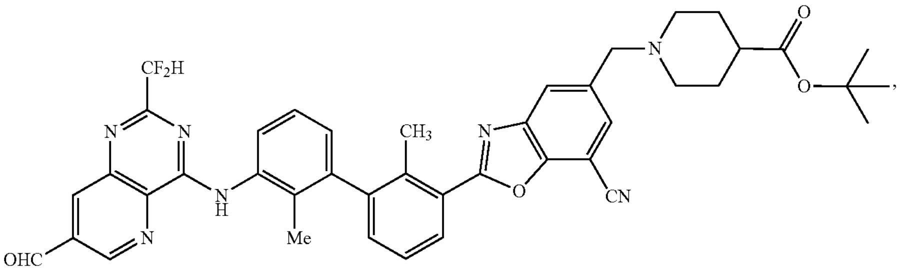

or a salt thereof.

56. The process of embodiment 35, wherein the process comprises: reacting a compound of formula A-3a:

A-3a

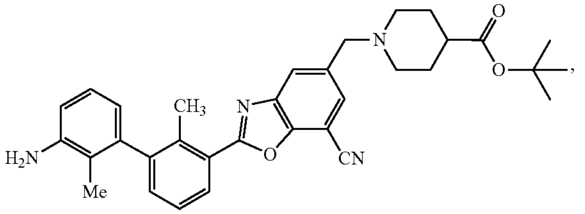

or a salt thereof, with a compound of formula A-4a:

A-4a

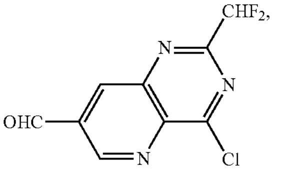

or a salt thereof, in the presence of an alkali metal halide and a base, to form a compound of formula A-5a:

A-5a

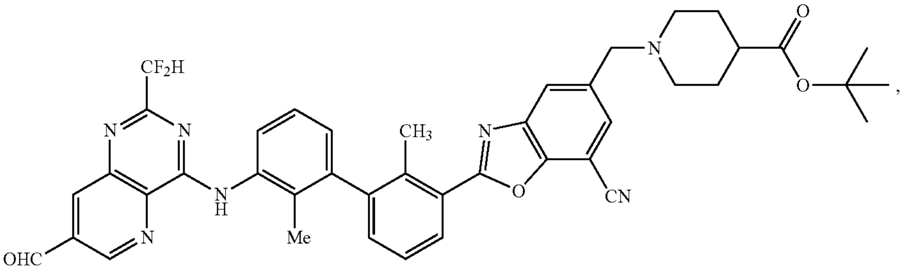

or a salt thereof.

57. A process of preparing (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidine-4-carboxylic acid (compound of formula 1), or a salt thereof, comprising:

reacting a compound of formula A-5:

A-5

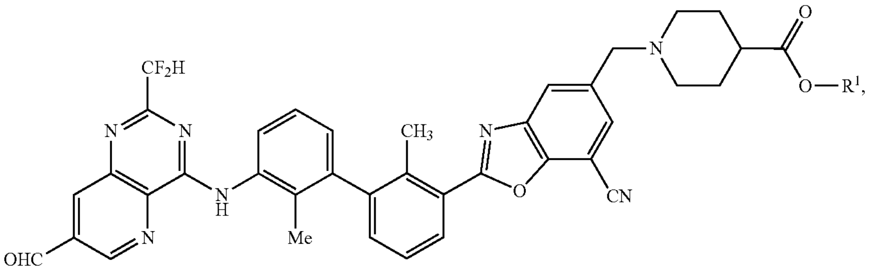

or a salt thereof, with a compound of formula A-6:

A-6

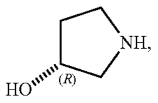

or a salt thereof, in the presence of a reducing agent to form a compound of formula A-7:ke

A-7

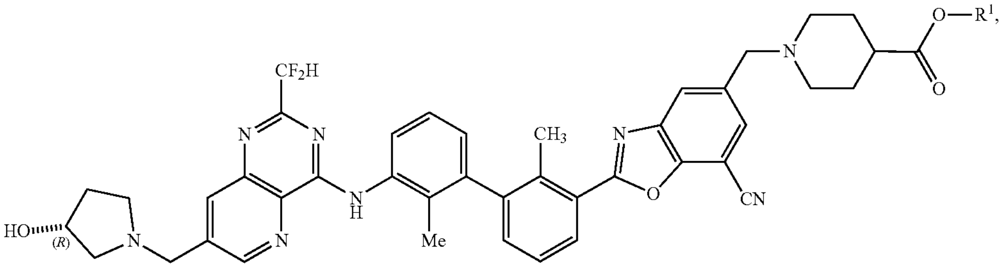

or a salt thereof, wherein $R^1$ is $C_{1-6}$ alkyl.

58. The process of any one of embodiments 35-56, wherein the process further comprises:

reacting a compound of formula A-5:

A-5

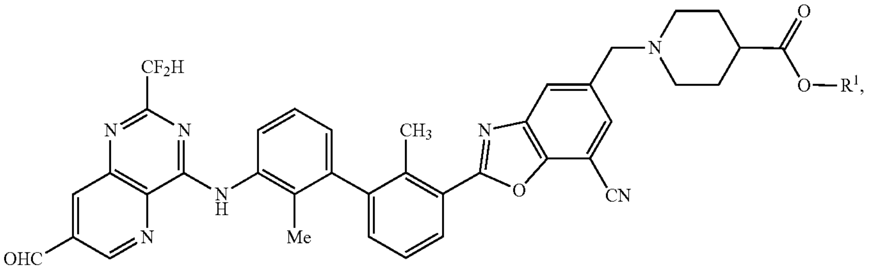

or a salt thereof, with a compound of formula A-6:

A-6

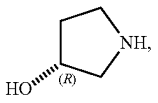

or a salt thereof, in the presence of a reducing agent to form a compound of formula A-7:

A-7

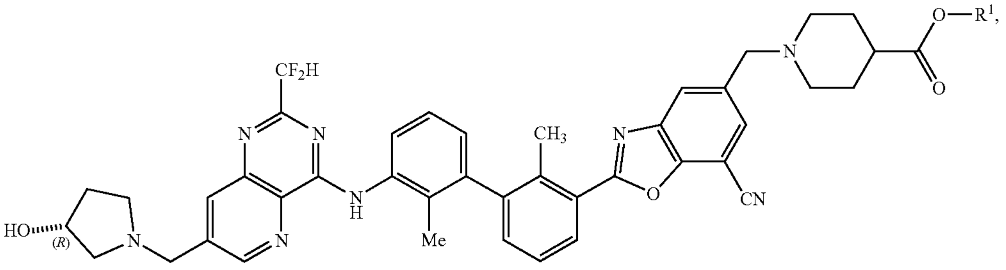

or a salt thereof, wherein $R^1$ is $C_{1-6}$ alkyl.

59. The process of embodiment 57 or 58, wherein the reducing agent is a borohydride reducing agent.

60. The process of any one of embodiments 57-59, wherein the reducing agent is selected from $NaBH_4$, $NaBH_3CN$ and $NaBH(OAc)_3$.

61. The process of any one of embodiments 57-59, wherein the reducing agent is $NaBH(OAc)_3$.

62. The process of any one of embodiments 57-61, wherein the reacting of the compound of formula A-5, or the salt thereof, with the compound of formula A-6, or the salt thereof, is carried out in the presence of a catalyst.

63. The process of embodiment 62, wherein the catalyst is trimethyl borate.

64. The process of any one of embodiments 57-63, wherein from about 1 to about 4 molar equivalents of the compound of formula A-6, or the salt thereof, is utilized relative to the compound of formula A-5, or the salt thereof.

65. The process of any one of embodiments 57-63, wherein from about 2 to about 3 molar equivalents of the compound of formula A-6, or the salt thereof, is utilized relative to the compound of formula A-5, or the salt thereof.

66. The process of any one of embodiments 57-63, wherein from about 1.5 to about 2.5 molar equivalents of the compound of formula A-6, or the salt thereof, is utilized relative to the compound of formula A-5, or the salt thereof.

67. The process of any one of embodiments 57-63, wherein from about 2 to about 2.5 molar equivalents of the compound of formula A-6, or the salt thereof, is utilized relative to the compound of formula A-5, or the salt thereof.

68. The process of any one of embodiments 57-63, wherein about 2 molar equivalents of the compound of formula A-6, or the salt thereof, is utilized relative to the compound of formula A-5, or the salt thereof.

69. The process of any one of embodiments 62-68, wherein from about 1 to about 4 molar equivalents of the catalyst is utilized relative to the compound of formula A-5, or the salt thereof.

70. The process of any one of embodiments 62-68, wherein from about 1.5 to about 2.5 molar equivalents of the catalyst is utilized relative to A-5, or the salt thereof.

71. The process of any one of embodiments 62-68, wherein about 2 molar equivalents of the catalyst is utilized relative to the compound of formula A-5, or the salt thereof.

72. The process of any one of embodiments 57-71, wherein from about 1 to about 4 molar equivalents of the reducing agent is utilized relative to the compound of formula A-5, or the salt thereof.

73. The process of any one of embodiments 57-71, wherein from about 2 to about 3 molar equivalents of the reducing agent is utilized relative to the compound of formula A-5, or the salt thereof.

74. The process of any one of embodiments 57-71, wherein from about 1.5 to about 2.5 molar equivalents of the reducing agent is utilized relative to the compound of formula A-5, or the salt thereof.

75. The process of any one of embodiments 57-71, wherein from about 2 to about 2.5 molar equivalents of the reducing agent is utilized relative to the compound of formula A-5, or the salt thereof.

76. The process of any one of embodiments 57-71, wherein about 2 molar equivalents of the reducing agent is utilized relative to the compound of formula A-5, or the salt thereof.

77. The process of any one of embodiments 57-76, wherein the reacting of the compound of formula A-5, or the salt thereof, with the compound of formula A-6, or salt thereof, is carried out at a temperature of about 15° C. to about 25° C.

78. The process of any one of embodiments 57-77, wherein the reacting of the compound of formula A-5, or the salt thereof, with the compound of formula A-6, or salt thereof, is carried out in a solvent component.

79. The process of embodiment 78, wherein the reacting of the compound of formula A-5, or the salt thereof, with the compound of formula A-6, or salt thereof, is carried out in a solvent component comprising a polar aprotic solvent.

80. The process of embodiment 78 or 79, wherein the reacting of the compound of formula A-5, or the salt thereof, with the compound of formula A-6, or salt thereof, is carried out in a solvent component comprising an organonitrile and an organohalide.

81. The process of any one of embodiments 78-80, wherein the reacting of the compound of formula A-5, or the salt thereof, with the compound of formula A-6, or salt thereof, is carried out in a solvent component comprising dichloromethane and acetonitrile.

82. The process of any one of embodiments 57-81, wherein the compound of formula A-5, or the salt thereof, is a compound of formula A-5a:

A-5a

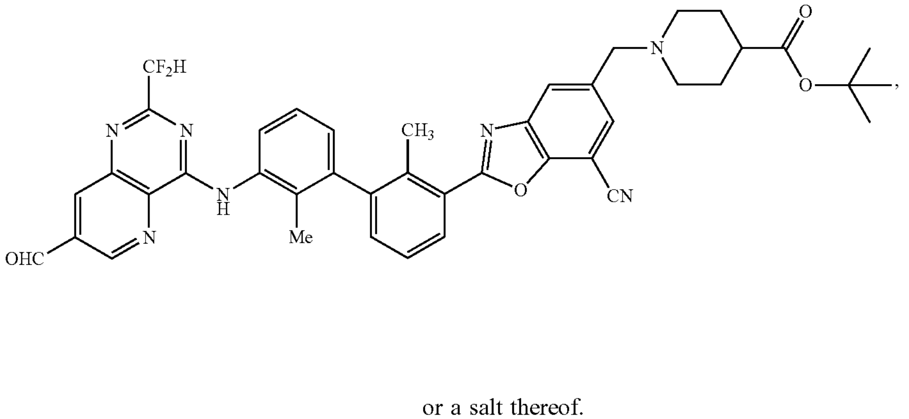

or a salt thereof.

83. The process of any one of embodiments 57-82, wherein the compound of formula A-7, or the salt thereof, is a compound of formula A-7a:

A-7a

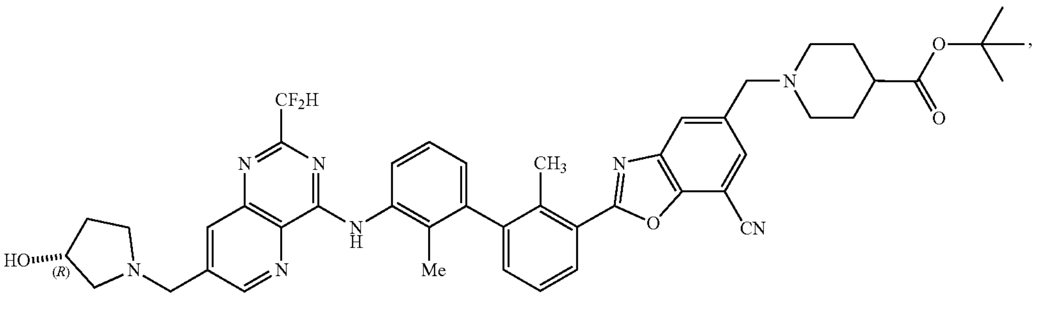

or a salt thereof.

84. The process of embodiment 57 or 58, wherein the process comprises:

reacting a compound of formula A-5a:

A-5a

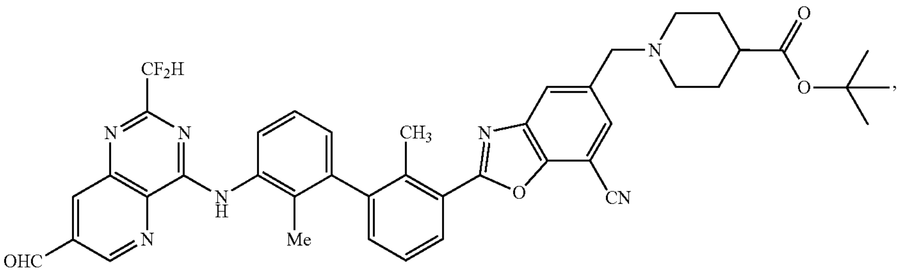

or a salt thereof, with a compound of formula A-6:

A-6

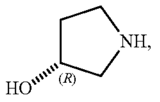

or a salt thereof, in the presence of a reducing agent to form a compound of formula A-7a:

A-7a

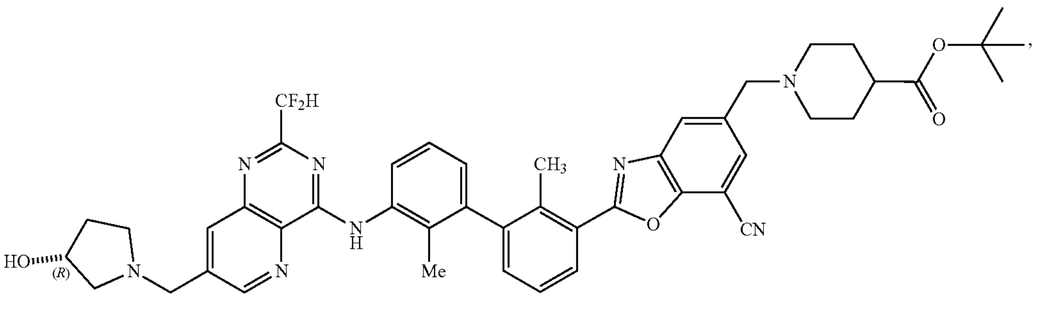

or a salt thereof.

85. A process of preparing (R)-1-((7-cyano-2-(3'-((2-(difluoromethyl)-7-((3-hydroxypyrrolidin-1-yl)methyl) pyrido[3,2-d]pyrimidin-4-yl)amino)-2,2'-dimethyl-[1,1'-biphenyl]-3-yl)benzo[d]oxazol-5-yl)methyl)piperidine-4-carboxylic acid (compound of formula 1), or a salt thereof, comprising:

reacting a compound of formula A-3:

A-3

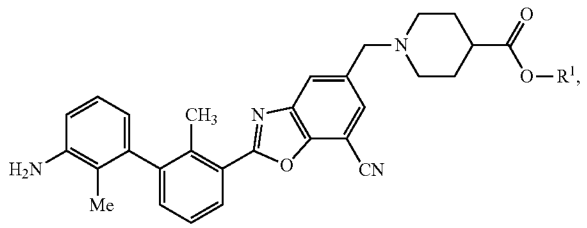

or a salt thereof, with a compound of formula B-1:

B-1

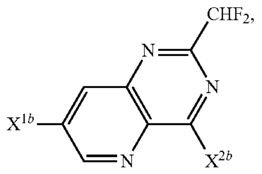

or a salt thereof, in the presence of a base to form a compound of formula B-2:

B-2

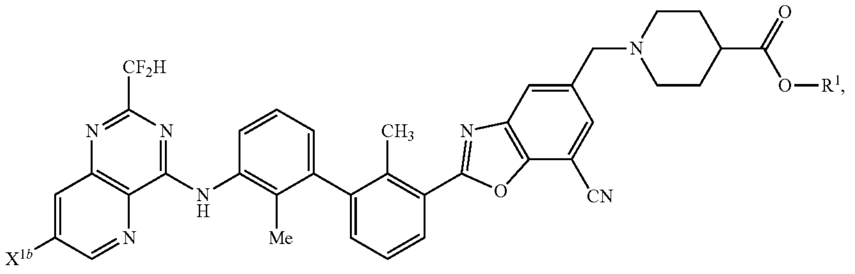

or a salt thereof, wherein $R^1$ is $C_{1-6}$ alkyl; and $X^{1b}$ and $X^{2b}$ are independently halo.

86. The process of embodiment 85, wherein the base, present in the reacting of the compound of formula A-3, or the salt thereof, with the compound of formula B-1, or the salt thereof, is an alkali metal base.

87. The process of embodiment 85 or 86, wherein the base, present in the reacting of the compound of formula A-3, or the salt thereof, with the compound of formula B-1, or the salt thereof, is an alkali metal carbonate.

88. The process of any one of embodiments 85-87, wherein the base, present in the reacting of the compound of formula A-3, or the salt thereof, with the compound of formula B-1, or the salt thereof, is selected from cesium carbonate, lithium carbonate, sodium carbonate, and potassium carbonate.

89. The process of any one of embodiments 85-88, wherein the base, present in the reacting of the compound of formula A-3, or the salt thereof, with the compound of formula B-1, or the salt thereof, is potassium carbonate.

90. The process of any one of embodiments 85-89, wherein from about 1 to about 1.5 molar equivalents of the compound of formula B-1, or the salt thereof, is utilized relative to the compound of formula A-3, or the salt thereof.

91. The process of any one of embodiments 85-89, wherein about 1 molar equivalent of the compound of formula B-1, or the salt thereof, is utilized relative to the compound of formula A-3, or the salt thereof.

92. The process of any one of embodiments 85-91, wherein from about 1 to about 4 molar equivalents of the base is utilized relative to the compound of formula A-3, or the salt thereof.

93. The process of any one of embodiments 85-91, wherein from about 1.5 to about 2.5 molar equivalents of the base is utilized relative to the compound of formula A-3, or the salt thereof.

94. The process of any one of embodiments 85-91, wherein from about 2 to about 3 molar equivalents of the base is utilized relative to the compound of formula A-3, or the salt thereof.

95. The process of any one of embodiments 85-91, wherein from about 2 to about 2.5 molar equivalents of the base is utilized relative to the compound of formula A-3, or the salt thereof.

96. The process of any one of embodiments 85-91, wherein about 2 molar equivalents of the base is utilized relative to the compound of formula A-3, or the salt thereof.

97. The process of any one of embodiments 85-96, wherein the reacting of the compound of formula A-3, or the salt thereof, with the compound of formula B-1, or the salt thereof, is carried out at a temperature of about 70° C. to about 90° C.

98. The process of any one of embodiments 85-96, wherein the reacting of the compound of formula A-3, or the salt thereof, with the compound of formula B-1, or the salt thereof, is carried out at a temperature of about 80° C.

99. The process of any one of embodiments 85-99, wherein the reacting of the compound of formula A-3, or the salt thereof, with the compound of formula B-1, or the salt thereof, is carried out in a solvent component.

100. The process of embodiment 99, wherein the reacting of the compound of formula A-3, or the salt thereof, with the compound of formula B-1, or the salt thereof, is carried out in a solvent component comprising an organic ether.

101. The process of embodiment 99 or 100, wherein the reacting of the compound of formula A-3, or the salt thereof, with the compound of formula B-1, or the salt thereof, is carried out in a solvent component comprising diglyme.

102. The process of any one of embodiments 85-101, wherein $X^{1b}$ is bromo.

103. The process of any one of embodiments 85-102, wherein $X^{2b}$ is chloro.

104. The process of any one of embodiments 85-103, wherein the compound of formula A-3, or the salt thereof, is a compound of formula A-3a:

A-3a

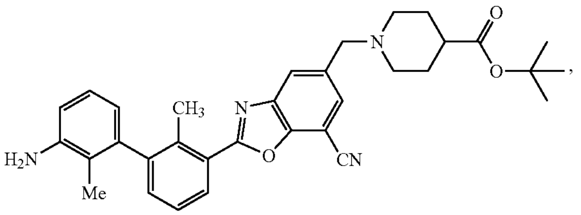

or a salt thereof.

105. The process of any one of embodiments 85-104, wherein the compound of formula B-1, or the salt thereof, is a compound of formula B-1a:

B-1a

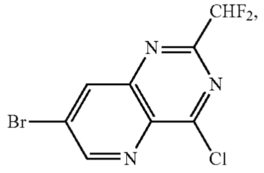

or a salt thereof.

106. The process of any one of embodiments 85-105, wherein the compound of formula B-2, or the salt thereof, is a compound of formula B-2a:

B-2a

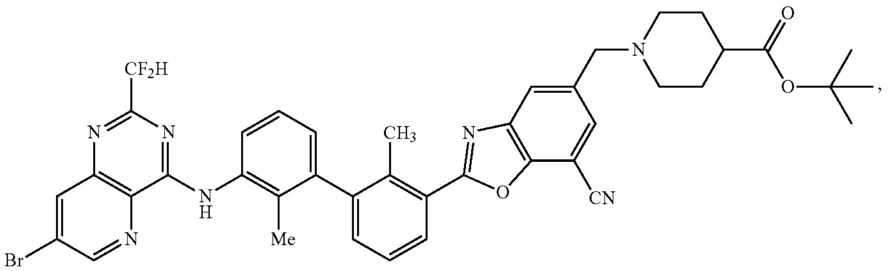

or a salt thereof.

107. The process of embodiment 85, wherein the process comprises:

reacting a compound of formula A-3a:

A-3a

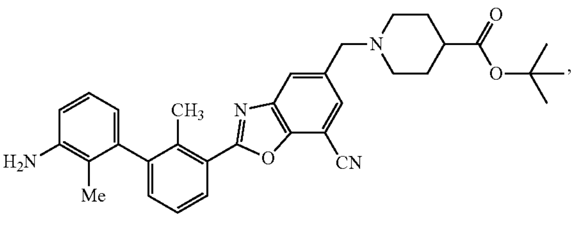

or a salt thereof, with a compound of formula B-1a:

B-1a

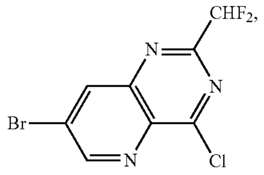

or a salt thereof, in the presence of a base, to form a compound of formula B-2a:

B-2a

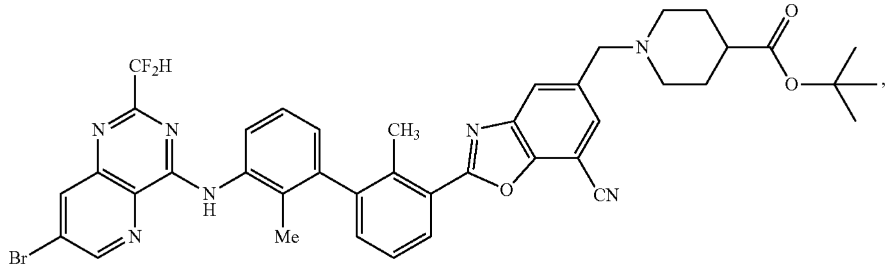

or a salt thereof.

108. A process of preparing (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidine-4-carboxylic acid (compound of formula 1), or a salt thereof, comprising:

reacting a compound of formula B-2:

B-2

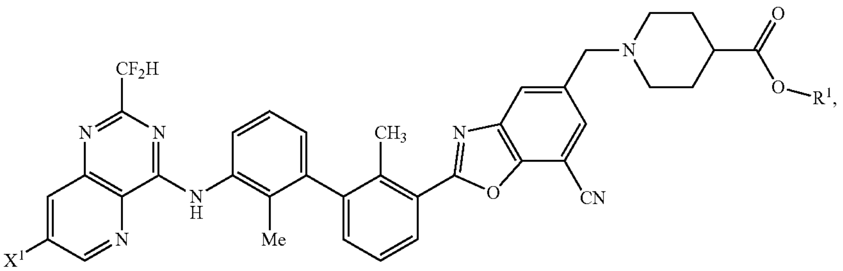

or a salt thereof, with a salt of formula B-3:

B-3

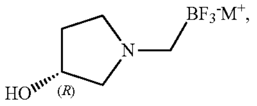

wherein $M^+$ is $Li^+$, $Na^+$, $K^+$, or $Cs^+$, in the presence of a Suzuki catalyst and a base to form a compound of formula A-7:

A-7

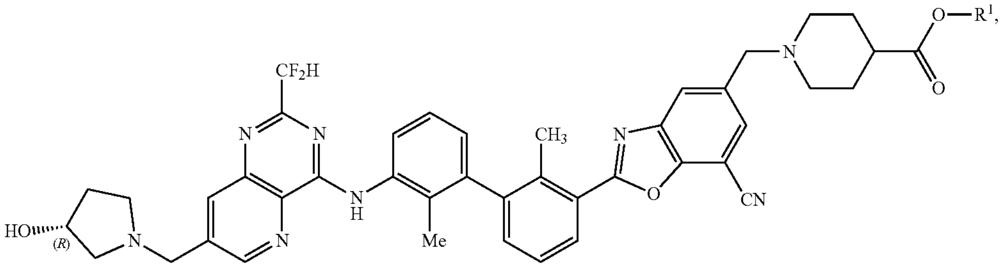

or a salt thereof, wherein $R^1$ is $C_{1-6}$ alkyl and $X^1$ is halo.

109. The process of any one of embodiments 85-107, wherein the process further comprises:

reacting a compound of formula B-2:

B-2

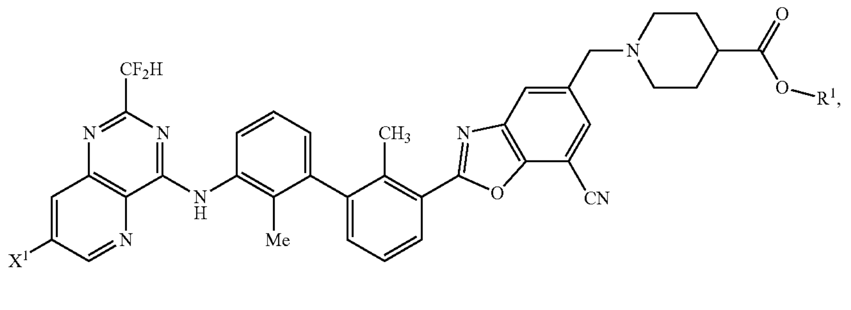

or a salt thereof, with a salt of formula B-3:

B-3

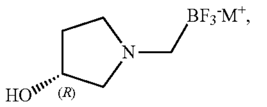

wherein $M^+$ is $Li^+$, $Na^+$, $K^+$, or $Cs^+$, in the presence of a Suzuki catalyst and a base to form a compound of formula A-7:

A-7

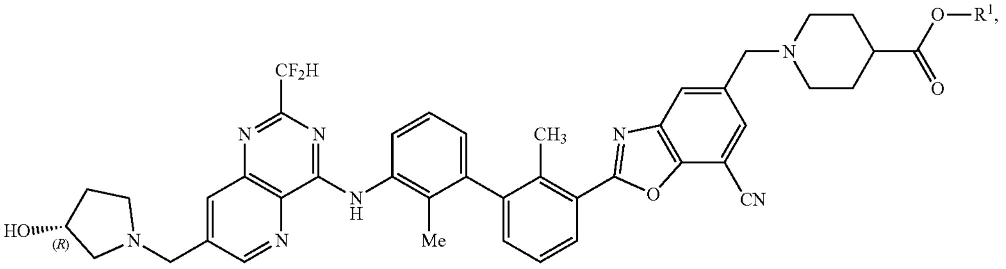

or a salt thereof, wherein $R^1$ is $C_{1-6}$ alkyl and $X^{1b}$ is halo.

110. The process of embodiment 108 or 109, wherein $X^{1b}$ is bromo.

111. The process of any one of embodiments 108-110, wherein the Suzuki catalyst is a palladium catalyst.

112. The process of any one of embodiments 108-111, wherein the Suzuki catalyst is selected from CataCXium® Pd G4 ((2'-(methylamino)-[1,1'-biphenyl]-2-yl)((methylsulfonyl)oxy)palladium di(1-adamantyl)-n-butylphosphine complex), $Pd(PPh_3)_4$, $Pd(dppf)_2Cl_2$, dichlorobis[di-tert-butyl(p-dimethylaminophenyl)phosphino]palladium and $PdCl_2$(dtbpf) (Pd-118).

113. The process of any one of embodiments 108-112, wherein the Suzuki catalyst is CataCXium® Pd G4 ((2'-(methylamino)-[1,1'-biphenyl]-2-yl)((methylsulfonyl)oxy) palladium di(1-adamantyl)-n-butylphosphine complex).

114. The process of any one of embodiments 108-113, wherein the base, present in the reacting of the compound of formula B-2, or the salt thereof, with the salt of formula B-3, is an alkali metal base.

115. The process of any one of embodiments 108-113, wherein the base, present in the reacting of the compound of formula B-2, or the salt thereof, with the salt of formula B-3, is an alkali metal carbonate.

116. The process of any one of embodiments 108-113, wherein the base, present in the reacting of the compound of formula B-2, or the salt thereof, with the salt of formula B-3, is selected from cesium carbonate, lithium carbonate, sodium carbonate, and potassium carbonate.

117. The process of any one of embodiments 108-113, wherein the base, present in the reacting of the compound of formula B-2, or the salt thereof, with the salt of formula B-3, is cesium carbonate.

118. The process of any one of embodiments 108-117, wherein from about 1 to about 4 molar equivalents of the salt of formula B-3 is utilized relative to the compound of formula B-2, or the salt thereof.

119. The process of any one of embodiments 108-117, wherein from about 1.5 to about 2.5 molar equivalents of the salt of formula B-3 is utilized relative to the compound of formula B-2, or the salt thereof.

120. The process of any one of embodiments 108-117, wherein from about 2 to about 3 molar equivalents of the salt of formula B-3 is utilized relative to the compound of formula B-2, or the salt thereof.

121. The process of any one of embodiments 108-117, wherein from about 2 to about 2.5 molar equivalents of the salt of formula B-3 is utilized relative to the compound of formula B-2, or the salt thereof.

122. The process of any one of embodiments 108-117, wherein about 2 molar equivalents of the salt of formula B-3 is utilized relative to the compound of formula B-2, or the salt thereof.

123. The process of any one of embodiments 108-122, wherein from about 3 to about 9 molar equivalents of the base is utilized relative to the compound of formula B-2, or the salt thereof.

124. The process of any one of embodiments 108-122, wherein from about 5 to about 7 molar equivalents of the base is utilized relative to the compound of formula B-2, or the salt thereof.

125. The process of any one of embodiments 108-122, wherein about 6 molar equivalents of the base is utilized relative to the compound of formula B-2, or the salt thereof.

126. The process of any one of embodiments 108-125, wherein from about 0.01 to about 0.5 molar equivalent of the Suzuki catalyst is utilized relative to the compound of formula B-2, or the salt thereof.

127. The process of any one of embodiments 108-125, wherein from about 0.01 to about 0.1 molar equivalent of the Suzuki catalyst is utilized relative to the compound of formula B-2, or the salt thereof.

128. The process of any one of embodiments 108-125, wherein from about 0.03 to about 0.05 molar equivalent of the Suzuki catalyst is utilized relative to the compound of formula B-2, or the salt thereof.

129. The process of any one of embodiments 108-125, wherein about 0.04 molar equivalent of the Suzuki catalyst is utilized relative to the compound of formula B-2, or the salt thereof.

130. The process of any one of embodiments 108-129, wherein the reacting of the compound of formula B-2, or the salt thereof, with the salt of formula B-3, is carried out at a temperature of about 80° C. to about 120° C.

131. The process of any one of embodiments 108-129, wherein the reacting of the compound of formula B-2, or the salt thereof, with the salt of formula B-3, is carried out at a temperature of about 100° C.

132. The process of any one of embodiments 108-131, wherein the reacting of the compound of B-2, or the salt thereof, with the salt of formula B-3, is carried out in a solvent component.

133. The process of embodiment 132, wherein the reacting of the compound of B-2, or the salt thereof, with the salt of formula B-3, is carried out in a solvent component comprising a non-protic organic solvent.

134. The process of embodiment 132 or 133, wherein the reacting of the compound of B-2, or the salt thereof, with the salt of formula B-3, is carried out in a solvent component comprising a di-$C_{1-6}$ alkyl ether or a 4-10 membered heterocycloalkyl ether.

135. The process of any one of embodiments 132-134, wherein the reacting of the compound of B-2, or the salt thereof, with the salt of formula B-3, is carried out in a solvent component comprising dioxane.

136. The process of any one of embodiments 108-135, wherein the compound of formula B-2, or the salt thereof, is a compound of formula B-2a:

B-2a

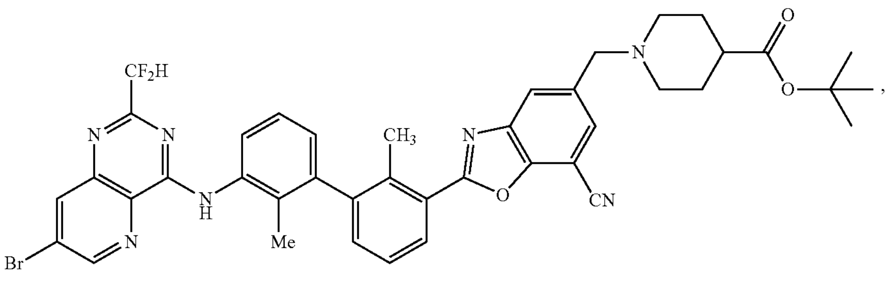

or a salt thereof.

137. The process of any one of embodiments 108-136, wherein the salt of formula B-3, or the salt thereof, is a salt of formula B-3a:

B-3a

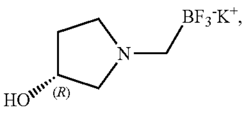

or a salt thereof.

138. The process of any one of embodiments 108-137, wherein the compound of formula A-7, or the salt thereof, is a compound of formula A-7a:

A-7a

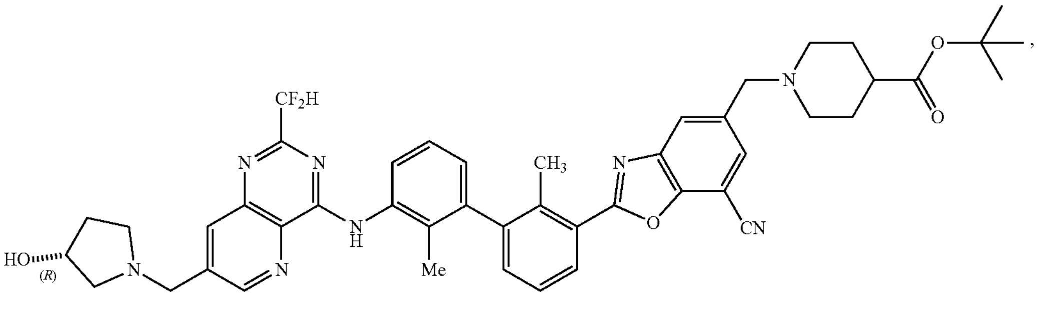

or a salt thereof.

139. The process of embodiment 108 or 109, wherein the process comprises:

reacting a compound of formula B-2a:

B-2a

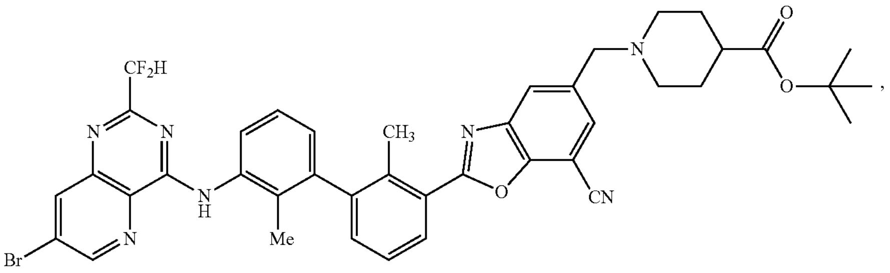

or a salt thereof, with a salt of formula B-3a:

B-3a

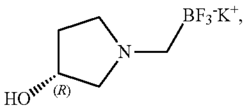

in the presence of a Suzuki catalyst and a base to form a compound of formula A-7a:

A-7a

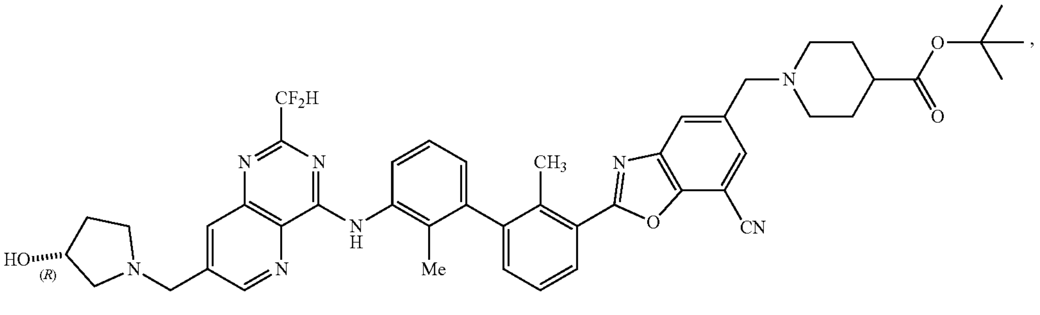

or a salt thereof.

140. The process of any one of embodiments 35-55, 58-83, 85-106, and 108-139, wherein the compound of formula A-3 or the salt thereof is prepared by a process comprising:

reacting a compound of formula A-1:

A-1

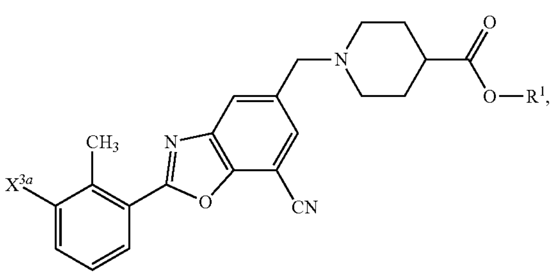

or a salt thereof, with a compound of formula A-2:

A-2

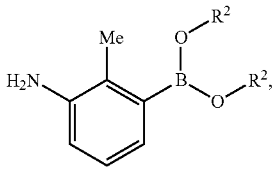

or a salt thereof, in the presence of a Suzuki catalyst and a base, wherein $X^{3a}$ is halo;

$R^1$ is $C_{1-6}$ alkyl; and each $R^2$ is independently selected from H and $C_{1-6}$ alkyl; or each $R^2$ together form an $C_{2-3}$ alkylene linker, which is optionally substituted by 1, 2, 3, or 4 independently selected $C_{1-4}$ alkyl groups.

141. The process of embodiment 140, wherein the Suzuki catalyst, present in the reacting of the compound of formula A-1, or the salt thereof, with the compound of formula A2, or the salt thereof, is a palladium catalyst.

142. The process of embodiment 140 or 141, wherein the Suzuki catalyst, present in the reacting of the compound of formula A-1, or the salt thereof, with the compound of formula A2, or the salt thereof, is selected from Cat-aCXium® Pd G4 ((2'-(methylamino)-[1,1'-biphenyl]-2-yl) ((methylsulfonyl)oxy)palladium di(1-adamantyl)-n-butylphosphine complex), $Pd(PPh_3)_4$, $Pd(dppf)_2Cl_2$, dichlorobis[di-tert-butyl(p-dimethylaminophenyl)phosphino]palladium and $PdCl_2$(dtbpf) (Pd-118).

143. The process of any one of embodiments 140-142, wherein the Suzuki catalyst, present in the reacting of the compound of formula A-1, or the salt thereof, with the compound of formula A2, or the salt thereof, is $PdCl_2$(dtbpf) (Pd-118).

144. The process of any one of embodiments 140-143, wherein the base, present in the reacting of the compound of formula A-1, or the salt thereof, with the compound of formula A2, or the salt thereof, is an alkali metal base.

145. The process of any one of embodiments 140-144, wherein the base, present in the reacting of the compound of formula A-1, or the salt thereof, with the compound of formula A2, or the salt thereof, is an alkali metal phosphate.

146. The process of any one of embodiments 140-145, wherein the base, present in the reacting of the compound of formula A-1, or the salt thereof, with the compound of formula A2, or the salt thereof, is potassium phosphate dibasic.

147. The process of any one of embodiments 140-146, wherein from about 1 to about 2 molar equivalents of the compound of formula A-2, or the salt thereof, is utilized relative to the compound of formula A-1, or the salt thereof.

148. The process of any one of embodiments 140-146, wherein from about 1 to about 1.5 molar equivalents of the compound of formula A-2, or the salt thereof, is utilized relative to the compound of formula A-1, or the salt thereof.

149. The process of any one of embodiments 140-146, wherein about 1 molar equivalent of the compound of formula A-2, or the salt thereof, is utilized relative to the compound of formula A-1, or the salt thereof.

150. The process of any one of embodiments 140-149, wherein from about 1 to about 9 molar equivalents of the base is utilized relative to the compound of formula A-1, or the salt thereof.

151. The process of any one of embodiments 140-149, wherein from about 3 to about 5 molar equivalents of the base is utilized relative to the compound of formula A-1, or the salt thereof.

152. The process of any one of embodiments 140-149, wherein about 4 molar equivalents of the base is utilized relative to the compound of formula A-1, or the salt thereof.

153. The process of any one of embodiments 140-152, wherein from about 0.001 to about 0.1 molar equivalent of the Suzuki catalyst is utilized relative to the compound of formula A-1, or the salt thereof.

154. The process of any one of embodiments 140-152, wherein about 0.008 molar equivalent of the Suzuki catalyst is utilized relative to the compound of formula A-1, or the salt thereof.

155. The process of any one of embodiments 140-154, wherein the reacting of the compound of formula A-1, or the salt thereof, with the compound of formula A-2 or the salt thereof, is carried out at a temperature of about 70° C. to about 100° C.

156. The process of any one of embodiments 140-154, wherein the reacting of the compound of formula A-1, or the salt thereof, with the compound of formula A-2 or the salt thereof, is carried out at a temperature of about 80° C.

157. The process of any one of embodiments 140-156, wherein the reacting of the compound of A-1, or the salt thereof, with the compound of formula A-2, or the salt thereof, is carried out in a solvent component.

158. The process of embodiment 157, wherein the reacting of the compound of A-1, or the salt thereof, with the compound of formula A-2, or the salt thereof, is carried out in a solvent component comprising a polar protic solvent.

159. The process of embodiment 157 or 158, wherein the reacting of the compound of A-1, or the salt thereof, with the compound of formula A-2, or the salt thereof, is carried out in a solvent component comprising $C_{1-6}$ alkanol and water.

160. The process of any one of embodiments 157-159, wherein the reacting of the compound of A-1, or the salt thereof, with the compound of formula A-2, or the salt thereof, is carried out in a solvent component comprising water and tert-butanol.

161. The process of any one of embodiments 140-160, wherein the compound of A-1, or the salt thereof, is a compound of formula A-1a:

A-1a

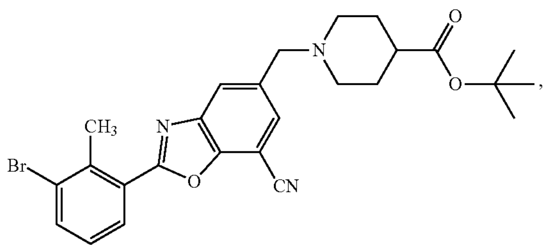

or a salt thereof.

162. The process of any one of embodiments 140-161, wherein the compound of A-2, or the salt thereof, is a compound of formula A-2a:

A-2a

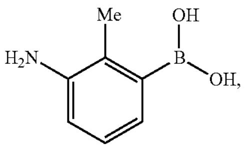

or a salt thereof.

163. The process of embodiment 140, wherein the process comprises:

reacting a compound of formula A-1a:

A-1a

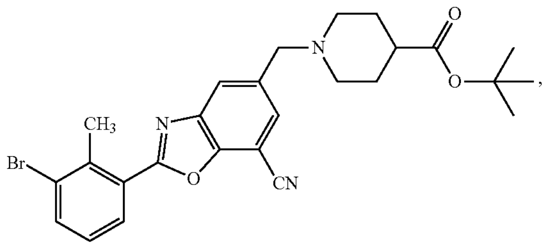

or a salt thereof, with a compound of formula A-2a:

A-2a

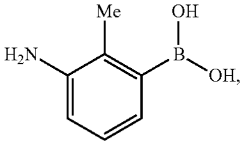

or a salt thereof, in the presence of a Suzuki catalyst and a base.

164. The process of any one of embodiments 57-83 and 108-163, wherein the compound of formula 1, or the salt thereof, is prepared by a process comprising:

converting a compound of formula A-7:

A-7

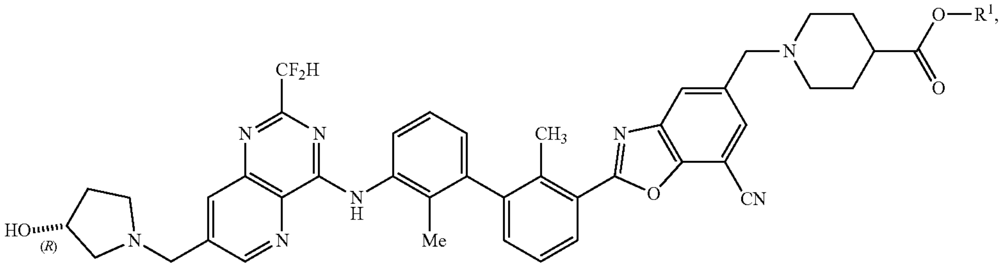

or a salt thereof, to the compound of formula 1:

1

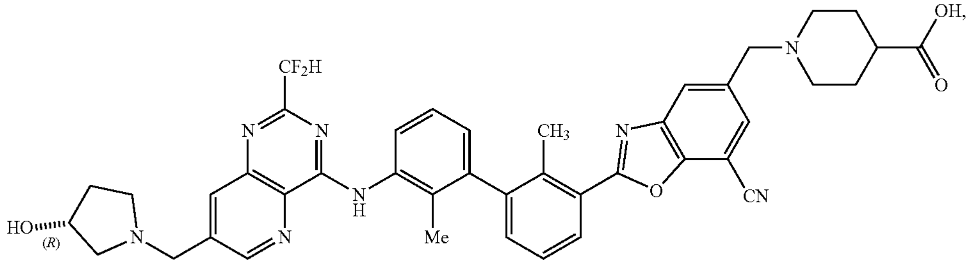

or a salt thereof, wherein $R^1$ is $C_{1-6}$ alkyl.

165. The process of embodiment 164, wherein the converting of the compound of formula A-7, or the salt thereof, to the compound of formula 1, or the salt thereof, comprises treating the compound of formula A-7, or the salt thereof, with a Lewis acid.

166. The process of embodiment 165, wherein the Lewis acid, present in the converting of the compound of formula A-7, or the salt thereof, is iodotrimethylsilane.

167. The process of embodiment 165 or 166, wherein from about 1 to about 5 molar equivalents of the Lewis acid is utilized relative to the compound of formula A-7, or the salt thereof.

168. The process of embodiment 165 or 166, wherein from about 2 to about 4 molar equivalents of the Lewis acid is utilized relative to the compound of formula A-7, or the salt thereof.

169. The process of embodiment 165 or 166, wherein about 3 molar equivalents of the Lewis acid is utilized relative to the compound of formula A-7, or the salt thereof.

170. The process of any one of embodiments 164-169, wherein the converting of the compound of formula A-7, or the salt thereof, is carried out at a temperature of about room temperature.

171. The process of any one of embodiments 164-170, wherein the converting of the compound of formula A-7, or the salt thereof, is carried out in a solvent component.

172. The process of embodiment 171, wherein the converting of the compound of formula A-7, or the salt thereof, is carried out in a solvent component comprising a polar aprotic solvent.

173. The process of any one of embodiments 171 or 172, wherein the converting of the compound of formula A-7, or the salt thereof, is carried out in a solvent component comprising an organohalide.

174. The process of any one of embodiments 171-173, wherein the converting of the compound of formula A-7, or the salt thereof, is carried out in a solvent component comprising dichloromethane.

175. The process of any one of embodiments 164-174, wherein the compound of A-7, or the salt thereof, is a compound of formula A-7a:

A-7a

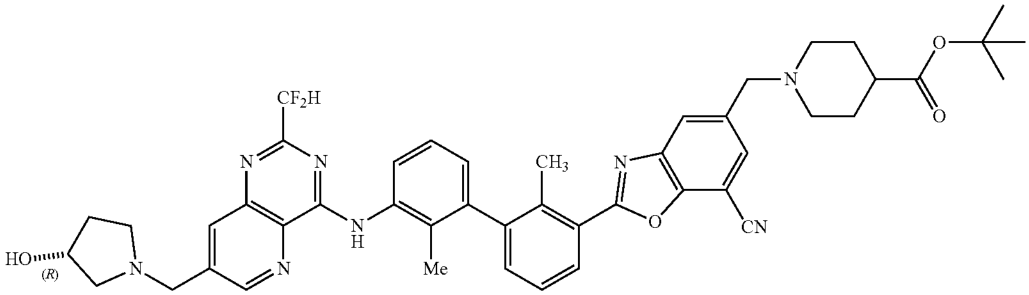

, or a salt thereof.

176. The process of any one of embodiments 164-175, wherein the compound of formula 1, or the salt thereof, is prepared by a process comprising:

reacting a compound of formula A-7a:

A-7a

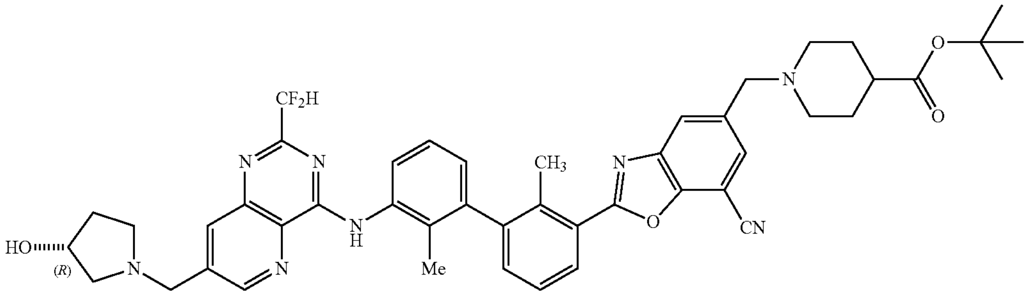

, or a salt thereof, with a Lewis acid to form the compound of formula 1:

1

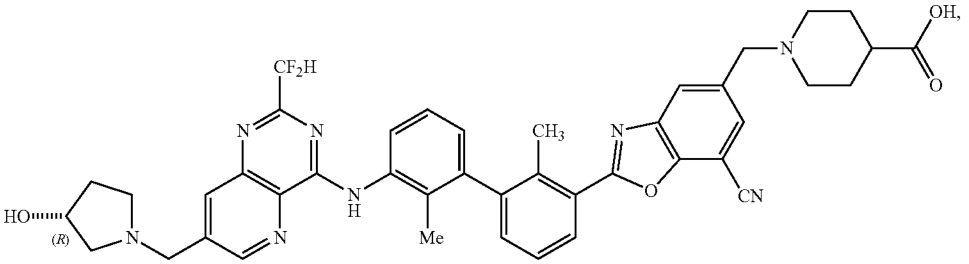

or a salt thereof.

177. A process of preparing (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidine-4-carboxylic acid (compound of formula 1), or a salt thereof, comprising:

a) reacting a compound of formula A-3a:

A-3a

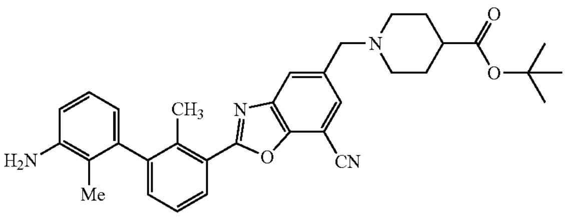

, or a salt thereof, with a compound of formula A-4a:

A-4a

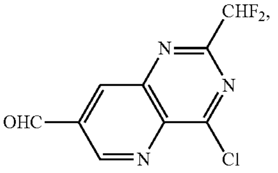

or a salt thereof, in the presence of an alkali metal halide and a base, to form a compound of formula A-5a:

A-5a

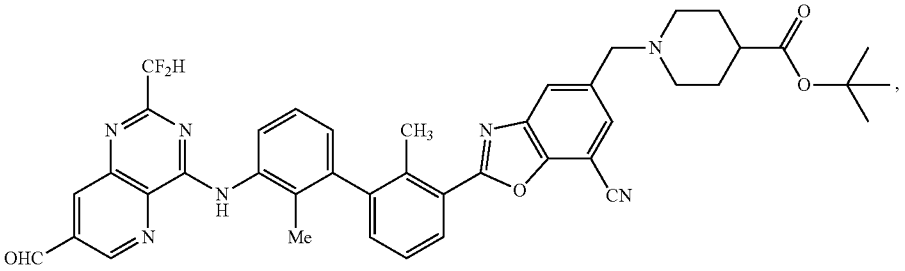

or a salt thereof;

b) reacting the compound of formula A-5a:

A-5a

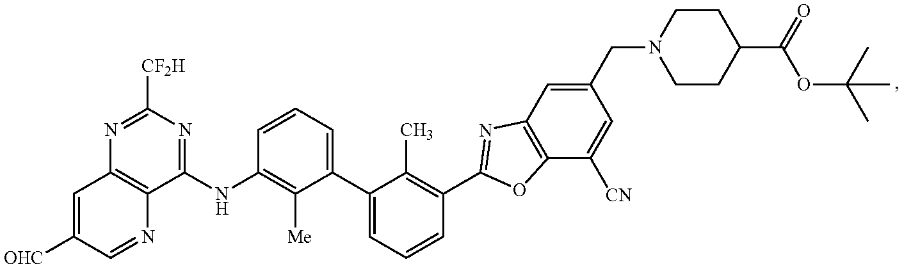

or a salt thereof, with a compound of formula A-6:
A-6
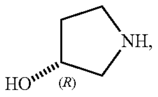
or a salt thereof, in the presence of a reducing agent to form a compound of formula A-7a:
A-7a
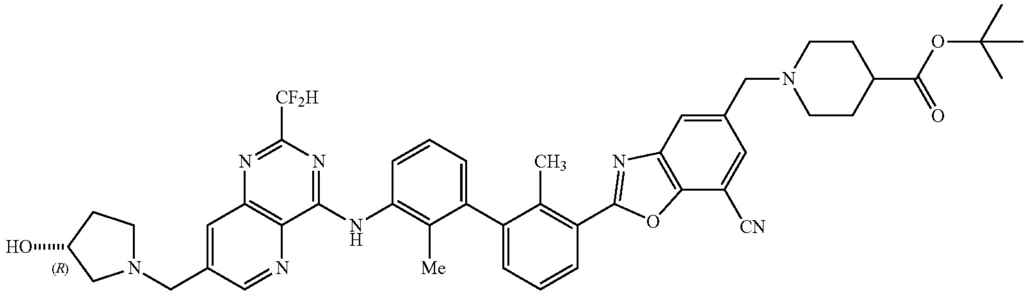
,
or a salt thereof, and
c) reacting the compound of formula A-7a:
A-7a
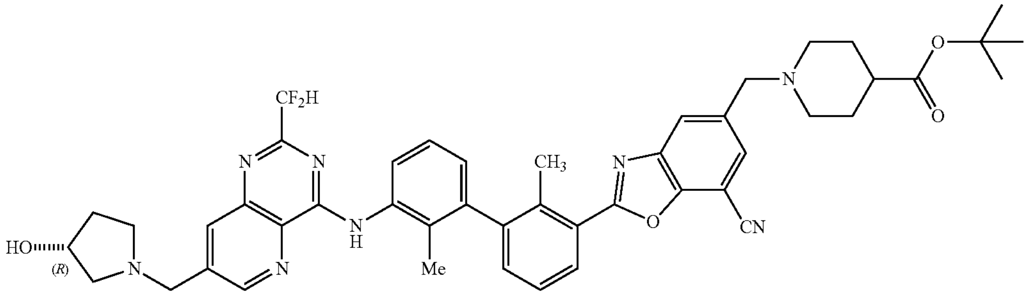
,
or a salt thereof, with a Lewis acid to form the compound of formula 1:
1
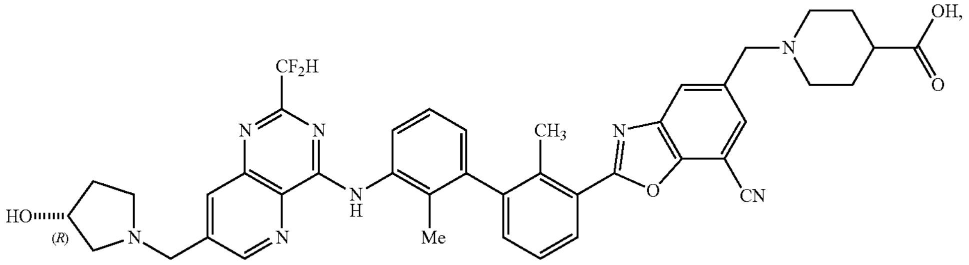
or a salt thereof.

178. A process of preparing (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidine-4-carboxylic acid (compound of formula 1), or a salt thereof, comprising:

a) reacting a compound of formula A-3a:

A-3a

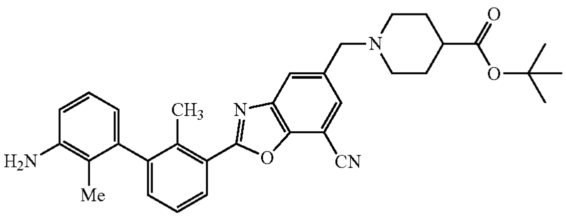

, or a salt thereof, with a compound of formula B-1a:

B-1a

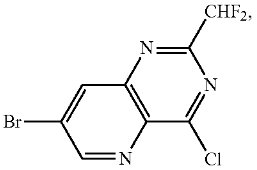

, or a salt thereof, in the presence of a base, to form a compound of formula B-2a:

B-2a

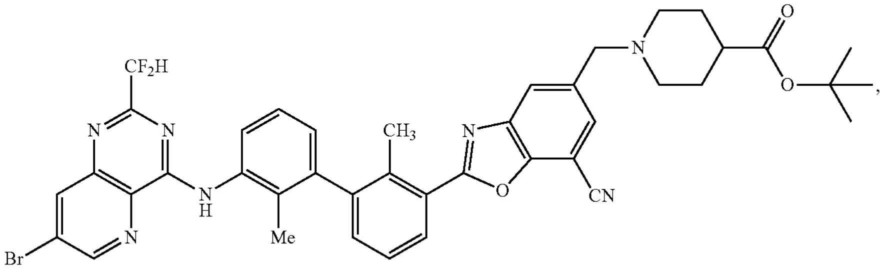

, or a salt thereof;

b) reacting the compound of formula B-2a or a salt thereof, with a salt of formula B-3a:

B-3a

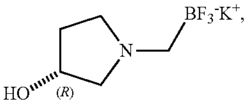

, in the presence of a Suzuki catalyst and a base to form a compound of formula A-7a:

A-7a

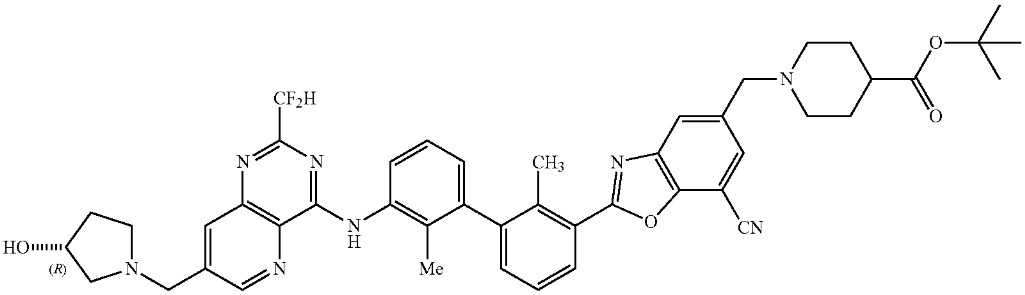

, or a salt thereof, and c) reacting the compound of formula A-7a:

A-7a

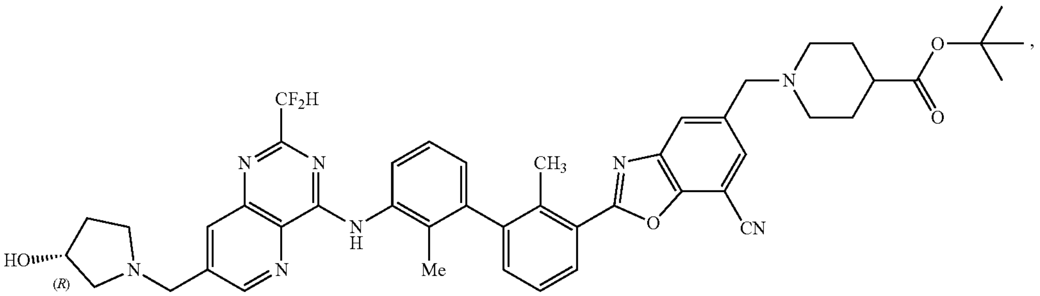

or a salt thereof, with a Lewis acid to form the compound of formula 1:

1

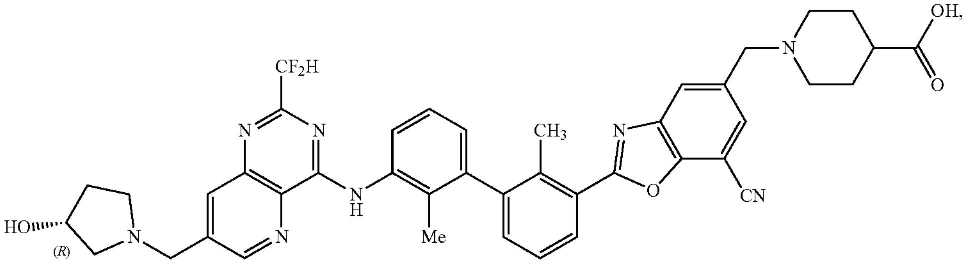

or a salt thereof.

179. A process of preparing a compound of formula A-1:

A-1

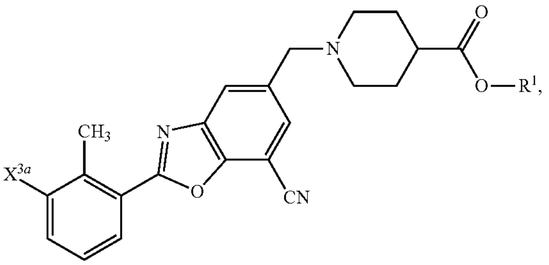

or a salt thereof, comprising: converting a compound of formula 6:

6

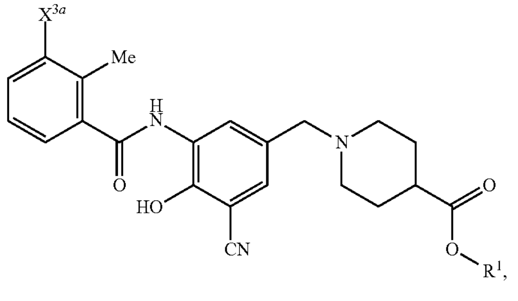

or a salt thereof, under oxidation conditions to form the compound of formula A-1, or the salt thereof, wherein $R^1$ is $C_{1-6}$ alkyl and $X^{3a}$ is halo.

180. The process of embodiment 179, wherein $X^{3a}$ is bromo.

181. The process of embodiment 179 or 180, wherein the oxidation conditions of converting the compound of formula 6, or the salt thereof, to the compound of formula A-1, or the salt thereof, comprise treating with a free radical initiator and $P(R^3)_3$, wherein $R^2$ is $C_{1-6}$ alkyl, $C_{5-6}$ cyclohexyl, or $C_{6-9}$ aryl.

182. The process of embodiment 181, wherein the $P(R^3)_3$ is triphenylphosphine.

183. The process of embodiment 181 or 182, wherein the free radical initiator is a diazo compound or a peroxide compound.

184. The process of embodiment 181 or 182, wherein the free radical initiator is a diazo compound.

185. The process of any one of embodiments 181-184, wherein the free radical initiator has formula $R^4$—OC(═O)—N═N—C(O)—$OR^{4'}$, wherein $R^4$ and $R^{4'}$ are independently selected from $C_{1-6}$ alkyl and benzyl.

186. The process of any one of embodiments 181-185, wherein the free radical initiator is diisopropylazodicarboxylate.

187. The process of any one of embodiments 181-186, wherein from about 1 to about 2 molar equivalents of $P(R^3)_3$ is utilized relative to the compound of formula 6, or the salt thereof.

188. The process of any one of embodiments 181-186, wherein about 1.7 molar equivalents of $P(R^2)_3$ is utilized relative to the compound of formula 6, or the salt thereof.

189. The process of any one of embodiments 181-188, wherein from about 1 to about 2 molar equivalents of the free radical initiator is utilized relative to the compound of formula 6, or the salt thereof.

190. The process of any one of embodiments 181-188, wherein about 1.7 molar equivalents of the free radical initiator is utilized relative to the compound of formula 6, or the salt thereof.

191. The process of any one of embodiments 179-190, wherein the converting of the compound of formula 6 or the salt thereof to the compound of formula A-1, or the salt thereof, is carried out at a temperature of from about 50° C. to about 80° C.

192. The process of any one of embodiments 179-190, wherein the converting of the compound of formula 6 or the salt thereof to the compound of formula A-1, or the salt thereof, is carried out at a temperature of about 65° C.

193. The process of any one of embodiments 179-192, wherein the converting of compound 6, or the salt thereof, to the compound of formula A-1, or the salt thereof, is carried out in a solvent component.

194. The process of embodiment 193, wherein the converting of compound 6, or the salt thereof, to the compound of formula A-1, or the salt thereof, is carried out in a solvent component comprising a di-$C_{1-6}$ alkyl ether or a 4-10 membered heterocycloalkyl ether.

195. The process of embodiment 193 or 194, wherein the converting of compound 6, or the salt thereof, to the compound of formula A-1, or the salt thereof, is carried out in a solvent component comprising tetrahydrofuran.

196. The process of any one of embodiments 179-195, wherein the compound of A-1 or the salt thereof is a compound of formula A-1a:

A1-a

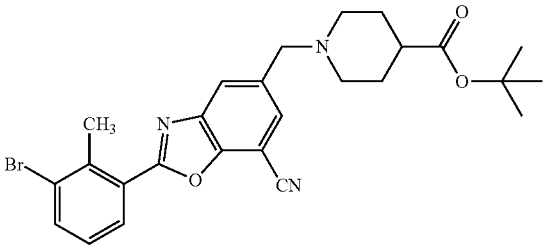

, or a salt thereof.

197. The process of any one of embodiments 179-196, wherein the compound of formula 6, or the salt thereof, is a compound of formula 6a:

6a

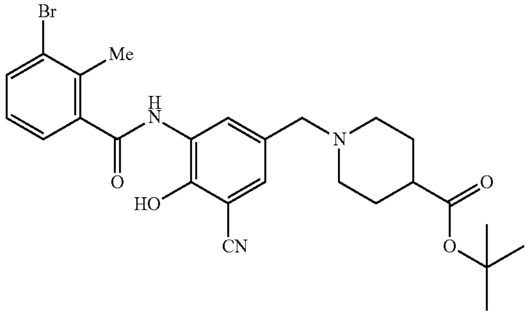

, or a salt thereof.

198. The process of any one of embodiments 179-196, wherein the compound of formula 6, or the salt thereof, is prepared by a process comprising:

reacting a compound of formula 5:

5

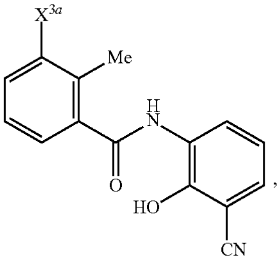

, or a salt thereof, with a compound of formula 9:

9

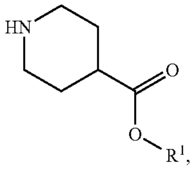

or a salt thereof, wherein $R^1$ is $C_{1-6}$ alkyl, and paraformaldehyde; and $X^{3a}$ is halo.

199. The process of embodiment 198, wherein $X^{3a}$ is bromo.

200. The process of embodiment 198 or 199, wherein from about 1 to about 1.5 molar equivalents of paraformaldehyde is utilized relative to the compound of formula 5, or the salt thereof.

201. The process of embodiment 198 or 199, wherein about 1 molar equivalent of paraformaldehyde is utilized relative to the compound of formula 5, or the salt thereof.

202. The process of any one of embodiments 198-201, wherein from about 1 to about 1.5 molar equivalents of the compound of formula 9, or the salt thereof, is utilized relative to the compound of formula 5, or the salt thereof.

203. The process of any one of embodiments 198-201, wherein about 1 molar equivalent of the compound of formula 9 or the salt thereof is utilized relative to the compound of formula 5, or the salt thereof.

204. The process of any one of embodiments 198-203, wherein the reacting of the compound of formula 5, or the salt thereof, with the compound of formula 9, or the salt thereof, and paraformaldehyde, is carried out at a temperature of from about 60° C. to about 80° C.

205. The process of any one of embodiments 198-203, wherein the reacting of the compound of formula 5, or the salt thereof, with the compound of formula 9, or the salt thereof, and paraformaldehyde, is carried out at a temperature of about 70° C.

206. The process of any one of embodiments 198-205, wherein the reacting of the compound of formula 5, or the salt thereof, with the compound of formula 9, or the salt thereof, and paraformaldehyde, is carried out in a solvent component.

207. The process of embodiment 206, wherein the reacting of the compound of formula 5, or the salt thereof, with the compound of formula 9, or the salt thereof, and paraformaldehyde, is carried out in a solvent component comprising a polar aprotic solvent.

208. The process of embodiment 206, wherein the reacting of the compound of formula 5, or the salt thereof, with the compound of formula 9, or the salt thereof, and paraformaldehyde, is carried out in a solvent component comprising acetonitrile.

209. The process of any one of embodiments 198-208, wherein the compound of formula 6, or the salt thereof, is a compound of formula 6a:

6a

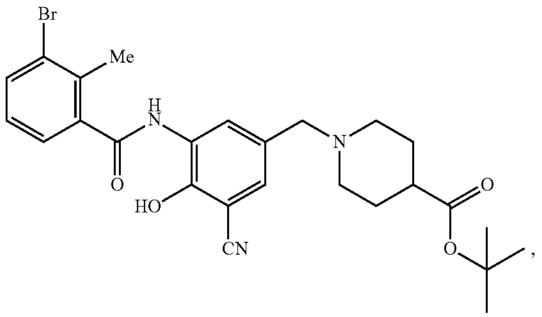

or a salt thereof.

210. The process of any one of embodiments 198-209, wherein the compound of formula 9, or the salt thereof, is a compound of formula 9a:

9a

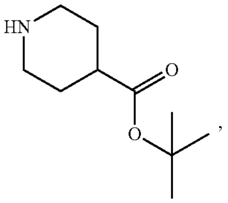

or a salt thereof.

211. The process of any one of embodiments 198-210, wherein the compound of formula 5, or the salt thereof, is prepared by a process comprising:

hydrolyzing a compound of formula 4:

4

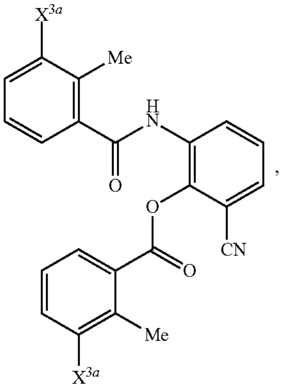

to the compound of formula 5, or a salt thereof, wherein $X^{3a}$ is halo.

212. The process of embodiment 211, wherein $X^{3a}$ is bromo.

213. The process of embodiment 211 or 212, wherein the hydrolyzing of the compound of formula 4 is conducted in the presence of a base.

214. The process of embodiment 213, wherein the base, present in the hydrolyzing of the compound of formula 4, is an alkali metal base.

215. The process of embodiment 213 or 214, wherein the base, present in the hydrolyzing of the compound of formula 4, is an alkali metal hydroxide.

216. The process of any one of embodiments 213-215, wherein the base, present in the hydrolyzing of the compound of formula 4, is selected from lithium hydroxide, sodium hydroxide, potassium hydroxide, rubidium hydroxide, lithium hydroxide, sodium hydroxide, potassium hydroxide, rubidium hydroxide, and cesium hydroxide.

217. The process of any one of embodiments 213-216, wherein the base, present in the hydrolyzing of the compound of formula 4, is sodium hydroxide.

218. The process of any one of embodiments 211-217, wherein the hydrolyzing of the compound of formula 4 is carried out at a temperature of about room temperature.

219. The process of any one of embodiments 211-218, wherein the hydrolyzing of the compound of formula 4 is carried out in a solvent component.

220. The process of embodiment 219, wherein the hydrolyzing of the compound of formula 4 is carried out in a solvent component comprising a di-$C_{1-6}$ alkyl ether or a 4-10 membered heterocycloalkyl ether, and water.

221. The process of embodiment 219 or 220, wherein the hydrolyzing of the compound of formula 4 is carried out in a solvent component comprising tetrahydrofuran and water.

222. The process of any one of embodiments 211-221, wherein the compound of formula 4 is prepared by a process comprising:

reacting a compound of formula 3:

3

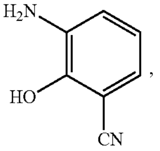

or a salt thereof, with a compound of formula 8A:

8A

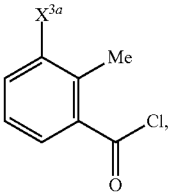

in the presence of a base, wherein $X^{3a}$ is halo.

223. The process of embodiment 222, wherein $X^{3a}$ is bromo.

224. The process of embodiment 222 or 223, wherein the base, present in the reacting of the compound of formula 3, or the salt thereof, with the compound of formula 8A, is an amine base.

225. The process of any one of embodiments 222-224, wherein the base, present in the reacting of the compound of formula 3, or the salt thereof, with the compound of formula 8A, is selected from N,N-diisopropylamine, methylamine, dimethylamine, trimethylamine, and ethylamine.

226. The process of any one of embodiments 222-225, wherein the base, present in the reacting of the compound of formula 3, or the salt thereof, with the compound of formula 8A, is trimethylamine.

227. The process of any one of embodiments 222-226, wherein from about 1 to about 3 molar equivalents of the compound of formula 8A is utilized relative to the compound of formula 3, or the salt thereof.

228. The process of any one of embodiments 222-226, wherein from about 1.5 to about 2.5 molar equivalents of the compound of formula 8A is utilized relative to the compound of formula 3, or the salt thereof.

229. The process of any one of embodiments 222-226, wherein from about 2 to about 3 molar equivalents of the compound of formula 8A is utilized relative to the compound of formula 3, or the salt thereof.

230. The process of any one of embodiments 222-226, wherein from about 2 to about 2.5 molar equivalents of the compound of formula 8A is utilized relative to the compound of formula 3, or the salt thereof.

231. The process of any one of embodiments 222-226, wherein about 2 molar equivalents of the compound of formula 8A is utilized relative to the compound of formula 3, or the salt thereof.

232. The process of any one of embodiments 222-231, wherein from about 2 to about 4 molar equivalents of the base is utilized relative to the compound of formula 3, or the salt thereof.

233. The process of any one of embodiments 222-231, wherein about 3 molar equivalents of the base is utilized relative to the compound of formula 3, or the salt thereof.

234. The process of any one of embodiments 222-233, wherein the reacting of the compound of formula 3, or the salt thereof, with the compound of formula 8A, is carried out at room temperature.

235. The process of any one of embodiments 222-233, wherein the reacting of the compound of formula 3, or the salt thereof, with the compound of formula 8A, is carried out at a temperature of from about 20° C. to about 30° C.

236. The process of any one of embodiments 222-235, wherein the reacting of the compound of formula 3, or the salt thereof, with the compound of formula 8A is carried out in a solvent component.

237. The process of embodiment 236, wherein the reacting of the compound of formula 3, or the salt thereof, with the compound of formula 8A is carried out in a solvent component comprising a di-$C_{1-6}$ alkyl ether or a 4-10 membered heterocycloalkyl ether.

238. The process of embodiment 236, wherein the reacting of the compound of formula 3, or the salt thereof, with the compound of formula 8A is carried out in a solvent component comprising tetrahydrofuran.

239. The process of any of embodiments 222-238, wherein the compound of formula 8A is prepared by a process comprising:

reacting a compound of formula 8:

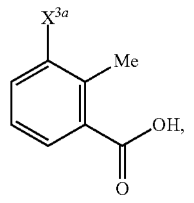

8 or a salt thereof, with a chlorinating agent, wherein $X^{3a}$ is halo.

240. The process of embodiment 239, wherein $X^{3a}$ is bromo.

241. The process of embodiment 239 or 240, wherein the chlorinating agent is selected from oxalyl chloride, phosphorus oxychloride, diphosgene, thionyl chloride, sulfuryl chloride and phosphorus pentachloride.

242. The process of any one of embodiments 239-241, wherein the chlorinating agent is oxalyl chloride.

243. The process of any one of embodiments 239-242, wherein the reacting of the compound of formula 8, or the salt thereof, with the chlorinating agent is conducted in the presence of a catalyst.

244. The process of embodiment 243, wherein the catalyst is dimethylformamide.

245. The process of any one of embodiments 239-244, wherein from about 1 to about 1.5 molar equivalents of the chlorinating agent is utilized relative to the compound of formula 8, or the salt thereof.

246. The process of any one of embodiments 239-244, wherein about 1 molar equivalent of the chlorinating agent is utilized relative to the compound of formula 8, or the salt thereof.

247. The process of any one of embodiments 239-246, wherein the reacting of the compound of formula 8, or the salt thereof, with the chlorinating agent is carried out at a temperature of from about 20° C. to about 30° C.

248. The process of any one of embodiments 239-247, wherein the reacting of the compound of formula 8, or the salt thereof, with the chlorinating agent is carried out in a solvent component.

249. The process of embodiment 248, wherein the reacting of the compound of formula 8, or the salt thereof, with the chlorinating agent is carried out in a solvent component comprising a di-$C_{1-6}$ alkyl ether or a 4-10 membered heterocycloalkyl ether.

250. The process of embodiment 248 or 249, wherein the reacting of the compound of formula 8, or the salt thereof, with the chlorinating agent is carried out in a solvent component comprising tetrahydrofuran.

251. The process of any one of embodiments 248-250, wherein the reacting of the compound of formula 8, or the salt thereof, with the chlorinating agent is carried out in a solvent component comprising dimethylformamide.

252. The process of any one of embodiments 85-106, wherein a compound of formula B-1, or the salt thereof, is prepared by a process comprising:

reacting a compound of formula 12:

12

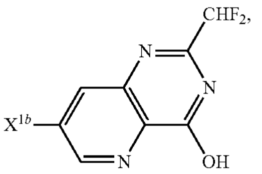

or a salt thereof, with a halogenating agent, wherein $X^{1b}$ is halo.

253. The process of embodiment 252, wherein $X^{1b}$ is bromo.

254. The process of embodiment 252 or 253, wherein the compound of formula B-1 has formula B-1a.

255. The process of any one of embodiments 252-254, wherein the reacting of the compound of formula 12 with the halogenating agent is conducted in the presence of a base and a catalyst.

256. The process of embodiment 255, wherein the base, present in the reacting of the compound of formula 12 with the halogenating agent, is an amine base.

257. The process of embodiment 255 or 256, wherein the base, present in the reacting of the compound of formula 12 with the halogenating agent, is selected from N,N-diethylaniline, N,N-diisopropylamine, methylamine, dimethylamine, trimethylamine, and ethylamine.

258. The process of any one of embodiments 255-257, wherein the base, present in the reacting of the compound of formula 12 with the halogenating agent, is N,N-diethylaniline.

259. The process of any one of embodiments 252-258, wherein the halogenating agent is a chlorinating agent.

260. The process of embodiment 259, wherein the halogenating agent is selected from oxalyl chloride, phosphorus oxychloride, triphosgene, thionyl chloride, sulfuryl chloride and phosphorus pentachloride.

261. The process of embodiment 259 or 260, wherein the halogenating agent is phosphorus oxychloride.

262. The process of any one of embodiments 255-261, wherein the catalyst, present in the reacting of the compound of formula 12 with the halogenating agent, is benzyltriethylammonium chloride.

263. The process of any one of embodiments 255-262, wherein from about 1 to about 2 molar equivalents of the base is utilized relative to the compound of formula 12, or the salt thereof.

264. The process of any one of embodiments 255-262, wherein about 1.5 molar equivalents of the base is utilized relative to the compound of formula 12, or the salt thereof.

265. The process of any one of embodiments 252-264, wherein from about 2 to about 4 molar equivalents of the halogenating agent is utilized relative to the compound of formula 12, or the salt thereof.

266. The process of any one of embodiments 252-264, wherein from about 2.5 to about 3.5 molar equivalents of the halogenating agent is utilized relative to the compound of formula 12, or the salt thereof.

267. The process of any one of embodiments 252-264, wherein about 3 molar equivalents of the halogenating agent is utilized relative to the compound of formula 12, or the salt thereof.

268. The process of any one of embodiments 255-267, wherein from about 1 to about 3 molar equivalents of the catalyst is utilized relative to the compound of formula 12, or the salt thereof.

269. The process of any one of embodiments 255-267, wherein about 2 molar equivalents of the catalyst is utilized relative to the compound of formula 12, or the salt thereof.

270. The process of any one of embodiments 252-269, wherein the reacting of the compound of formula 12, or the salt thereof, with the halogenating agent is carried out at a temperature of from about 70° C. to about 80° C.

271. The process of any one of embodiments 252-269, wherein the reacting of the compound of formula 12, or the salt thereof, with the halogenating agent is carried out at a temperature of about 75° C.

272. The process of any one of embodiments 252-269, wherein the reacting of the compound of formula 12, or the salt thereof with the halogenating agent is carried out in a solvent component.

273. The process of embodiment 272, wherein the reacting of the compound of formula 12, or the salt thereof with the halogenating agent is carried out in a solvent component comprising a polar aprotic solvent.

274. The process of embodiment 272 or 273, wherein the reacting of the compound of formula 12, or the salt thereof with the halogenating agent is carried out in a solvent component comprising acetonitrile.

275. The process of any one of embodiments 35-55, wherein the compound of formula A-4, or the salt thereof, is prepared by a process comprising:

oxidizing a compound of formula 14:

14

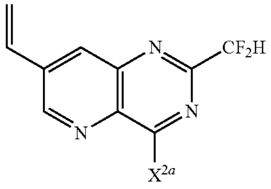

or a salt thereof, to form the compound of formula A-4, wherein $X^{2a}$ is halo.

276. The process of embodiment 275, wherein, $X^{2a}$ is chloro.

277. The process of embodiments 275 or 276, wherein the compound of formula A-4, or a salt thereof, is a compound of formula A-4a, A-4a

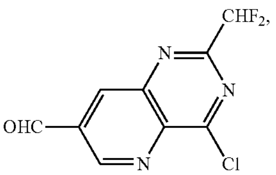

or a salt thereof.

278. The process of any one of embodiments 275-277, wherein the oxidizing of the compound of formula 14, or the salt thereof, is carried out in the presence of a catalyst.

279. The process of embodiment 278, wherein the catalyst, present in the oxidizing of the compound of formula 14, or the salt thereof, is osmium tetroxide.

280. The process of any one of embodiments 275-279, wherein the oxidizing of the compound of formula 14, or the salt thereof, is carried out in the presence of an oxidizing agent.

281. The process of embodiment 280, wherein the oxidizing agent, present in the oxidizing of the compound of formula 14, or the salt thereof, is sodium periodate.

282. The process of any one of embodiments 275-281, wherein the oxidizing of the compound of formula 14, or the salt thereof, is carried out in the presence of a base.

283. The process of embodiment 282, wherein the base, present in the oxidizing of the compound of formula 14, or the salt thereof, is an aromatic base.

284. The process of embodiment 282 or 283, wherein the base, present in the oxidizing of the compound of formula 14, or the salt thereof, is 2,6-dimethylpyridine.

285. The process of any one of embodiments 278-284, wherein from about 0.001 to about 0.1 molar equivalent of the catalyst is utilized relative to the compound of formula 14, or the salt thereof.

286. The process of any one of embodiments 278-284, wherein from about 0.01 molar equivalent of the catalyst is utilized relative to the compound of formula 14, or the salt thereof.

287. The process of any one of embodiments 280-286, wherein from about 3 to about 5 molar equivalents of the oxidizing agent is utilized relative to the compound of formula 14, or the salt thereof.

288. The process of any one of embodiments 280-286, wherein from about 4 molar equivalents of the oxidizing agent is utilized relative to the compound of formula 14, or the salt thereof.

289. The process of any one of embodiments 282-288, wherein from about 1 to about 3 molar equivalents of the base is utilized relative to the compound of formula 14, or the salt thereof.

290. The process of any one of embodiments 282-288, wherein from about 2 molar equivalents of the base is utilized relative to the compound of formula 14, or the salt thereof.

291. The process of any one of embodiments 275-290, wherein the oxidizing of the compound of formula 14, or the salt thereof is carried out at a temperature of from about 10° C. to about 15° C.

292. The process of any one of embodiments 275-291, wherein the oxidizing of the compound of formula 14, or the salt thereof is carried out in a solvent component.

293. The process of embodiment 292, wherein the oxidizing of the compound of formula 14, or the salt thereof is carried out in a solvent component comprising a di-$C_{1-6}$ alkyl ether, a 4-10 membered heterocycloalkyl ether, a polar protic solvent, or a mixture thereof.

294. The process of embodiment 292 or 293, wherein the oxidizing of the compound of formula 14, or the salt thereof is carried out in a solvent component comprising tetrahydrofuran and water.

295. The process of any one of embodiments 275-294, wherein the compound of formula 14, or the salt thereof, is prepared by a process comprising:

reacting a compound of formula 13:

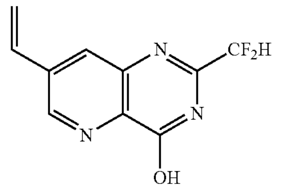

13 or a salt thereof, with a halogenating agent to form the compound of formula 14, or the salt thereof.

296. The process of embodiment 295, wherein the reacting of the compound of formula 13, or the salt thereof, with the halogenating agent is conducted in the presence of a base.

297. The process of embodiment 296, wherein the base, present in the reacting of the compound of formula 13, or the salt thereof, with the halogenating agent, is an amine base.

298. The process of embodiment 296 or 297, wherein the base, present in the reacting of the compound of formula 13, or the salt thereof, with the halogenating agent, is selected from N,N-diethylaniline, N,N-diisopropylamine, methylamine, dimethylamine, trimethylamine, and ethylamine.

299. The process of any one of embodiments 296-298, wherein the base, present in the reacting of the compound of formula 13, or the salt thereof, with the halogenating agent, is N,N-diethylaniline.

300. The process of any one of embodiments 295-299, wherein the halogenating agent, utilized in the reacting with the compound of formula 13, or the salt thereof, is a chlorinating agent.

301. The process of embodiment 300, wherein the halogenating agent, utilized in the reacting with the compound of formula 13, or the salt thereof, is selected from oxalyl chloride, phosphorus oxychloride, triphosgene, thionyl chloride, sulfuryl chloride and phosphorus pentachloride.

302. The process of embodiment 300 or 301, wherein the halogenating agent, utilized in the reacting with the compound of formula 13, or the salt thereof, is phosphorus oxychloride.

303. The process of any one of embodiments 296-302, wherein from about 1 to about 2 molar equivalents of the base is utilized relative to the compound of formula 13, or the salt thereof.

304. The process of any one of embodiments 296-302, wherein about 1 molar equivalent of the base is utilized relative to the compound of formula 13, or the salt thereof.

305. The process of any one of embodiments 295-304, wherein from about 1 to about 2 molar equivalents of the halogenating agent is utilized relative to the compound of formula 13, or the salt thereof.

306. The process of any one of embodiments 295-304, wherein about 1 molar equivalent of the halogenating agent is utilized relative to the compound of formula 13, or the salt thereof.

307. The process of any one of embodiments 295-306, wherein the reacting of the compound of formula 13, or the salt thereof, with the halogenating agent is carried out at a temperature of from about 100° C. to about 150° C.

308. The process of any one of embodiments 295-306, wherein the reacting of the compound of formula 13, or the salt thereof, with the halogenating agent is carried out at a temperature of about 130° C.

309. The process of any one of embodiments 295-308, wherein the reacting of the compound of formula 13, or the salt thereof, with the halogenating agent is carried out in a solvent component.

310. The process of embodiment 309, wherein the reacting of the compound of formula 13, or the salt thereof, with the halogenating agent is carried out in a solvent component comprising an aromatic hydrocarbon.

311. The process of embodiment 309 or 310, wherein the reacting of the compound of formula 13, or the salt thereof, with the halogenating agent is carried out in a solvent component comprising toluene.

312. The process of any one of embodiments 295-311, wherein the compound of formula 13, or the salt thereof, is prepared by a process comprising:

reacting a compound of formula 12:

12

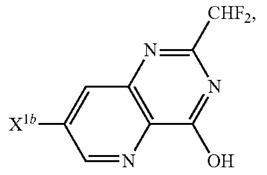

or a salt thereof, with 4,4,5,5-tetramethyl-2-vinyl-1,3,2-dioxaborolane in the presence of a Suzuki catalyst and a base to form the compound of formula 13, or the salt thereof, wherein $X1^b$ is halo.

313. The process of embodiment 312, wherein $X^{1b}$ is bromo.

314. The process of embodiment 312 or 313, wherein the Suzuki catalyst, present in the reacting of the compound of formula 12, or the salt thereof, with the 4,4,5,5-tetramethyl-2-vinyl-1,3,2-dioxaborolane, is a palladium catalyst.

315. The process of any one of embodiments 312-314, wherein the Suzuki catalyst, present in the reacting of the compound of formula 12, or the salt thereof, with the 4,4,5,5-tetramethyl-2-vinyl-1,3,2-dioxaborolane, is selected from RuPhos Pd G4, CataCXium® Pd G4 ((2'-(methylamino)-[1,1'-biphenyl]-2-yl)((methylsulfonyl)oxy)palladium di(1-adamantyl)-n-butylphosphine complex), $Pd(PPh_3)_4$, $Pd(dppf)_2Cl_2$, dichlorobis[di-tert-butyl(p-dimethylaminophenyl)phosphino]palladium and $PdCl_2(dtbpf)$ (Pd-118).

316. The process of any one of embodiments 312-315, wherein the Suzuki catalyst, present in the reacting of the compound of formula 12, or the salt thereof, with the 4,4,5,5-tetramethyl-2-vinyl-1,3,2-dioxaborolane, is $Pd(dppf)_2Cl_2$.

317. The process of any one of embodiments 312-316, wherein the base, present in the reacting of the compound of formula 12, or the salt thereof, with the 4,4,5,5-tetramethyl-2-vinyl-1,3,2-dioxaborolane, is an alkali metal base.

318. The process of any one of embodiments 312-317, wherein the base, present in the reacting of the compound of formula 12, or the salt thereof, with the 4,4,5,5-tetramethyl-2-vinyl-1,3,2-dioxaborolane, is an alkali metal carbonate.

319. The process of any one of embodiments 312-318, wherein the base, present in the reacting of the compound of formula 12, or the salt thereof, with the 4,4,5,5-tetramethyl-2-vinyl-1,3,2-dioxaborolane, is selected from cesium carbonate, lithium carbonate, sodium carbonate and potassium carbonate.

320. The process of any one of embodiments 312-319, wherein the base, present in the reacting of the compound of formula 12, or the salt thereof, with the 4,4,5,5-tetramethyl-2-vinyl-1,3,2-dioxaborolane, is potassium carbonate.

321. The process of any one of embodiments 312-320, wherein from about 1 to about 2 molar equivalents of the 4,4,5,5-tetramethyl-2-vinyl-1,3,2-dioxaborolane is utilized relative to the compound of formula 12, or the salt thereof.

322. The process of any one of embodiments 312-320, wherein from about 1.5 molar equivalents of the 4,4,5,5-tetramethyl-2-vinyl-1,3,2-dioxaborolane is utilized relative to the compound of formula 12, or the salt thereof.

323. The process of any one of embodiments 312-322, wherein from about 1 to about 5 molar equivalents of the base is utilized relative to the compound of formula 12, or the salt thereof.

324. The process of any one of embodiments 312-322, wherein from about 2 to about 4 molar equivalents of the base is utilized relative to the compound of formula 12, or the salt thereof.

325. The process of any one of embodiments 312-322, wherein about 3 molar equivalents of the base is utilized relative to the compound of formula 12, or the salt thereof.

326. The process of any one of embodiments 312-325, wherein from about 0.01 to about 0.1 molar equivalent of the Suzuki catalyst is utilized relative to the compound of formula 12, or the salt thereof.

327. The process of any one of embodiments 312-325, wherein about 0.04 molar equivalent of the Suzuki catalyst is utilized relative to the compound of formula 12, or the salt thereof.

328. The process of any one of embodiments 312-327, wherein the reacting of the compound of formula 12, or the salt thereof, with the 4,4,5,5-tetramethyl-2-vinyl-1,3,2-dioxaborolane is carried out at a temperature of from about 80° C. to about 85° C.

329. The process of any one of embodiments 312-328, wherein the reacting of the compound of formula 12, or the salt thereof, with the 4,4,5,5-tetramethyl-2-vinyl-1,3,2-dioxaborolane is carried out in a solvent component.

330. The process of embodiment 329, wherein the reacting of the compound of formula 12, or the salt thereof, with the 4,4,5,5-tetramethyl-2-vinyl-1,3,2-dioxaborolane is carried out in a solvent component comprising a polar protic solvent, a $C_{1-6}$ alkanol, or a mixture thereof.

331. The process of embodiment 329 or 330, wherein the reacting of the compound of formula 12, or the salt thereof, with the 4,4,5,5-tetramethyl-2-vinyl-1,3,2-dioxaborolane is carried out in a solvent component comprising water and ethanol.

332. The process of any one of embodiments 312-331, wherein the compound of formula 12, or the salt thereof, is prepared by a process comprising:

reacting a compound of formula 11:

11

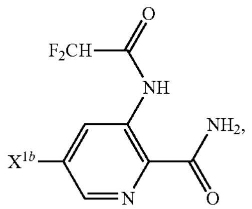

or a salt thereof, with a base, wherein $X^{1b}$ is halo.

333. The process of embodiment 332, wherein $X^{1b}$ is bromo.

334. The process of embodiment 332 or 333, wherein the base, utilized in the reacting with the compound of formula 11, or the salt thereof, is an alkali metal base.

335. The process of any one of embodiments 332-334, wherein the base, utilized in the reacting with the compound of formula 11, or the salt thereof, is an alkali metal hydroxide.

336. The process of any one of embodiments 332-335, wherein the base, utilized in the reacting with the compound of formula 11, or the salt thereof, is selected from lithium hydroxide, sodium hydroxide, potassium hydroxide, rubidium hydroxide, and cesium hydroxide.

337. The process of any one of embodiments 332-336, wherein the base, utilized in the reacting with the compound of formula 11, or the salt thereof, is sodium hydroxide.

338. The process of any one of embodiments 332-337, wherein from about 1 to about 3 molar equivalents of the base is utilized relative to the compound of formula 11, or the salt thereof.

339. The process of any one of embodiments 332-337, wherein about 2 molar equivalents of the base is utilized relative to the compound of formula 11, or the salt thereof.

340. The process of any one of embodiments 332-339, wherein the reacting of the compound of formula 11, or the salt thereof, with the base, is carried out at a temperature of from about 80° C. to about 90° C.

341. The process of any one of embodiments 332-339, wherein the reacting of the compound of formula 11, or the salt thereof, with the base, is carried out at a temperature of about 85° C.

342. The process of any one of embodiments 332-341, wherein the reacting of the compound of formula 11, or the salt thereof, with the base, is carried out in a solvent component.

343. The process of embodiment 342, wherein the reacting of the compound of formula 11, or the salt thereof, with the base is carried out in a solvent component comprising a protic solvent.

344. The process of embodiment 342 or 343, wherein the reacting of the compound of formula 11, or the salt thereof, with the base is carried out in a solvent component comprising a $C_{1-6}$ alkanol.

345. The process of any one of embodiments 342-344, wherein the reacting of the compound of formula 11, or the salt thereof, with the base is carried out in a solvent component comprising ethanol.

346. The process of any one of embodiments 332-345, wherein the compound of formula 11, or the salt thereof, is prepared by a process comprising:

reacting a compound of formula 10:

10

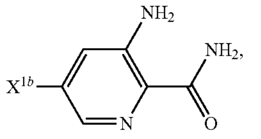

or a salt thereof, with 2,2-difluoroacetic anhydride, wherein $X^{1b}$ is halo.

347. The process of embodiment 346, wherein $X^{1b}$ is bromo.

348. The process of embodiment 346 or 347, wherein from about 1 to about 2 molar equivalents of the 2,2-difluoroacetic anhydride is utilized relative to the compound of formula 10, or the salt thereof.

349. The process of any one of embodiments 346-348, wherein about 1.5 molar equivalents of the 2,2-difluoroacetic anhydride is utilized relative to the compound of formula 10, or the salt thereof.

350. The process of any one of embodiments 346-349, wherein the reacting of the compound of formula 10, or the salt thereof, with the 2,2-difluoroacetic anhydride, is carried out at a temperature of about 50° C. to about 70° C.

351. The process of any one of embodiments 346-349, wherein the reacting of the compound of formula 10, or the salt thereof, with the 2,2-difluoroacetic anhydride, is carried out at a temperature of about 60° C.

352. The process of any one of embodiments 346-351, wherein the reacting of the compound of formula 10, or the salt thereof, with the 2,2-difluoroacetic anhydride, is carried out in a solvent component.

353. The process of embodiment 352, wherein the reacting of the compound of formula 10, or the salt thereof, with the 2,2-difluoroacetic anhydride, is carried out in a solvent component solvent component comprising a di-$C_{1-6}$ alkyl ether or a 4-10 membered heterocycloalkyl ether.

354. The process of embodiment 352 or 353, wherein the reacting of the compound of formula 10, or the salt thereof, with the 2,2-difluoroacetic anhydride, is carried out in a solvent component solvent component comprising 1,4-dioxane.

355. A compound of formula A-1:

A-1

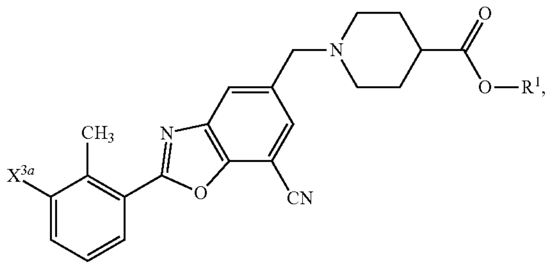

or a salt thereof, wherein $R^1$ is $C_{1-6}$ alkyl; and $X^{3a}$ is halo.

356. The compound of embodiment 355, wherein the compound is a compound of formula A-1a:

A-1a

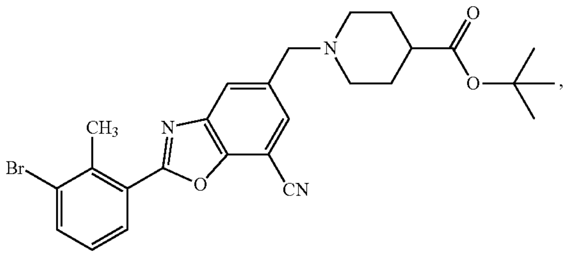

or a salt thereof.

357. A compound of formula A-3:

A-3

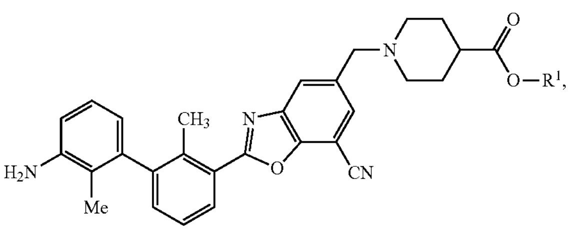

or a salt thereof, wherein $R^1$ is $C_{1-6}$ alkyl.

358. The compound of embodiment 357, wherein the compound is a compound of formula A-3a:

A-3a

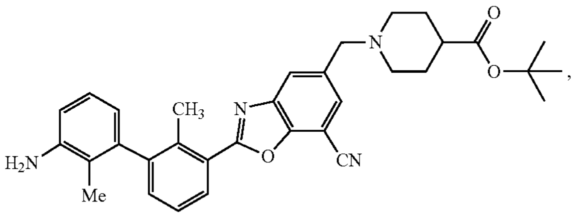

or a salt thereof.

359. A compound of formula A-4:

A-4

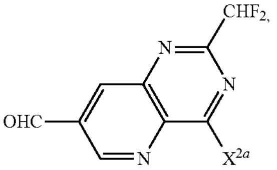

or a salt thereof, wherein $X^{2a}$ is halo.

360. The compound of embodiment 359, wherein the compound is a compound of formula A-4a:

A-4a

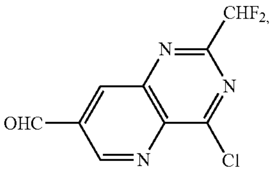

or a salt thereof.

361. A compound of formula A-5:

A-5

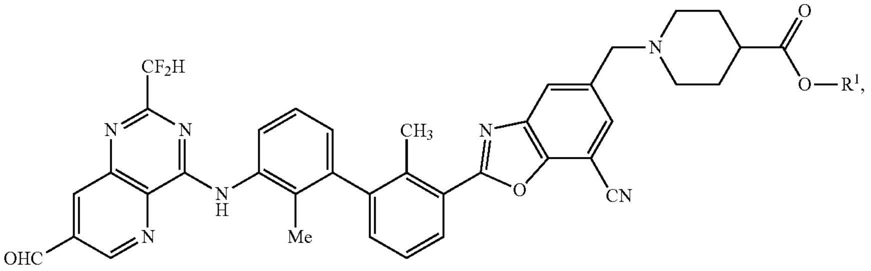

or a salt thereof, wherein $R^1$ is $C_{1-6}$ alkyl.

362. The compound of embodiment 361, wherein the compound is a compound of formula A-5a, A-5a

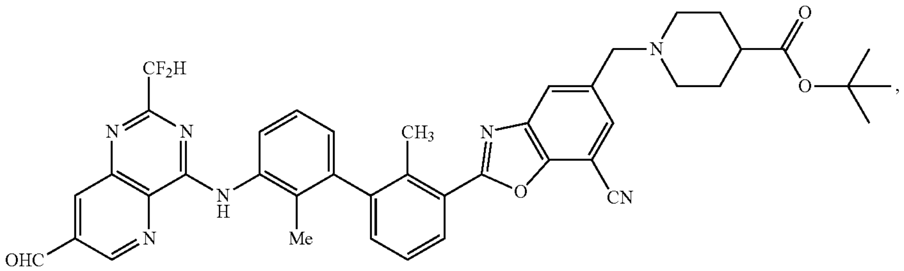

or a salt thereof.

363. A compound of formula A-7:
A-7
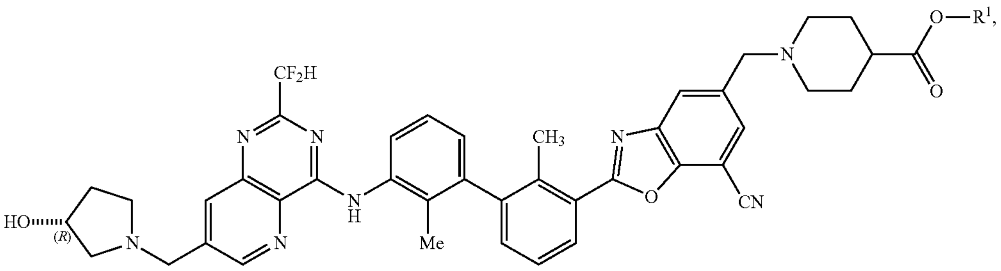
or a salt thereof, wherein $R^1$ is $C_{1-6}$ alkyl.
364. The compound of embodiment 363, wherein the compound is a compound of formula A-7a:
A-7a
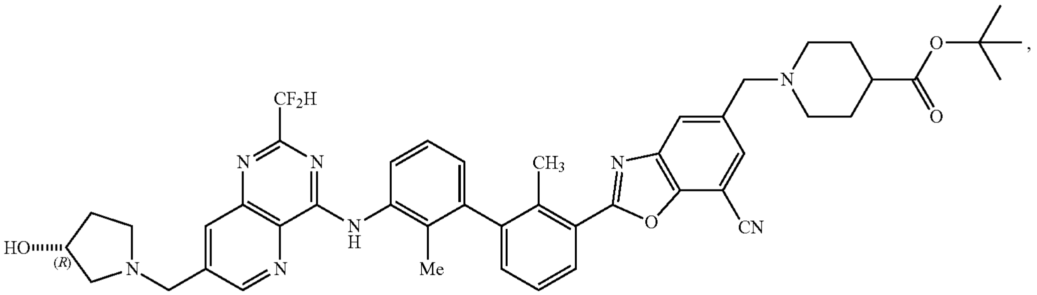
or a salt thereof.
365. A compound of formula B-2:
B-2
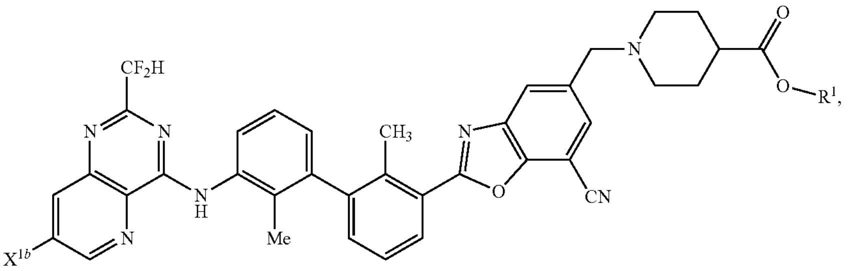
or a salt thereof, wherein $R^1$ is $C_{1-6}$ alkyl, wherein $X^{1b}$ is halo.

366. The compound of embodiment 365, wherein the compound is a compound of formula B-2a:

B-2a

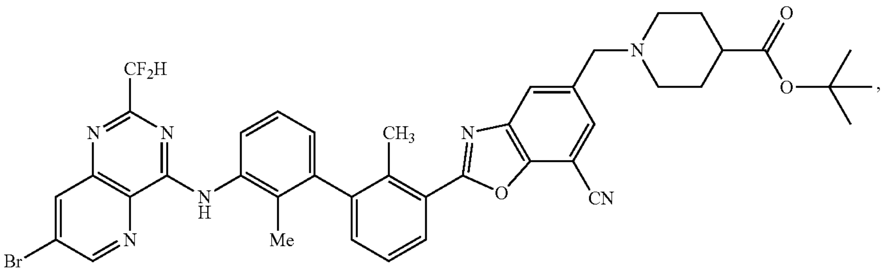

or a salt thereof.

367. A compound selected from a compound of formula 4, a compound of formula 5, and a compound of formula 6:

4

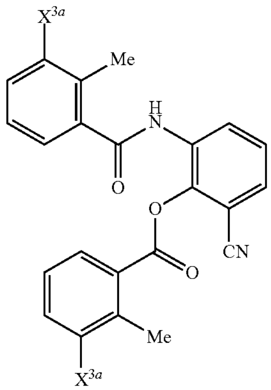

5

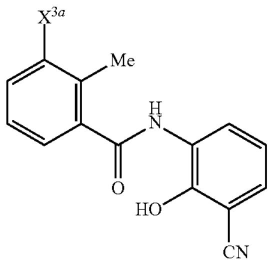

6

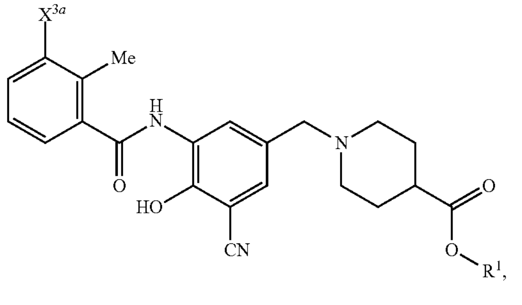

or a salt thereof, wherein each $X^{3a}$ is independently halo; and $R^1$ is t-butyl.

368. The compound of embodiment 367, wherein the compound is a compound of formula 4a:

4a

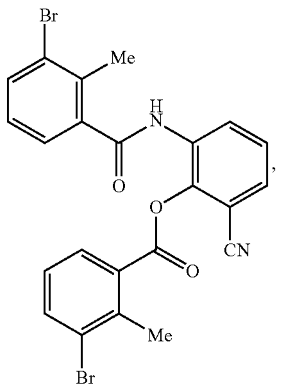

or a salt thereof.

369. The compound of embodiment 367, wherein the compound is a compound of formula 5a:

5a

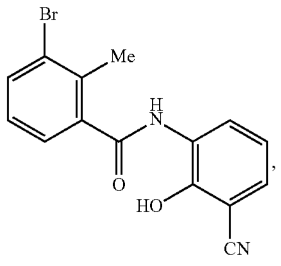

or a salt thereof.

370. The compound of embodiment 367, wherein the compound is a compound of formula 6a:

6a

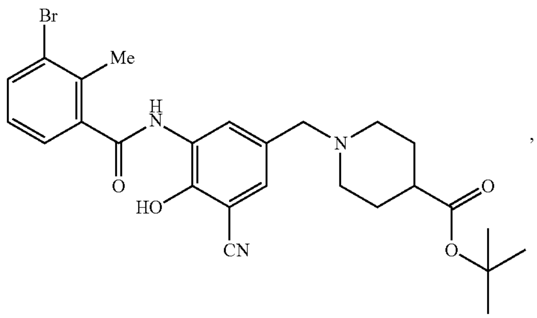

or a salt thereof.

371. A compound of formula 11:

11

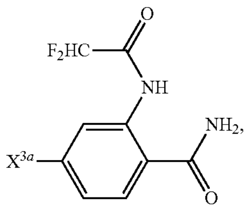

or a salt thereof, wherein $X^{3a}$ is halo.

372. The compound of embodiment 371, wherein the compound is a compound of formula 11a:

11a

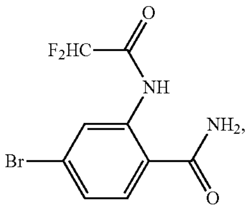

or a salt thereof.

EXAMPLES

Experimental Methods

In some examples below, X-Ray Powder Diffraction analysis was carried out on a Bruker D8 X-ray Powder Diffractometer (XRPD) instrument using Cu Kα radiation (40 kV, 40 mA) and a θ-2θ goniometer fitted with a Ge monochromator. The incident beam passes through a 2.0 mm divergence slit followed by a 0.2 mm anti-scatter slit and knife edge. The diffracted beam passes through an 8.0 mm receiving slit with 2.5° Soller slits followed by the Lynxeye Detector. The software used for data collection and analysis was Diffrac Plus XRD Commander and Diffrac Plus EVA respectively. Samples were run under ambient conditions as flat plate specimens using powder as received. The sample was prepared on a polished, zero-background (510) silicon wafer by gently pressing onto the flat surface or packed into a cut cavity. The sample was rotated in its own plane. The general experimental procedures for XRPD were: (1) angular range: 2 to 42° 2θ; (2) step size: 0.05° 2θ; and collection time: 0.5 s/step (total collection time: 6.40 min). The extended data collection experimental procedures for XRPD were: (1) angular range: 3 to 30° 2θ; (2) step size: 0.05° 2θ; and collection time: 4 s/step (total collection time: 38.00 min).

In some examples below, X-Ray Powder Diffraction analysis was carried out on a PANalytical Empyrean X-ray Powder Diffractometer (XRPD) instrument using Cu Kα radiation (45 kV, 40 mA) in transmission geometry. A 0.5° slit, 4 mm mask and 0.04 rad Soller slits with a focusing mirror were used on the incident beam. A $PIXcel^{3D}$ detector, placed on the diffracted beam, was fitted with a receiving slit and 0.04 rad Soller slits. The software used for data collection was X'Pert Data Collector using X'Pert Operator Interface. The data were analysed and presented using Diffrac Plus EVA or HighScore Plus. Samples were prepared and analysed in either a metal or Millipore 96 well-plate in transmission mode. X-ray transparent film was used between the metal sheets on the metal well-plate and powders (approximately 1-2 mg) were used as received. The Millipore plate was used to isolate and analyse solids from suspensions by adding a small amount of suspension directly to the plate before filtration under a light vacuum. The scan mode for the metal plate used the gonio scan axis, whereas a 2θ scan was utilised for the Millipore plate. The general experimental procedures for XRPD were: (1) angular range: 2.5 to 32.0° 2θ; step size: 0.0130° 2θ; and collection time: 12.75 s/step (total collection time of 2.07 min).

Qualitative NMR analysis (H) was conducted on a Bruker 400 MHz instrument equipped with an auto-sampler and controlled by a DRX400 console. Samples were prepared in DMSO-$d_6$ solvent, unless otherwise stated. Automated experiments were acquired using ICON-NMR configuration, using standard Bruker-loaded experiments ($^1H$, $^{13}C$ {$^1H$}, DEPT135).

Differential Scanning Calorimetry (DSC) was carried out on a TA Instruments Differential Scanning Calorimetry, Model Q2000 with autosampler. The DSC instrument conditions were as follows: 25-300° C. at 10° C./min; pin-holed aluminum sample pan; and nitrogen gas flow at 50 mL/min. Modulated temperature DSC was carried out using an underlying heating rate of 2° C./min and temperature modulation parameters of 0.636° C. (amplitude) every 60 seconds (period). Some experiments were run on a TA Instruments Differential Scanning Calorimetry with autosampler. The DSC instrument conditions were as follows: 25-300° C. at 10° C./min; pin-holed aluminum sample pan; and nitrogen gas flow at 50 mL/min.

Thermogravimetric analysis (TGA) was carried out on a TA Instruments Thermogravimetric Analyzer with autosampler. The general experimental conditions for TGA were: ramp from 25° C.-350° C. at 10° C./min; nitrogen purge, gas flow at 25 mL/min; aluminum pan. Some experiments were run on a TA Instruments Thermogravimetric Analyzer, TGA Q500 with autosampler. The general experimental conditions for TGA were: ramp from 25° C.-600° C. at 20° C./min; nitrogen purge, gas flow at 25 mL/min; platinum sample pan.

Polarized light microscopy (PLM) was carried out on a Leica LM/DM polarised light microscope with a digital video camera for image capture. A small amount of each sample was placed on a glass slide, with or without immersion oil, and covered with a glass slip. The sample was viewed with appropriate magnification and partially polarised light, coupled to a λ false-colour filter. Images were captured using StudioCapture or Image ProPlus software.

Scanning electron microscopy (SEM) data was collected on a Phenom Pro Scanning Electron Microscope. A small quantity of sample was mounted onto an aluminium stub using conducting double-sided adhesive tape. A thin layer of gold was applied using a sputter coater (20 mA, 120 s).

Gravimetric Vapour sorption (GVS) was carried out using a SMS DVS Intrinsic moisture sorption analyser, controlled by DVS Intrinsic Control software. The sample temperature was maintained at 25° C. by the instrument controls. The humidity was controlled by mixing streams of dry and wet nitrogen, with a total flow rate of 200 ml/min. The relative humidity was measured by a calibrated Rotronic probe (dynamic range of 1.0-100% RH), located near the sample. The weight change, (mass relaxation) of the sample as a function of % RH was constantly monitored by a microbalance (accuracy±0.005 mg).

Typically, 5-30 mg of sample was placed in a tared mesh stainless steel basket under ambient conditions. The sample was loaded and unloaded at 40% RH and 25° C. (typical room conditions). A moisture sorption isotherm was performed as outlined below (2 scans per complete cycle). The standard isotherm was performed at 25° C. at 10% RH intervals over a 0-90% RH range. Typically, a double cycle (4 scans) was carried out.

Method for SMS DVS Intrinsic experiments

| Parameter | Value |
|---|---|
| Adsorption-Scan 1 | 40-90 |
| Desorption, Adsorption-Scan 2 | 90-0, 0-40 |
| Intervals (% RH) | 10 |
| Number of Scans | 4 |
| Flow rate (ml/min) | 200 |
| Temperature (° C.) | 25 |
| Stability (° C./min) | 0.2 |
| Sorption Time (hours) | 6 hour time out |
| Number of cycles | 2 |

The sample was recovered after completion of the isotherm and re-analysed by XRPD.

Purity analysis was performed on an Agilent HP1100/Infinity II 1260 series system equipped with a diode array detector. The full method details are provided below:

HPLC method for chemical purity determinations

| Parameter | Value | | |
|---|---|---|---|
| Type of method | Reverse phase with gradient elution | | |
| Sample Preparation | 0.5 mg/ml in acetonitrile:water 1:1 | | |
| Column | Supelco Ascentis Express C18 2.7 μm 100 × 4.6 mm | | |
| Column Temperature (° C.) | 25 | | |
| Injection (μl) | 5 | | |
| Detection: Wavelength, Bandwidth (nm) | 255, 90 | | |
| Flow Rate (ml/min) | 2 | | |
| Phase A | 0.1% TFA in water | | |
| Phase B | 0.085% TFA in acetonitrile | | |
| Timetable | Time (min) | % Phase A | % Phase B |
| | 0 | 95 | 5 |
| | 6 | 5 | 95 |
| | 6.2 | 95 | 5 |
| | 8 | 95 | 5 |

The water content of each sample was measured by Karl Fischer Titration (KF) on a Metrohm 874 Oven Sample Processor at 150° C. with 851 Titrano Coulometer using Hydranal Coulomat AG oven reagent and nitrogen purge. Weighed solid samples were introduced into a sealed sample vial. Approximately 10 mg of sample was used per titration and duplicate determinations were made. An average of these results is presented unless otherwise stated.

A Crystal16 crystallisation system (Technobis, NL) was used to determine the solubility and metastable zone of the material as a function of temperature. Slurries of the API, in different overall concentrations, were prepared by adding a known amount of solid to a known amount of chilled solvent (between 0.5 and 1.5 ml) and stirred at 600 rpm using a magnetic bar. The saturation temperature was measured through cycles of heating and cooling from −8 to 60° C. at 0.5° C./min.

Upon increasing the temperature, the solid completely dissolved and the suspension became a clear solution such that the light transmission reached its maximum value. This temperature is assigned at the clear point, which was assumed to coincide with the saturation temperature. Then, by cooling the solution at a rate of 0.5° C./min, the temperature at which particles first formed was detected by a decrease in the light transmission. This is assigned as the cloud point. The points were fitted by a Van't Hoff equation and the difference between the cloud and the clear points defined the metastable zone width (MSZW) of the system.

Example 1A. Preparation of (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidine-4-carboxylic acid (Compound of Formula 1)

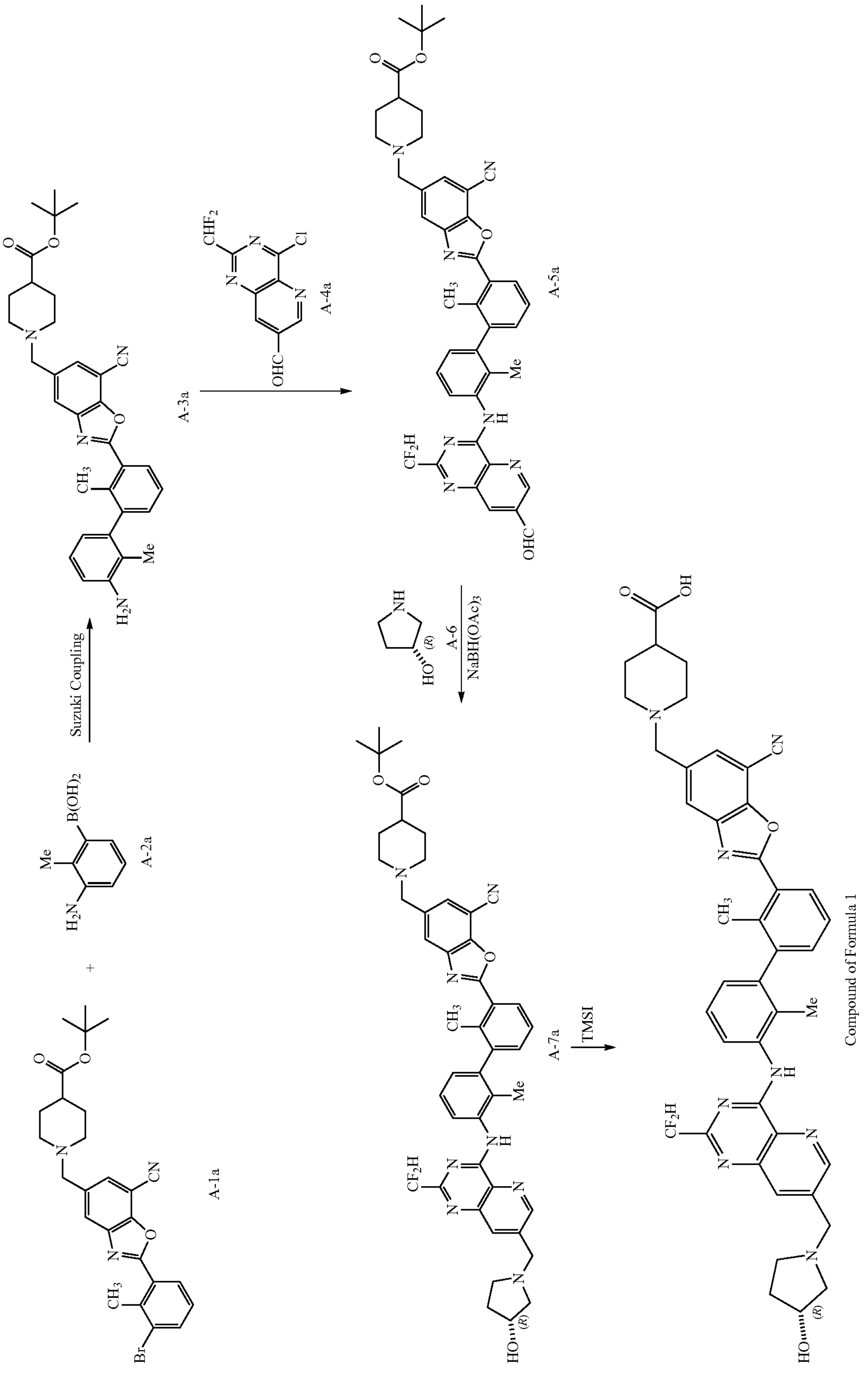
A-1a
A-2a
Suzuki Coupling
A-3a
A-4a
A-5a
A-6
NaBH(OAc)$_3$
A-7a
TMSI
Compound of Formula 1

Step 1: tert-Butyl-1-((2-(3'-amino-2,2'-dimethyl-[1,1'-biphenyl]-3-yl)-7-cyanobenzo[d]oxazol-5-yl)methyl)piperidine-4-carboxylate (A-3a)

To an inerted reactor was charged A-1a (675 g, 1.32 mol), A-2a·HCl (258 g, 1.38 mol) and potassium phosphate dibasic (894 g, 5.13 mol) followed by tert-butanol (6.75 L), and water (10.13 L). While stirring, nitrogen gas was bubbled through the mixture for not longer than 20 minutes. The mixture was then heated to 40-50° C. while maintaining nitrogen bubbling through the mixture. $PdCl_2$(dtbpf) (Pd-118) (6.79 g, 0.01 mol) was next charged to the reactor. The mixture was next heated to 75-85° C. while being continually sparged with nitrogen. The sub-surface bubbling was ceased upon reaching temperature, and the reaction mixture was stirred at 75-85° C. for NLT 1.5 hours until starting material was consumed according to HPLC. The reaction mixture was then cooled to 15-30° C. and the stirring stopped, upon which the layers separated. The aqueous layer was discarded and the organic layer was then distilled until approximately 3.5-4.5 volumes remained. The organic layer was then weighed and stored for use until several lots could be combined for work up.

Workup: Several concentrated solutions (4970 g) were pooled and charged to an inerted 200 L reactor, with the containers rinsed with MTBE (9.5 L). An aqueous solution of 20% sodium chloride (28.3 kg) was then charged to the reactor. The mixture was next stirred for NLT 20 minutes and the layers were allowed to separate. After the aqueous layer was removed, silica gel (3782 g), SiliaMetS® Thiol (946 g), and activated carbon C-941 (946 g) were then charged to the reactor slowly, followed by MTBE (61.5 L). The reaction mixture was warmed to 25-35° C. and stirred for NLT 4 hours after which solids were filtered and the cake washed with MTBE (94.5 L). The filtrate and the wash were then distilled by rotovap until approximately 2-4 volumes remained. Solvent was then evaporated using the rotovap while slowly charging THF (94.5 L) until the volume remaining was approximately 2-4 volumes (approx. 6 L, HPLC purity of 98.4%). The organic layer was next transferred to drums with THF (9.0 L) then weighed (21.65 kg, theoretically 4970 kg of (A-3a)) and stored for use in the next step.

Step 2: tert-butyl 1-((7-cyano-2-(3'-((2-(difluoromethyl)-7-formylpyrido[3,2-d]pyrimidin-4-yl)amino)-2,2'-dimethyl-[1,1'-biphenyl]-3-yl)benzo[d]oxazol-5-yl)methyl)piperidine-4-carboxylate (A-5a)

A-3a in THF (21.65 kg), lithium bromide (402 g, 4.63 mol, 0.5 equiv), and N,N-diisopropylamine (6.5 L, 37 mol, 4.0 equiv) were charged to a 100 L reactor. The mixture was next heated to 40-50° C. Next, A-4a (2.48 kg, 10.2 mol, 1.1 equiv) was dissolved in THF (10 L) and then slowly charged to the reactor via additional funnel over not longer than 1 hour. The containers and addition funnel were then rinsed with THF (5 L) and the rinse added to the reactor. The mixture was then stirred at 40-50° C. for not longer than 4 hours and an IPC test was performed. Upon meeting the IPC acceptance criterion, the mixture was then cooled to 15-30° C. Next, the reaction mixture was transferred to a 200 L reactor, and the vessel was rinsed with ethyl acetate (25 L). The batch was then washed twice with a 1 N HCl solution (64 L total) leaving the organic layer in the reactor. Next, the batch was washed twice with 5% sodium bicarbonate ($NaHCO_3$) solution (38 L total), leaving the organic layer in the reactor. Finally, the batch was washed with 10% sodium chloride (NaCl) solution (22 L).

Next, the organic layer was concentrated to approximately 4-5 volumes, while slowly charging 5 volumes of EtOAc (25 L). The solution was then charged to the 200 L reactor and stirred at 15-30° C. for NLT 1 hour. The solution was then warmed to 40-50° C. and heptane (75 L) was slowly charged to the reactor and the mixture was then stirred at 40-50° C. for NLT 2 hours. Next, the mixture was cooled to 15-30° C. and then filtered and washed with heptane (25 L). After pulling nitrogen through the cake, the solids were transferred to drying trays and dried under vacuum at NMT 55° C. to obtain (A-5a) (6228 g, 90% based on (A-1a), 94.8% purity). $^1H$ NMR (600 MHz, DMSO) δ 10.74 (s, 1H), 10.36 (s, 1H), 9.37 (d, J=1.8 Hz, 1H), 8.80 (d, J=1.9 Hz, 1H), 8.18 (dd, J=7.9, 1.4 Hz, 1H), 8.13 (s, 1H), 7.88 (s, 1H), 7.66 (d, J=8.1 Hz, 1H), 7.58 (t, J=7.7 Hz, 1H), 7.47 (dd, J=7.7, 1.5 Hz, 1H), 7.42 (t, J=7.7 Hz, 1H), 7.17 (d, J=7.6 Hz, 1H), 6.78 (t, J=54.4 Hz, 1H), 3.64 (s, 2H), 2.78 (d, J=9.8 Hz, 2H), 2.50 (s, 3H), 2.26-2.16 (m, 1H), 2.16-2.02 (m, 2H), 1.97 (s, 3H), 1.81-1.74 (m, 2H), 1.64-1.51 (m, 2H), 1.40 (s, 9H); LCMS, $C_{42}H_{39}F_2N_7O_4(M+H)^+$: calculated 744.3, found 744.3

Step 3: (R)-tert-butyl-1-((7-cyano-2-(3'-(2-(difluoromethyl)-7-((3-hydroxypyrrolidin-1-yl)methyl)pyrido[3,2-d]pyrimidin-4-ylamino)-2,2'-dimethylbiphenyl-3-yl)benzo[d]oxazol-5-yl)methyl)piperidine-4-carboxylate (A-7a)

To an inert reactor was added A-5a (5.99 kg, 8.05 mol), acetonitrile (29.9 L), dichloromethane (29.9 L), trimethyl borate (1.79 L, 16.1 mol, 2 equiv.), and A-6 (1.4 kg, 16.1 mol, 2 equiv.). The mixture was stirred at 15-25° C. for not longer than 30 minutes. Sodium triacetoxyborohydride (3.58 kg, 16.9 mol, 2.1 equiv.) was then added in portions to the reactor to maintain the temperature at 15-25° C. The mixture was then stirred at 15-25° C. for NLT 12 hours until an IPC test by HPLC passed. Additional sodium triacetoxyborohydride and agitation time could be added to drive the reaction to completion. Methanol (6.0 L) was then charged slowly to the reactor, followed by methylene chloride (29.9 L). Next, the organic layer was washed twice with a 5% sodium bicarbonate ($NaHCO_3$) solution (59 L total) and the mixture stirred for NLT 20 minutes. The aqueous layer was then back extracted twice with methylene chloride (30 L total). The organic layers were combined and concentrated to dryness to afford (A-7a) (7.35 kg, 93.79 LCAP purity) which was used directly in the next step. $^1H$ NMR (600 MHz, DMSO-$d_6$) δ 10.74 (s, 1H), 10.36 (s, 1H), 9.37 (d, J=1.9 Hz, 1H), 8.80 (d, J=1.9 Hz, 1H), 8.18 (dd, J=7.9, 1.4 Hz, 1H), 8.13 (d, J=1.5 Hz, 1H), 7.88 (d, J=1.5 Hz, 1H), 7.66 (d, J=7.8 Hz, 1H), 7.58 (t, J=7.8 Hz, 1H), 7.47 (d, J=7.8 Hz, 1H), 7.42 (t, J=7.8 Hz, 1H), 7.17 (dd, J=7.8, 1.0 Hz, 1H), 6.78 (t, J=54.4 Hz, 1H), 3.64 (s, 2H), 2.78 (d, J=10.7 Hz, 2H), 2.50 (s, 3H), 2.21 (m, 1H), 2.09 (m, 2H), 1.97 (s, 3H), 1.77 (dd, J=12.1, 3.9 Hz, 2H), 1.58 (m, 2H), 1.40 (s, 9H); $^{13}C$ NMR (151 MHz, DMSO-$d_6$) δ 192.63, 174.21, 164.38, 159.47, 158.28, 149.60, 148.98, 144.56, 143.48, 142.83, 142.06, 139.23, 137.23, 137.04, 136.84, 135.21, 134.44, 133.40, 132.69, 130.07, 127.90, 126.92, 126.53, 126.09, 126.00, 125.91, 115.01, 112.86, 94.58, 79.93, 61.36, 52.43, 41.47, 28.45, 28.18, 18.40, 15.83.

Step 4: (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidine-4-carboxylic acid (Compound of Formula 1)

A-7a from the previous step and dichloromethane were charged to a rotary evaporator and the resulting solution was azeotroped to remove water until a level of 0.5% was obtained by Karl Fischer Titration. The solution was then charged to a 100 L reactor and dichloromethane used to assist the rinse and bring the total amount of dichloromethane to 7 volumes. The solution was cooled to 0-5° C. and trimethylsilyl iodide (3.43 L, 24.1 mol, 3.0 equiv) was added slowly to maintain a temperature of 0-15° C. The reaction mixture was then allowed to warm to 15-25° C. while stirring for not longer than 6 h until an IPC test by HPLC passed. The reaction mixture was then transferred to clean and dry containers and the reactor rinsed with dichloromethane. The reaction mixture was next partitioned into two equal portions and the following workup was performed on each portion.

Workup: To a 200 L reactor was added water (49.2 L) and ammonium hydroxide (1.5 L, 12.07 mol, 1.5 equiv) and the solution cooled to 0-5° C. A 50% portion of the reaction mixture was then charged slowly to maintain a temperature of 0-15° C. The mixture was then allowed to warm to 15-25° C. while stirring for NLT 1 h. Next methanol (49.2 L) was then charged and the mixture stirred at 15-25° C. for NLT 2 h. The pH of the mixture was then adjusted to 5.0-6.0 with 6 N HCl (2.3 L) and the mixture was stirred at 15-25° C. for NLT 4 h. The pH was then adjusted to 7.3-7.5 with 2 N NaOH (1.55 L). Agitation was ceased, and the layers were allowed to partition. The organic layer containing the product was removed and the aqueous layer back extracted with dichloromethane (16.4 L). The remaining aqueous layer was then discarded. The organic layers were next combined and methanol (9.8 L) was added followed by phosphate buffer (pH 7.16, 23 L). The mixture was stirred for NLT 2 h. After that period stirring was ceased and the layers were partitioned and separated. The phosphate buffer wash could be repeated if residual iodide is noted by HPLC. Next, the organic layer was charged to a rotavapor and distilled to dryness. Tetrahydrofuran was charged to the rotavapor and the mixture agitated until a solution was obtained. The solution was then distilled until 2.5-3 volumes remained. The workup procedure was repeated for the second portion. The organic layers were then transferred to a 100 L reactor and THF used to assist the rinse to bring the total THF to 5 volumes. Silica gel (1.3 kg) and activated carbon C-941 (657 g) were then charged to the reactor. The mixture was then warmed to 30-40° C. and stirred for about 2 hours. The mixture was then filtered and the filter cake washed with THF (19.7 L). The filtrate and wash were then charged to the rotavapor through a 10 μm polish filter and distilled to dryness to afford crude Compound of Formula 1 (7.23 kg, 95.0% purity). Next, the mixture was dissolved with polish filtered THF (13.1 L) and polish filtered 2-butanone (72.1 L) and transferred to an inert reactor. The mixture was then warmed to 35-45° C. Filtered USP water (13.1 L) was then charged and the temperature maintained at 35-45° C. The solution was then stirred at 35-45° C. for not longer than 2 hours. Next, Compound of Formula 1 seed crystals (6.1 g) were charged and the mixture was stirred at 35-45° C. for NLT 4 hours. The mixture was then allowed to cool to 15-25° C. over 4 hours. The mixture was then stirred at 15-25° C. for 14 hours. The mixture was then filtered and the filter cake was washed with filtered 2-butanone (13.1 L). Nitrogen was then pulled through the filter for 3 d. The filter cake was then transferred to drying trays, placed in a vacuum oven, and dried under vacuum at not more than 55° C. to give Compound of Formula 1 (4220 g, 69% yield based on A-5a, 98.97 LCAP purity).

Compound of Formula 1 recrystallization and hydration. To a reactor was charged filtered 2-butanone (54.6 L) and Compound of Formula 1 (4200 g). The mixture was warmed to 55-65° C. to obtain a solution. Filtered USP water (8.4 L) was then charged slowly to maintain the temperature at 55-65° C. The solution was then stirred at 55-65° C. for about 1 hour. Next, Compound of Formula 1 seeds (4.26 g) were charged to the reactor. The mixture was then stirred at 55-65° C. for about 2 hrs. The mixture was then allowed to cool to 15-25° C. over about 4 hrs and then stirred at 15-25° C. for not longer than 12 hours. The mixture was filtered and the filter cake washed with filtered MEK (8.4 L). Nitrogen was then pulled through the filter for about 6 hours. The solids were transferred to trays and dried at 55° C. under vacuum with nitrogen sweep. Upon meeting specification for residual solvent, the oven was purged with humidified nitrogen until the solids contained between 7.5 and 9.5% water by Karl Fischer Titration upon which the product was removed from the oven, weighed and packaged (4351 g, 102% yield, 7.89% water by Karl Fischer Titration).

Example 1B. Preparation of (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidine-4-carboxylic acid (Compound of Formula 1)

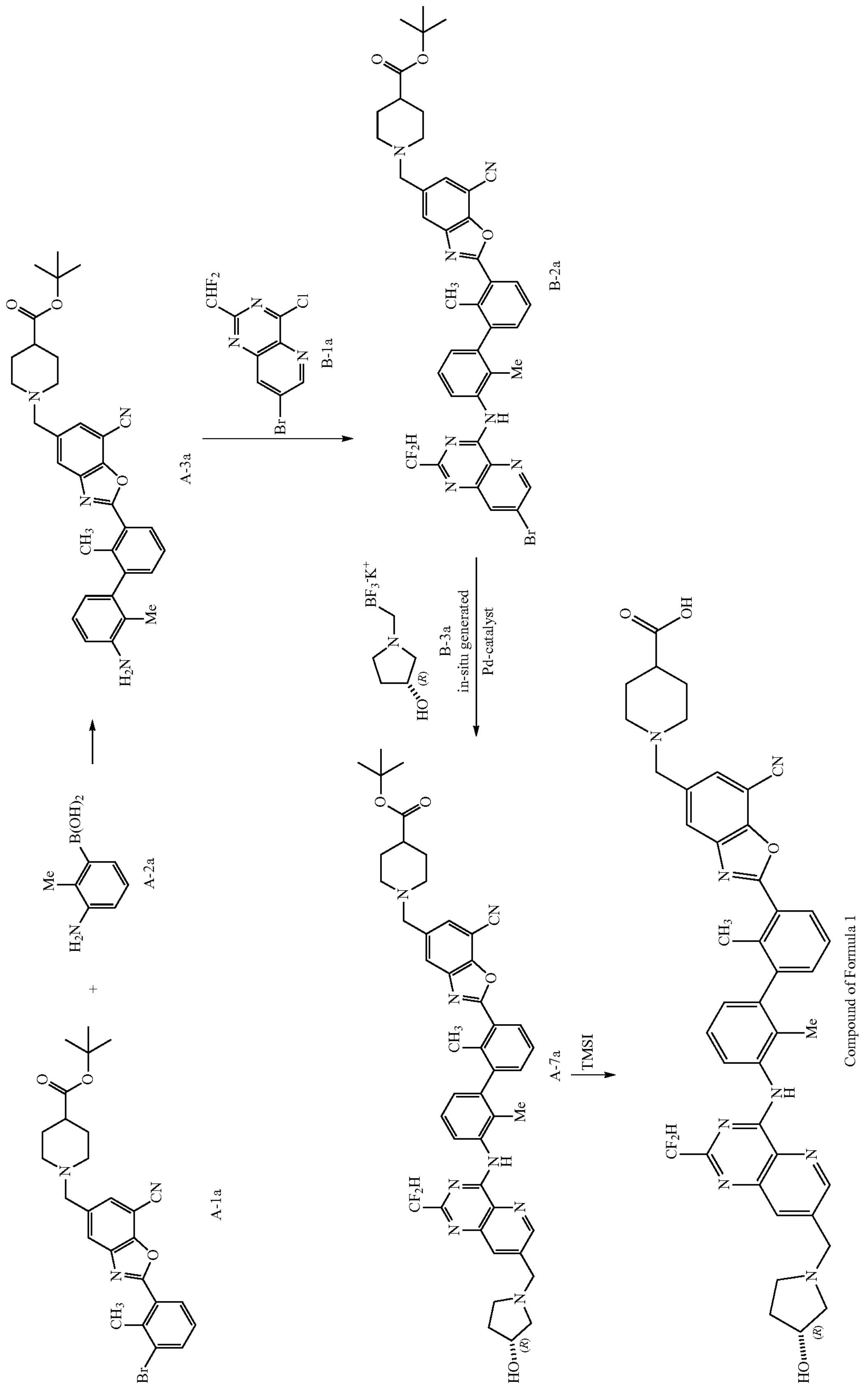
A-1a
A-2a
A-3a
B-1a
B-2a
B-3a
in-situ generated
Pd-catalyst
A-7a
TMSI
Compound of Formula 1

Step 1: tert-Butyl-1-((2-(3'-amino-2,2'-dimethyl-[1,1'-biphenyl]-3-yl)-7-cyanobenzo[d]oxazol-5-yl)methyl)piperidine-4-carboxylate (A-3a)

To a 22 L RBF was added A-1a (0.70 kg, 1.37 mol, 1 eq), A-2a (0.27 kg, 1.43 mol, 1.04 eq), and potassium phosphate dibasic (0.93 kg, 5.3 mol, 3.88 eq). The solids were dissolved in tert-BuOH (7 L, 10 v) and water (7 L, 10 v) and degassed with subsurface nitrogen for 1 h. To the degassed solution, $PdCl_2$(dtbpf) (Pd-118) (6.97 g, 10.7 mmol, 0.0078 eq) was added and degassing continued while warming until ~40° C. The reaction mixture was heated to reflux for 1.5 h and deemed complete by HPLC analysis (>98% conversion). The reaction was cooled to rt, transferred to a 22 L separatory funnel. The reactor was rinsed with MTBE (1 L) and combined into the separatory funnel. The aqueous layer was removed and the organics were washed with saturated brine (3.5 L, 5 v). The organic layer was concentrated to minimal volume via rotavap, diluted with diglyme (3.7 L, 5 v), and with distillation continued until the ratio of t-BuOH to diglyme was <5% by $^1$H-NMR. The crude (A-3a) was used as a solution in diglyme directly in the next reaction. $^1$H NMR (500 MHz, DMSO) δ 8.14-8.07 (m, 2H), 7.86 (s, 1H), 7.50 (t, J=7.7 Hz, 1H), 7.35 (dd, J=7.6, 1.4 Hz, 1H), 6.98 (t, J=7.7 Hz, 1H), 6.69 (dd, J=8.0, 1.2 Hz, 1H), 6.35 (dd, J=7.4, 1.2 Hz, 1H), 4.96 (s, 2H), 3.62 (s, 2H), 2.79-2.73 (m, 2H), 2.41 (s, 3H), 2.21-2.16 (m, 1H), 2.11-2.02 (m, 2H), 1.78-1.73 (m, 5H), 1.62-1.54 (m, 2H), 1.39 (s, 9H). LCMS, $C_{33}H_{37}N_4O_3$ $(M+H)^+$: calculated 537.3, found 537.6.

Step 2: tert-Butyl-1-((2-(3'-((7-bromo-2-(difluoromethyl)pyrido[3,2-d]pyrimidin-4-yl)amino)-2,2'-dimethyl-[1,1'-biphenyl]-3-yl)-7-cyanobenzo[d]oxazol-5-yl)methyl)piperidine-4-carboxylate (B-2a)

B-1a (0.42 kg, 1.43 mol, 1.04 eq) and potassium carbonate (0.38 kg, 2.74 mol, 2 eq) were charged to the crude (A-3a) (0.74 kg, 1.37 mol, 1 eq) in diglyme (5 v) at rt. The reaction mixture was warmed at 80° C. for 4 hours until complete by HPLC (2.6% remaining A-3a). The reaction mixture was cooled to rt and transferred via vacuum cannula to a second flask containing cold water (11 L, 15 v) maintaining ≤20° C. to precipitate (B-2a). The resultant slurry was agitated for 3 h at rt, filtered, washed with water (2.5 L, 3 v) and dried on the filter with vacuum under a nitrogen atmosphere. The resultant off-white powder of (B-2a) (1.13 kg, 104% yield) was used directly in the next reaction. $^1$H NMR (600 MHz, DMSO) δ 10.60 (s, 1H), 9.09 (d, J=2.1 Hz, 1H), 8.66 (d, J=2.1 Hz, 1H), 8.17 (d, J=7.8 Hz, 1H), 8.12 (m, 1H), 7.88 (bs, 1H), 7.64 (dd, J=8.1, 1.2 Hz, 1H), 7.58 (t, J=7.7 Hz, 1H), 7.46 (d, J=7.5 Hz, 1H), 7.40 (t, J=7.7 Hz, 1H), 7.15 (dd, J=7.6, 1.3 Hz, 1H), 6.76 (t, J=54.5 Hz, 1H), 3.63 (bs, 2H), 2.77 (bs, 2H), 2.49 (s, 3H), 2.29-2.15 (m, 1H), 2.14-1.99 (m, 2H), 1.94 (s, 3H), 1.84-1.74 (m, 2H), 1.67-1.57 (m, 2H), 1.39 (s, 9H). LCMS, $C_{41}H_{39}BrF_2N_7O_3$ $(M+H)^+$: calculated 795.2/793.2, found 795.3/793.3.

Step 3: (R)-tert-Butyl 1-((7-cyano-2-(3'-(2-(difluoromethyl)-7-((3-hydroxypyrrolidin-1-yl)methyl)pyrido[3,2-d]pyrimidin-4-ylamino)-2,2'-dimethylbiphenyl-3-yl)benzo[d]oxazol-5-yl)methyl)piperidine-4-carboxylate (A-7a)

Potassium trifluoroborate salt: To a 22 L round bottom flask was added (R)-pyrrolidin-3-ol (187 g, 2.1 mol, 1.4 eq), potassium (bromomethyl)trifluoroborate (311 g, 1.55 mol, 1 eq), Dioxane (4.6 L, 15 v), and water (1.5 L, 5 v). The reaction mixture was warmed at 40° C. for 6 h and judged complete by fluorine NMR with subsequent cooling to rt. The reagent solution was used directly with no further manipulation.

To the 22 L round bottom flask containing the previously prepared trifluoroborate salt (1.55 mol, 2 eq) was charged B-2a (0.62 kg, 0.774 mol, 1 eq) and cesium carbonate (1.5 kg, 4.67 mol, 6.04 eq). The reaction mixture was diluted with dioxane (8 L, 13 v) and degassed with subsurface nitrogen for 1 h. With continuous degassing, CataCXium® Pd G4 (23 g, 31 mmol, 0.04 eq) was charged and the reaction was warmed at reflux (the nitrogen degassing was ceased at 50° C.). The reaction was heated at reflux for 7 h and was judged complete by HPLC then cooled to rt. The aqueous layer was removed, and the organics were washed with saturated brine (2 L, 1.2 vol). The organic layer was concentrated to minimal volume (thick oil/foam), dissolved in ethyl acetate (2 L), and silica (1.2 kg, 2×/wt) was charged. Concentration to dryness afforded crude A-7a adhered to silica. The impregnated silica was slurried in ethyl acetate and loaded upon a silica (1.8 kg, 3×/wt) column (18 cm×30 cm). The product was eluted with methanol/ethyl acetate (0-25%) and the fractions were concentrated in vacuo to afford A-7a (567.8 g, 90% yield) as a voluminous foam. $^1$H NMR (500 MHz, DMSO) δ 10.2 (s, 1H), 8.96 (d, J=1.9 Hz, 1H), 8.20-8.14 (m, 2H), 8.12 (d, J=1.5 Hz, 1H), 7.87 (d, J=1.4 Hz, 1H), 7.72 (d, J=7.8 Hz 1H), 7.57 (t, J=7.7 Hz, 1H), 7.48-7.44 (m, 1H), 7.40 (t, J=7.8 Hz, 1H), 7.14 (d, J=7.1 Hz, 1H), 6.72 (t, J=54.6 Hz, 1H), 4.73 (d, J=4.6 Hz, 1H), 4.28-4.19 (bs, 1H), 3.91 (d, J=14.0 Hz, 1H), 3.84 (d, J=14.0 Hz, 1H), 3.63 (s, 2H), 2.81-2.65 (m, 4H), 2.51 (m, 1H) 2.49 (s, 3H), 2.42 (dd, J=9.6, 3.5 Hz, 1H), 2.19 (tt, J=11.0, 4.0 Hz, 1H), 2.11-2.01 (m, 3H), 1.97 (s, 3H), 1.80-1.73 (m, 2H), 1.64-1.52 (m, 3H), 1.39 (s, 9H); LCMS, $C_{46}H_{49}F_2N_8O_4$ $(M+H)^+$: calculated 815.4, found 815.3

Step 4: (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidine-4-carboxylic acid (Compound of Formula 1)

To a 22 L round bottom flask was charged A-7a (0.67 kg, 0.82 mol, 1 eq) and dichloromethane (4.6 L, 7 v). The reaction mixture was cooled to 0° C. and iodotrimethylsilane (0.33 L, 2.5 mol, 3 eq) was charged dropwise via addition funnel maintaining the internal temperature≤5° C. The reaction mixture was allowed to warm to room temperature and following 16 h the reaction was complete by HPLC. In a separate 22 L round bottom flask a mixture of water (3.4 L, 5 vol) and ammonium hydroxide (0.33 L, 2.5 mol, 3 eq) was cooled to 0° C. The reaction mixture was slowly quenched into the ammonium hydroxide mixture maintaining <10° C., and the flask was rinsed with dichloromethane (2 L, 3 v). The reaction mixture was diluted with Methanol (6 L, 9 vol) and the pH was adjusted to ~6-7 using hydrochloric acid (6N, ~475 mL). The aqueous layer was drained, and back extracted twice with dichloromethane (1.3 L, 2 vol). The organic layers were combined over silica (1.2 kg, 2×/wt) and concentrated to dryness. The resultant crude Compound of Formula 1 on silica was slurried in dichloromethane (2 L) twice and concentrated to dryness to remove residual solvents. The impregnated silica was slurried in dichloromethane and loaded upon a silica (1.8 kg, 3×/wt) column (18 cm×30 cm). The column was eluted with methanol/dichloromethane (10-80%, 90 v) and all fractions containing product were combined to afford Compound of Formula 1

(629 g) contaminated with HI. The aqueous layer was concentrated to remove methanol, at which point a sticky oil of Compound of Formula 1 (100 g) was isolated by decanting the remaining water and dissolving in methanol/dichloromethane. The combined impure Compound of Formula 1 was then further processed. $^{1}$H NMR (500 MHz, DMSO) δ 12.12 (bs, 1H), 10.41 (s, 1H), 8.96 (d, J=1.9 Hz, 1H), 8.19-8.14 (m, 2H), 8.11 (d, J=1.5 Hz, 1H), 7.86 (d, J=1.5 Hz, 1H), 7.72 (dd, J=8.1, 1.3 Hz, 1H), 7.57 (t, J=7.7 Hz, 1H), 7.46 (dd, J=7.7, 1.5 Hz, 1H), 7.40 (t, J=7.8 Hz, 1H), 7.13 (dd, J=7.6, 1.4 Hz, 1H), 6.72 (t, J=54.6 Hz, 1H), 4.75 (bs, 1H), 4.23 (dq, J=9.5, 3.5 Hz, 1H), 3.91 (d, J=13.9 Hz, 1H), 3.84 (d, J=14.0 Hz, 1H), 3.63 (m, 2H), 2.83-2.65 (m, 4H), 2.51 (m, 1H), 2.49 (s, 3H), 2.42 (dd, J=9.6, 3.5 Hz, 1H), 2.20 (tt, J=11.1, 3.9 Hz, 1H), 2.12-2.00 (m, 3H), 1.97 (s, 3H), 1.84-1.76 (m, 2H), 1.64-1.53 (m, 3H); $C_{42}H_{41}F_2N_8O_4$(M+H)$^+$: calculated 759.3, found 759.3

Example 1C. Preparation of (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidine-4-carboxylic acid (Compound of Formula 1)

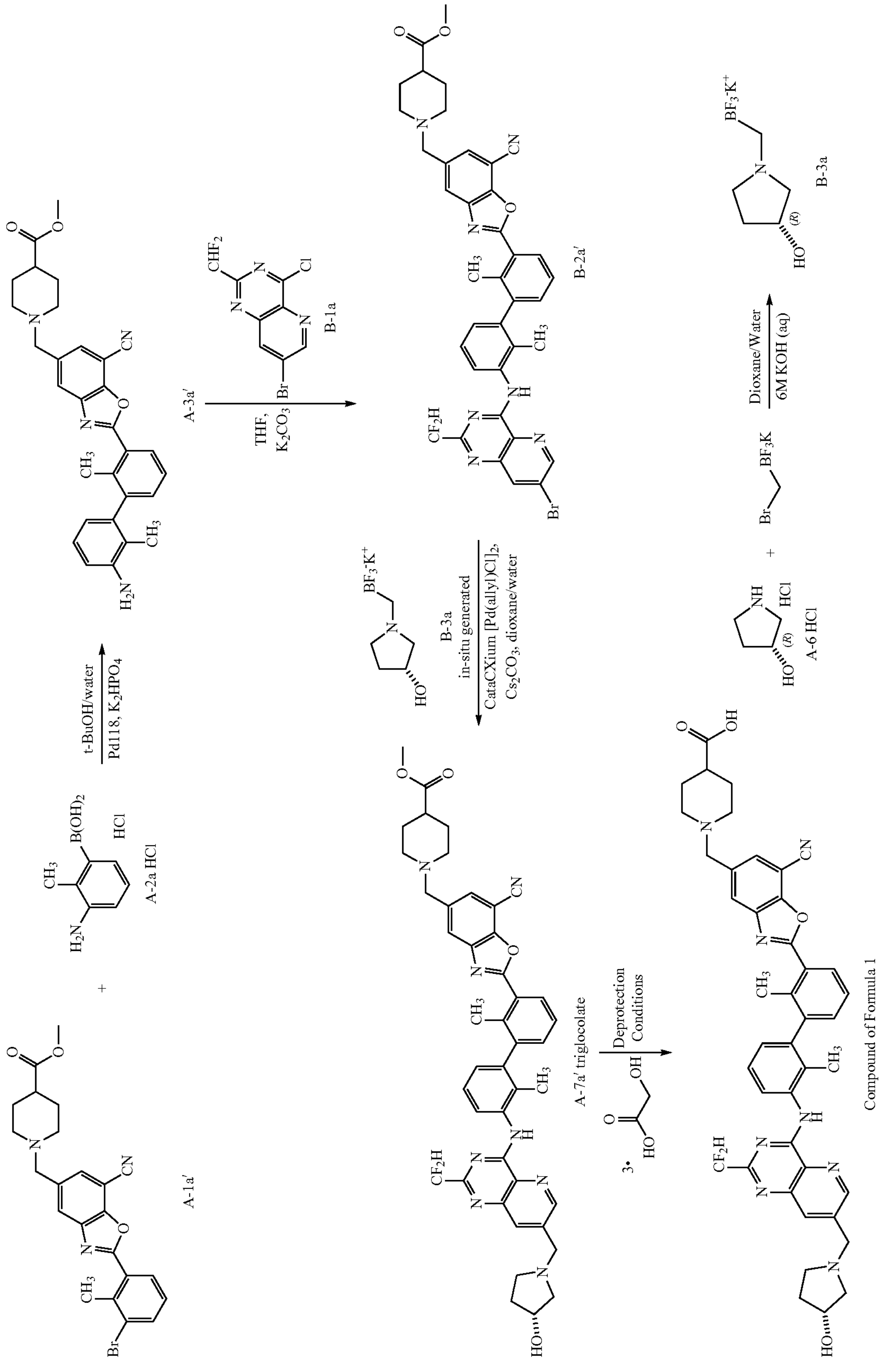
A-1a'
A-2a HCl
A-3a'
B-1a
B-2a'
B-3a
A-6 HCl
A-7a' triglocolate
Compound of Formula 1

Step 1: methyl 1-((2-(3'-amino-2,2'-dimethyl-[1,1'-biphenyl]-3-yl)-7-cyanobenzo[d]oxazol-5-yl)methyl) piperidine-4-carboxylate (A-3a')

A-1a' (353 g, 1.0 eq), A-2a HCl (156 g, 1.1 eq), and potassium phosphate dibasic (510 g, 3.88 eq.) were slurried in water (10 v) and t-BuOH (5 v). The mixture was degassed, charged with Pd-118 (3.84 g, 0.0078 eq.), and warmed at 80° C. for 1.5 h until complete by HPLC. Upon completion NAC/$K_3PO_4$ (2 v, 0.5M:0.55M) was charged and the mixture was cooled to 60° C. At 60° C., A-3a' seed crystals (0.35 g, 0.1 wt %) were charged and the mixture was slowly (1.5 h) cooled to 0° C. The mixture was filtered (fast), washed with water (2×5 v), and dried in a vacuum oven at 45° C. to afford A-3a' (358.7 g, 96% yield, 99.1% pure; 136 ppm Pd; 0.14% water). $^1$H NMR (400 MHz, DMSO) δ 8.11 (m, 2H), 7.86 (d, J=1.5 Hz, 1H), 7.50 (t, J=7.7 Hz, 1H), 7.35 (dd, J=7.5, 1.4 Hz, 1H), 6.98 (t, J=7.7 Hz, 1H), 6.69 (dd, J=8.0, 1.3 Hz, 1H), 6.35 (dd, J=7.4, 1.2 Hz, 1H), 4.96 (s, 2H), 3.63 (s, 2H), 3.60 (s, 3H), 2.79 (m, 2H), 2.41 (s, 3H), 2.34 (tt, J=11.1, 4.0 Hz, 1H), 2.07 (dd, J=12.5, 9.9 Hz, 2H), 1.81 (dd, J=13.1, 3.6 Hz, 2H), 1.76 (s, 3H), 1.62 (m, 2H). $C_{30}H_{31}N_4O_3$ $(M+H)^+$: calculated 495.2, found $(M+H)^+$: 495.2

Step 2: methyl 1-((2-(3'-((7-bromo-2-(difluoromethyl)pyrido[3,2-d]pyrimidin-4-yl)amino)-2,2'-dimethyl-[1,1'-biphenyl]-3-yl)-7-cyanobenzo[d]oxazol-5-yl)methyl)piperidine-4-carboxylate (B-2a')

A slurry of A-3a' (305 g, 1.0 eq), B-1a (200 g, 1.1 eq), and potassium carbonate (89 g, 1.05 eq) in THF (3 L, 10 v) was warmed at 50° C. for 9 h until complete by HPLC. The reaction mixture was quenched by the addition of water (1.5 L, 5 v) and MEK (1.5 L, 5 v), which dissolves solids precipitated during the reaction. The aqueous layer was separated and the organics were washed twice with aqueous potassium hydrogen carbonate (8%, 0.6 L, 2 v). The reaction mixture was concentrated to 5 v, diluted with EtOAc (1.5 L, 5 v) and concentrated to 5 v three times to reduce water. The reaction mixture was warmed at 50° C. and seeded with B-2a' to induce crystallization (seeding is not needed if thick seed bed precipitates during distillation). The thick seed bed forming the slurry was diluted with heptane (3 L, 10 v) and slowly cooled to rt. The slurry was filtered, washed with heptane (0.6 L, 2 v) and dried in a vacuum oven at 45° C. to afford B-2a' (458 g, 99% yield, 99.0% pure; KF 0.05%; 95 ppm Pd). $^1$H NMR (400 MHz, DMSO) δ 10.60 (s, 1H), 9.09 (d, J=2.2 Hz, 1H), 8.67 (d, J=2.1 Hz, 1H), 8.17 (dd, J=7.9, 1.4 Hz, 1H), 8.13 (d, J=1.5 Hz, 1H), 7.88 (d, J=1.5 Hz, 1H), 7.64 (d, J=8.0 Hz, 1H), 7.58 (t, J=7.7 Hz, 1H), 7.50-7.44 (m, 1H), 7.41 (t, J=7.8 Hz, 1H), 7.19-7.12 (m, 1H), 6.72 (t, J=54.4 Hz, 1H), 3.64 (s, 2H), 3.61 (s, 3H), 2.79 (m, 2H), 2.49 (s, 3H), 2.33 (m, 1H), 2.08 (m, 2H), 1.95 (s, 3H), 1.82 (m, 2H), 1.63 (m, 2H). $C_{38}H_{33}BrF_2N_7O_3$ $(M+H)^+$: calculated 752.2, found $(M+H)^+$: 752.2

Step 3: methyl (R)-1-((7-cyano-2-(3'-((2-(difluoromethyl)-7-((3-hydroxypyrrolidin-1-yl)methyl) pyrido[3,2-d]pyrimidin-4-yl)amino)-2,2'-dimethyl-[1,1'-biphenyl]-3-yl)benzo[d]oxazol-5-yl)methyl) piperidine-4-carboxylate tris(2-hydroxyacetate) (A-7a')

To a solution of preformed Molander reagent B-3a (1.6 eq; 2 v dioxane; 1.5 v water) was charged cesium carbonate (78, 6 eq), B-2a' (30 g, 1 eq) and dioxane (270 mL, 9 v). The slurry was degassed (3× vacuum) and the pre-mixed catalyst (allylPd(II)Cl 0.0085 eq; CataCXium A 0.037 eq; dioxane 2 v) was charged and the mixture degassed (3× vacuum) followed by warming at reflux (91° C.). Following reaction completion (16 h) the reaction was cooled to 45° C. and diluted with water (30 mL, 1 v). The layers were separated at 35° C. and the organics were washed twice with NAC/$K_3PO_4$ (0.5:0.55 M, 90 mL; 3 v) and with aqueous $K_3PO_4$ (0.1 M; 60 mL; 2 v). The organics were concentrated to 3 v and azeotropically dried via THF addition and distillation (300 mL, 18 v) until a KF<0.2% was obtained. The A-7a' in THF was charged over 30 min to a solution of glycolic acid (9.09 g, 3 eq) in MTBE (450 mL, 15 v), cooled to 0° C. and filtered, washing twice with MTBE (60 mL, 2 v) to afford A-7a' triglycolate (35.1 g; 88% yield; 96.8% pure; 146 ppm Pd; KF 2.6%) $^1$H NMR (400 MHz, DMSO) (trigylcolate) δ 10.43 (s, 1H), 8.96 (d, J=1.9 Hz, 1H), 8.18 (dd, J=7.7, 1.6 Hz, 2H), 8.13 (d, J=1.5 Hz, 1H), 7.88 (d, J=1.5 Hz, 1H), 7.72 (d, J=7.8 Hz, 1H), 7.58 (t, J=7.7 Hz, 1H), 7.46 (dd, J=7.6, 1.5 Hz, 1H), 7.41 (t, J=7.8 Hz, 1H), 7.14 (m, 1H), 6.73 (t, J=54.5 Hz, 1H), 4.75 (s, 1H), 4.24 (s, 1H), 3.91 (s, 7H), 3.65 (s, 2H), 3.61 (s, 3H), 3.08 (s, 1H), 2.75 (m, 4H), 2.49 (s, 2H), 2.44 (dd, J=9.6, 3.5 Hz, 1H), 2.34 (m, 1H), 2.06 (m, 2H), 1.97 (s, 3H), 1.82 (m, 2H), 1.61 (m, 3H), 1.11 (s, 3H). $^1$H NMR (500 MHz, DMSO) (Freebase) δ 10.42 (s, 1H), 8.96 (d, J=2.0 Hz, 1H), 8.17 (m, 2H), 8.12 (d, J=1.5 Hz, 1H), 7.87 (d, J=1.4 Hz, 1H), 7.72 (d, J=8.0 Hz, 1H), 7.57 (t, J=7.7 Hz, 1H), 7.46 (dd, J=7.6, 1.4 Hz, 1H), 7.40 (t, J=7.8 Hz, 1H), 7.13 (m, 1H), 6.72 (t, J=54.6 Hz, 1H), 4.76 (s, 1H), 4.24 (m, 1H), 3.93 (m, 2H), 3.64 (s, 2H), 3.60 (s, 3H), 2.79 (m, 3H), 2.71 (m, 1H), 2.50 (m, 1H) 2.49 (s, 3H), 2.45 (m, 1H), 2.34 (m, 1H), 2.06 (m, 3H), 1.97 (s, 3H), 1.82 (m, 2H), 1.61 (m, 3H). $C_{43}H_{43}F_2N_8O_4(M+H)^+$: calculated 773.3, found $(M+H)^+$: 773.3

Step 4: (R)-1-((7-cyano-2-(3'-((2-(difluoromethyl)-7-((3-hydroxypyrrolidin-1-yl)methyl)pyrido[3,2-d] pyrimidin-4-yl)amino)-2,2'-dimethyl-[1,1'-biphenyl]-3-yl)benzo[d]oxazol-5-yl)methyl)piperidine-4-carboxylic acid (Compound of Formula 1)

Salt Break: A-7a' triglycolate (100 g) was added portion-wise to 3 v (300 mL) water and allowed to dissolve. Impurities were extracted with 3 v (300 mL) 2-Methyl THF at 40° C. the layers were separated and the aqueous phase containing product is kept. The organic layer was back extracted with 1 v (100 mL) water and combined with the product solution. The product aqueous layer (pH~4.1) was made basic (pH~9.5) with 2 v (200 mL) 30% aqueous $K_3PO_4$ and extracted with 3 v (300 mL) THF. Ester Hydrolysis: The 300 mL THF solution was cooled to internal temperature 0-10° C. target of 5° C. followed by addition of 5° C. chilled 1.0M NaOH (2 equiv., ~2 v, 200 mL) maintaining the IT below 10° C. Target 5° C. The reaction was stirred at 5° C. until SM A-7a' was <1% (~3 h). The reaction was neutralized with 20% Phosphoric acid to pH~7.2-7.5 (~0.3 v, ~30 mL) and warmed to room temp where the pH was adjusted to 6.8-6.9 using 20% phosphoric acid and 1.0M NaOH. 3 v (300 mL) 2-MeTHF were added then the mixture was warmed to 45° C. to achieve a phase separation and the organic phase was distilled to ~300 mL with 2×500 mL THF azeotropic distillations. The 300 mL organic solution was treated with 0.4× (40 g) SilicaThiol and 0.2× (20 g) charcoal C-941 at 45° C. for 3 h. The mixture was filtered through celite and washed with 2×300 mL THF then concentrated to ~225 mL (3 v based on theoretical yield). The organic solution was warmed to 45° C. and 975 mL (13 v based on TY) MEK was added and continued to heat to 60° C. 105 mL (1.4 v based on TY) water was added and the homogenous mixture was cooled to 40° C. then seeded and stirred for 2 h. The mixture was cooled to 15° C. and filtered. Solids were dried in a vacuum oven at 50° C. with a nitrogen sweep (80% yield, >99% purity).

Example 2. Preparation of tert-Butyl 1-((2-(3-bromo-2-methylphenyl)-7-cyanobenzo[d]oxazol-5-yl)methyl)piperidine-4-carboxylate (A-1a)

A-1a

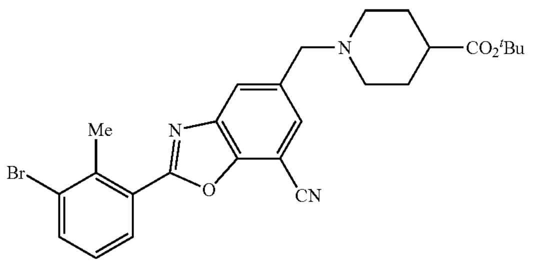

Step 1: 3-Amino-2-hydroxybenzonitrile (3)

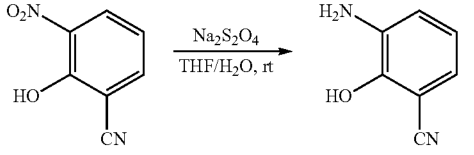

2 3

Sodium hydrosulfite (1.825 kg, 10.5 mol, 2.87 equiv) was added in portions over approximately 30 minutes using an external ice/water bath as necessary to keep the temperature below 30° C. to a solution of 2-hydroxy-3-nitrobenzonitrile (600 g, 3.66 mol, 1 equiv) in tetrahydrofuran (6 L) and water (5.4 L). The mixture was stirred for 30 minutes and sodium bicarbonate (752 g, 4.08 mol, 1.12 equiv) was added in portions using an external ice/water bath as necessary to keep the temperature below 22° C. After 1 hour, LCMS analysis indicated complete conversion to compound 3. The mixture was poured to a separatory funnel and extracted with dichloromethane (6 L). The organic layer was washed with saturated sodium chloride (4 L). The combined aqueous layers were extracted with a mixture of dichloromethane (1.5 L) and THF (1.2 L). The combined organic layers were dried over sodium sulfate and concentrated under reduced pressure to dryness. The residue was dried under vacuum at 40° C. overnight to give compound 3 (338 g, 69% yield) as a dark solid.

Step 2: 3-Bromo-N-(3-cyano-2-hydroxyphenyl)-2-methylbenzamide (5a)

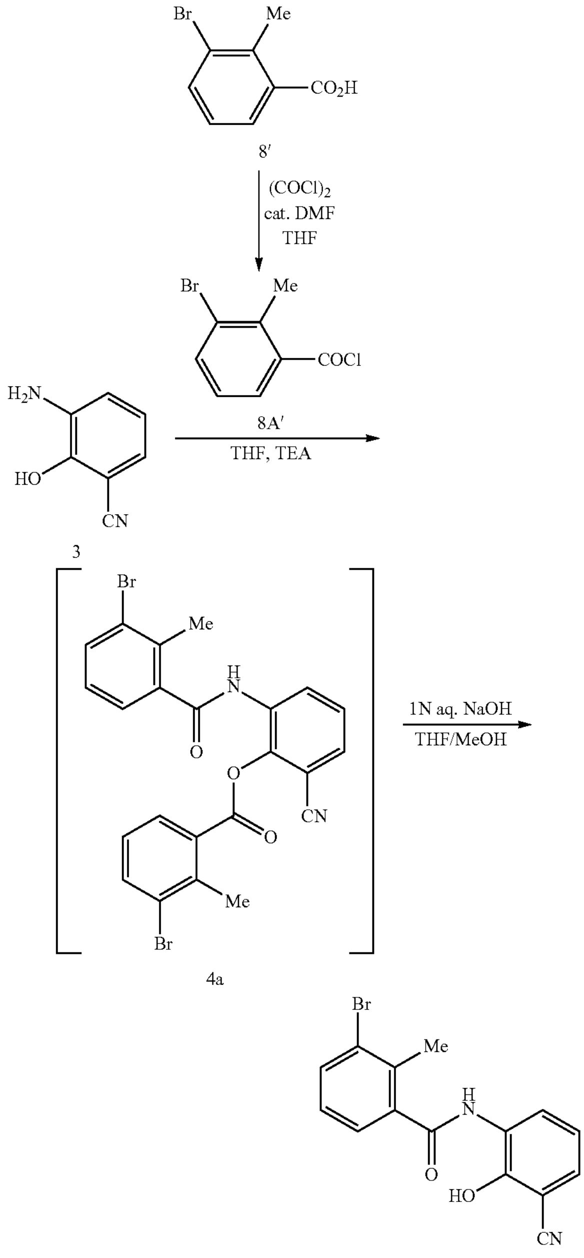

8′ 3 4a 5a

Two reactions of equal size were run in parallel. Dimethylformamide (18 L) was added, followed by the dropwise addition of oxalyl chloride (860 mL, 10.12 mol, 2.14 equiv) to a slurry of 3-bromo-2-methylbenzoic acid (2.1 kg, 9.4 mol, 2.1 equiv) and anhydrous tetrahydrofuran (8 L) at a rate that the temperature did not exceed 25° C. The reactions were stirred at room temperature for 1 hour, an aliquot was analyzed by 1H NMR and the reaction was determined to be complete. The reactions were concentrated separately to oils and each were transferred to separate 50 L flasks with anhydrous tetrahydrofuran (3 L). To each 50 L reaction flask was added a solution of compound 3 (600 g, 4.47 mol, 1 equiv) in anhydrous tetrahydrofuran (4 L) via a cannula. Triethylamine (2.0 L, 14.16 mol, 3 equiv) was added to each flask over the course of 1 hour using an external ice/water bath to keep the temperature below 25° C. The reactions were stirred for 1 hour and an aliquot of each was analyzed by HPLC to show the reaction was complete with 3 main products (mono-, di-, and tri-substituted). An aqueous sodium bicarbonate (540 g, 2.93 mol, 0.63 equiv) solution in water (18 L) was added to each of the reactions and the mixture was stirred overnight. The resulting slurries were filtered on the same funnel, the solids were washed with water (2×5 L) and dried on a filter for 6 hours under a stream of nitrogen to give the mixture of compounds 4 (6.2 kg wet weight). The wet cake was divided in half (3.1 kg each) and was charged to two separate 50 L flasks and slurried in THF (12 L) and 1N sodium hydroxide (5.5 L). The mixture was stirred overnight and analysis showed all the di- and tri-substituted compounds had been hydrolyzed to compound 5. 1N HCl (5.5 L) was added and the reaction was stirred overnight at room temperature. The resulting solids were filtered and washed with water (2×4 L) and heptane (2×4 L). The solids were dried on the filter overnight and then under vacuum at 40° C. overnight to give compound 5 (2064 g, 70% yield) as a light gray solid.

Step 3: tert-Butyl 1-(3-(3-bromo-2-methylbenzamido)-5-cyano-4-hydroxybenzyl)piperidine-4-carboxylate (6a)

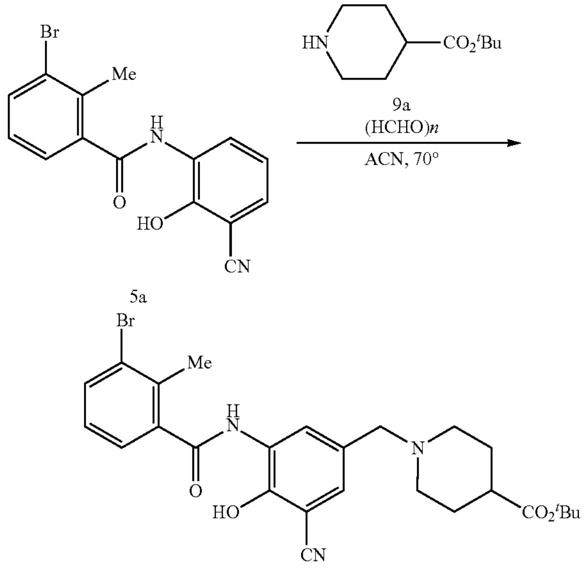

5a, 9a, 6a

Two reactions of equal size were run in parallel. Paraformaldehyde (107 g, 3.59 mol, 1.15 equiv) and tert-butyl piperidine-4-carboxylate (663 g, 3.59 mol, 1.15 equiv) were sequentially added to a solution of compound 5 (1032 g, 3.12 mol, 1 equiv) in acetonitrile (8 L) in each flask. The two reactions were heated at 70° C. for 3 hours, an aliquot was analyzed by HPLC and the reaction was determined to be complete. The reactions were cooled to room temperature overnight and the resulting solids were filtered together, washed with acetonitrile (2×2 L) and dried under a stream of nitrogen on the filter to give compound 6 (3194 g, 97% yield) as an off white solid. $^1$H NMR (400 MHz, $CDCl_3$) δ

8.77 (s, 1H), 8.32 (d, J=2.4 Hz, 1H), 7.56 (dd, J=8.0, 1.3 Hz, 1H), 7.32 (dd, J=7.7, 1.3 Hz, 1H), 7.03 (t, J=7.8 Hz, 1H), 6.91 (d, J=2.3 Hz, 1H), 3.85 (s, 2H), 3.31 (brs, 2H), 2.89 (brs, 2H), 2.46 (s, 3H), 2.42-2.32 (m, 1H), 2.12-2.00 (m, 4H), 1.39 (s, 9H). LCMS, $C_{26}H_{31}BrN_3O_4$ calculated 528.1, found 528.2

Step 4: tert-Butyl 1-((2-(3-bromo-2-methylphenyl)-7-cyanobenzo[d]oxazol-5-yl)methyl)piperidine-4-carboxylate (A-1a)

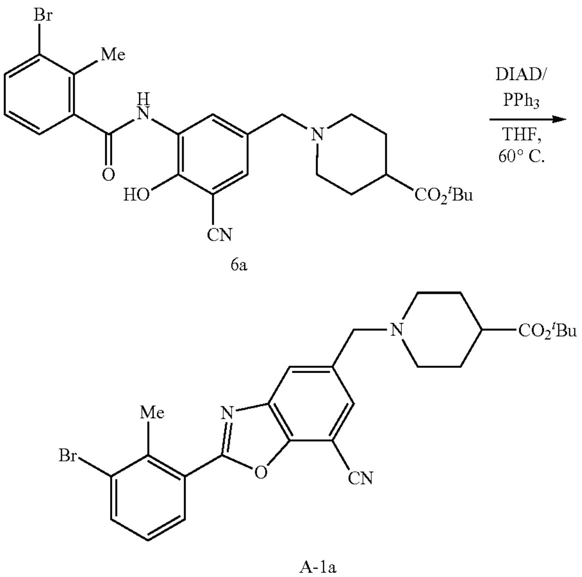

6a, A-1a

Diisopropylazodicarboxylate (1012 g, 5.01 mol, 1.65 equiv) was added in three portions (~340 g each) to a solution of compound 6 (1597 g, 3.02 mol, 1 equiv) and triphenylphosphine (1312 g, 5.01, 1.65 equiv) in tetrahydrofuran (10.5 L) in each flask resulting in an exotherm from 17° C. to 40° C. The reactions were then heated at 66° C. for 5 hours at which time LCMS indicated the reaction was complete. After cooling overnight to room temperature, each of the hazy solutions were clarified separately through a pad of celite (~3 inches on a 6 L glass fritted funnel) rinsing the celite with THF (2×2 L). The filtrates were concentrated separately under reduced pressure. Ethanol (4 L) was added to each of the residues and the mixtures were re-concentrated under reduced pressure. The residues were suspended in ethanol (8 L), heated at 40° C. for 1 hour and cooled to room temperature while stirring overnight. The mixtures were filtered on the same funnel and the solids were washed with ethanol (2×3 L) and was then dried on the filter under a stream of nitrogen overnight. The solids were further dried under vacuum at 40° C. overnight to give compound 7 (2526 g, 82% yield) as an off-white solid. $^1$H NMR (600 MHz, DMSO-d6) δ 8.11 (dd, J=7.9, 1.3 Hz, 2H), 7.93 (dd, J=8.0, 1.2 Hz, 1H), 7.89 (d, J=1.6 Hz, 1H), 7.42 (t, J=7.9 Hz, 1H), 3.63 (s, 2H), 2.82 (s, 3H), 2.76 (m, 2.80-2.71, 2H), 2.20 (tt, J=11.1, 3.8 Hz, 1H), 2.14-1.97 (m, 2H), 1.81-1.71 (m, 2H), 1.63-1.52 (m, 2H), 1.40 (s, 9H). LC-MS calculated for $C_{26}H_{29}BrN_3O_3(M+H)^+$: m/z=510.1 and 512.1; found: 510.0 and 512.0.

Example 3. Preparation of 7-bromo-2-(difluoromethyl)pyrido[3,2-d]pyrimidin-4-ol (12a)

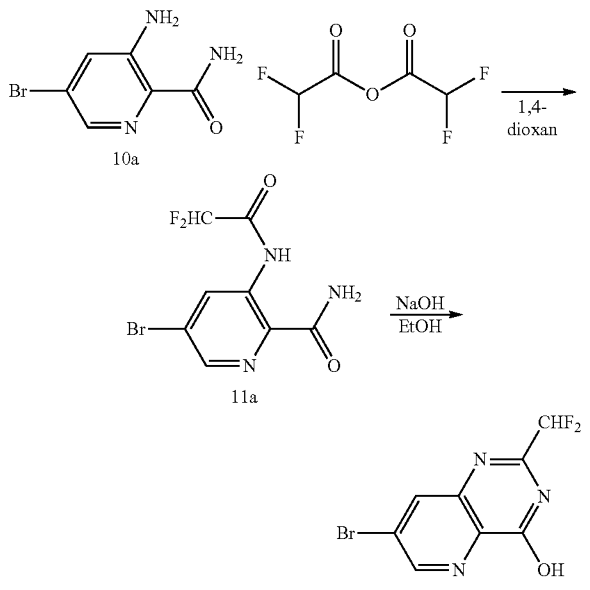

10a

11a

12a

To a 1 L 3-neck round bottom flask equipped with a mechanical stirrer was added 3-amino-5-bromopicolinamide (10a) (100 g, 444 mmol), 2,2-difluoroacetic anhydride (73 ml, 569 mmol) and 2 V 1,4-Dioxane (200 ml). Upon addition, the solution warmed from ~22° C. to 50° C. then continued to heat to 60° C. with external heating mantle and stirred. The reaction was complete after 1.5 h. Next the mixture was allowed to cool to room temperature over 3 h and placed in an ice bath. The cooled solution was quenched by the addition of water (400 mL) and the slurry was stirred for about 1 h. The precipitate was filtered and dried on a medium porosity filter overnight. The isolated material was used without further purification. Next, the crude solid was treated with sodium hydroxide (40 g, 979 mmol) in Ethanol (500 ml) and heated to 85° C. for 2 h. Upon completion by HPLC, the reaction was cooled to room temperature. The mixture was next cooled further in an ice bath and neutralized with 12 N hydrochloric acid. Water (500 ml) was added and the cooled mixture was allowed to stir for 1 h. The precipitate was filtered and dried under vacuum on filter funnel overnight. $^1H$ NMR (500 MHz, DMSO) δ 8.93-8.87 (d, J=2.1 Hz, 1H), 8.48-8.43 (d, J=2.1 Hz, 1H), 6.91-6.67 (t, J=52.9 Hz, 1H).

Example 4. 7-bromo-4-chloro-2-(difluoromethyl)pyrido[3,2-d]pyrimidine (B-1a)

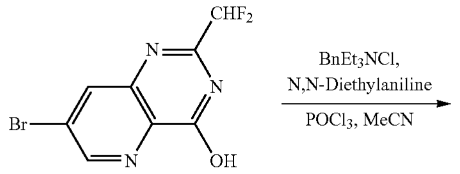

12a

-continued

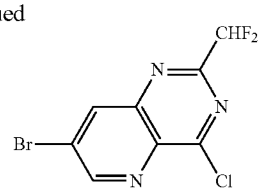

B-1a

To a 2 L 3-neck round bottom flask was added 7-bromo-2-(difluoromethyl)pyrido[3,2-d]pyrimidin-4-ol (12a) (120 g, 435 mmol), Benzyltriethylammonium chloride (198 g, 869 mmol), and N,N-Diethylaniline (104 ml, 652 mmol) in Acetonitrile (500 ml). Phosphorus oxychloride (122 ml, 1304 mmol) was added dropwise to the mixture via addition funnel over 20 min. During addition the solution temperature increased from 15° C. to 29° C. After complete addition, the solution was heated to 75° C. for about 1 h and deemed complete by LCMS and HPLC. The reaction was then transferred via cannula to 1 L of cold water, maintaining internal temperature below 15° C. Yellow solids formed upon addition and the suspension was allowed to stir for 1 h. The precipitate was filtered, washed with heptane (400 mL) and dried on a filter funnel under vacuum/nitrogen for 3 h. The solids were then transferred to dry in a vacuum oven at 35° C. for 72 h (112 g, 88% isolated, 98.5% LCAP). $^1H$ NMR (500 MHz, DMSO) δ 8.93-8.87 (d, J=2.1 Hz, 1H), 8.48-8.43 (d, J=2.1 Hz, 1H), 6.91-6.67 (t, J=52.9 Hz, 1H); LC-MS calculated for $C_{26}H_{29}BrN_3O_3(M+H)^+$: m/z=510.1 and 512.1; found: 510.0 and 512.0.

Example 5. 2-(difluoromethyl)-7-vinylpyrido[3,2-d]pyrimidin-4-ol (13)

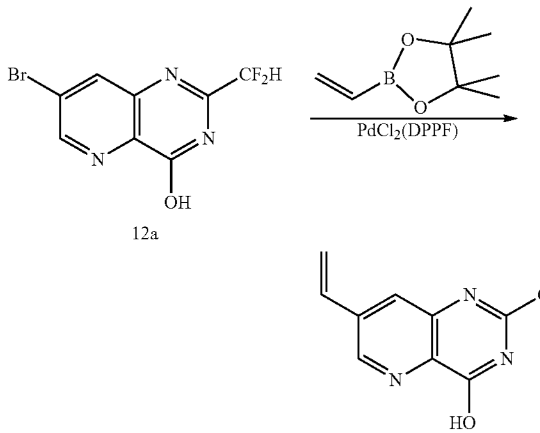

12a

13

To a 100 L reactor was charged 7-bromo-2-(difluoromethyl)pyrido[3,2-d]pyrimidin-4-ol (12a) (7 kg, 27.3 mol), ethanol (31.5 L), $H_2O$ (31.5 L), $K_2CO_3$, (11.3 kg, 81.9 mol), $PdCl_2(DPPF)$ (700 g, 1.0 mol) and 4,4,5,5-tetramethyl-2-vinyl-1,3,2-dioxaborolane (5.5 kg, 35.5 mol). The mixture was heated to 80-85° C. for 35 hours until starting material was consumed according to HPLC analysis. The mixture was then cooled and filtered through celite. The celite was washed with a minimum amount of ethyl acetate and added to the filtrate. HCl (36%, 10 L) was added to the mixture to adjust the pH to 2-3. The organic layer was partitioned and the aqueous layer washed with ethyl acetate (3×30 L). The organic layers were combined and washed with brine (20 L). The organic layer was evaporated to dryness and petroleum ether (10 L) was added. The resulting solids were filtered and dried on the funnel to give 2-(difluoromethyl)-7-vinylpyrido[3,2-d]pyrimidin-4-ol (13) (2.8 kg, 50%, 97% LCAP) as a brown solid. $^1H$ NMR (400 MHz, DMSO) 13.28 (1H, S), 8.99 (1H, d, J=2 Hz), 8.25 (1H, d, J=2 Hz), 6.83 (1H, t, J=53 Hz), 6.90-6.98 (1H, m), 6.30 (1H, d, J=17.6 Hz), 5.65 (1H, d, J=11.2 Hz) ppm.

Example 6. 4-chloro-2-(difluoromethyl)-7-vinylpyrido[3,2-d]pyrimidine (14a)

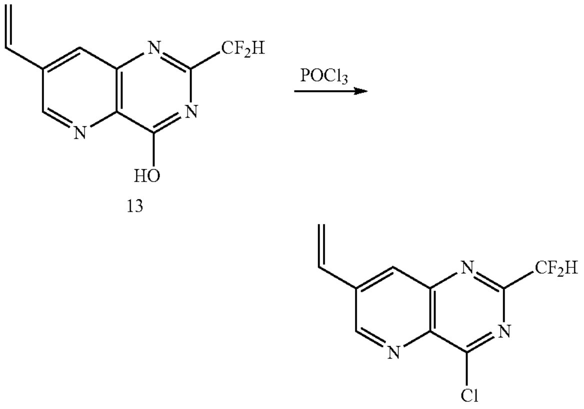

13

14a

To a 20 L reactor was charged 2-(difluoromethyl)-7-vinylpyrido[3,2-d]pyrimidin-4-ol (13) followed by toluene (7 L). Slowly, $POCl_3$ (1.5 kg, 9.5 mol) was charged followed by N,N-dimethyl aniline (1.4 kg, 9.5 mol). Next the mixture was heated to 130° C. for 3 hours and deemed complete by HPLC. The mixture was then cooled to ambient temperature and poured onto ice water (6 L). Ethyl acetate was added and the mixture was agitated for 1 h. The organic layer was separated and the aqueous layer back extracted with ethyl acetate (4.0 L). After combining, the organic layers were washed with brine (5 L). The organic layer was concentrated to an oil and diluted with dichloromethane (0.5 L). The material was then passed through a silica gel plug and eluted with ethyl acetate/hexanes (1:5, 30 L). The fraction containing the product was concentrated to give the product 4-chloro-2-(difluoromethyl)-7-vinylpyrido[3,2-d]pyrimidine (14a) (1.7 kg, 82% yield, 99% LCAP) as a yellow solid. $^1H$ NMR (400 MHz, DMSO) 9.84 (1H, s), 8.68 (1H, s), 7.15 (1H, t, J=53 Hz), 7.02-7.14 (1H, m), 6.51 (1H, d, J=17.6 Hz), 5.81 (1H, d, J=11.2 Hz).

Example 7. 4-chloro-2-(difluoromethyl)pyrido[3,2-d]pyrimidine-7-carbaldehyde (A-4a)

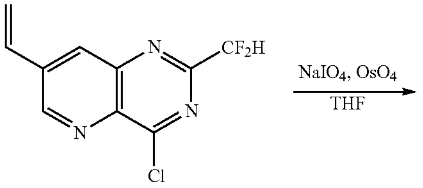

14a

-continued

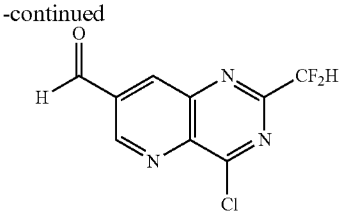

A-4a

To a 50 L reactor was charged tetrahydrofuran (10 L), $H_2O$ (6 L), and $NaIO_4$ (3.0 kg, 14 mol). The mixture was then cooled to 5-10° C. and 2,6 dimethylpyridine (749 g, 7.0 mol) was added followed by $OsO_4$ (9 g, 35 mmol). Next a solution of 4-chloro-2-(difluoromethyl)-7-vinylpyrido[3,2-d]pyrimidine (14a) (1.2 kg, 3.5 mol) in THF (14 L) was slowly added over 2 h, while maintaining the temperature between 10-15° C. The mixture was then agitated at that range for 4 h and was deemed complete by HPLC. Next, ethyl acetate (15 L) was charged to the vessel and the mixture was filtered to remove insoluble material. The mixture was washed with brine (10 L) and the organic layer concentrated to give a brown oil. Next, petroleum ether (2 L) was added to the resulting oil and the mixture agitated overnight whereupon crude product precipitated. The solids were collected by filtration and further triturated with MTBE (5 L) for 2 h at 50° C. The mixture was filtered to give the final product 4-chloro-2-(difluoromethyl)pyrido[3,2-d]pyrimidine-7-carbaldehyde (A-4a) as a yellow solid (650 g, 54%, 98% LCAP). $^1H$ NMR (400 MHz, DMSO) 10.42 (1H, s), 9.61 (1H, s), 8.91 (1H, s), 6.79 (1H, t, J=53 Hz).

Example 8. Preparation of Crystalline Free Base of Form I of (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl) piperidine-4-carboxylic acid (Form I of Compound of Formula 1)

Procedure 1: Compound of Formula 1 was dissolved at 40° C. in THF (5 vol) under stirring. The sample was then cooled to 32° C. at which temperature seeds of free form Form I (ca. 5% w/w) are added. MEK:$H_2O$ (11:2, 1 vol) is added and the sample is cooled to 5° C. at 0.1° C./min under stirring. Predicted yield: 90%.

Procedure 2: Compound of Formula 1 dissolved at 40° C. in THF (5 vol) under stirring. MEK:$H_2O$ (11:2, 0.7 vol) is added and seeds of free form Form I (ca. 5% w/w) are added. MEK:$H_2O$ (11:2, 0.3 vol) was added and the sample is cooled to 5° C. at 0.1° C./min under stirring. Predicted yield: 90%

Free form Form I was crystalline by XRPD. The $^1H$-NMR was consistent with the proposed structure with no signs of residual solvents remaining. HPLC purity analysis revealed the material to be 96.8% pure. Thermal analysis showed a 3.49% w/w loss between 30° C. and 95° C., corresponding to 1.5 mol eq of water, suggesting the material is likely a sesquihydrate. Degradation occurred at 275° C. Water loss was observed in the DSC at 34.9° C. (endothermic) and was followed by the endothermic melt at 160.6° C. The sample was also analysed by XRPD following the material loss and was found to remain unchanged. Furthermore, the XRPD remained unchanged following static storage for 7 days at elevated temperature and relative humidity conditions.

TABLE 1

| XRPD Peak Data for Form I of Compound of Formula 1 | |
|---|---|
| 2-Theta (°) | Relative Intensity (%) |
| 6.96 | 47.3 |
| 8.54 | 63.9 |
| 9.97 | 52.4 |
| 14.61 | 100 |
| 15.18 | 72.9 |
| 15.76 | 62.7 |
| 17.19 | 87.3 |
| 20.06 | 92.8 |
| 21.07 | 45.8 |
| 23.94 | 49.1 |
| 24.77 | 73.2 |
| 26.14 | 72.9 |
| 28.14 | 28.3 |
| 29.56 | 28.3 |
| 30.25 | 25.6 |
| 10.55 | 33.1 |

Example 9. Preparation of Crystalline Free Base of Form II of (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidine-4-carboxylic acid (Form II of Compound of Formula 1)

The compound of Formula 1 (50 mg) was dissolved in MEK (20 vol, 1 ml) at 50° C. To the sample was added 1 mol eq of counterion L-arginine and $H_2O$ (5% w/w, 100 µl) The samples were then cooled from 50° C. to 5° C. at a rate of 0.1° C./min. Suspensions were isolated using a filter canular and analysed by XRPD. The material is a crystalline sample (99.0% purity) and the $^1$H-NMR was consistent with the proposed structure. The TGA analysis showed a 4.68% w/w loss between 30° C. and 100° C., corresponding to 2.1 mol eq of water. The DSC contained endotherm at 75.8° C. (153 J/g), an endotherm at 165.2° C. (41 J/g) and the endothermic melt at 205.9° C. (27 J/g).

TABLE 2

| XRPD Peak Data for Form II of Compound of Formula 1 | |
|---|---|
| 2-Theta (°) | Relative Intensity (%) |
| 8.5 | 100 |
| 15.0 | 89.2 |
| 15.7 | 95.5 |
| 17.0 | 74.8 |
| 18.6 | 82 |
| 20.2 | 94.1 |
| 20.5 | 91.9 |
| 21.7 | 81.1 |
| 25.5 | 82.9 |
| 26.7 | 79.3 |

Example 10. Preparation of Methanesulfonic Acid Salt of (R)-1-((7-cyano-2-(3'-((2-(difluoromethyl)-7-((3-hydroxypyrrolidin-1-yl)methyl)pyrido[3,2-d]pyrimidin-4-yl)amino)-2,2'-dimethyl-[1,1'-biphenyl]-3-yl)benzo[d]oxazol-5-yl)methyl)piperidine-4-carboxylic acid (Compound of Formula 1 Methanesulfonic Acid Salt)

The compound of Formula 1 (500 mg) was treated with MEK (10 ml, 20 vol) at 50° C. Methanesulfonic acid (1 mol eq from a 1 M stock solution in THF) was added. Water (5% w/w) was added to give a suspension. The suspension was slowly cooled to 5° C. at 0.1° C./min. The mother liquor was decanted, leaving behind powder on the sides of the vial and a gummy solid in the center of the vial. Both were analyzed by XRPD. The gummy solid was isolated as Form III, and $^1$H-NMR was consistent with the proposed structure, with 1 mol eq of methanesulfonic acid present.

TGA of the compound of Formula 1 methanesulfonic acid salt Form III showed a 4.51% w/w loss between 27° C.-140° C., equating to approximately 2 mol eq of water. The material was also analysed by Karl Fischer, which showed the material contained 5.8% (approximately 2 mol eq) water. The DSC contained a broad endothermic event between 30° C.-130° C. which is likely due to solvent loss. The DSC of the compound of Formula 1 methanesulfonic acid salt Form III also showed an endothermic melt event at 179.3° C. The sample was visually assessed by PLM and SEM and was found to consist of agglomerated particles. The material was very hygroscopic, with a weight uptake of 19.5% w/w between 0-90% RH. XRPD analysis following the GVS experiment showed the material remained unchanged.

XRPD analysis following static storage of the compound of Formula 1 methanesulfonic acid salt Form III at 25° C./97% RH and 40° C./75% RH for 5 days revealed the material remained unchanged, however a loss in crystallinity was observed in both conditions. The compound of Formula 1 methanesulfonic acid salt Form III was found to have a purity of 99.4% by HPLC.

The methanesulfonic acid salt (20 mg) was treated with solvent (20 vol) and matured (RT–50° C., 4 h) for 3 days. Samples were then analyzed by XRPD. Attempts in improve the crystallinity of the scaled up methanesulfonic acid salt was undertaken by subjecting the material to maturation for 72 h in a variety of solvents. A slight improvement in crystallinity was observed from maturing in 2-propanol, ethyl acetate, and tert-butyl methyl ether. Interestingly, complete dissolution was observed in ethanol and water and XRPD analysis was not performed for these samples.

TABLE 3

| XRPD Peak Data for the compound of Formula 1 methanesulfonic acid salt Form III | |
|---|---|
| 2-Theta (°) | Relative Intensity (%) |
| 5.19 | 53.5 |
| 7.51 | 69.4 |
| 8.25 | 68.8 |
| 8.85 | 38.4 |
| 9.45 | 39.6 |
| 12.43 | 56.5 |
| 11.65 | 42.6 |
| 12.96 | 58.3 |
| 14.04 | 70.9 |
| 17.93 | 100 |
| 17.31 | 66.7 |
| 16.93 | 72.7 |
| 16.57 | 72.7 |
| 15.76 | 57.7 |
| 14.75 | 48 |
| 19.15 | 62.2 |
| 23.55 | 67 |
| 24.53 | 60.4 |
| 25.51 | 62.2 |
| 26.61 | 61 |

Example A. Homogeneous Time-Resolved Fluorescence (HTRF) PD-1/PD-L1 Binding Assay The assays are conducted in a standard black 384-well polystyrene plate with a final volume of 20 µL. Inhibitors are first serially diluted in DMSO and then added to the plate wells before the addition of other reaction components. The final concentration of DMSO in the assay is 1%. The assays are carried out at 25° C. in the PBS buffer (pH 7.4) with 0.05% Tween-20 and 0.1% BSA. Recombinant human PD-L1 protein (19-238) with a His-tag at the C-terminus can be purchased from AcroBiosystems (PD1-H5229). Recombinant human PD-1 protein (25-167) with Fc tag at the C-terminus can be purchased from AcroBiosystems (PD1-H5257). PD-L1 and PD-1 proteins are diluted in the assay buffer and 10 μL are added to the plate well. Plates are centrifuged and proteins are preincubated with inhibitors for 40 minutes. The incubation is followed by the addition of 10 μL of HTRF detection buffer supplemented with Europium cryptate-labeled anti-human IgG (PerkinElmer-AD0212) specific for Fc and anti-His antibody conjugated to SureLight®-Allophycocyanin (APC, PerkinElmer-AD0059H). After centrifugation, the plate is incubated at 25° C. for 60 min. before reading on a PHERAstar FS plate reader (665 nm/620 nm ratio). Final concentrations in the assay are—3 nM PD1, 10 nM PD-L1, 1 nM europium anti-human IgG and 20 nM anti-His-Allophycocyanin. $IC_{50}$ determination is performed by fitting the curve of percent control activity versus the log of the inhibitor concentration using the GraphPad Prism 5.0 software.

Example B. Src Homology Region 2 Domain-Containing Phosphatase (SHP) Assay

U2OS/PD-L1 cells (DiscoveRx Corporation) are maintained in McCoy's 5A medium with addition of 10% FBS, 0.25 μg/ml Puromycin. After removing the culture media, the cell medium is replaced with assay medium (RPMI1640 medium with 1% FBS). The U2OS/PD-L1 cells are then added in 384-well black clear bottom assay plate (CELLCOAT® Tissue Culture Plates, Greiner Bio-One) at 5000 cells per well in 20 μL assay medium. Test compounds are prepared by serial dilution in DMSO and 125 nL compound are first transferred to the 384 REMP plate well (Thermofisher) by ECHO liquid handler (Labcyte) followed with addition of 27.5 μL assay medium. 5 μL/well compounds in the assay medium are transferred to the cell plate with 0.05% DMSO in the final assay at 0.25 μM. Jurkat-PD-1-SHP cells (DiscoveRx Corporation) are cultured in RPMI1640 medium supplemented with 10% FBS, 250 μg/ml Hygromycin B, 500 μg/ml G418. After the replacement of culture media with assay medium, 5,000 Jurkat-PD-1-SHP cells in 20 μL are dispensed into each well. The assay plate is incubated at 37° C., 5% $CO_2$ for 2 hours before 2.5 μL PathHunter reagent 1 (DiscoveRx Corporation) are added to each well. The assay plate is shaken for 1 min at 350 rpm in the dark followed with addition of 10 μL PathHunter reagent 2 (DiscoveRx Corporation). Chemiluminescent signal is recorded with TopCount reader (Perkin Elmer) after incubation at room temperature for 1 hour. Wells with DMSO are served as the positive controls and wells containing no cells are used as negative controls. $IC_{50}$ determination is performed by fitting the curve of percentage of control activity versus the log of the compound concentration using the GraphPad Prism 6.0 software.

Example C. Nuclear Factor of Activated T-cells (NFAT) Assay

PD-L1 aAPC/CHO-K1 cells (Promega) are maintained in F-12 medium with addition of 10% FBS, 200 μg/ml Hygromycin B, 250 μg/ml Geneticin (G418). Jurkat-PD-1-NFAT effector cells (Promega) are cultured in RPMI 1640 medium supplemented with 10% FBS, 100 μg/ml Hygromycin B, 500 μg/ml G418. The culture media of PD-L1 aAPC/CHO-K1 cells are first replaced with assay medium (RPMI1640 medium with 1% FBS). The PD-L1 aAPC/CHO-K1 cells are then added in a white 384-well white clear bottom assay plate (CELLCOAT® Tissue Culture Plates, Greiner Bio-One) at 8000 per well in 10 μL assay medium. Test compounds are prepared by serial dilution in DMSO and 0.8 μL test compounds in DMSO are first transferred to the 384 REMP plate well (Thermofisher) by PlateMate Plus (Thermofisher) followed with addition of 50 μL plating medium. 5 μL compounds in the assay medium are transferred to the cells with 0.4% DMSO in the final assay at 2 μM. After removing the culture media, 10,000 Jurkat-PD-1-NFAT effector cells in 5 μL assay medium is dispensed into each well. The assay plate is incubated at 37° C., 5% $CO_2$ for 24 hours. After the assay plate is equilibrated to room temp for 15 minutes, 20 L/well of Bio-Glo™ reagent (Promega) are added. After 8 minutes incubation at room temperature, luminescence is read at with Pherastar microplate reader (BMG Labtech). The fold of induction (FOI) is calculated based on the ratio of luminescence normalized to the DMSO wells within each assay plate. The maximum percentage of induction is reported based on the ratio between the highest FOI of each compound and the maximum FOI of control compound within each assay plate. Wells with DMSO are served as the negative controls and wells containing control compound with the highest FOI are used as positive controls. EC50 determination is performed by fitting the curve of percent control activity versus the log of the compound concentration using the GraphPad Prism 6.0 software.

Example D. PD-L1 Whole Blood Internalization Assay

To determine PD-L1 internalization in human whole blood, normal human blood (Biological Specialty Corp, Colmar. PA) is incubated in the presence or absence of a concentration range of test compounds and 1 ng/ml human interferon γ (R&D Systems Inc. Minn. MN) in a 96 well "2 ml Assay Block" (Corning, Corning NY) for 18-20 hours at 37° C. Blood is then stained with PD-L1 (MIH1, eBioscience; or BD Biosciences San Jose, CA), CD14 (Life Technologies, Carlsbad, CA) for 30 minutes in the dark at room temperature. Whole Blood/red cells are lysed/fixed (lysis buffer BD Biosciences) for 5 minutes at 37° C. in the dark and then centrifuged at 1600 RPM for 5 minutes. Cells are resuspended in Stain Buffer (BD Bioscience, San Jose, CA) and transferred into 96 well round bottom plates (Corning). Cells are gated on CD14+(BD Biosciences) and PD-L1 expression determined by mean fluorescence intensity (MFI) (BD LSRFortessa™ X-20). $IC_{50}$ determination are performed by fitting the curve of compound percent inhibition versus the log of the compound concentration using the GraphPad Prism 7.0 software.

Example E. In Vivo Pharmacokinetics in Rats, Monkeys and Dogs

For in vivo pharmacokinetic experiments, test compounds are administered to male Sprague Dawley rats, male beagle dogs, or male and female Cynomolgus monkeys intravenously or via oral gavage. For IV dosing, test compounds are dosed at 0.5 to 1 mg/kg using a formulation of 10% dimethylacetamide (DMAC) in acidified saline via IV bolus for rat and 5 min or 10 min IV infusion for dog and monkey respectively. For oral dosing, test compounds are dosed at 1.0 to 3.0 mg/kg using 5% DMAC in 0.5% methylcellulose in citrate buffer (pH 3.5). Blood samples are collected at predose and various time points up to 24 hours postdose. All blood samples are collected using EDTA as the anticoagulant and centrifuged to obtain plasma samples. The plasma concentrations of test compounds are determined by LC-MS methods. The measured plasma concentrations are used to calculate PK parameters by standard noncompartmental methods using Phoenix® WinNonlin software program (version 7.0, Pharsight Corporation). In rats and monkeys, cassette dosing of up to six test compounds are conducted to obtain preliminary PK parameters.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A crystalline form of the compound of formula 1, or a pharmaceutically acceptable salt thereof:

(formula 1)

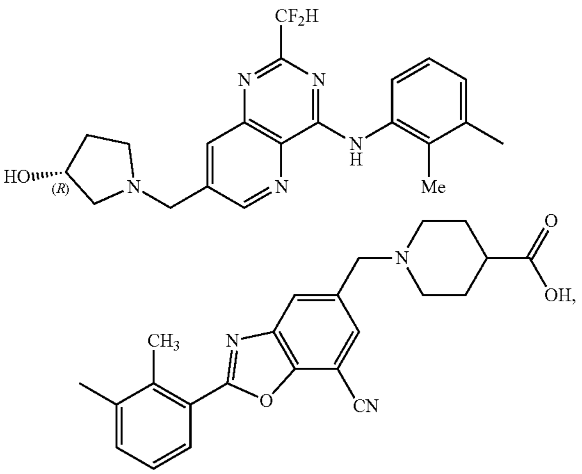

wherein:

the compound of formula 1 is the free base sesquihydrate of the compound of formula 1 having Form I, which has at least one XRPD peak, in terms of 2-theta (±0.2 degrees), selected from 7.0, 8.5, 10.0, 10.6, 14.6, 15.2, 15.8, 17.2, 20.1, 21.1, 23.9, 24.8, 26.1, 28.1, 29.6, and 30.2 degrees;

the compound of formula 1 is the free base of the compound of formula 1 having Form II, which has at least one XRPD peaks, in terms of 2-theta (±0.2 degrees), selected from 8.5, 15.0, 15.7, 17.0, 18.6, 20.2, 20.5, 21.7, 25.5, and 26.7 degrees; or the compound of formula 1 is a methanesulfonic acid salt having Form III, which has at least one XRPD peaks, in terms of 2-theta (±0.2 degrees), selected from 5.2, 7.5, 8.2, 8.8, 9.4, 11.6, 12.4, 13.0, 14.0, 14.8, 15.8, 16.6, 16.9, 17.3, 17.9, 19.2, 23.6, 24.5, 25.5, and 26.6 degrees.

2. The crystalline form of claim 1, having Form I.

3. The crystalline form of claim 2, having at least four XRPD peaks, in terms of 2-theta (±0.2 degrees), selected from 7.0, 8.5, 10.0, 10.6, 14.6, 15.2, 15.8, 17.2, 20.1, 21.1, 23.9, 24.8, 26.1, 28.1, 29.6, and 30.2 degrees.

4. The crystalline form of claim 2, having two endothermic peaks with an onset temperature (±3° C.) at 35° C. and a maximum temperature (±3° C.) at 68° C., and an onset temperature (±3° C.) at 161° C. and a maximum temperature (±3° C.) at 169° C. in a DSC thermogram.

5. The crystalline form of claim 1, having Form II.

6. The crystalline form of claim 5, having at least four XRPD peaks, in terms of 2-theta (±0.2 degrees), selected from 8.5, 15.0, 15.7, 17.0, 18.6, 20.2, 20.5, 21.7, 25.5, and 26.7 degrees.

7. The crystalline form of claim 5, having three endothermic peaks with a maximum temperature (±3° C.) at 76° C., an onset temperature (±3° C.) at 165° C. and a maximum temperature (±3° C.) at 173° C., an onset temperature (±3° C.) at 206° C. and a maximum temperature (±3° C.) at 224° C. in a DSC thermogram.

8. The crystalline form of claim 1, having Form III.

9. The crystalline form of claim 8, having at least four XRPD peaks, in terms of 2-theta (±0.2 degrees), selected from 5.2, 7.5, 8.2, 8.8, 9.4, 11.6, 12.4, 13.0, 14.0, 14.8, 15.8, 16.6, 16.9, 17.3, 17.9, 19.2, 23.6, 24.5, 25.5, and 26.6 degrees.

10. The crystalline form of claim 8, having two endothermic peaks with an onset temperature (±3° C.) at 30° C. and a maximum temperature (±3° C.) at 67° C., an onset temperature (±3° C.) at 179° C. and a maximum temperature (±3° C.) at 202° C. in a DSC thermogram.

11. A pharmaceutical composition comprising the crystalline form of claim 1, and a pharmaceutically acceptable carrier or excipient.

12. A method of treating a disease or disorder associated with inhibition of PD-1/PD-L1 interaction, said method comprising administering to a patient in need thereof a therapeutically effective amount of the crystalline form of claim 1, wherein the disease or disorder is cancer selected from lung cancer, small cell lung cancer, non-small cell lung cancer, hepatic cancer, hepatocellular carcinoma, melanoma, cancer of the bladder, cancer of the urethra, renal cancer, clear cell renal carcinoma, and cutaneous squamous cell carcinoma.

13. The method of claim 12, wherein the cancer is lung cancer.

14. The method of claim 12, wherein the cancer is small cell lung cancer.

15. The method of claim 12, wherein the cancer is non-small cell lung cancer.

16. The method of claim 12, wherein the cancer is hepatic cancer.

17. The method of claim 12, wherein the cancer is hepatocellular carcinoma.

18. The method of claim 12, wherein the cancer is melanoma.

19. The method of claim 12, wherein the cancer is cancer of the bladder.

20. The method of claim 12, wherein the cancer is cancer of the urethra.

21. The method of claim 12, wherein the cancer is renal cancer.

22. The method of claim 12, wherein the cancer is clear cell renal carcinoma.

23. The method of claim 12, wherein the cancer is cutaneous squamous cell carcinoma.

24. The crystalline form of claim 2, having an X-ray powder diffraction (XRPD) pattern as shown in FIG. 1.

25. The crystalline form of claim 2, having a differential scanning calorimetry (DSC) thermogram as depicted in FIG. 2.

26. The crystalline form of claim 2, having a thermogravimetric analysis (TGA) thermogram as depicted in FIG. 2.

27. The crystalline form of claim 2, having at least two XRPD peaks, in terms of 2-theta (±0.2 degrees), selected from 7.0, 8.5, 10.0, 10.6, 14.6, 15.2, 15.8, 17.2, 20.1, 21.1, 23.9, 24.8, 26.1, 28.1, 29.6, and 30.2 degrees.

28. The crystalline form of claim 2, having at least three XRPD peaks, in terms of 2-theta (±0.2 degrees), selected from 7.0, 8.5, 10.0, 10.6, 14.6, 15.2, 15.8, 17.2, 20.1, 21.1, 23.9, 24.8, 26.1, 28.1, 29.6, and 30.2 degrees.

29. The crystalline form of claim 2, having characteristic XRPD peaks, in terms of 2-theta (±0.2 degrees), at 7.0, 8.5, 10.0, 10.6, 14.6, 15.2, 15.8, 17.2, 20.1, 21.1, 23.9, 24.8, 26.1, 28.1, 29.6, and 30.2 degrees.

30. The crystalline form of claim 5, having an XRPD pattern as shown in FIG. 3.

31. The crystalline form of claim 5, having a DSC thermogram as depicted in FIG. 4.

32. The crystalline form of claim 5, having a TGA thermogram as depicted in FIG. 4.

33. The crystalline form of claim 5, having at least two XRPD peaks, in terms of 2-theta (±0.2 degrees), selected from 8.5, 15.0, 15.7, 17.0, 18.6, 20.2, 20.5, 21.7, 25.5, and 26.7 degrees.

34. The crystalline form of claim 5, having at least three XRPD peaks, in terms of 2-theta (±0.2 degrees), selected from 8.5, 15.0, 15.7, 17.0, 18.6, 20.2, 20.5, 21.7, 25.5, and 26.7 degrees.

35. The crystalline form of claim 5, having characteristic XRPD peaks, in terms of 2-theta (±0.2 degrees), at 8.5, 15.0, 15.7, 17.0, 18.6, 20.2, 20.5, 21.7, 25.5, and 26.7 degrees.

36. The crystalline form of claim 8, having an XRPD pattern as shown in FIG. 5.

37. The crystalline form of claim 8, having a DSC thermogram as depicted in FIG. 6.

38. The crystalline form of claim 8, having a TGA thermogram as depicted in FIG. 6.

39. The crystalline form of claim 8, having at least two XRPD peaks, in terms of 2-theta (±0.2 degrees), selected from 5.2, 7.5, 8.2, 8.8, 9.4, 11.6, 12.4, 13.0, 14.0, 14.8, 15.8, 16.6, 16.9, 17.3, 17.9, 19.2, 23.6, 24.5, 25.5, and 26.6 degrees.

40. The crystalline form of claim 8, having at least three XRPD peaks, in terms of 2-theta (±0.2 degrees), selected from 5.2, 7.5, 8.2, 8.8, 9.4, 11.6, 12.4, 13.0, 14.0, 14.8, 15.8, 16.6, 16.9, 17.3, 17.9, 19.2, 23.6, 24.5, 25.5, and 26.6 degrees.

41. The crystalline form of claim 8, having characteristic XRPD peaks, in terms of 2-theta (±0.2 degrees), at 5.2, 7.5, 8.2, 8.8, 9.4, 11.6, 12.4, 13.0, 14.0, 14.8, 15.8, 16.6, 16.9, 17.3, 17.9, 19.2, 23.6, 24.5, 25.5, and 26.6 degrees.

* * * * *

UNITED STATES PATENT AND TRADEMARK OFFICE

CERTIFICATE OF CORRECTION

PATENT NO. : 11,866,434 B2
APPLICATION NO. : 17/520174
DATED : January 9, 2024
INVENTOR(S) : Dengjin Wang et al.

It is certified that error appears in the above-identified patent and that said Letters Patent is hereby corrected as shown below:

On the Title Page

Column 2, item (56) (Other Publications), Line 13, delete "p. 97,"" and insert -- p97," --.

Signed and Sealed this
Fifth Day of March, 2024

Katherine Kelly Vidal
*Director of the United States Patent and Trademark Office*